(12) United States Patent
Toda et al.

(10) Patent No.: US 8,222,281 B2
(45) Date of Patent: Jul. 17, 2012

(54) CARBOXYLIC ACID COMPOUND

(75) Inventors: Narihiro Toda, Tokyo (JP); Masao Yoshida, Tokyo (JP); Rieko Takano, Tokyo (JP); Masahiro Inoue, Tokyo (JP); Takeshi Honda, Tokyo (JP); Koji Matsumoto, Tokyo (JP); Ryutaro Nakashima, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 12/893,592

(22) Filed: Sep. 29, 2010

(65) Prior Publication Data
US 2011/0053974 A1    Mar. 3, 2011

Related U.S. Application Data

(63) Continuation of application No. PCT/JP2009/061350, filed on Jun. 23, 2009.

(30) Foreign Application Priority Data

Jun. 25, 2008   (JP) ................................. 2008-165756

(51) Int. Cl.
*A61K 31/44*   (2006.01)
*C07D 211/94*   (2006.01)
(52) U.S. Cl. ........................................ 514/345; 546/303
(58) Field of Classification Search .................. 514/470, 514/345; 549/466; 546/303
See application file for complete search history.

(56) References Cited

U.S. PATENT DOCUMENTS

| 2008/0319077 A1 | 12/2008 | Suzuki et al. |
| 2009/0170908 A1 | 7/2009 | Shimada et al. |

FOREIGN PATENT DOCUMENTS

| WO | WO 2005/051890 A1 | 6/2005 |
| WO | WO 2005/086661 A2 | 9/2005 |
| WO | WO 2006/011615 A1 | 2/2006 |
| WO | WO 2009/054479 A1 | 4/2009 |

OTHER PUBLICATIONS

Bénéchie, M. et al., "Total Synthesis of Maytansinoids. Approach to 4,6-bisdemethylmaytansine and 4-demethylmaytansine", *Tetrahedron*, 48(10), 1895-1910, 1992.

de Haan, R. et al., "Intramolecular Photocycloaddition of a Vinyl Ether to $CF_3$-substituted 2-methoxy-5-phenylpent-1-enes", *Journal of Photochemistry and Photobiology A: Chemistry*, 102(2-3), 179-188, 1997.

Marzi, E. et al., "Fluorophenols and (Trifluoromethyl)phenols as Substrates of Site-Selective Metalation Reactions: To Protect or Not to Protect", *Eur. J. Org. Chem.*, 2001, 2911-2915, 2001.

Musso, D.L. et al., "Indanylidenes. 1. Design and Synthesis of (E)-2-(4,6-Difluoro-1-indanylidene)acetamide, a Potent, Centrally Acting Muscle Relaxant with Antiinflammatory and Analgesic Activity", *J. Med. Chem.*, 46(3), 399-408, 2003.

Ohtani, I. et al., "High-Field FT NMR Application of Mosher's Method. The Absolute Configurations of Marine Terpenoids", *J. Am. Chem. Soc.*, 113(11), 4092-4096, 1991.

International Search Report for International Application No. PCT/JP2009/061350, mailed on Sep. 8, 2009 (English & Japanese).

*Primary Examiner* — Taofiq A Solola
(74) *Attorney, Agent, or Firm* — Locke Lord LLP

(57) ABSTRACT

To find a therapeutic agent and/or a preventive agent for diabetes mellitus or the like having excellent activity and safety. A compound represented by the following general formula (I), or a pharmacologically acceptable salt thereof. In the formula, X represents $=C(R5)-$ or $=N-$; Y represents $-O-$ or $-NH-$; L represents a bond or a substitutable C1-C3 alkylene group; M represents a substitutable C3-C10 cycloalkyl group, a substitutable C6-C10 aryl group, or a substitutable heterocyclic group; $R^1$ represents a C1-C6 alkyl group, a C3-C10 cycloalkyl group, a C1-C6 haloalkyl group, a C2-C6 alkenyl group, a C2-C6 alkynyl group, a C1-C6 aliphatic acyl group, a C1-C6 alkoxy C1-C6 alkyl group, or a C6-C10 aryl group; and $R^2$, $R^3$, $R^4$, and $R^5$ may be the same or different and each represent a hydrogen atom, a halogen atom, a C1-C3 alkyl group, a C1-C3 haloalkyl group, a C1-C3 alkoxy group, or a nitro group. In this connection, the alkyl group moieties of $R^1$ and $R^2$ may be bonded to each other to form a 5- to 6-membered heterocyclic ring containing one oxygen atom.

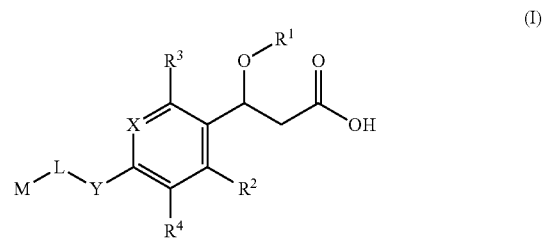

(I)

27 Claims, No Drawings

CARBOXYLIC ACID COMPOUND

This application is a national application filed under 35 U.S.C. §111 (a) which claims the benefit of International Application Number PCT/JP2009/061350, filed on Jun. 23, 2009, entitled "CARBOXYLIC ACID COMPOUND", which claims the benefit of Japanese Patent Application Number 2008-165756, filed on Jun. 25, 2008, all of which are hereby incorporated by reference.

FIELD OF THE INVENTION

The present invention relates to a novel compound and a pharmacologically acceptable salt thereof having a blood glucose lowering effect and the like.

Further, the invention relates to a therapeutic agent and/or a preventive agent for diabetes mellitus, postprandial hyperglycemia, impaired glucose tolerance, ketosis, acidosis, diabetic neuropathy, diabetic nephropathy, diabetic retinopathy, hyperlipidemia, sexual dysfunction, a skin disease, a joint disease, osteopenia, arteriosclerosis, a thrombotic disease, dyspepsia, memory learning disorder, obesity, hypertension, edema, insulin resistance, unstable diabetes mellitus, lipoatrophy, insulin allergy, insulinoma, lipotoxicity, hyperinsulinemia, cancer, or the like (preferably, a therapeutic agent and/or a preventive agent for diabetes mellitus) containing the above-mentioned compound or a pharmacologically acceptable salt thereof as an active ingredient.

Further, the invention relates to a composition for preventing or treating any of the above-mentioned diseases containing the above-mentioned compound as an active ingredient; use of the above-mentioned compound for manufacturing a pharmaceutical composition for preventing or treating any of the above-mentioned diseases; or a method for preventing or treating any of the above-mentioned diseases, comprising administering a pharmacologically effective amount of the above-mentioned compound to a mammal (preferably a human).

BACKGROUND OF THE INVENTION

Patent documents 1 to 3 disclose a compound having a substructure which is partly the same as that of the compound of the invention and described to be useful as a therapeutic agent for diabetes mellitus.

The compound disclosed in Patent document 2 has a substructure which is partly the same as that of the compound of the invention, however, the structure of the compound disclosed in Patent document 2 is completely different from that of the compound of the invention in that a cyclopropane ring is essential at the α-position of a carboxylic acid.

The compound disclosed in Patent document 3 has a substructure which is partly the same as that of the compound of the invention, however, the structure of the compound disclosed in Patent document 3 is completely different from that of the compound of the invention in that the compound disclosed in Patent document 3 does not have an alkoxy group at the β-position of a carboxylic acid, which is essential to the compound of the invention.

PRIOR ART DOCUMENTS

Patent Documents

Patent document 1: WO 2006/011615 (corresponding to US Patent Application Publication No. US 2008/319077)
Patent document 2: WO 2005/051890
Patent document 3: WO 2005/086661 (corresponding to US Patent Application Publication No. US 2007/142384)

SUMMARY OF THE INVENTION

Problems that the Invention is to Solve

The present inventors made intensive studies, and as a result, they found that a compound represented by the below-mentioned formula (I) unexpectedly has an excellent blood glucose lowering activity and the like based on its specific chemical structure, and further has excellent physical properties as a pharmaceutical preparation such as stability, and therefore can be a pharmaceutical which is safe and useful as a preventive or therapeutic agent for hyperglycemia, diabetes mellitus, and pathological conditions or diseases associated with these diseases, and thus, the invention has been completed based on these findings.

That is, the invention has a blood glucose lowering effect, an enhancing effect on insulin secretion, and the like, and is useful as a preventive or therapeutic agent for a disease such as diabetes mellitus (type I diabetes, type II diabetes, gestational diabetes, or the like), postprandial hyperglycemia, impaired glucose tolerance, ketosis, acidosis, diabetic neuropathy, diabetic nephropathy, diabetic retinopathy, hyperlipidemia (hypertriglyceridemia, hypercholesterolemia, hypohigh density lipoproteinemia, postprandial hyperlipidemia, or the like), sexual dysfunction, a skin disease, a joint disease, osteopenia, arteriosclerosis, a thrombotic disease, dyspepsia, memory learning disorder, obesity, hypertension, edema, insulin resistance, unstable diabetes mellitus, lipoatrophy, insulin allergy, insulinoma, lipotoxicity, hyperinsulinemia, or cancer, particularly for a disease such as type II diabetes or postprandial hyperglycemia.

Means for Solving the Problems

The invention is directed to:
(1) a compound represented by the following general formula (I) or a pharmacologically acceptable salt thereof:

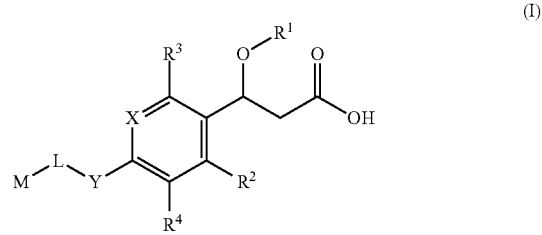

[wherein X represents =C($R^5$)— or =N—; Y represents —O— or —NH—; L represents a C1-C3 alkylene group optionally substituted with a halogen atom, a C1-C3 haloalkyl group or a C1-C3 alkyl group, or a bond; M represents a C3-C10 cycloalkyl group (the cycloalkyl group being optionally fused with one phenyl group or 4- to 10-membered heterocyclic ring containing 1 to 3 heteroatoms which may be the same or different and are selected from nitrogen, oxygen, and sulfur, and further optionally substituted with 1 to 5 substituents selected from substituent group α), a C6-C10 aryl group (the aryl group may be substituted with 1 to 5 groups selected from substituent group α), or a 4- to 10-membered heterocyclic group containing 1 to 3 heteroatoms which may be the same or different and are selected from nitrogen, oxygen, and sulfur (the heterocyclic group being optionally substituted with 1 to 5 substituents selected from substituent group α); $R^1$ represents a C1-C6 alkyl group, a C3-C10 cycloalkyl group, a C1-C6 haloalkyl group, a C2-C6 alkenyl group, a C2-C6 alkynyl group, a C1-C6 aliphatic acyl group, a C1-C6 alkoxy C1-C6 alkyl group or a C6-C10 aryl group; $R^2$, $R^3$, $R^4$, and $R^5$ may be the same or different and each represents a hydrogen atom, a halogen atom, a C1-C3 alkyl group, a C1-C3 haloalkyl group, a C1-C3 alkoxy group, or a nitro group; the alkyl group moieties of $R^1$ and $R^2$ being optionally bonded to each other to form a 5- to 6-membered heterocyclic ring containing one oxygen atom; and the substituent group α includes a halogen atom, a C1-C6 alkyl group, a C1-C6 haloalkyl group, a C1-C6 hydroxyalkyl group (the hydroxyalkyl group being optionally substituted with one C1-C6 alkyl group), a C1-C6 alkoxy C1-C6 alkyl group, a C1-C6 aminoalkyl group, a C1-C6 alkoxy group, a C1-C6 haloalkoxy group, a C6-C10 aryloxy group, a C1-C6 alkylthio group, a carboxy group, a C1-C6 alkoxycarbonyl group, a hydroxy group, a C1-C6 aliphatic acyl group, an amino group, a C1-C6 alkylamino group, a C3-C10 cycloalkylamino group, a C1-C6 dialkylamino group, a C1-C6 alkoxyamino group, a C1-C6 aliphatic acylamino group (the C1-C6 aliphatic acylamino group being optionally substituted with 1 to 3 halogen atoms), a cyano group, a nitro group, a C1-C6 alkylsulfonyl group, a C1-C6 dialkylaminosulfonyl group, a C3-C10 cycloalkyl group, and a C6-C10 aryl group (the aryl group being optionally substituted with one to five C1-C6 haloalkyl groups)];

(2) the compound according to the above (1), wherein X is $=C(R^5)$— and $R^5$ is a hydrogen atom;

(3) the compound according to the above (1) or (2), wherein Y is —O—;

(4) the compound according to any one of the above (1) to (3), wherein L is a bond or a C1-C3 alkylene group;

(5) the compound according to any one of the above (1) to (4), wherein M is a C3-C10 cycloalkyl group (the cycloalkyl group being optionally fused with one phenyl group, and further optionally substituted with 1 to 5 substituents selected from substituent group α), a C6-C10 aryl group (the aryl group may be substituted with 1 to 5 groups selected from substituent group α);

(6) the compound according to any one of the above (1) to (5), wherein $R^2$, $R^3$, and $R^4$ are each a hydrogen atom;

(7) a compound represented by the following general formula (II):

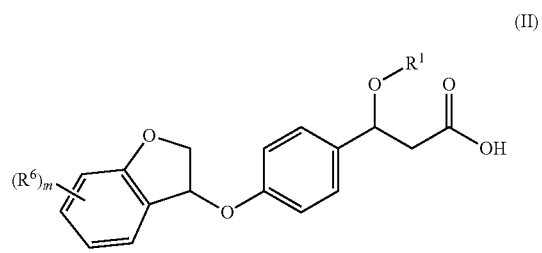

(II)

[wherein $R^1$ represents a C1-C6 alkyl group, a C3-C10 cycloalkyl group, a C1-C6 haloalkyl group, a C2-C6 alkenyl group, a C2-C6 alkynyl group, a C1-C6 aliphatic acyl group, a C1-C6 alkoxy C1-C6 alkyl group or a C6-C10 aryl group; m represents an integer of any one of 0 to 3; $R^6$'s may be the same or different and each represents a halogen atom, a C1-C6 alkyl group, a C1-C6 haloalkyl group, a C1-C6 hydroxyalkyl group (the hydroxyalkyl group being optionally substituted with one C1-C6 alkyl group), a C1-C6 alkoxy C1-C6 alkyl group, a C1-C6 aminoalkyl group, a C1-C6 alkoxy group, a C1-C6 haloalkoxy group, a C6-C10 aryloxy group, a C1-C6 alkylthio group, a carboxy group, a C1-C6 alkoxycarbonyl group, a hydroxy group, a C1-C6 aliphatic acyl group, an amino group, a C1-C6 alkylamino group, a C3-C10 cycloalkylamino group, a C1-C6 dialkylamino group, a C1-C6 alkoxyamino group, a C1-C6 aliphatic acylamino group (the C1-C6 aliphatic acylamino group being optionally substituted with 1 to 3 halogen atoms), a cyano group, a nitro group, a C1-C6 alkylsulfonyl group, a C1-C6 dialkylaminosulfonyl group, a C3-C10 cycloalkyl group, or a C6-C10 aryl group (the aryl group being optionally substituted with one to five C1-C6 haloalkyl groups)];

(8) the compound according to the above (7), wherein $R^1$ is a C1-C6 alkyl group;

(9) the compound according to the above (7), wherein $R^1$ is an ethyl group;

(10) the compound according to any one of the above (7) to (9), wherein m is 1 or 2;

(11) the compound according to any one of the above (7) to (10), wherein $R^6$'s may be the same or different and are each a halogen atom, a C1-C6 alkyl group, a C1-C6 haloalkyl group, a C1-C6 alkoxy group, or a C1-C6 haloalkoxy group;

(12) the compound according to any one of the above (7) to (10), wherein $R^6$'s may be the same or different and are each a C1-C6 haloalkyl group or a C1-C6 haloalkoxy group;

(13) a compound represented by the following general formula (III):

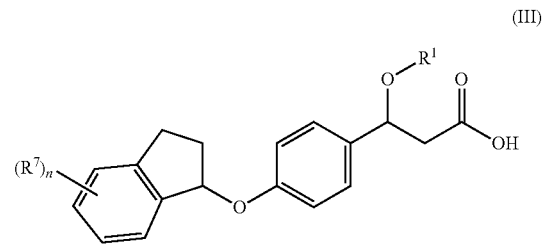

(III)

[wherein $R^1$ represents a C1-C6 alkyl group, a C3-C10 cycloalkyl group, a C1-C6 haloalkyl group, a C2-C6 alkenyl group, a C2-C6 alkynyl group, a C1-C6 aliphatic acyl group, a C1-C6 alkoxy C1-C6 alkyl group or a C6-C10 aryl group; n represents an integer of any one of 0 to 3; $R^7$'s may be the same or different and each represents a halogen atom, a C1-C6 alkyl group, a C1-C6 haloalkyl group, a C1-C6 hydroxyalkyl group (the hydroxyalkyl group being optionally substituted with one C1-C6 alkyl group), a C1-C6 alkoxy C1-C6 alkyl group, a C1-C6 aminoalkyl group, a C1-C6 alkoxy group, a C1-C6 haloalkoxy group, a C6-C10 aryloxy group, a C1-C6 alkylthio group, a carboxy group, a C1-C6 alkoxycarbonyl group, a hydroxy group, a C1-C6 aliphatic acyl group, an amino group, a C1-C6 alkylamino group, a C3-C10 cycloalkylamino group, a C1-C6 dialkylamino group, a C1-C6 alkoxyamino group, a C1-C6 aliphatic acylamino group (the C1-C6 aliphatic acylamino group being optionally substituted with 1 to 3 halogen atoms), a cyano group, a nitro group, a C1-C6 alkylsulfonyl group, a C1-C6 dialkylaminosulfonyl group, a C3-C10 cycloalkyl group, or a C6-C10 aryl group (the aryl group being optionally substituted with one to five C1-C6 haloalkyl groups)];

(14) the compound according to the above (13), wherein $R^1$ is a C1-C6 alkyl group;

(15) the compound according to the above (13), wherein $R^1$ is an ethyl group;

(16) the compound according to any one of the above (13) to (15), wherein n is 1 or 2;

(17) the compound according to any one of the above (13) to (16), wherein $R^7$'s may be the same or different and are each a halogen atom, a C1-C6 alkyl group, a C1-C6 haloalkyl group, a C1-C6 haloalkoxy group or a C3-C10 cycloalkyl group;

(18) the compound according to any one of the above (13) to (16), wherein $R^7$'s may be the same or different and are each a fluorine atom, a methyl group, an ethyl group, a difluoromethyl group, a trifluoromethyl group, or a trifluoromethoxy group;

(19) 3-{4-[(3,4-dichlorobenzyl)oxy]phenyl}-3-ethoxypropionic acid, (3S)-3-{4-[(3,4-dichlorobenzyl)oxy]phenyl}-3-ethoxypropionic acid, 3-ethoxy-3-(6-{[4-(trifluoromethyl)benzyl]oxy}pyridin-3-yl)propionic acid, (3S)-3-ethoxy-3-(6-{[4-(trifluoromethyl)benzyl]oxy}pyridin-3-yl) propionic acid, 3-ethoxy-3-{4-[(2-methylbenzyl)oxy] phenyl}propionic acid, 3-{4-[(4-cyano-1-naphthyl)oxy] phenyl}-3-ethoxypropionic acid, 3-[4-(3,5-dichlorophenoxy)phenyl]-3-ethoxypropionic acid, 3-[4-(2,5-dichlorophenoxy)phenyl]-3-ethoxypropionic acid, (3S)-3-ethoxy-3-(4-{[4-(trifluoromethyl)benzyl]oxy}phenyl) propionic acid, (3S)-3-(4-{[(1R)-4-chloro-2,3-dihydro-1H-inden-1-yl]oxy}phenyl)-3-ethoxypropionic acid, (3S)-3-ethoxy-3-(4-{[(1R)-4-(trifluoromethyl)-2,3-dihydro-1H-inden-1-yl]oxy}phenyl)propionic acid, (3S)-3-(4-{[(1S)-4-chloro-2,3-dihydro-1H-inden-1-yl]oxy}phenyl)-3-ethoxypropionic acid, or (3S)-3-ethoxy-3-(4-{[4-(trifluoromethyl)-2,3-dihydro-1H-inden-1-yl]oxy}phenyl) propionic acid;

(20) (3S)-3-ethoxy-3-(4-{[(1R)-4-(trifluoromethyl)-2,3-dihydro-1H-inden-1-yl]oxy}phenyl)propionic acid;

(21) (3S)-3-ethoxy-3-(4-{[4-(trifluoromethyl)-2,3-dihydro-1H-inden-1-yl]oxy}phenyl)propionic acid;

(22) (3S)-3-ethoxy-3-(4-{[(3S)-7-(trifluoromethoxy)-2,3-dihydro-1-benzofuran-3-yl]oxy}phenyl)propionic acid;

(23) (3S)-3-ethoxy-3-(4-{[(1R)-5-fluoro-4-(trifluoromethyl)-2,3-dihydro-1H-inden-1-yl]oxy}phenyl)-propionic acid;

(24) (3S)-3-ethoxy-3-(4-{[(1R)-4-ethyl-2,3-dihydro-1H-inden-1-yl]oxy}phenyl)propionic acid;

(25) (3S)-3-ethoxy-3-(4-{[(1R)-4-methyl-2,3-dihydro-1H-inden-1-yl]oxy}phenyl)propionic acid;

(26) (3S)-3-(4-{[(1R)-4-(difluoromethyl)-2,3-dihydro-1H-inden-1-yl]oxy}phenyl)-3-ethoxypropionic acid;

(27) (3S)-3-ethoxy-3-(4-{[(3S)-7-(trifluoromethyl)-2,3-dihydro-1-benzofuran-3-yl]oxy}phenyl)propionic acid;

(28) (3S)-3-ethoxy-3-(4-{[(1R)-6-fluoro-4-(trifluoromethyl)-2,3-dihydro-1H-inden-1-yl]oxy}phenyl)-propionic acid;

(29) (3S)-3-(4-{[(1R)-4,6-dimethyl-2,3-dihydro-1H-inden-1-yl]oxy}phenyl)-3-ethoxypropionic acid;

(30) (3S)-3-ethoxy-3-(4-{[(1R)-4-(trifluoromethoxy)-2,3-dihydro-1H-inden-1-yl]oxy}phenyl)propionic acid;

(31) (3S)-3-(4-{[(1R)-4-cyclopropyl-2,3-dihydro-1H-inden-1-yl]oxy}phenyl)-3-ethoxypropionic acid;

(32) a pharmacologically acceptable salt of the compound according to any one of the above (2) to (31);

(33) a pharmaceutical composition, containing the compound or a pharmacologically acceptable salt thereof according to any one of the above (1) to (31) as an active ingredient;

(34) a blood glucose lowering agent, containing the compound or a pharmacologically acceptable salt thereof according to any one of the above (1) to (32) as an active ingredient;

(35) an insulin secretion enhancer, containing the compound or a pharmacologically acceptable salt thereof according to any one of the above (1) to (32) as an active ingredient;

(36) a therapeutic agent or a preventive agent for diabetes mellitus, containing the compound or a pharmacologically acceptable salt thereof according to any one of the above (1) to (32) as an active ingredient;

(36-1) a therapeutic agent or a preventive agent for type II diabetes, containing the compound or a pharmacologically acceptable salt thereof according to any one of the above (1) to (32) as an active ingredient;

(36-2) a therapeutic agent for type II diabetes, containing the compound or a pharmacologically acceptable salt thereof according to any one of the above (1) to (32) as an active ingredient;

(37) a therapeutic agent or a preventive agent for postprandial hyperglycemia, containing the compound or a pharmacologically acceptable salt thereof according to any one of the above (1) to (32) as an active ingredient;

(38) a therapeutic agent or a preventive agent for impaired glucose tolerance, diabetic neuropathy, diabetic nephropathy, diabetic retinopathy, obesity, insulin resistance, unstable diabetes, insulin allergy, insulinoma, or hyperinsulinemia, containing the compound or a pharmacologically acceptable salt thereof according to any one of the above (1) to (32) as an active ingredient;

(39) a therapeutic agent or a preventive agent for ketosis, acidosis, hyperlipidemia, sexual dysfunction, a skin disease, a joint disease, osteopenia, arteriosclerosis, a thrombotic disease, dyspepsia, memory learning disorder, hypertension, edema, lipoatrophy, lipotoxicity, or cancer, containing the compound or a pharmacologically acceptable salt thereof according to any one of the above (1) to (32) as an active ingredient;

(40) use of the compound or a pharmacologically acceptable salt thereof according to any one of the above (1) to (32) for manufacturing an insulin secretion enhancer or a blood glucose lowering agent;

(41) use of the compound or a pharmacologically acceptable salt thereof according to any one of the above (1) to (32) for manufacturing a preventive agent or a therapeutic agent for a disease selected from diabetes mellitus, postprandial hyperglycemia, impaired glucose tolerance, diabetic neuropathy, diabetic nephropathy, diabetic retinopathy, obesity, insulin resistance, unstable diabetes, insulin allergy, insulinoma, and hyperinsulinemia;

(41-1) use of the compound or a pharmacologically acceptable salt thereof according to any one of the above (1) to (32) for manufacturing a preventive agent or a therapeutic agent for a disease selected from diabetes mellitus and postprandial hyperglycemia;

(41-2) use of the compound or a pharmacologically acceptable salt thereof according to any one of the above (1) to (32) for manufacturing a preventive agent or a therapeutic agent for type II diabetes;

(42) a method for preventing or treating a disease selected from diabetes mellitus, postprandial hyperglycemia, impaired glucose tolerance, diabetic neuropathy, diabetic nephropathy, diabetic retinopathy, obesity, insulin resistance, unstable diabetes, insulin allergy, insulinoma, and hyperinsulinemia, comprising administering a pharmacologically effective amount of the compound or a pharmacologically acceptable salt thereof according to any one of the above (1) to (32), or a pharmacologically acceptable ester thereof to a mammal;

(42-1) a method for preventing or treating a disease selected from diabetes mellitus and postprandial hyperglycemia, comprising administering a pharmacologically effective amount of the compound or a pharmacologically acceptable salt thereof according to any one of the above (1) to (32), or a pharmacologically acceptable ester thereof to a mammal; and (42-2) a method for preventing or treating type II diabetes, comprising administering a pharmacologically effective amount of the compound or a pharmacologically acceptable salt thereof according to any one of the above (1) to (32), or a pharmacologically acceptable ester thereof to a mammal.

In the invention, the "C1-C3 alkyl group" refers to a straight or branched chain alkyl group having 1 to 3 carbon atoms, and can be, for example, a methyl, ethyl, or n-propyl group. In the case of $R^2$, $R^3$, $R^4$, $R^5$, and the substituent of the C1-C3 alkylene represented by L, the C1-C3 alkyl group is preferably a methyl group.

In the invention, the "C1-C6 alkyl group" refers to a straight or branched chain alkyl group having 1 to 6 carbon atoms, and can be, for example, a group mentioned above as an example of the "C1-C3 alkyl group" or an n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, or 2-ethylbutyl group. In the case of R', the C1-C6 alkyl group is preferably an ethyl group. In the case of substituent group α, the C1-C6 alkyl group is preferably an alkyl group having 1 to 3 carbon atoms, and most preferably a methyl group. In the case of $R^6$ and $R^7$, the C1-C6 alkyl group is preferably an alkyl group having 1 to 3 carbon atoms, and most preferably an ethyl group or a methyl group.

In the invention, the "C3-C10 cycloalkyl group" refers to a 3- to 10-membered saturated cyclic hydrocarbon group which may be fused with another ring, and can be, for example, a cyclopropyl, cyclobutyl, cyclopentyl, cyclohexyl, cycloheptyl, norbornyl, adamantyl, 2,3-dihydroindenyl, 1,2,3,4-tetrahydronaphthalenyl, or 6,7,8,9-tetrahydro-5H-benzo[7]annulenyl group. In the case of M, the C3-C10 cycloalkyl group is preferably a 3- to 7-membered saturated cyclic hydrocarbon group or a C3-C7 cycloalkyl group fused with a phenyl group, and more preferably a cyclohexyl, 2,3-dihydroindenyl, 1,2,3,4-tetrahydronaphthalenyl, or 6,7,8,9-tetrahydro-5H-benzo[7]annulenyl group. In the case of $R^1$, $R^6$, $R^7$, and substituent group α, the C3-C10 cycloalkyl group is preferably a 3- to 7-membered saturated cyclic hydrocarbon group, and more preferably a cyclopropyl, cyclobutyl, cyclopentyl, or cyclohexyl group.

In the invention, the "C1-C3 haloalkyl group" refers to a group in which the above-mentioned "C1-C3 alkyl group" is substituted with halogen atom(s), and can be, for example, a trifluoromethyl, trichloromethyl, difluoromethyl, dichloromethyl, dibromomethyl, fluoromethyl, 2,2,2-trifluoroethyl, 2,2,2-trichloroethyl, 2-bromoethyl, 2-chloroethyl, 2-fluoroethyl, 2-iodoethyl, 3-chloropropyl, or 2,2-dibromoethyl group. In the case of the substituent of the C1-C3 alkyl represented by L, the C1-C3 haloalkyl group is preferably a trifluoromethyl group, and in the case of $R^2$, $R^3$, $R^4$, and $R^5$, the C1-C3 haloalkyl group is preferably a trifluoromethyl or difluoromethyl group.

In the invention, the "C1-C6 haloalkyl group" refers to a group in which the above-mentioned "C1-C6 alkyl group" is substituted with halogen atom(s), and can be, for example, a group mentioned above as an example of the "C1-C3 haloalkyl group" or a 4-fluorobutyl, 6-iodohexyl, or 2,2-dibromoethyl group. In the case of $R^1$, the C1-C6 haloalkyl group is preferably a trifluoromethyl or difluoroethyl group, and in the case of $R^6$, $R^7$, and substituent group α, the C1-C6 haloalkyl group is preferably a trifluoromethyl or difluoromethyl group.

In the invention, the "C1-C6 aminoalkyl group" refers to a group in which the above-mentioned "C1-C6 alkyl group" is substituted by an amino group, and can be, for example, an aminomethyl, aminoethyl, aminopropyl, or aminobutyl group. In the case of $R^6$, $R^7$, and substituent group α, the C1-C6 aminoalkyl group is preferably aminomethyl.

In the invention, the "C1-C6 hydroxyalkyl group" refers to a group in which the above-mentioned "C1-C6 alkyl group" is substituted with a hydroxy group, and can be, for example, a hydroxymethyl, hydroxyethyl, 1-hydroxyethyl, hydroxypropyl, hydroxybutyl, hydroxypentyl, or hydroxyhexyl group. In the case of $R^6$, $R^7$, and substituent group α, the C1-C6 hydroxyalkyl group is preferably a hydroxymethyl group or a 1-hydroxyethyl group.

In the invention, the "C1-C3 alkoxy group" refers to a group in which the above-mentioned "C1-C3 alkyl group" is bonded to an oxygen atom, and can be, for example, a straight or branched chain alkoxy group having 1 to 3 carbon atoms such as methoxy, ethoxy, n-propoxy, or isopropoxy. In the case of $R^2$, $R^3$, $R^4$, and $R^5$, the C1-C3 alkoxy group is preferably a methoxy or ethoxy group.

In the invention, the "C1-C6 alkoxy group" refers to a group in which the above-mentioned "C1-C6 alkyl group" is bonded to an oxygen atom, and can be, for example, a group mentioned above as an example of the "C1-C3 alkoxy group" or a straight or branched chain alkoxy group having 1 to 6 carbon atoms such as n-butoxy, isobutoxy, s-butoxy, tert-butoxy, n-pentoxy, isopentoxy, 2-methylbutoxy, neopentoxy, n-hexyloxy, 4-methylpentoxy, 3-methylpentoxy, 2-methylpentoxy, 3,3-dimethylbutoxy, 2,2-dimethylbutoxy, 1,1-dimethylbutoxy, 1,2-dimethylbutoxy, 1,3-dimethylbutoxy, or 2,3-dimethylbutoxy. In the case of $R^6$, $R^7$, and substituent group α, the C1-C6 alkoxy group is preferably a methoxy or ethoxy group.

In the invention, the "C1-C6 haloalkoxy group" refers to a group in which the above-mentioned "C1-C6 haloalkyl group" is bonded to an oxygen atom, and can be, for example, a trifluoromethoxy, trichloromethoxy, difluoromethoxy, dichloromethoxy, dibromomethoxy, fluoromethoxy, 2,2,2-trichloroethoxy, 2,2,2-trifluoroethoxy, 2-bromoethoxy, 2-chloroethoxy, 2-fluoroethoxy, or 2,2-dibromoethoxy group. In the case of $R^6$, $R^7$, and substituent group α, the C1-C6 haloalkoxy group is preferably a trifluoromethoxy or difluoromethoxy group.

In the invention, the "C1-C6 alkoxy C1-C6 alkyl group" refers to a group in which the above-mentioned "C1-C6 alkoxy group" is bonded to the above-mentioned "C1-C6 alkyl group", and can be, for example, a methoxymethyl, methoxyethyl, ethoxymethyl, ethoxyethyl, n-propoxymethyl, n-propoxyethyl, isopropoxymethyl, n-butoxymethyl, isobutoxymethyl, s-butoxymethyl, tert-butoxymethyl, n-pentoxymethyl, isopentoxymethyl, 2-methylbutoxymethyl, neopentoxymethyl, n-hexyloxymethyl, 4-methylpentoxymethyl, 3-methylpentoxymethyl, 2-methylpentoxymethyl, 3,3-dimethylbutoxymethyl, 2,2-dimethylbutoxymethyl, or 1,1-dimethylbutoxymethyl group. In the case of $R^1$, the C1-C6 alkoxy C1-C6 alkyl group is preferably a methoxymethyl group. In the case of $R^6$, $R^7$, and substituent group α, the C1-C6 alkoxy C1-C6 alkyl group is preferably a methoxymethyl group.

In the invention, the "C1-C6 alkylthio group" refers to a group in which the above-mentioned "C1-C6 alkyl group" is bonded to a sulfur atom, and can be, for example, a methylthio, ethylthio, or t-butylthio group. In the case of $R^6$, $R^7$, and substituent group α, the C1-C6 alkylthio group is preferably a methylthio group.

In the invention, the "C2-C6 alkenyl group" refers to a straight or branched chain alkenyl group having 2 to 6 carbon atoms, and can be, for example, an ethenyl, 1-propenyl, 2-propenyl, 1-methyl-2-propenyl, 1-methyl-1-propenyl, 2-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl, or 5-hexenyl group. In the case of $R^1$, the C2-C6 alkenyl group is preferably a straight or branched chain alkenyl group having 3 to 5 carbon atoms, and more preferably an ethenyl group.

In the invention, the "C2-C6 alkynyl group" refers to a straight or branched chain alkynyl group having 2 to 6 carbon atoms, and can be, for example, an ethynyl, 2-propynyl, 1-methyl-2-propynyl, 2-methyl-2-propynyl, 2-ethyl-2-propynyl, 2-butynyl, 1-methyl-2-butynyl, 2-methyl-2-butynyl, 1-ethyl-2-butynyl, 3-butynyl, 1-methyl-3-butynyl, 2-methyl-3-butynyl, 1-ethyl-3-butynyl, 2-pentynyl, 1-methyl-2-pentynyl, 2-methyl-2-pentynyl, 3-pentynyl, 1-methyl-3-pentynyl, 2-methyl-3-pentynyl, 4-pentynyl, 1-methyl-4-pentynyl, 2-methyl-4-pentynyl, 2-hexynyl, 3-hexynyl, 4-hexynyl, or 5-hexynyl group. In the case of $R^1$, the C2-C6 alkynyl group is preferably a straight or branched chain alkynyl group having 3 to 5 carbon atoms.

In the invention, the "C1-C3 alkylene group" refers to an alkylene group having 1 to 3 carbon atoms, and can be, for example, methylene, methylmethylene, dimethylmethylene, ethylene, or propylene. In the case of L, the C1-C3 alkylene group is preferably methylene or ethylene, and more preferably methylene.

In the invention, the "C6-C10 aryl group" refers to an aromatic hydrocarbon group having 6 to 10 carbon atoms, and can be, for example, a phenyl, indenyl, or naphthyl group. In the case of M, $R^1$, $R^6$, $R^7$, and substituent group α, the C6-C10 aryl group is preferably a phenyl group.

In the invention, the "C6-C10 aryloxy group" refers to a group in which the above-mentioned "C6-C10 aryl group" is bonded to an oxygen atom, and can be, for example, a phenyloxy, indenyloxy, or naphthyloxy group. In the case of $R^6$, $R^7$, and substituent group α, the C6-C10 aryloxy group is preferably a phenyloxy group.

In the invention, the "4- to 10-membered heterocyclic group containing 1 to 3 heteroatoms which may be the same or different and are selected from nitrogen, oxygen, and sulfur" refers to a 4- to 10-membered heterocyclic group containing 1 to 3 sulfur atoms, oxygen atoms, or nitrogen atoms, and can be, for example, an aromatic heterocyclic group such as furyl, thienyl, pyrrolyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyranyl, pyridyl, pyridazinyl, pyrimidinyl, or pyrazinyl; or a partially or completely reduced group corresponding to any of these aromatic heterocyclic groups such as morpholinyl, thiomorpholinyl, pyrrolidinyl, pyrrolinyl, imidazolidinyl, imidazolinyl, pyrazolidinyl, pyrazolinyl, piperidinyl, piperazinyl, or tetrahydropyranyl. Incidentally, the above-mentioned "4- to 10-membered heterocyclic group" may be fused with another cyclic group, and can be, for example, a benzofuranyl, chromenyl, indolidinyl, isoindolyl, indolyl, indazolyl, purinyl, quinolidinyl, isoquinolyl, quinolyl, phthalazinyl, naphthylidinyl, quinoxalinyl, quinazolinyl, isoindolinyl, 2,3-dihydro-1-benzofuranyl, 3,4-dihydro-1H-isochromenyl, 1,2,3,4-tetrahydroquinolinyl, or 1,2,3,4-tetrahydroisoquinolinyl group. In the case of M, the 4- to 10-membered heterocyclic group is preferably a 4- to 10-membered heterocyclic group containing at least one nitrogen atom and may contain an oxygen atom or a sulfur atom, and can be, for example, an aromatic heterocyclic group such as pyrrolyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyridyl, pyridazinyl, pyrimidinyl, or pyrazinyl; or a partially or completely reduced group corresponding to any of these aromatic heterocyclic groups such as morpholinyl, thiomorpholinyl, pyrrolidinyl, pyrrolinyl, imidazolidinyl, imidazolinyl, pyrazolidinyl, pyrazolinyl, piperidinyl, piperazinyl, or tetrahydropyranyl, and is more preferably a pyridyl, pyrimidyl, pyrazolyl, pyrrolidinyl, piperidinyl, piperazinyl, morpholinyl, or tetrahydropyranyl group.

In the invention, the "5- to 6-membered heterocyclic ring containing one oxygen atom" refers to a 5- or 6-membered heterocyclic ring containing one oxygen atom, and can be, for example, 2,5-dihydrofuran or 3,6-dihydro-2H-pyran. In the case where the alkyl group moieties of $R^1$ and $R^2$ are bonded to each other, the 5- to 6-membered heterocyclic ring containing one oxygen atom is preferably 2,5-dihydrofuran.

In the invention, the "C1-C6 alkoxycarbonyl group" refers to a group in which the above-mentioned "C1-C6 alkoxy group" is bonded to a carbonyl group, and can be, for example, a straight or branched chain alkoxycarbonyl group having 1 to carbon atoms such as methoxycarbonyl, ethoxycarbonyl, n-propoxycarbonyl, isopropoxycarbonyl, n-butoxycarbonyl, isobutoxycarbonyl, s-butoxycarbonyl, tert-butoxycarbonyl, n-pentoxycarbonyl, isopentoxycarbonyl, 2-methylbutoxycarbonyl, neopentoxycarbonyl, n-hexyloxycarbonyl, 4-methylpentoxycarbonyl, 3-methylpentoxycarbonyl, 2-methylpentoxycarbonyl, 3,3-dimethylbutoxycarbonyl, 2,2-dimethylbutoxycarbonyl, 1,1-dimethylbutoxycarbonyl, 1,2-dimethylbutoxycarbonyl, 1,3-dimethylbutoxycarbonyl, or 2,3-dimethylbutoxycarbonyl. In the case of $R^6$, $R^7$, and substituent group α, the C1-C6 alkoxycarbonyl group is preferably a methoxycarbonyl, ethoxycarbonyl, or tert-butoxycarbonyl group.

In the invention, the "C1-C6 aliphatic acyl group" refers to a group in which an aliphatic hydrocarbon group having 1 to 6 carbon atoms is bonded to a carbonyl group, and can be, for example, an alkylcarbonyl group such as a formyl, acetyl, propionyl, butylyl, isobutylyl, pentanoyl, pivaloyl, valeryl, or isovaleryl group; a haloalkylcarbonyl group such as chloroacetyl, dichloroacetyl, trichloroacetyl, or trifluoroacetyl; a lower alkoxyalkylcarbonyl group such as methoxyacetyl; an unsaturated alkylcarbonyl group such as (E)-2-methyl-2-butenoyl; or the like. In the case of $R^1$, $R^6$, $R^7$, and substituent group α, the C1-C6 aliphatic acyl group is preferably a formyl group, an acetyl group, or a trifluoroacetyl group.

In the invention, the "C1-C6 alkylamino group" refers to a group in which the above-mentioned "C1-C6 alkyl group" is bonded to an amino group, and can be, for example, a methylamino, ethylamino, n-propylamino, isopropylamino, n-butylamino, isobutylamino, s-butylamino, tert-butylamino, n-pentylamino, isopentylamino, 2-methylbutylamino, neopentylamino, 1-ethylpropylamino, n-hexylamino, isohexylamino, 4-methylpentylamino, 3-methylpentylamino, 2-methylpentylamino, 1-methylpentylamino, 3,3-dimethylbutylamino, 2,2-dimethylbutylamino, 1,1-dimethylbutylamino, 1,2-dimethylbutylamino, 1,3-dimethylbutylamino, 2,3-dimethylbutylamino, or 2-ethylbutylamino group. In the case of $R^6$, $R^7$, and substituent group α, the C1-C6 alkylamino group is preferably a methylamino group, an ethylamino group, or an isopropylamino group.

In the invention, the "C3-C10 cycloalkylamino group" refers to a group in which the above-mentioned "C3-C10 cycloalkyl" is bonded to an amino group, and can be, for example, a cyclopropylamino, cyclobutylamino, cyclopentylamino, cyclohexylamino, cycloheptylamino, norbornylamino, or adamantylamino group. In the case of $R^6$, $R^7$, and substituent group α, the C3-C10 cycloalkylamino group is preferably a 3- to 7-membered saturated cyclic hydrocarbon amino group.

In the invention, the "C1-C6 dialkylamino group" refers to a group in which an amino group is substituted with two of the above-mentioned "C1-C6 alkyl groups" which may be the same or different, and can be, for example, an N,N-dimethylamino, N,N-diethylamino, N,N-di-n-propylamino, N,N-diisopropylamino, N,N-di-n-butylamino, N,N-diisobutylamino, N,N-di-s-butylamino, N,N-di-tert-butylamino, N,N-di-n-pentylamino, N,N-diisopentylamino, N,N-di-2-methylbutylamino, N,N-dineopentylamino, N,N-di-1-ethylpropylamino, N,N-di-n-hexylamino, N,N-diisohexylamino, N,N-di-4-methylpentylamino, N,N-di-3-methylpentylamino, N,N-di-2-methylpentylamino, N,N-di-1-methylpentylamino, N,N-ethylmethylamino, or N,N-isopropylmethylamino group. In the case of $R^6$, $R^7$, and substituent group α, the C1-C6 dialkylamino group is preferably a dimethylamino or diethylamino group.

In the invention, the "C1-C6 alkoxyamino group" refers to a group in which the above-mentioned "C1-C6 alkoxy group" is bonded to an amino group, and can be, for example, a straight or branched chain alkoxyamino group having 1 to 6 carbon atoms such as methoxyamino, ethoxyamino, n-propoxyamino, isopropoxyamino, n-butoxyamino, isobutoxyamino, s-butoxyamino, tert-butoxyamino, n-pentoxyamino, isopentoxyamino, 2-methylbutoxyamino, neopentoxyamino, n-hexyloxyamino, 4-methylpentoxyamino, 3-methylpentoxyamino, 2-methylpentoxyamino, 3,3-dimethylbutoxyamino, 2,2-dimethylbutoxyamino, 1,1-dimethylbutoxyamino, 1,2-dimethylbutoxyamino, 1,3-dimethylbutoxyamino, or 2,3-dimethylbutoxyamino. In the case of $R^6$, $R^7$, and substituent group α, the C1-C6 alkoxyamino group is preferably a methoxyamino group, an ethoxyamino group, or an n-propoxyamino group.

In the invention, the "C1-C6 aliphatic acylamino group" refers to a group in which an aliphatic hydrocarbon group having 1 to 6 carbon atoms or a hydrogen atom is bonded to a carbonylamino group, and can be, for example, an alkylcarbonylamino group such as a formylamino, acetylamino, propionylamino, butylylamino, isobutylylamino, pentanoylamino, pivaloylamino, valerylamino, or isovalerylamino group; a haloalkylcarbonylamino group such as chloroacetylamino, dichloroacetylamino, trichloroacetylamino, or trifluoroacetylamino; a lower alkoxyalkylcarbonylamino group such as methoxyacetylamino; an unsaturated alkylcarbonylamino group such as (E)-2-methyl-2-butenoylamino; or the like. In the case of $R^6$, $R^7$, and substituent group α, the C1-C6 aliphatic acylamino group is preferably an acetylamino group.

In the invention, the "C1-C6 alkylsulfonyl group" refers to a group in which the above-mentioned "C1-C6 alkyl group" is bonded via a sulfonyl group, and can be, for example, a methanesulfonyl, ethanesulfonyl, n-propanesulfonyl, isopropanesulfonyl, n-butanesulfonyl, isobutanesulfonyl, s-butanesulfonyl, tert-butane sulfonyl, n-pentane sulfonyl, isopentanesulfonyl, 2-methylbutanesulfonyl, neopentanesulfonyl, n-hexanesulfonyl, 4-methylpentanesulfonyl, 3-methylpentanesulfonyl, 2-methylpentanesulfonyl, 3,3-dimethylbutanesulfonyl, 2,2-dimethylbutanesulfonyl, 1,1-dimethylbutanesulfonyl, 1,2-dimethylbutanesulfonyl, 1,3-dimethylbutanesulfonyl, or 2,3-dimethylbutanesulfonyl group. In the case of $R^6$, $R^7$, and substituent group α, the C1-C6 alkylsulfonyl group is preferably a straight or branched chain alkanesulfonyl group having 1 to 4 carbon atoms, and most preferably a methanesulfonyl group.

In the invention, the "C1-C6 dialkylaminosulfonyl group" refers to a group in which the above-mentioned "C1-C6 dialkylamino group" is bonded via a sulfonyl group, and can be, for example, an N,N-dimethylaminosulfonyl, N,N-diethylaminosulfonyl, N,N-di-n-propylaminosulfonyl, N,N-diisopropylaminosulfonyl, N,N-di-n-butylaminosulfonyl, N,N-diisobutylaminosulfonyl, N,N-di-s-butylaminosulfonyl, N,N-di-tert-butylaminosulfonyl, N,N-di-n-pentylaminosulfonyl, N,N-diisopentylaminosulfonyl, N,N-di-2-methylbutylaminosulfonyl, N,N-dineopentylaminosulfonyl, N,N-di-1-ethylpropylaminosulfonyl, N,N-di-n-hexylaminosulfonyl, N,N-diisohexylaminosulfonyl, N,N-di-4-methylpentylaminosulfonyl, N,N-di-3-methylpentylaminosulfonyl, N,N-di-2-methylpentylaminosulfonyl, N,N-di-1-methylpentylaminosulfonyl, N,N-ethylmethylaminosulfonyl, or N,N-isopropylmethylaminosulfonyl group. In the case of $R^6$, $R^7$, and substituent group α, the C1-C6 dialkylaminosulfonyl group is preferably a dimethylaminosulfonyl or diethylaminosulfonyl group.

In the invention, the "halogen atom" is a fluorine atom, a chlorine atom, a bromine atom, or an iodine atom. In the case of L, $R^2$, $R^3$, $R^4$, $R^5$, $R^6$, $R^7$, and substituent group α, the halogen atom is preferably a chlorine atom or a fluorine atom.

In the invention, the "pharmacologically acceptable salt" refers to a salt which can be formed by reacting with an acid when the compound of the invention has a basic group such as an amino group, or by reacting with a base when the compound of the invention has an acidic group such as a carboxyl group.

The salt derived from a basic group can be preferably an inorganic acid salt such as a hydrohalide salt (such as a hydrofluoride, a hydrochloride, a hydrobromide, or a hydroiodide), a nitrate, a perchlorate, a sulfate, or a phosphate; an organic acid salt such as a lower alkanesulfonate (such as a methanesulfonate, a trifluoromethanesulfonate, or an ethanesulfonate), an arylsulfonate (such as a benzenesulfonate or a p-toluenesulfonate), an acetate, a malate, a fumarate, a succinate, a citrate, an ascorbate, a tartrate, an oxalate, or a maleate; or an amino acid salt such as a glycine salt, a lysine salt, an arginine salt, an ornithine salt, a glutamic acid salt, or an aspartic acid salt. The salt is preferably a hydrohalide salt or an inorganic acid salt.

On the other hand, the salt derived from an acidic group can be preferably a metal salt such as an alkali metal salt (such as a sodium salt, a potassium salt, or a lithium salt), an alkaline earth metal salt (such as a calcium salt or a magnesium salt), an aluminum salt, or an iron salt; an amine salt such as an inorganic amine salt (such as an ammonium salt) or an organic amine salt (such as a t-octylamine salt, a dibenzylamine salt, a morpholine salt, a glucosamine salt, a phenylglycine alkyl ester salt, an ethylenediamine salt, an N-methylglucamine salt, a guanidine salt, a diethylamine salt, a triethylamine salt, a dicyclohexylamine salt, an N,N'-dibenzylethylenediamine salt, a chloroprocaine salt, a procaine salt, a diethanolamine salt, an N-benzylphenethylamine salt, a piperazine salt, a tetramethylammonium salt, or a tris(hydroxymethyl)aminomethane salt); or an amino acid salt such as a glycine salt, a lysine salt, an arginine salt, an ornithine salt, a glutamic acid salt, or an aspartic acid salt.

Incidentally, the carboxylic acid compound having the above-mentioned general formula (I) may have various isomers. As for the above-mentioned general formula (I), these isomers and racemic and non-racemic mixtures of these isomers are all represented by a single formula. Therefore, the invention includes all of these isomers and mixtures of these isomers in various proportions. Further, the invention also includes compounds labeled with any of various radioisotopes [tritium ($^3H$), iodine-125 ($^{125}I$), carbon-14 ($^{14}C$), and the like] or non-radioisotopes [deuterium ($^2H$) and the like].

Further, in the case where the carboxylic acid compounds having the above-mentioned general formula (I) and salts thereof form solvates (for example, hydrates), the invention also includes all of these solvates.

Further, the invention also includes all of the compounds that are metabolized in the body and converted to carboxylic acid compounds having the above-mentioned general formula (I) or salts thereof (for example, derivatives in which the carboxylic acid moiety of the above-mentioned general formula (I) is esterified, and the like).

The above-mentioned general formula (I) is preferably the above-mentioned general formula (II), the above-mentioned general formula (III), or the following general formula (Ia).

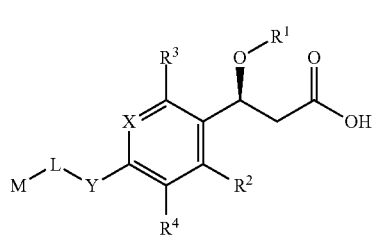

(Ia)

In this formula, X, Y, L, M, $R^1$, $R^2$, $R^3$, $R^4$, and $R^5$ represent the same definitions as described above.

The above-mentioned general formula (II) is preferably the following general formula (IIa).

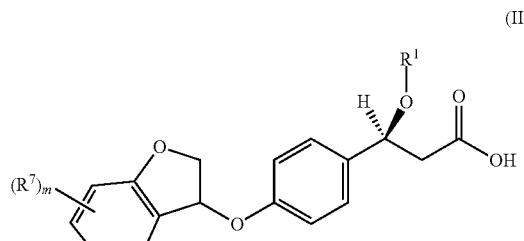

(IIa)

In this formula, $R^1$ represents the same definition as described above; m represents an integer of any one of 0 to 3; $R^6$'s may be the same or different and each represents a halogen atom, a C1-C6 alkyl group, a C1-C6 haloalkyl group, a C1-C6 hydroxyalkyl group (the hydroxyalkyl group being optionally substituted with one C1-C6 alkyl group), a C1-C6 alkoxy C1-C6 alkyl group, a C1-C6 aminoalkyl group, a C1-C6 alkoxy group, a C1-C6 haloalkoxy group, a C6-C10 aryloxy group, a C1-C6 alkylthio group, a carboxy group, a C1-C6 alkoxycarbonyl group, a hydroxy group, a C1-C6 aliphatic acyl group, an amino group, a C1-C6 alkylamino group, a C3-C10 cycloalkylamino group, a C1-C6 dialkylamino group, a C1-C6 alkoxyamino group, a C1-C6 aliphatic acylamino group (the C1-C6 aliphatic acylamino group being optionally substituted with 1 to 3 halogen atoms), a cyano group, a nitro group, a C1-C6 alkylsulfonyl group, a C1-C6 dialkylaminosulfonyl group, a C3-C10 cycloalkyl group, or a C6-C10 aryl group (the aryl group being optionally substituted with one to five C1-C6 haloalkyl groups). The above-mentioned general formula (II) is particularly preferably the following general formula (IIb).

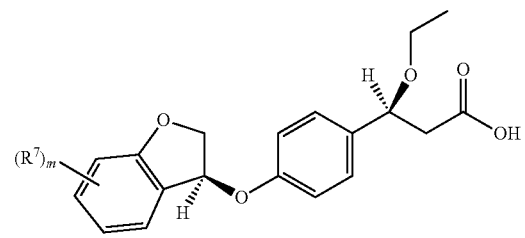

(IIb)

In this formula, $R^6$ and m represent the same definitions as described above.

The above-mentioned general formula (III) is preferably the following general formula (IIIa).

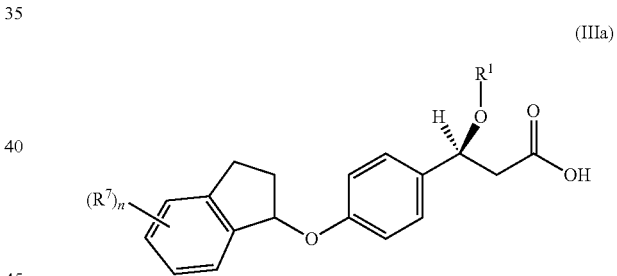

(IIIa)

In this formula, $R^1$ represents the same definition as described above; n represents an integer of any one of 0 to 3; $R^7$'s may be the same or different and each represents a halogen atom, a C1-C6 alkyl group, a C1-C6 haloalkyl group, a C1-C6 hydroxyalkyl group (the hydroxyalkyl group being optionally substituted with one C1-C6 alkyl group), a C1-C6 alkoxy C1-C6 alkyl group, a C1-C6 aminoalkyl group, a C1-C6 alkoxy group, a C1-C6 haloalkoxy group, a C6-C10 aryloxy group, a C1-C6 alkylthio group, a carboxy group, a C1-C6 alkoxycarbonyl group, a hydroxy group, a C1-C6 aliphatic acyl group, an amino group, a C1-C6 alkylamino group, a C3-C10 cycloalkylamino group, a C1-C6 dialkylamino group, a C1-C6 alkoxyamino group, a C1-C6 aliphatic acylamino group (the C1-C6 aliphatic acylamino group being optionally substituted with 1 to 3 halogen atoms), a cyano group, a nitro group, a C1-C6 alkylsulfonyl group, a C1-C6 dialkylaminosulfonyl group, a C3-C10 cycloalkyl group, or a C6-C10 aryl group (the aryl group being optionally substituted with one to five C1-C6 haloalkyl groups). The above-mentioned general formula (III) is particularly preferably the following general formula (IIIb).

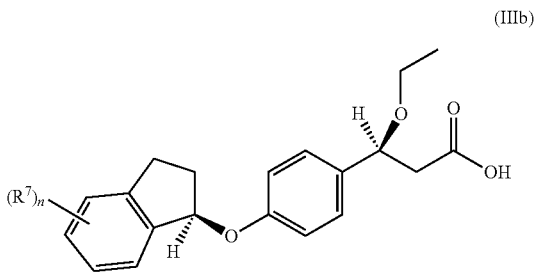

(IIIb)

In this formula, $R^7$ and n represent the same definitions as described above.

X is preferably $=C(R^5)-$, and more preferably $=CH-$.

Y is preferably $-O-$.

L is preferably a bond or a C1-C3 alkylene group, and more preferably a bond.

M is preferably a C3-C10 cycloalkyl group (the cycloalkyl group being optionally fused with one phenyl group or 4- to 10-membered heterocyclic group containing 1 to 3 heteroatoms which may be the same or different and are selected from nitrogen, oxygen, and sulfur, and further optionally substituted with 1 to 5 substituents selected from substituent group α), or a C6-C10 aryl group (the aryl group being optionally substituted with 1 to 5 substituents selected from substituent group α), more preferably a C3-C10 cycloalkyl group (the cycloalkyl group being optionally fused with one phenyl group and further optionally substituted with 1 to 5 substituents selected from substituent group α) or a phenyl group (the phenyl group being optionally substituted with 1 to 5 substituents selected from substituent group α), and particularly preferably a 2,3-dihydroindenyl group (the 2,3-dihydroindenyl group being optionally substituted with 1 to 5 substituents selected from substituent group α) or a 2,3-dihydrobenzofuranyl group (the 2,3-dihydrobenzofuranyl group being optionally substituted with 1 to 5 substituents selected from substituent group α).

$R^1$ is preferably a C1-C6 alkyl group or a C1-C6 haloalkyl group, more preferably a C1-C6 alkyl group, and particularly preferably an ethyl group.

$R^2$ is preferably a hydrogen atom.

$R^3$ is preferably a hydrogen atom.

$R^4$ is preferably a halogen atom or a hydrogen atom, and more preferably a hydrogen atom.

$R^5$ is preferably a halogen atom or a hydrogen atom, and more preferably a hydrogen atom.

$R^6$ is preferably a C1-C6 haloalkyl group or a C1-C6 haloalkoxy group, and more preferably a trifluoromethyl group or a trifluoromethoxy group.

$R^7$ is preferably a halogen atom, a C1-C6 alkyl group, a C1-C6 haloalkyl group, a C1-C6 haloalkoxy group, or a C3-C10 cycloalkyl group, and more preferably, a fluorine atom, a methyl group, an ethyl group, a difluoromethyl group, a trifluoromethyl group, or a trifluoromethoxy group.

m is preferably 1 or 2.

n is preferably 1 or 2.

In the case where the C3-C10 cycloalkyl group represented by M is substituted, substituent group α is preferably a halogen atom.

In the case where the C3-C10 cycloalkyl group fused with a phenyl group represented by M is substituted, substituent group α is preferably a halogen atom, a C1-C6 alkyl group, and a C1-C6 haloalkyl group.

In the case where the C3-C10 cycloalkyl group fused with a 4- to 10-membered heterocyclic group containing 1 to 3 heteroatoms which may be the same or different and are selected from nitrogen, oxygen, and sulfur represented by M is substituted, substituent group α is preferably a halogen atom, a C1-C6 alkyl group, and a C1-C6 haloalkyl group.

In the case where the C6-C10 aryl group represented by M is substituted, substituent group α is preferably a halogen atom, a C1-C6 alkyl group, a C1-C6 haloalkyl group, and a 4- to 10-membered heterocyclic group containing 1 to 3 heteroatoms which may be the same or different and are selected from nitrogen, oxygen, and sulfur.

In the case where the 4- to 10-membered heterocyclic group containing 1 to 3 heteroatoms which may be the same or different and are selected from nitrogen, oxygen, and sulfur represented by M is substituted, substituent group α is preferably a C1-C6 alkyl group and a C6-C10 aryl group.

Specific examples of the carboxylic acid compound having the above-mentioned general formula (I) of the invention include the compounds illustrated below. However, the invention is not limited to the following illustrative compounds.

Incidentally, in the following Table 1 to Table 2, "Me" represents a methyl group; "Et" represents an ethyl group; "$^n$Pr" represents a normal propyl group; "$^i$Pr" represents an isopropyl group; "$^c$Pr" represents a cyclopropyl group; "$^i$Bu" represents an isobutyl group; "$^t$Bu" represents a tertiary butyl group; "$^c$Hex" represents a cyclohexyl group; "$^c$Pn" represents a cyclopentyl group; "MeO" represents a methoxy group; "EtO" represents an ethoxy group; "Ph" represents a phenyl group; "Bn" represents a benzyl group; "Naph" represents a naphthyl group; "Pyr" represents a pyridyl group; "piperidinyl" represents a piperidinyl group; "pirazolyl" represents a pyrazolyl group; "pyrazinyl" represents a pyrazinyl group; "thiazolyl" represents a thiazolyl group; "Bzthiazolyl" represents a benzothiazolyl group; "1,2,3-triazolyl" represents a 1,2,3-triazolyl group; "quinolinyl" represents a quinolinyl group; "furanyl" represents a furanyl group; "Bzfuranyl" represents a benzofuranyl group; "pyrrolyl" represents a pyrrolyl group; "thienyl" represents a thienyl group; "$^c$Hexenyl" represents a cyclohexenyl group; "CN" represents a cyano group; "$NO_2$" represents a nitro group; "$CF_3$" represents a trifluoromethyl group; "$CF_3O$" represents a trifluoromethoxy group; "3,4-di-Cl-Bn" represents a 3,4-dichlorobenzyl group; "$^t$BuO—C(=O)" represents a tertiary butoxycarbonyl group; "Ind" represents an indenyl group; "DHInd" represents a 2,3-dihydroindenyl group; "DHBzf" represents a 2,3-dihydrobenzofuranyl group; "DHoxazolyl" represents a 4,5-dihydrooxazolyl group; "THNaph" represents a 1,2,3,4-tetrahydronaphthalenyl group; "THannul" represents a 6,7,8,9-tetrahydro-5H-benzo[7]annulenyl group; and "DH$^c$PentaPyridyl" represents a 6,7-dihydro-5H-cyclopenta[b]pyridyl group.

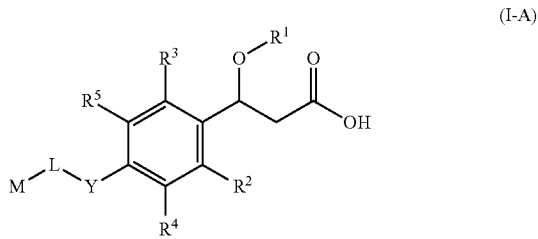

(I-A)

TABLE 1

| No. | Y | M-L- | $R^1$ | $R^2$ | $R^3$ | $R^4$ | $R^5$ |
|---|---|---|---|---|---|---|---|
| 1-1 | O | Ph- | Et | H | H | H | H |
| 1-2 | O | 4-CF$_3$-Ph- | Et | H | H | H | H |
| 1-3 | O | 2-Cl-Ph- | Et | H | H | H | H |
| 1-4 | O | 3-Cl-Ph- | Et | H | H | H | H |
| 1-5 | O | 4-Ph-Ph- | Et | H | H | H | H |
| 1-6 | O | 3-Ph-Ph- | Et | H | H | H | H |
| 1-7 | O | 2-Ph-Ph- | Et | H | H | H | H |
| 1-8 | O | 4-Bn-Ph- | Et | H | H | H | H |
| 1-9 | O | 4-Bn-Ph- | Me | H | H | H | H |
| 1-10 | O | 2-Bn-Ph- | Et | H | H | H | H |
| 1-11 | O | 3,5-di-Cl-Ph- | Me | H | H | H | H |
| 1-12 | O | 2,4-di-Cl-Ph- | Et | H | H | H | H |
| 1-13 | O | 3,4-di-Cl-Ph- | Et | H | H | H | H |
| 1-14 | O | 2,3-di-Cl-Ph- | Et | H | H | H | H |
| 1-15 | O | 3,5-di-Cl-Ph- | Et | H | H | H | H |
| 1-16 | O | 2,5-di-Cl-Ph- | Et | H | H | H | H |
| 1-17 | O | 2,6-di-Cl-4-CF$_3$-Ph- | Et | H | H | H | H |
| 1-18 | O | 2-Br-4-Cl-Ph- | Et | H | H | H | H |
| 1-19 | O | 3-Cl-6-Ph-Ph- | Et | H | H | H | H |
| 1-20 | O | 3-F-6-Ph-Ph- | Et | H | H | H | H |
| 1-21 | O | 2-Cl-4-CF$_3$-Ph- | Et | H | H | H | H |
| 1-22 | O | 2-Cl-5-CF$_3$-Ph- | Et | H | H | H | H |
| 1-23 | O | 2-Br-5-F-Ph- | Et | H | H | H | H |
| 1-24 | O | 2-(4-Cl)PhO-4-CF$_3$-Ph- | Et | H | H | H | H |
| 1-25 | O | 2-(4-Cl)PhO-Ph- | Et | H | H | H | H |
| 1-26 | O | 2-Cl-4-F-Ph- | Et | H | H | H | H |
| 1-27 | O | 3-Cl-5-F-Ph- | Et | H | H | H | H |
| 1-28 | O | 2-F-5-CF$_3$-Ph- | Et | H | H | H | H |
| 1-29 | O | 2,4-di-CF$_3$-Ph- | Et | H | H | H | H |
| 1-30 | O | 2-Br-4-CF$_3$-Ph- | Et | H | H | H | H |
| 1-31 | O | 2,4-di-Cl-3,5-di-Me-Ph- | Et | H | H | H | H |
| 1-32 | O | 2,4,5-tri-Cl-Ph- | Et | H | H | H | H |
| 1-33 | O | 2,4-di-Cl-3,5-di-Me-Ph- | $^n$Pr | H | H | H | H |
| 1-34 | O | 4-CF$_3$-Ph-CF$_2$— | Et | H | H | H | H |
| 1-35 | O | 3-Cl-Ph-C(Me)H— | Et | H | H | H | H |
| 1-36 | O | 4-CF$_3$-Ph-C(Me)H— | Et | H | H | H | H |
| 1-37 | O | 4-Cl-Ph-(CH$_2$)$_2$— | Et | H | H | H | H |
| 1-38 | O | 2-Me-Ph-(CH$_2$)$_2$— | Et | H | H | H | H |
| 1-39 | O | 3,4-di-Cl-Ph-(CH$_2$)$_2$— | Et | H | H | H | H |
| 1-40 | O | 3,4-di-Cl-Ph-(CH$_2$)$_3$— | Et | H | H | H | H |
| 1-41 | O | 4-Cl-Ph-C(CF$_3$)H— | Et | H | H | H | H |
| 1-42 | O | 3-$^i$PrO-Bn- | Et | H | H | H | H |
| 1-43 | O | 3-NO$_2$-Bn- | Et | H | H | H | H |
| 1-44 | O | 4-NO$_2$-Bn- | Et | H | H | H | H |
| 1-45 | O | 3-CF$_3$O-Bn- | Et | H | H | H | H |
| 1-46 | O | 4-CF$_3$O-Bn- | Et | H | H | H | H |
| 1-47 | O | 2-CF$_3$-Bn- | Et | H | H | H | H |
| 1-48 | O | 4-CF$_3$-Bn- | Et | H | H | H | H |
| 1-49 | O | 3-CN-Bn- | Et | H | H | H | H |
| 1-50 | O | 3-Me-Bn- | Et | H | H | H | H |
| 1-51 | O | 3-Cl-Bn- | Et | H | H | H | H |
| 1-52 | O | 4-Me-Bn- | Et | H | H | H | H |
| 1-53 | O | 2-Me-Bn- | $^i$Pr | H | H | H | H |
| 1-54 | O | 2-Me-Bn- | MeC(=O)— | H | H | H | H |
| 1-55 | O | 4-Cl-Bn- | Et | H | H | H | H |
| 1-56 | O | 2-Cl-Bn- | Et | H | H | H | H |
| 1-57 | O | 2-F-Bn- | Et | H | H | H | H |
| 1-58 | O | 3-F-Bn- | Et | H | H | H | H |
| 1-59 | O | 4-F-Bn- | Et | H | H | H | H |
| 1-60 | O | 3-PhO-Bn- | Et | H | H | H | H |
| 1-61 | O | 2-N(Me$_2$)-Bn- | Et | H | H | H | H |
| 1-62 | O | 4-N(Me$_2$)-Bn- | Et | H | H | H | H |
| 1-63 | O | 2-PhO-Bn- | Et | H | H | H | H |
| 1-64 | O | 3-N(Me$_2$)-Bn- | Et | H | H | H | H |
| 1-65 | O | 3-N(Me$_2$)SO$_2$-Bn- | Et | H | H | H | H |
| 1-66 | O | 3-MeSO$_2$-Bn- | Et | H | H | H | H |
| 1-67 | O | 2-Me-Bn- | Et | H | H | H | H |
| 1-68 | O | 3,4-di-Cl-Bn- | CF$_3$CH$_2$— | H | H | H | H |
| 1-69 | O | 3,4-di-Cl-Bn- | $^c$Pr- | H | H | H | H |
| 1-70 | O | 3,4-di-Cl-Bn- | Ph- | H | H | H | H |
| 1-71 | O | 3,4-di-Cl-Bn- | Et | H | MeO | H | H |
| 1-72 | O | 3,4-di-Cl-Bn- | Et | H | H | H | Me |
| 1-73 | O | 3,4-di-Cl-Bn- | Et | H | H | H | NO$_2$ |
| 1-74 | O | 3,4-di-Cl-Bn- | Et | H | Cl | H | H |
| 1-75 | O | 3,4-di-Cl-Bn- | Et | H | H | H | F |
| 1-76 | O | 3,4-di-Cl-Bn- | Me | F | H | H | H |
| 1-77 | O | 3,4-di-Cl-Bn- | CHF$_2$—CH$_2$— | H | H | H | H |
| 1-78 | O | 3,5-di-Cl-Bn- | Et | H | H | H | H |

TABLE 1-continued

| No. | Y | M-L- | R¹ | R² | R³ | R⁴ | R⁵ |
|---|---|---|---|---|---|---|---|
| 1-79 | O | 2,3-di-Cl-Bn- | Et | H | H | H | H |
| 1-80 | O | 3,4-di-Cl-Bn- | Et | H | H | H | H |
| 1-81 | O | 3,4-di-Cl-Bn- | Et | F | H | H | H |
| 1-82 | O | 3,4-di-Cl-Bn- | Et | H | H | H | Br |
| 1-83 | O | 3,4-di-Cl-Bn- | Et | H | H | Br | Br |
| 1-84 | NH | 3,4-di-Cl-Bn- | Et | H | H | H | H |
| 1-85 | O | 2-Cl-3-CF₃-Bn- | Et | H | H | H | H |
| 1-86 | O | 3-MeO-Bn- | Et | H | H | H | H |
| 1-87 | O | 3-MeOCH₂O-Bn- | Et | H | H | H | H |
| 1-88 | O | 3,5-di-MeO-Bn- | Et | H | H | H | H |
| 1-89 | O | 2-Br-5-MeO-Bn- | Et | H | H | H | H |
| 1-90 | O | 3-MeO-2-Me-Bn- | Et | H | H | H | H |
| 1-91 | O | 2-MeO-3-Me-Bn- | Et | H | H | H | H |
| 1-92 | O | 3-Cl-6-MeO-Bn- | Et | H | H | H | H |
| 1-93 | O | 4-Cl-6-MeO-Bn- | Et | H | H | H | H |
| 1-94 | O | 3,5-di-CF₃-Bn- | Et | H | H | H | H |
| 1-95 | O | 4-F-6-Me-Bn- | Et | H | H | H | H |
| 1-96 | O | 2-Cl-3-CF₃-Bn- | Et | H | H | H | H |
| 1-97 | O | 2,4-di-CF₃-Bn- | Et | H | H | H | H |
| 1-98 | O | 2-Cl-5-CF₃-Bn- | Et | H | H | H | H |
| 1-99 | O | 3-F-4-CF₃-Bn- | Et | H | H | H | H |
| 1-100 | O | 4-CF₃-5-ⁱPrO-Bn- | Et | H | H | H | H |
| 1-101 | O | 4-Cl-5-CF₃O-Bn- | Et | H | H | H | H |
| 1-102 | O | 3-Cl-5-CF₃O-Bn- | Et | H | H | H | H |
| 1-103 | O | 4-Cl-5-CF₃-Bn- | Et | H | H | H | H |
| 1-104 | O | 4-CHF₂-Bn- | Et | H | H | H | H |
| 1-105 | O | 3-N(Me)₂C(=O)-Bn- | Et | H | H | H | H |
| 1-106 | O | 4-F-6-CF₃-Bn- | Et | H | H | H | H |
| 1-107 | O | 4-CF₃-6-Ph-Bn- | Et | H | H | H | H |
| 1-108 | O | 2,3-di-F-Bn- | Et | H | H | H | H |
| 1-109 | O | 3,4-di-F-Bn- | Et | H | H | H | H |
| 1-110 | O | 4-N(Me)₂C(=O)-Bn- | Et | H | H | H | H |
| 1-111 | O | 4-MeSO₂-Bn- | Et | H | H | H | H |
| 1-112 | O | 3-NH₂-4-CF₃-Bn- | Et | H | H | H | H |
| 1-113 | O | 3-CF₃(C=O)NH-4-CF₃-Bn- | Et | H | H | H | H |
| 1-114 | O | 3-(1-pyrrolyl)-4-CF₃-Bn- | Et | H | H | H | H |
| 1-115 | O | 3-(1-pyrrolyl)-Bn- | Et | H | H | H | H |
| 1-116 | O | 3-NH(Me)-4-CF₃-Bn- | Et | H | H | H | H |
| 1-117 | O | 4-F-5-CF₃-Bn- | Et | H | H | H | H |
| 1-118 | O | 3,4-di-CF₃-Bn- | Et | H | H | H | H |
| 1-119 | O | 3,5-di-CF₃-Bn- | Et | H | H | H | H |
| 1-120 | O | 3-Cl-4-CF₃-Bn- | Et | H | H | H | H |
| 1-121 | O | 2-F-3-CF₃-Bn- | Et | H | H | H | H |
| 1-122 | O | 3-Cl-4-F-Bn- | Et | H | H | H | H |
| 1-123 | O | 4-Cl-5-F-Bn- | Et | H | H | H | H |
| 1-124 | O | 3-F-2-CF₃-Bn- | Et | H | H | H | H |
| 1-125 | O | 2,4-di-Cl-5-F-Bn- | Et | H | H | H | H |
| 1-126 | O | 2-Cl-3-F-Bn- | Et | H | H | H | H |
| 1-127 | O | 2,4,5-tri-F-Bn- | Et | H | H | H | H |
| 1-128 | O | 3-Cl-4-CF₃O-Bn- | Et | H | H | H | H |
| 1-129 | O | 2,3-di-F-4-CF₃-Bn- | Et | H | H | H | H |
| 1-130 | O | 3-F-4-CF₃O-Bn- | Et | H | H | H | H |
| 1-131 | O | 4-F-5-CF₃O-Bn- | Et | H | H | H | H |
| 1-132 | O | 4-Cl-6-F-Bn- | Et | H | H | H | H |
| 1-133 | O | 3-Cl-2-PhO-Bn- | Et | H | H | H | H |
| 1-134 | O | 4-Cl-6-PhO-Bn- | Et | H | H | H | H |
| 1-135 | O | 3-Cl-6-PhO-Bn- | Et | H | H | H | H |
| 1-136 | O | 2-(3-Pyr-O)Bn- | Et | H | H | H | H |
| 1-137 | O | 2-(4-Pyr-O)Bn- | Et | H | H | H | H |
| 1-138 | O | 2-(5-Cl-2-Pyr-O)-Bn- | Et | H | H | H | H |
| 1-139 | O | 2-(4-Cl)PhO-4-Cl-Bn- | Et | H | H | H | H |
| 1-140 | O | 3-(2-Me)Pyr-CH₂— | Et | H | H | H | H |
| 1-141 | O | 3-(6-CF₃)Pyr-CH₂— | Et | H | H | H | H |
| 1-142 | O | 2-(5-CF₃)Pyr-CH₂— | Et | H | H | H | H |
| 1-143 | O | 2-(6-Me)Pyr-CH₂— | Et | H | H | H | H |
| 1-144 | O | 2-(3-Cl-5-CF₃)Pyr- | Et | H | H | H | H |
| 1-145 | O | 2-(6-Me)Pyr- | Et | H | H | H | H |
| 1-146 | O | 3-(1-Ph)piperidinyl-CH₂— | Et | H | H | H | H |
| 1-147 | O | 4-(1-Ph)piperidinyl-CH₂— | Et | H | H | H | H |
| 1-148 | O | 4-(1-ᵗBuO—C(=O)-piperidinyl-CH₂— | Et | H | H | H | H |
| 1-149 | O | 2-pyrazinyl-CH₂— | Et | H | H | H | H |
| 1-150 | O | 5-(1,3-di-Me)-pirazolyl- | Et | H | H | H | H |
| 1-151 | O | 1-(4-CN)Naph- | Et | H | H | H | H |
| 1-152 | O | 4-(1-F-Naph)-CH₂- | Et | H | H | H | H |
| 1-153 | O | 4-Cl-Naph- | Et | H | H | H | H |
| 1-154 | O | 1-(4-CF₃)Naph- | Et | H | H | H | H |
| 1-155 | O | 4-(2-Ph)DHoxazolyl-CH₂— | Et | H | H | H | H |

TABLE 1-continued

| No. | Y | M-L- | R¹ | R² | R³ | R⁴ | R⁵ |
|---|---|---|---|---|---|---|---|
| 1-156 | O | 2-(5-CF₃)thienyl-CH₂— | Et | H | H | H | H |
| 1-157 | O | 6-(1,1,4,4-tetra-Me)THNaph-CH₂— | Et | H | H | H | H |
| 1-158 | O | 1-THNaph- | Et | H | H | H | H |
| 1-159 | O | 1-(5-CF₃)THNaph- | Et | H | H | H | H |
| 1-160 | O | 4-(8-CF₃)quinolinyl- | Et | H | H | H | H |
| 1-161 | O | 4-(7-Cl)quinolinyl- | Et | H | H | H | H |
| 1-162 | O | 4-(2-Me)quinolinyl- | Et | H | H | H | H |
| 1-163 | O | 5-(2-(4-CF₃)Ph-4-Me)Thiazolyl-CH₂— | Et | H | H | H | H |
| 1-164 | O | 2-Bzthiazolyl-CH₂— | Et | H | H | H | H |
| 1-165 | O | 4-(2-Ph-5-Me-1,2,3-triazolyl)-CH₂— | Et | H | H | H | H |
| 1-166 | O | 4-[2-(4-Cl-Ph)thiazolyl]-CH₂— | Et | H | H | H | H |
| 1-167 | O | 2-(4-CF₃)thiazolyl-CH₂— | Et | H | H | H | H |
| 1-168 | O | 2-(5-CF₃)furanyl-CH₂— | Et | H | H | H | H |
| 1-169 | O | 3-DHBzf- | Et | H | H | H | H |
| 1-170 | O | 3-(7-CF₃)DHBzf- | Et | H | H | H | H |
| 1-171 | O | 3-(7-CF₃)Bzfuranyl- | Et | H | H | H | H |
| 1-172 | O | ᶜHex-CH₂— | Et | H | H | H | H |
| 1-173 | O | ᶜHex-(CH₂)₂— | Et | H | H | H | H |
| 1-174 | O | 4-CF₃-ᶜHex-CH₂— | Et | H | H | H | H |
| 1-175 | O | 4-ᶜHexenyl-CH₂— | Et | H | H | H | H |
| 1-176 | O | 1-(4-CF₃)Ind- | Et | H | H | H | H |
| 1-177 | O | 1-DHInd- | Et | H | H | H | H |
| 1-178 | O | 2-DHInd- | Et | H | H | H | H |
| 1-179 | O | 1-(5-F)DHInd- | Et | H | H | H | H |
| 1-180 | O | 1-(6-F)DHInd- | Et | H | H | H | H |
| 1-181 | O | 1-(4-F)DHInd- | Et | H | H | H | H |
| 1-182 | O | 1-(4,6-di-F)DHInd- | Et | H | H | H | H |
| 1-183 | O | 1-(4-Me)DHInd- | Et | H | H | H | H |
| 1-184 | O | 1-(6-Me)DHInd- | Et | H | H | H | H |
| 1-185 | O | 1-(5-Me)DHInd- | Et | H | H | H | H |
| 1-186 | O | 1-(3,3-di-Me)DHInd- | Et | H | H | H | H |
| 1-187 | O | 1-(4-Et)DHInd- | Et | H | H | H | H |
| 1-188 | O | 1-(4-ⁿPr)DHInd- | Et | H | H | H | H |
| 1-189 | O | 1-(4-ⁱPr)DHInd- | Et | H | H | H | H |
| 1-190 | O | 1-(4-ᶜPr)DHInd- | Et | H | H | H | H |
| 1-191 | O | 1-(4-ᶜHex)DHInd- | Et | H | H | H | H |
| 1-192 | O | 1-(5-MeO)DHInd- | Et | H | H | H | H |
| 1-193 | O | 1-(6-MeO)DHInd- | Et | H | H | H | H |
| 1-194 | O | 1-(4-MeO)DHInd- | Et | H | H | H | H |
| 1-195 | O | 1-(4-Cl-5-MeO)DHInd- | Et | H | H | H | H |
| 1-196 | O | 1-(4-Cl)DHInd- | Et | H | H | H | H |
| 1-197 | O | 1-(5-Cl)DHInd- | Et | H | H | H | H |
| 1-198 | O | 1-(6-Cl)DHInd- | Et | H | H | H | H |
| 1-199 | O | 1-(7-Cl)DHInd- | Et | H | H | H | H |
| 1-200 | O | 1-(4-Cl)DHInd- | Et | H | H | H | H |
| 1-201 | O | 1-(4,6-di-Cl)DHInd- | Et | H | H | H | H |
| 1-202 | O | 1-(4-CF₃)DHInd- | Et | H | H | H | H |
| 1-203 | O | 1-(6-CF₃)DHInd- | Et | H | H | H | H |
| 1-204 | O | 1-(4-CF₃)DHInd- | Et | F | H | H | H |
| 1-205 | O | 5-(1-CF₃)THannul- | Et | H | H | H | H |
| 1-206 | O | 5-(1-Cl)THannul- | Et | H | H | H | H |
| 1-207 | O | 7-(4-CF₃)DHᶜPentaPyridyl- | Et | H | H | H | H |
| 1-208 | O | 3-(7-CF₃O)DHBzf- | Et | H | H | H | H |
| 1-209 | O | 3-(7-Et)DHBzf- | Et | H | H | H | H |
| 1-210 | O | 1-(5-F-4-CF₃)DHInd- | Et | H | H | H | H |
| 1-211 | O | 1-(4-CHF₂)DHInd- | Et | H | H | H | H |
| 1-212 | O | 1-(6-F-4-CF₃)DHInd- | Et | H | H | H | H |
| 1-213 | O | 1-(4,6-di-Me)DHInd- | Et | H | H | H | H |
| 1-214 | O | 1-(4-CF₃O)DHInd- | Et | H | H | H | H |
| 1-215 | O | 1-(6-Me-4-CF₃)DHInd- | Et | H | H | H | H |
| 1-216 | O | 1-(6-F-3-Me)DHInd- | Et | H | H | H | H |
| 1-217 | O | 1-(5-Me-4-CF₃)DHInd- | Et | H | H | H | H |
| 1-218 | O | 1-(5-Cl-4-CF₃)DHInd- | Et | H | H | H | H |
| 1-219 | O | 1-(4-CF₃-6-OH)DHInd- | Et | H | H | H | H |
| 1-220 | O | 1-(2-F-4-CF₃)DHInd- | Et | H | H | H | H |
| 1-221 | O | 1-(6-MeO-4-CF₃)DHInd- | Et | H | H | H | H |
| 1-222 | O | 1-(5-CF₃)DHInd- | Et | H | H | H | H |
| 1-223 | O | 1-(7-Me-4-CF₃)DHInd- | Et | H | H | H | H |
| 1-224 | O | 1-(6-Cl-4-Me)DHInd- | Et | H | H | H | H |
| 1-225 | O | 1-(5-F-4-Me)DHInd- | Et | H | H | H | H |
| 1-226 | O | 1-(5-Cl-4-Me)DHInd- | Et | H | H | H | H |
| 1-227 | NH | 1-(4-CF₃)DHInd- | Et | H | H | H | H |

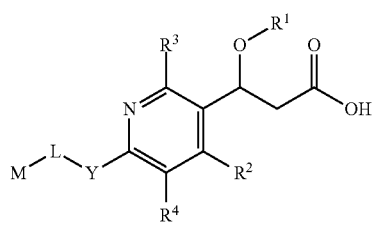

(I-B)

TABLE 2

| No. | Y | M-L- | $R^1$ | $R^2$ | $R^3$ | $R^4$ |
|---|---|---|---|---|---|---|
| 2-1 | O | 2-Me-Bn- | Et | H | H | H |
| 2-2 | O | 2-MeO-Bn- | Et | H | H | H |
| 2-3 | O | 3-MeO-Bn- | Et | H | H | H |
| 2-4 | O | 3-PhO-Bn- | Et | H | H | H |
| 2-5 | O | 4-$CF_3$-Bn- | Et | H | H | H |
| 2-6 | O | 4-$CF_3$-Bn- | Me | H | H | H |
| 2-7 | O | 4-$CF_3$-Bn- | —$CH_2$— | | H | H |
| 2-8 | O | 3-(2,6-di-Me-Ph)Bn- | HC≡C—$CH_2$— | H | H | H |
| 2-9 | O | 3-(2,6-di-Me-Ph)Bn- | $H_2$C=CH—$CH_2$— | H | H | H |
| 2-10 | O | 3-(2,6-di-Me-Ph)Bn- | MeO—$CH_2$— | H | H | H |
| 2-11 | O | 3-(2,6-di-Me-Ph)Bn- | MeC(=O)— | H | H | H |
| 2-12 | O | 3-(2,6-di-Me-Ph)Bn- | Me | H | H | H |
| 2-13 | O | 3-(2,6-di-Me-Ph)Bn- | Et | H | H | H |
| 2-14 | O | 3-(2,6-di-Me-Ph)Bn- | —$CH_2$— | | H | H |
| 2-15 | O | 3,4-di-Cl-Bn- | Et | H | H | H |
| 2-16 | O | 1-DHInd- | Et | H | H | H |
| 2-17 | O | 1-(4-Cl)DHInd- | Et | H | H | H |
| 2-18 | O | 1-(4-$CF_3$)DHInd- | Et | H | H | H |
| 2-19 | O | 2-furanyl-$CH_2$— | Et | H | H | H |
| 2-20 | O | 3-furanyl-$CH_2$— | Et | H | H | H |
| 2-21 | NH | 4-$CF_3$-Bn- | Et | H | H | H |

In the above tables, a preferred compound is 1-15, 1-16, 1-48, 1-67, 1-80, 1-151, 1-170, 1-183, 1-187, 1-190, 1-200, 1-202, 1-208, 1-210, 1-211, 1-212, 1-213, 1-214 or 2-5, a more preferred compound is 1-170, 1-183, 1-187, 1-190, 1-202, 1-208, 1-210, 1-211, 1-212, 1-213 or 1-214, and a particularly preferred compound is 1-170, 1-183, 1-202, 1-208, 1-212 or 1-214.

A compound having the following general formula (I) of the invention can be produced by, for example, using a known compound as a starting material according to the processes described below.

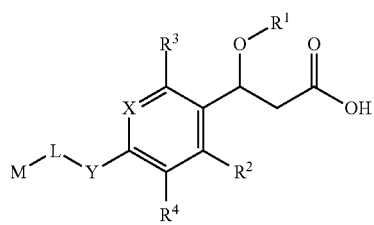

(I)

In the above-mentioned formula and the following description, X, Y, L, M, $R^1$, $R^2$, $R^3$, $R^4$, and $R^5$ represent the same definitions as described above.

Process A

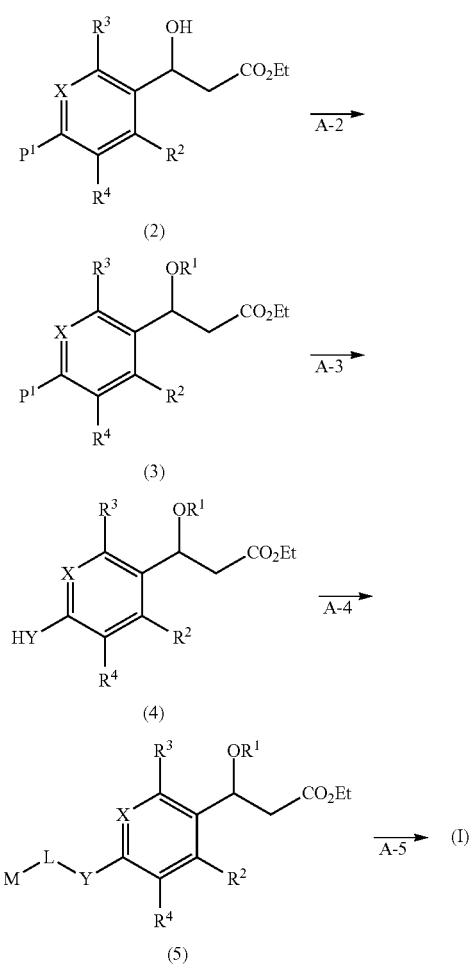

Process B

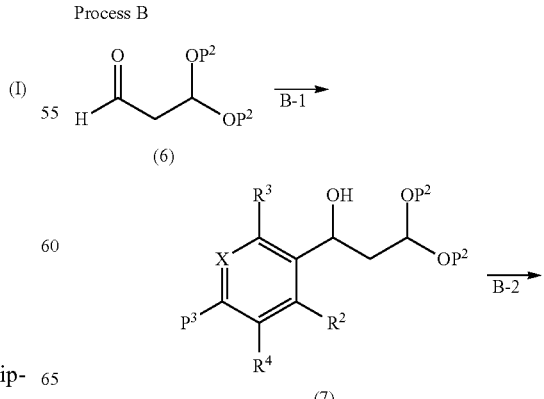

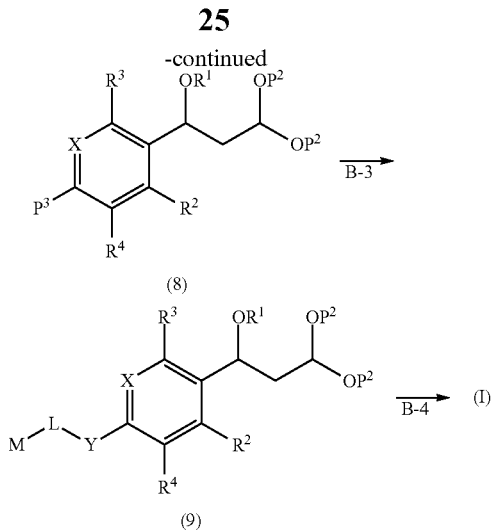

(Process A-2)

This process is a process for manufacturing Compound (3) by introducing an alkyl group into the protected hydroxy group at the β-position of the carboxylic acid of Compound (2).

The solvent is not particularly limited as long as it does not inhibit the reaction. However, examples thereof include halogenated hydrocarbons such as dichloromethane, chloroform, carbon tetrachloride, dichloroethane, chlorobenzene, and dichlorobenzene; and aromatic hydrocarbons such as benzene, toluene, and xylene, and preferred is an aromatic hydrocarbon.

The reagent is not particularly limited as long as it is a reagent to be used for the alkylation of a hydroxy group. However, preferred is a metal oxide such as silver oxide(I) or an alkyl halide such as ethyl iodide.

The reaction temperature is from room temperature to 150° C., and preferably from 50° C. to 120° C.

The reaction time is from 0.5 hour to 24 hours, and preferably from 0.5 hour to 12 hours.

(Process A-3)

This process is a process for manufacturing Compound (4) by, in the case where $P^1$ of Compound (3) is a protected hydroxy group, deprotecting the hydroxy group, and in the case where $P^1$ is a nitro group, reducing the nitro group to form an amino group.

The deprotection of a hydroxy group can be carried out in accordance with a method well known in the field of organic synthetic chemistry such as the method described in "Protective Groups in Organic Synthesis (Third Edition)" written by Greene and Wuts (Wiley Interscience, USA).

The reduction of a nitro group to an amino group can be carried out in accordance with a reduction method well known in the field of organic synthetic chemistry. A preferred reduction method is a hydrogenation reaction performed in the presence of a catalyst and hydrogen gas.

(Process A-4)

This process is a process for manufacturing Compound (5) by reacting H—Y— (HO— or $H_2N$—) of Compound (4) with an M-L group in which a desired substitution position has been halogenated in an inert solvent in the presence of a base to introduce the M-L group into H—Y—.

The halogenated M-L group can be produced by or in accordance with a known method.

The solvent is not particularly limited as long as it does not inhibit the reaction and can dissolve the starting material to some extent. However, examples thereof include ethers such as diethyl ether, diisopropyl ether, tetrahydrofuran, dioxane, dimethoxyethane, and diethylene glycol dimethyl ether; amides such as formamide, dimethylformamide, dimethylacetamide, N-methyl-2-pyrrolidone, and hexamethylphosphorotriamide; and ketones such as acetone, methyl ethyl ketone, methyl isobutyl ketone, isophorone, and cyclohexanone, and preferred is acetone, dimethylformamide, or tetrahydrofuran.

The base is not particularly limited as long as it does not affect a portion other than the substitution position in Compound (4), and examples thereof include alkali metal carbonates such as lithium carbonate, sodium carbonate, and potassium carbonate; alkali metal bicarbonates such as lithium bicarbonate, sodium bicarbonate, and potassium bicarbonate; metal alkoxides such as lithium methoxide, sodium methoxide, sodium ethoxide, and potassium-t-butoxide; organic amines such as triethylamine, tributylamine, diisopropylethylamine, N-methylmorpholine, pyridine, 2,6-lutidine, 4-(N,N-dimethylamino)pyridine, N,N-dimethylaniline, N—N-diethylaniline, 1,5-diazabicyclo[4.3.0]nona-5-ene, 1,4-diazabicylo[2.2.2]octane (DABCO), and 1,8-diazabicyclo[5.4.0]-7-undecene (DBU); organic metal bases such as In the above-mentioned processes and the following description, $P^1$ represents a halogen atom, a nitro group, or a hydroxy group which may be protected by a silyl group; $P^2$ represents a C1-C6 alkyl group; and $P^3$ represents a halogen atom.

In the above-mentioned processes and the following description, the "silyl group" which protects a hydroxy group in the definition of $P^1$ is not particularly limited as long as it is a group to be used in the field of organic synthetic chemistry. However, examples thereof include various silyl groups which are suitable for protecting a hydroxy group and described in, for example, "Protective Groups in Organic Synthesis (Third Edition)" written by Greene and Wuts (Wiley Interscience, USA).

A process for manufacturing Compound (I) of the invention can be selected from the above-mentioned Process A and Process B according to a desired compound.

Hereinafter, the respective processes will be described.

(Process A)

(Process A-1)

This process is a process for manufacturing Compound (2) by introducing a corresponding substituent into Compound (1) by an aldol reaction with an acetate ester.

The solvent is not particularly limited as long as it does not inhibit the reaction and can dissolve the starting material to some extent. However, examples thereof include ethers such as diethyl ether, diisopropyl ether, tetrahydrofuran, dioxane, dimethoxyethane, and diethylene glycol dimethyl ether, and preferred is diethyl ether, dimethoxyethane, or tetrahydrofuran.

Examples of the reagent include an organolithium reagent such as an alkyllithium; a Grignard reagent such as an alkylmagnesium halide; an organozinc reagent such as an alkylzinc; an organotin reagent such as an alkyltin; and an organosilicon reagent such as an alkylsilane, and preferred is an organolithium reagent, a Grignard reagent, or an organosilicon reagent, and if necessary, a Lewis acid, a metal salt, or the like may be allowed to coexist with such a reagent.

The acetate ester is not particularly limited as long as it is an alkyl ester of acetic acid, however, preferred is ethyl acetate.

The reaction temperature is from −100° C. to 100° C., and preferably from −78° C. to 0° C.

The reaction time is from 0.5 hour to 12 hours, and preferably from 0.5 hour to 3 hours.

butyllithium, lithium diisopropylamide (LDA), and lithium bis(trimethylsilyl)amide; and combinations of any of the above-mentioned bases. Preferred is a metal carbonate.

The reaction temperature is from room temperature to 150° C., and preferably from room temperature to 100° C.

The reaction time is from 0.5 hour to 24 hours, and preferably from 1 hour to 12 hours.

Further, Process A-4 can also be carried out by reacting Compound (4) with an alcohol corresponding to M-L-OH under usual Mitsunobu reaction conditions.

(Process A-5)

This process is a process for manufacturing the objective Compound (I) and is carried out by hydrolyzing the ester of the carboxylic acid of Compound (5).

The method for hydrolyzing the ester can be generally carried out by a method well known in the art of organic synthetic chemistry such as the method described in "Protective Groups in Organic Synthesis (Third Edition)" written by Greene and Wuts (Wiley Interscience, USA).

Incidentally, in the case where $P^1$ represents a halogen atom or a hydroxy group, the synthesis of the objective Compound (I) can also be carried out by subjecting Compound (1) to Process A-4 prior to Process A-1.

(Process B)

(Process B-1)

This process is a process for manufacturing Compound (7) by reacting Compound (6) which can be prepared in accordance with a known method with a halogenated aromatic cyclic group in the presence of a base.

The halogenated aromatic cyclic group can be produced by or in accordance with a known method.

The solvent is not particularly limited as long as it does not inhibit the reaction and can dissolve the starting material. However, preferred examples thereof include ethers such as diethyl ether, diisopropyl ether, tetrahydrofuran, dioxane, dimethoxyethane, and diethylene glycol dimethyl ether, and more preferred is diethyl ether, dimethoxyethane, or tetrahydrofuran.

Examples of the base to be used include organic metal bases such as butyllithium, lithium diisopropylamide (LDA), and lithium bis(trimethylsilyl)amide.

The reaction temperature is from −100° C. to 100° C., and preferably from −78° C. to 0° C.

The reaction time is from 0.5 hour to 12 hours, and preferably from 0.5 hour to 3 hours.

(Process B-2)

This process is a process for manufacturing Compound (8) by introducing an $R^1$ group into the hydroxy group of Compound (7).

As the reagent, a halogenated $R^1$ group which can be produced by or in accordance with a known method is used.

The solvent is not particularly limited as long as it does not inhibit the reaction and can dissolve the starting material to some extent. However, examples thereof include ethers such as diethyl ether, diisopropyl ether, tetrahydrofuran, dioxane, dimethoxyethane, and diethylene glycol dimethyl ether; and amides such as formamide, dimethylformamide, dimethylacetamide, N-methyl-2-pyrrolidone, and hexamethylphosphorotriamide, and preferred is dimethylformamide or tetrahydrofuran.

The reaction is preferably carried out in the presence of a base, and the base to be used is not particularly limited as long as it is a base to be used in a usual alkylation reaction. However, examples thereof include alkali metal carbonates such as lithium carbonate, sodium carbonate, and potassium carbonate; alkali metal bicarbonates such as lithium bicarbonate, sodium bicarbonate, and potassium bicarbonate; and alkali metal hydroxides such as lithium hydroxide, sodium hydroxide, and potassium hydroxide, and preferred is an alkali metal hydroxide.

The reaction temperature is from 0° C. to 100° C., and preferably from 0° C. to 50° C.

The reaction time is from 0.5 hour to 24 hours, and preferably from 1 hour to 12 hours.

(Process B-3)

This process is a process for manufacturing Compound (9) by, in the case where Y is —O—, subjecting Compound (8) and an alcohol corresponding to M-L-OH to a nucleophilic substitution reaction, and in the case where Y is —NH—, subjecting Compound (8) and an amine corresponding to M-L-NH$_2$ to an amination reaction.

(a) In the case where Y is —O—

As the reagent, an alcohol which can be produced by or in accordance with a known method is used.

The reaction is preferably carried out in the presence of a base, and the base to be used is not particularly limited as long as it is abase to be used in a usual alkylation reaction. However, examples thereof include alkali metal carbonates such as lithium carbonate, sodium carbonate, and potassium carbonate; alkali metal bicarbonates such as lithium bicarbonate, sodium bicarbonate, and potassium bicarbonate; and alkali metal hydroxides such as lithium hydroxide, sodium hydroxide, and potassium hydroxide, and preferred is an alkali metal hydroxide.

The solvent is not particularly limited as long as it does not inhibit the reaction and can dissolve the starting material to some extent. However, examples thereof include ethers such as diethyl ether, diisopropyl ether, tetrahydrofuran, dioxane, dimethoxyethane, and diethylene glycol dimethyl ether; and amides such as formamide, dimethylformamide, dimethylacetamide, N-methyl-2-pyrrolidone, and hexamethylphosphorotriamide, and preferred is an ether.

The reaction temperature is from 0° C. to 150° C., and preferably from 0° C. to 100° C.

The reaction time is from 0.5 hour to 24 hours, and preferably from 1 hour to 12 hours.

(b) In the case where Y is —NH—

As the reagent, an amine which can be produced by or in accordance with a known method is used.

The reaction is preferably carried out in the presence of a catalyst, and the catalyst to be used is not particularly limited as long as it is a catalyst to be used in a usual alkylation reaction. However, examples thereof include transition metal catalysts such as PEPPSI [1,3-bis(2,6-diisopropylphenyl)imidazol-2-ylidene](3-chloropyridyl)palladium(II) dichloride catalyst; alkali metal carbonates such as lithium carbonate, sodium carbonate, and potassium carbonate; alkali metal bicarbonates such as lithium bicarbonate, sodium bicarbonate, and potassium bicarbonate; metal alkoxides such as lithium methoxide, sodium methoxide, sodium ethoxide, and potassium-t-butoxide; organic amines such as triethylamine, tributylamine, diisopropylethylamine, N-methylmorpholine, pyridine, 2,6-lutidine, 4-(N,N-dimethylamino)pyridine, N,N-dimethylaniline, N—N-diethylaniline, 1,5-diazabicyclo[4.3.0]nona-5-ene, 1,4-diazabicylo[2.2.2]octane (DABCO), and 1,8-diazabicyclo[5.4.0]-7-undecene (DBU); and organic metal bases such as butyllithium, lithium diisopropylamide (LDA), and lithium bis(trimethylsilyl)amide. Preferred is a transition metal catalyst or a metal alkoxide.

The solvent is not particularly limited as long as it does not inhibit the reaction and can dissolve the starting material to some extent. However, examples thereof include ethers such as diethyl ether, diisopropyl ether, tetrahydrofuran, dioxane, dimethoxyethane, and diethylene glycol dimethyl ether; and amides such as formamide, dimethylformamide, dimethylacetamide, N-methyl-2-pyrrolidone, and hexamethylphosphorotriamide, and preferred is dimethylformamide or tetrahydrofuran.

The reaction temperature is from room temperature to 150° C., and preferably from 50° C. to 120° C.

The reaction time is from 0.5 hour to 24 hours, and preferably from 3 hours to 12 hours.

(Process B-4)

This process is a process for manufacturing the objective Compound (I) and is carried out by deprotecting the protecting group $P^1$ of the aldehyde of Compound (9) in an inert solvent in the presence of an acid and further oxidizing the aldehyde to form a carboxylic acid.

The solvent to be used and the type of the acid vary depending on the protecting group, however, the process can be generally carried out by a method well known in the art of organic synthetic chemistry such as the method described in "Protective Groups in Organic Synthesis (Third Edition)" written by Greene and Wuts (Wiley Interscience, USA).

The solvent to be used in the oxidation of the aldehyde is not particularly limited as long as it does not inhibit the reaction and can dissolve the starting material to some extent. However, examples thereof include ethers such as diethyl ether, diisopropyl ether, tetrahydrofuran, dioxane, dimethoxyethane, and diethylene glycol dimethyl ether; alcohols such as methanol, ethanol, t-butanol, and isopropanol; water; and mixed solvents thereof, and preferred is t-butanol, tetrahydrofuran, water, or a mixed solvent thereof.

The reagent to be used in the oxidation reaction is not particularly limited as long as it is a reagent to be generally used in an oxidation reaction from an aldehyde to a carboxylic acid, however, examples thereof include metal chlorites such as sodium chlorite and chlorine scavengers such as 2-methyl-2-butene.

The reaction temperature is from 0° C. to 60° C., and preferably from 0° C. to room temperature.

The reaction time is from 0.5 hour to 24 hours, and preferably from 0.5 hour to 6 hours.

After completion of the reactions of the above-mentioned respective processes, the objective compound is collected from the reaction mixture according to a common procedure. For example, the reaction mixture is appropriately neutralized, or in the case where insoluble matter is contained therein, the insoluble matter is removed by filtration, and then, water and an organic solvent immiscible with water such as ethyl acetate are added to the filtrate, and the organic layer is washed with water or the like. Then, the organic layer containing the objective compound is separated and dried over anhydrous magnesium sulfate or the like, and then, the solvent is distilled off, whereby the objective compound can be obtained.

If necessary, the obtained objective compound can be separated and purified by a common procedure such as recrystallization or reprecipitation, or by appropriately combining a method commonly and usually used for the separation and purification of an organic compound, for example, a method using a synthetic adsorbent such as adsorption column chromatography or partition column chromatography, a method using ion exchange chromatography, or normal and reverse phase column chromatography using silica gel or alkylated silica gel and performing elution with an appropriate eluent.

Further, if necessary, the separation and purification of optically active compounds can also be performed using a chiral column.

The carboxylic acid compound having the above-mentioned general formula (I) or a pharmacologically acceptable salt thereof of the invention is administered in various forms. The administration route is not particularly limited and is determined according to the dosage form of various preparations, the age and gender of a patient, other conditions, the severity of a disease, and the like. For example, in the case of a tablet, a pill, a powder, a granule, a syrup, a liquid, a suspension, an emulsion, a granule, or a capsule, the compound is orally administered. Further, in the case of an injection, the compound is intravenously administered singly or in admixture with a common fluid replacement such as glucose or an amino acid, and further if necessary, the compound is intramuscularly, intradermally, subcutaneously, or intraperitoneally administered singly. In the case of a suppository, the compound is intrarectally administered. The administration route is preferably oral administration.

These various preparations can be formulated according to a common procedure using a known pharmaceutical aid which can be commonly used in the known field of pharmaceutical preparations such as an excipient, a binder, a disintegrant, a lubricant, a solubilizer, a corrigent, or a coating agent, as well as a base component.

When the compound is formed into a tablet, a broad variety of substances conventionally known as a carrier in this field can be used, and examples thereof include excipients such as lactose, sucrose, sodium chloride, glucose, urea, starch, calcium carbonate, kaolin, crystalline cellulose, and silicic acid; binders such as water, ethanol, propanol, simple syrup, glucose syrup, a starch solution, a gelatin solution, carboxymethyl cellulose, shellac, methyl cellulose, potassium phosphate, and polyvinylpyrrolidone; disintegrants such as dried starch, sodium alginate, agar powder, laminaran powder, sodium hydrogen carbonate, calcium carbonate, a polyoxyethylene sorbitan fatty acid ester, sodium lauryl sulfate, stearyl monoglyceride, starch, and lactose; disintegration inhibitors such as sucrose, stearin, cacao butter, and a hydrogenated oil; absorption enhancers such as a quaternary ammonium base and sodium lauryl sulfate; humectants such as glycerin and starch; adsorbents such as starch, lactose, kaolin, bentonite, and colloidal silicic acid; and lubricants such as purified talc, a stearate salt, boric acid powder, and polyethylene glycol. Further, if necessary, the tablet can be formed into a tablet coated with a usual coating composition such as a sugar-coated tablet, a gelatin-coated tablet, an enteric-coated tablet, a film-coated tablet, a double-layer tablet, or a multi-layer tablet.

When the compound is formulated into a pill, a broad variety of substances conventionally known as a carrier in this field can be used, and examples thereof include excipients such as glucose, lactose, starch, cacao butter, a hydrogenated vegetable oil, kaolin, and talc; binders such as arabic gum powder, tragacanth powder, gelatin, and ethanol; and disintegrants such as laminaran and agar.

When the compound is formulated into a suppository, a broad variety of substances conventionally known as a carrier in this field can be used, and examples thereof include polyethylene glycol, cacao butter, a higher alcohol, a higher alcohol ester, gelatin, and a semi-synthetic glyceride.

When the compound is formulated into an injection, a liquid or a suspension is sterilized and is preferably isotonic to blood. When the compound is formulated into a liquid, an emulsion or a suspension, any substance commonly used as a diluent in this field can be used, and examples thereof include water, ethyl alcohol, propylene glycol, ethoxylated isostearyl alcohol, polyoxylated isostearyl alcohol, and a polyoxyethylene sorbitan fatty acid ester. In this case, sodium chloride, glucose, or glycerin can be added to the pharmaceutical preparation in an amount sufficient to prepare an isotonic solution. Further, a common solubilizing agent, buffer, soothing agent, or the like may also be added to the preparation.

Further, if necessary, a coloring agent, a preservative, a perfume, a flavor, a sweetener, or the like, or another pharmaceutical product may be added to the preparation.

The amount of the active ingredient compound contained in the above-mentioned pharmaceutical preparation is not particularly limited and is suitably selected from a broad range, however, it is preferred to set the amount in a range generally from 1 to 70% by weight, preferably from 1 to 30% by weight of the total composition.

The dose of the active ingredient compound varies depending on the symptoms, age, body weight, administration method, dosage form, and the like, however, the compound can be administered to an adult at a daily dose of generally 0.001 mg/kg (preferably 0.01 mg/kg, more preferably 0.1 mg/kg) as the lower limit and 200 mg/kg (preferably 20 mg/kg, more preferably 10 mg/kg) as the upper limit once or several times.

The compound of the invention can be used in combination with any of various therapeutic or preventive agents for the above-mentioned diseases in which the invention is considered to be effective. In the case where the compound is used in combination with another agent, these can be administered simultaneously, or separately and continuously or at a desired time interval. The preparations to be co-administered may be formulated as a combination preparation or separate preparations.

Advantage of the Invention

The carboxylic acid compound and a pharmacologically acceptable salt thereof which are each the compound of the invention have an excellent blood glucose lowering effect, enhancing effect on insulin secretion, and the like, and are useful as a therapeutic agent or a preventive agent for diabetes mellitus (particularly, type II diabetes), postprandial hyperglycemia, impaired glucose tolerance, ketosis, acidosis, diabetic neuropathy, diabetic nephropathy, diabetic retinopathy, hyperlipidemia, sexual dysfunction, a skin disease, a joint disease, osteopenia, arteriosclerosis, a thrombotic disease, dyspepsia, memory learning disorder, obesity, hypertension, edema, insulin resistance, unstable diabetes mellitus, lipoatrophy, insulin allergy, insulinoma, lipotoxicity, hyperinsulinemia, cancer, or the like.

Further, the compound of the invention has a low plasma protein binding ratio, and is less likely to be metabolized in the body by an enzyme such as UDP-glucuronosyltransferase (UGT) or cytochrome P450 (CYP), and therefore, it is considered that the compound exhibits an excellent effect and also has a characteristic that the effect is long-lasting. Further, the compound has low toxicity, and has excellent safety, and therefore is extremely useful as a pharmaceutical.

DETAILED DESCRIPTION OF THE INVENTION

Subsequently, the invention will be described in more detail with reference to Examples and the like, however, the invention is not limited to these.

EXAMPLES

Example 1

3-{4-[(3,4-Dichlorobenzyl)oxy]phenyl}-3-ethoxypropionic acid (Illustrative Compound No: 1-80)

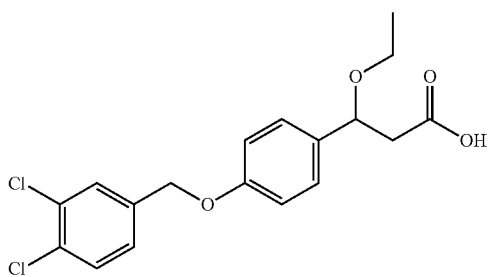

(1A) Ethyl 3-(4-{[tert-butyl(dimethyl)silyl]oxy}phenyl)-3-hydroxypropionate

Ethyl acetate (15 mL, 0.15 mol) was dissolved in tetrahydrofuran (120 mL), and a 1 M lithium bis(trimethylsilyl)amide tetrahydrofuran solution (130 mL, 0.13 mmol) was added thereto at −78° C., and then, the resulting mixture was stirred under a nitrogen atmosphere at −78° C. for 30 minutes. Thereafter, 4-{[tert-butyl(dimethyl)silyl]oxy}benzaldehyde (18.2 g, 77.0 mmol) dissolved in tetrahydrofuran (100 mL) was added thereto at −78° C., and the resulting mixture was stirred under a nitrogen atmosphere at −78° C. for 1 hour.

To the reaction solution, a saturated aqueous solution of ammonium chloride was added at −78° C., and the organic matter was extracted with ethyl acetate. The organic layer was washed with water and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=90:10 to 75:25 (v/v)), whereby the objective title compound was obtained as a colorless oily substance (24.9 g, quantitative).

$^1$H NMR (CDCl$_3$, 400 MHz): δ0.18 (6H, s), 0.98 (9H, s), 1.26 (3H, t, J=7.1 Hz), 2.65-2.79 (2H, m), 3.15 (1H, d, J=3.2 Hz), 4.18 (2H, q, J=7.1 Hz), 5.08 (1H, dt, J=3.2, 9.1 Hz), 6.82 (2H, d, J=8.6 Hz), 7.24 (2H, d, J=8.6 Hz)

(1B) Ethyl 3-(4-{[tert-butyl(dimethyl)silyl]oxy}phenyl)-3-ethoxypropionate

Ethyl 3-(4-{[tert-butyl(dimethyl)silyl]oxy}phenyl)-3-hydroxypropionate (4.00 g, 12.3 mmol) produced in (1A) was dissolved in toluene (100 mL), and ethyl iodide (4.92 mL, 61.5 mmol) and silver oxide (I) (12.0 g, 61.5 mmol) were added thereto at room temperature, and then, the resulting mixture was stirred under a nitrogen atmosphere at 100° C. for 4 hours. After cooling to room temperature, the reaction solution was filtered, and the solvent was distilled off under reduced pressure. Then, the resulting residue was purified by silica gel column chromatography (hexane:ethyl acetate=100:0 to 30:70 (v/v)), whereby the objective title compound was obtained as a colorless oily substance (3.06 g, yield: 70%).

$^1$H NMR (CDCl$_3$, 400 MHz): δ0.19 (6H, s), 0.98 (9H, s), 1.13 (3H, t, J=7.0 Hz), 1.22 (3H, t, J=7.0 Hz), 2.54 (1H, dd, J=5.1, 14.8 Hz), 2.76 (1H, dd, J=9.0, 15.2 Hz), 3.30-3.40 (2H, m), 4.13 (2H, q, J=7.2 Hz), 4.68 (1H, dd, J=5.1, 9.0 Hz), 6.80 (2H, d, J=8.6 Hz), 7.19 (2H, d, J=8.6 Hz)

(1C) Ethyl 3-ethoxy-3-(4-hydroxyphenyl)propionate

Ethyl 3-(4-{[tert-butyl(dimethyl)silyl]oxy}phenyl)-3-ethoxypropionate (3.06 g, 8.68 mmol) produced in (1B) was dissolved in tetrahydrofuran (100 mL). The reaction solution was cooled to 0° C., and a tetrabutyl ammonium fluoride tetrahydrofuran solution (1.0 M, 13.0 mL, 13.0 mmol) was added dropwise thereto, and then, the resulting mixture was stirred at room temperature for 3 hours. Water was added to the reaction solution, and the organic matter was extracted with ethyl acetate. The organic layer was washed with a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 75:25 (v/v)), whereby the objective title compound was obtained as a white solid (2.11 g, yield: 98%).

¹H NMR (CDCl₃, 400 MHz): δ1.14 (3H, t, J=7.1 Hz), 1.23 (3H, t, J=7.0 Hz), 2.55 (1H, dd, J=5.0, 14.8 Hz), 2.80 (1H, dd, J=9.0, 15.2 Hz), 3.29-3.41 (2H, m), 4.13 (2H, q, J=7.1 Hz), 4.68 (1H, dd, J=5.0, 8.9 Hz), 6.81 (2H, d, J=8.6 Hz), 7.21 (2H, d, J=8.6 Hz)

(1D) Ethyl 3-{4-[(3,4-dichlorobenzyl)oxy]phenyl}-3-ethoxypropionate

Ethyl 3-ethoxy-3-(4-hydroxyphenyl)propionate (124 mg, 0.520 mmol) produced in (1C) was dissolved in acetone (5 mL), and 3,4-dichlorobenzyl bromide (87 µL, 0.62 mmol) and potassium carbonate (108 mg. 0.78 mmol) were added thereto at room temperature, and then, the resulting mixture was stirred under a nitrogen atmosphere at 60° C. for 4 hours. After cooling to room temperature, the reaction solution was filtered, and the solvent was distilled off under reduced pressure, whereby a crude product was obtained. Then, this crude product was purified by silica gel column chromatography (hexane:ethyl acetate=100:0 to 60:40 (v/v)), whereby the objective title compound was obtained as a colorless oily substance (164 mg, yield: 79%).

¹H NMR (CDCl₃, 400 MHz): δ1.15 (3H, t, J=7.0 Hz), 1.24 (3H, t, J=7.0 Hz), 2.54 (1H, dd, J=5.5, 15.3 Hz), 2.80 (1H, dd, J=9.0, 15.3 Hz), 3.30-3.41 (2H, m), 4.14 (2H, q, J=7.0 Hz), 4.71 (1H, dd, J=5.5, 9.0 Hz), 5.01 (2H, s), 6.93 (2H, d, J=9.0 Hz), 7.25-7.29 (3H, m), 7.46 (1H, d, J=8.2 Hz), 7.54 (1H, d, J=2.0 Hz)

(1E) 3-{4-[(3,4-Dichlorobenzyl)oxy]phenyl}-3-ethoxypropionic acid

Ethyl 3-{4-[(3,4-dichlorobenzyl)oxy]phenyl}-3-ethoxypropionate (164 mg, 0.413 mmol) produced in (1D) was dissolved in tetrahydrofuran (3 mL) and ethanol (3 mL), and a 1 normal (hereinafter referred to as 1 N) aqueous solution of sodium hydroxide (2 mL) was added thereto at room temperature, and then, the resulting mixture was stirred at room temperature for 4 hours.

The solvent was distilled off under reduced pressure, and to the resulting residue, 1 N hydrochloric acid was added, and the organic matter was extracted with ethyl acetate. The organic layer was washed with a saturated sodium chloride solution, then dried over anhydrous magnesium sulfate and filtered. Then, the solvent was distilled off under reduced pressure, whereby a crude product was obtained. This crude product was washed with hexane/ethyl acetate (5/1 (v/v)), whereby the objective title compound was obtained as a white solid (121 mg, yield: 79%).

¹H NMR (CDCl₃, 400 MHz): δ1.19 (3H, t, J=7.0 Hz), 2.63 (1H, dd, J=4.3, 15.6 Hz), 2.83 (1H, dd, J=9.8, 15.6 Hz), 3.35-3.46 (2H, m), 4.70 (1H, dd, J=4.3, 9.8 Hz), 5.01 (2H, s), 6.94 (2H, d, J=8.6 Hz), 7.25-7.28 (3H, m), 7.46 (1H, d, J=8.2 Hz), 7.54 (1H, d, J=2.0 Hz)

MS (ESI) m/z: 367 (M−H)⁻

Example 2

3-Ethoxy-3-[4-({4-methyl-2-[4-(trifluoromethyl)phenyl]-1,3-thiazol-5-yl}methoxy)phenyl]propionic acid (Illustrative Compound No: 1-163)

(2A) Ethyl 3-ethoxy-3-[4-({4-methyl-2-[4-(trifluoromethyl)phenyl]-1,3-thiazol-5-yl}methoxy)phenyl]propionate Ethyl 3-ethoxy-3-(4-hydroxyphenyl)propionate (108 mg, 0.453 mmol) produced in Example 1 (1C) and {4-methyl-2-[4-(trifluoromethyl)phenyl]-1,3-thiazol-5-yl}methanol (124 mg, 0.453 mmol) were dissolved in tetrahydrofuran (10 mL), and triphenylphosphine (178 mg, 0.680 mmol) and a 40% diethyl azodicarboxylate toluene solution (309 µL, 0.680 mmol) were added thereto at room temperature, and then, the resulting mixture was stirred under a nitrogen atmosphere at 50° C. for 4 hours.

After the reaction solution was cooled to room temperature, the solvent was distilled off under reduced pressure, and the resulting residue was purified by silica gel column chromatography (hexane:ethyl acetate=100:0 to 50:50 (v/v)), whereby the objective title compound was obtained as a colorless oily substance (120 mg, yield: 54%).

¹H NMR (CDCl₃, 500 MHz): δ1.15 (3H, t, J=7.3 Hz), 1.23 (3H, t, J=7.3 Hz), 2.52 (3H, s), 2.55 (1H, dd, J=4.9, 15.1 Hz), 2.80 (1H, dd, J=8.8, 15.1 Hz), 3.32-3.41 (2H, m), 4.11-4.16 (2H, m), 4.70 (1H, dd, J=4.9, 8.8 Hz), 5.19 (2H, s), 6.97 (2H, d, J=8.3 Hz), 7.30 (2H, d, J=8.3 Hz), 7.68 (2H, d, J=8.3 Hz), 8.03 (2H, d, J=8.3 Hz)

(2B) 3-Ethoxy-3-[4-({4-methyl-2-[4-(trifluoromethyl)phenyl]-1,3-thiazol-5-yl}methoxy)phenyl]propionic acid Ethyl 3-ethoxy-3-[4-({4-methyl-2-[4-(trifluoromethyl)phenyl]-1,3-thiazol-5-yl}methoxy)phenyl]propionate (120 mg, 0.243 mmol) produced in (2A) was dissolved in tetrahydrofuran (3 mL) and ethanol (3 mL), and a 1 N aqueous solution of sodium hydroxide (2 mL) was added thereto at room temperature, and then, the resulting mixture was stirred at room temperature for 4 hours.

The solvent was distilled off from the reaction solution under reduced pressure, and to the resulting residue, 1 N hydrochloric acid was added, and the organic matter was extracted with ethyl acetate. The organic layer was washed with a saturated sodium chloride solution, then dried over anhydrous magnesium sulfate and filtered. Then, the solvent was distilled off under reduced pressure, whereby a crude product was obtained. This crude product was washed with hexane/ethyl acetate (5/1 (v/v)), whereby the objective title compound was obtained as a white solid (50 mg, yield: 44%).

¹H NMR (CDCl₃, 400 MHz): δ1.20 (3H, t, J=7.0 Hz), 2.52 (3H, s), 2.63 (1H, dd, J=4.3, 15.6 Hz), 2.84 (1H, dd, J=9.4, 15.6 Hz), 3.38-3.46 (2H, m), 4.70 (1H, dd, J=4.3, 9.4 Hz), 5.20 (2H, s), 6.99 (2H, d, J=8.6 Hz), 7.30 (2H, d, J=8.6 Hz), 7.68 (2H, d, J=8.2 Hz), 8.03 (2H, d, J=8.2 Hz).

MS (ESI) m/z: 464 (M−H)⁻

Example 3

3-Ethoxy-3-{4-[(3-isopropyloxybenzyl)oxy]phenyl}propionic acid (Illustrative Compound No: 1-42)

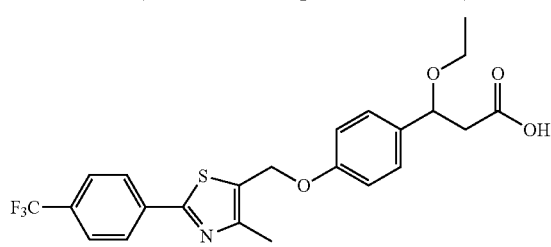

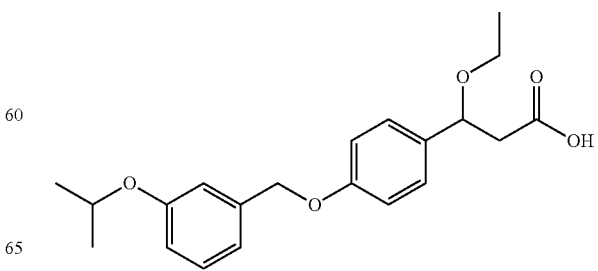

(3A) Ethyl 3-ethoxy-3-{4-[(3-isopropyloxybenzyl)oxy]phenyl}propionate

Ethyl 3-ethoxy-3-(4-hydroxyphenyl)propionate (100 mg, 0.420 mmol) produced in Example 1 (1C) and 3-isopropyloxybenzyl alcohol (118 mg, 0.710 mmol) were dissolved in tetrahydrofuran (2 mL), and triphenylphosphine (165 mg, 0.629 mmol) and a diethyl azodicarboxylate toluene solution (2.2 M, 290 μL, 0.640 mmol) were added thereto at room temperature, and then, the resulting mixture was stirred under a nitrogen atmosphere at room temperature for 4 hours.

The solvent in the reaction solution was distilled off under reduced pressure, and the resulting residue was purified by silica gel column chromatography (hexane:ethyl acetate=100:0 to 95:5 (v/v)), whereby the objective title compound was obtained as a colorless oily substance (115 mg, 71%).

$^1$H NMR (CDCl$_3$, 400 MHz): δ1.12 (3H, t, J=7.0 Hz), 1.21 (3H, t, J=7.0 Hz), 1.31 (6H, d, J=6.3 Hz), 2.53 (1H, dd, J=5.1, 15.2 Hz), 2.77 (1H, dd, J=9.0, 15.2 Hz), 3.26-3.39 (2H, m), 4.11 (2H, q, J=7.0 Hz), 4.54 (1H, h, J=6.3 Hz), 4.67 (1H, dd, J=5.1, 9.0 Hz), 5.00 (2H, s), 6.82 (1H, m), 6.90-6.97 (4H, m), 7.21-7.28 (3H, m)

(3B) 3-Ethoxy-3-{4-[(3-isopropyloxybenzyl)oxy]phenyl}propionic acid

Ethyl 3-ethoxy-3-{4-[(3-isopropyloxybenzyl)oxy]phenyl}propionate (115 mg, 0.298 mmol) produced in (3A) was dissolved in tetrahydrofuran (1 mL) and ethanol (1 mL), and a 1 N aqueous solution of sodium hydroxide (0.5 mL) was added thereto at room temperature, and then, the resulting mixture was stirred at room temperature for 4 hours.

To the reaction solution, 1 N hydrochloric acid was added, and the organic matter was extracted with ethyl acetate. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=80:20 to 50:50 (v/v)), whereby the objective title compound was obtained as a white solid (102 mg, 96%).

$^1$H NMR (CDCl$_3$, 500 MHz): δ1.18-1.22 (3H, m), 1.36 (6H, d, J=6.3 Hz), 2.65 (1H, dd, J=4.4, 15.6 Hz), 2.86 (1H, dd, J=9.8, 15.6 Hz), 3.35-3.48 (2H, m), 4.59 (1H, h, J=6.3 Hz), 4.71 (1H, dd, J=4.4, 9.8 Hz), 5.05 (2H, s), 6.88 (1H, m), 6.97-7.02 (4H, m), 7.26-7.33 (3H, m)

Example 4

3-Ethoxy-3-{4-[(3-nitrobenzyl)oxy]phenyl}propionic acid (Illustrative Compound No: 1-43)

(4A) Ethyl 3-ethoxy-3-{4-[(3-nitrobenzyl)oxy]phenyl}propionate

Ethyl 3-ethoxy-3-(4-hydroxyphenyl)propionate (200 mg, 0.839 mmol) produced in Example 1 (1C) and 3-nitrobenzyl alcohol (200 mg, 0.926 mmol) were dissolved in acetone (4 mL), and potassium carbonate (136 mg, 0.984 mmol) were added thereto at room temperature, and then, the resulting mixture was stirred at room temperature for 12 hours.

The reaction solution was filtered, and the solvent was distilled off under reduced pressure. Then, to the resulting residue, a saturated aqueous solution of ammonium chloride was added, and the organic matter was extracted with ethyl acetate. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=95:5 to 90:10 (v/v)), whereby the objective title compound was obtained as a light yellow oily substance (278 mg, 89%).

$^1$H NMR (CDCl$_3$, 500 MHz): δ1.17 (3H, t, J=7.0 Hz), 1.26 (3H, t, J=7.0 Hz), 2.58 (1H, dd, J=5.4, 15.1 Hz), 2.82 (1H, dd, J=8.8, 15.1 Hz), 3.33-3.44 (2H, m), 4.16 (2H, q, J=7.0 Hz), 4.73 (1H, dd, J=5.4, 8.8 Hz), 5.18 (2H, s), 6.99 (2H, d, J=8.8 Hz), 7.32 (2H, d, J=8.8 Hz), 7.60 (1H, dd, J=7.8, 8.3 Hz), 7.80 (1H, d, J=7.8 Hz), 8.22 (1H, d, J=8.3 Hz), 8.35 (1H, s)

(4B) 3-Ethoxy-3-{4-[(3-nitrobenzyl)oxy]phenyl}propionic acid

Ethyl 3-ethoxy-3-{4-[(3-nitrobenzyl)oxy]phenyl}propionate (50 mg, 0.13 mmol) produced in (4A) was dissolved in tetrahydrofuran (1 mL) and ethanol (1 mL), and a 1 N aqueous solution of sodium hydroxide (0.5 mL) was added thereto at room temperature, and then, the resulting mixture was stirred at room temperature for 4 hours.

To the reaction solution, 1 N hydrochloric acid was added, and the organic matter was extracted with ethyl acetate. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=80:20 to 50:50 (v/v)), whereby the objective title compound was obtained as a light yellow solid (30 mg, 70%).

$^1$H NMR (CDCl$_3$, 400 MHz): δ1.15 (3H, t, J=7.0 Hz), 2.59 (1H, dd, J=4.3, 16.0 Hz), 2.80 (1H, dd, J=9.4, 16.0 Hz), 3.31-3.44 (2H, m), 4.65 (1H, dd, J=4.3, 9.4 Hz), 5.12 (2H, s), 6.94 (2H, d, J=8.8 Hz), 7.25 (2H, d, J=8.8 Hz), 7.54 (1H, dd, J=7.8, 8.2 Hz), 7.74 (1H, d, J=7.8 Hz), 8.16 (1H, d, J=8.2 Hz), 8.29 (1H, s)

Example 5

3-Ethoxy-3-(4-{[3-(trifluoromethoxy)benzyl]oxy}phenyl)propionic acid (Illustrative Compound No: 1-45)

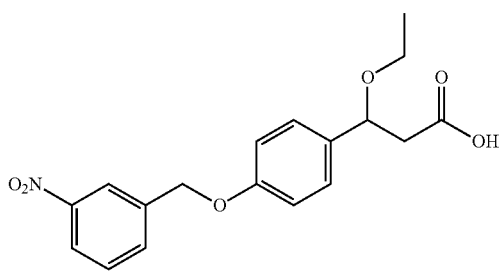

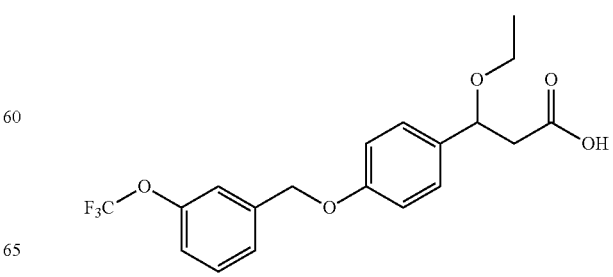

(5A) Ethyl 3-ethoxy-3-(4-{[3-(trifluoromethoxy)benzyl]oxy}phenyl)propionate

Ethyl 3-ethoxy-3-(4-hydroxyphenyl)propionate (100 mg, 0.420 mmol) produced in Example 1 (1C) and 3-trifluoromethoxybenzyl alcohol (123 mg, 0.640 mmol) were dissolved in tetrahydrofuran (2 mL), and triphenylphosphine (165 mg, 0.629 mmol) and a diethyl azodicarboxylate toluene solution (2.2 M, 290 µL, 0.638 mmol) were added thereto at room temperature, and then, the resulting mixture was stirred under a nitrogen atmosphere at room temperature for 4 hours. The solvent in the reaction solution was distilled off under reduced pressure, and the resulting residue was purified by silica gel column chromatography (hexane:ethyl acetate=100:0 to 95:5 (v/v)), whereby the objective title compound was obtained as a colorless oily substance (124 mg, 72%).

$^1$H NMR (CDCl$_3$, 400 MHz): δ1.12 (3H, t, J=7.0 Hz), 1.21 (3H, t, J=7.0 Hz), 2.54 (1H, dd, J=5.1, 14.9 Hz), 2.78 (1H, dd, J=9.0, 14.9 Hz), 3.27-3.40 (2H, m), 4.11 (2H, q, J=7.0 Hz), 4.68 (1H, dd, J=5.1, 9.0 Hz), 5.05 (2H, s), 6.93 (1H, d, J=8.6 Hz), 7.16 (1H, m), 7.24-7.31 (3H, m), 7.34 (1H, m), 7.40 (1H, dd, J=7.8, 7.8 Hz)

(5B) 3-Ethoxy-3-(4-{[3-(trifluoromethoxy)benzyl]oxy}phenyl)propionic acid

Ethyl 3-ethoxy-3-(4-{[3-(trifluoromethoxy)benzyl]oxy}phenyl)propionate (75 mg, 0.18 mmol) produced in (5A) was dissolved in tetrahydrofuran (1 mL) and ethanol (1 mL), and a 1 N aqueous solution of sodium hydroxide (0.5 mL) was added thereto at room temperature, and then, the resulting mixture was stirred at room temperature for 4 hours. 1 N Hydrochloric acid was added to the reaction solution, and the organic matter was extracted with ethyl acetate. The organic layer was washed with a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=80:20 to 50:50 (v/v)), whereby the objective title compound was obtained as a colorless oily substance (60 mg, 86%).

$^1$H NMR (CDCl$_3$, 400 MHz): δ1.16 (3H, t, J=7.0 Hz), 2.61 (1H, dd, J=4.3, 15.6 Hz), 2.82 (1H, dd, J=9.4, 15.6 Hz), 3.31-3.44 (2H, m), 4.67 (1H, dd, J=4.3, 9.4 Hz), 5.06 (2H, s), 6.94 (1H, d, J=8.6 Hz), 7.17 (1H, m), 7.23-7.30 (3H, m), 7.34 (1H, m), 7.40 (1H, dd, J=7.8, 7.8 Hz)

Example 6

3-Ethoxy-3-(4-{[3-(1H-pyrrol-1-yl)benzyl]oxy}phenyl)propionic acid (Illustrative Compound No: 1-115)

(6A) Ethyl 3-ethoxy-3-(4-{[3-(1H-pyrrol-1-yl)benzyl]oxy}phenyl)propionate

Ethyl 3-ethoxy-3-(4-hydroxyphenyl)propionate (100 mg, 0.420 mmol) produced in Example 1 (1C) and 3-(1H-pyrrol-1-yl)phenylmethanol (104 mg, 0.600 mmol) were dissolved in tetrahydrofuran (2 mL), and triphenylphosphine (165 mg, 0.629 mmol) and a diethyl azodicarboxylate toluene solution (2.2 M, 290 µL, 0.638 mmol) were added thereto at room temperature, and then, the resulting mixture was stirred under a nitrogen atmosphere at room temperature for 2 hours. The solvent in the reaction solution was distilled off under reduced pressure, and the resulting residue was purified by silica gel column chromatography (hexane:ethyl acetate=100:0 to 90:10 (v/v)), whereby the objective title compound was obtained as a light yellow oily substance (107 mg, yield: 65%).

$^1$H NMR (CDCl$_3$, 400 MHz): δ1.12 (3H, t, J=7.0 Hz), 1.21 (3H, t, J=7.0 Hz), 2.53 (1H, dd, J=5.1, 15.2 Hz), 2.77 (1H, dd, J=9.0, 15.2 Hz), 3.27-3.40 (2H, m), 4.11 (2H, q, J=7.0 Hz), 4.68 (1H, dd, J=5.1, 9.0 Hz), 5.09 (2H, s), 6.33-6.35 (2H, m), 6.94 (2H, d, J=8.6 Hz), 7.08-7.09 (2H, m), 7.25 (2H, d, J=8.6 Hz), 7.28 (1H, m), 7.34 (1H, m), 7.42 (1H, dd, J=7.4, 7.8 Hz), 7.46 (1H, dd, J=1.6, 2.0 Hz)

(6B) 3-Ethoxy-3-(4-{[3-(1H-pyrrol-1-yl)benzyl]oxy}phenyl)propionic acid

Ethyl 3-ethoxy-3-(4-{[3-(1H-pyrrol-1-yl)benzyl]oxy}phenyl)propionate (107 mg, 0.272 mmol) produced in (6A) was dissolved in tetrahydrofuran (1 mL) and ethanol (1 mL), and a 1 N aqueous solution of sodium hydroxide (0.5 mL) was added thereto at room temperature, and then, the resulting mixture was stirred at room temperature for 4 hours. 1 N Hydrochloric acid was added to the reaction solution, and the organic matter was extracted with ethyl acetate. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=80:20 to 50:50 (v/v)), whereby the objective title compound was obtained as a yellow oily substance (80 mg, yield: 80%).

$^1$H NMR (CDCl$_3$, 400 MHz): δ1.15 (3H, t, J=7.0 Hz), 2.61 (1H, dd, J=4.3, 15.6 Hz), 2.82 (1H, dd, J=9.4, 15.6 Hz), 3.31-3.44 (2H, m), 4.67 (1H, dd, J=4.3, 9.4 Hz), 5.09 (2H, s), 6.32-6.35 (2H, m), 6.96 (2H, d, J=8.6 Hz), 7.07-7.09 (2H, m), 7.25 (2H, d, J=8.6 Hz), 7.28 (1H, m), 7.34 (1H, m), 7.42 (1H, dd, J=7.8, 7.8 Hz), 7.46 (1H, dd, J=1.6, 2.0 Hz)

Example 7

3-Ethoxy-3-(4-{[4-(trifluoromethyl)benzyl]oxy}phenyl)propionic acid (Illustrative Compound No: 1-48)

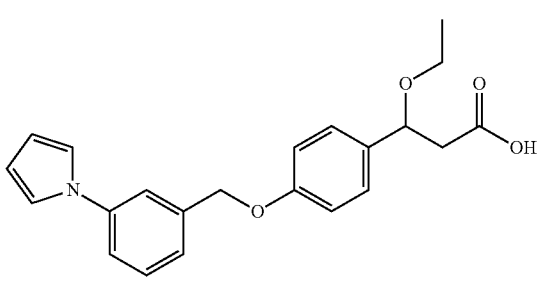

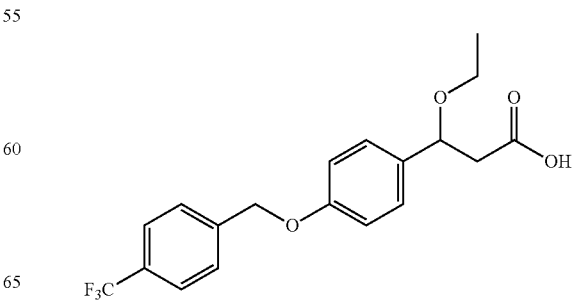

(7A) Ethyl 3-ethoxy-3-(4-{[4-(trifluoromethyl)benzyl]oxy}phenyl)propionate

Ethyl 3-ethoxy-3-(4-hydroxyphenyl)propionate (100 mg, 0.420 mmol) produced in Example 1 (1C) and [4-(trifluoromethyl)phenyl]methanol (111 mg, 0.630 mmol) were dissolved in tetrahydrofuran (10 mL), and triphenylphosphine (178 mg, 0.680 mmol) and a 40% diethyl azodicarboxylate toluene solution (309 µL, 0.680 mmol) were added thereto at room temperature, and then, the resulting mixture was stirred under a nitrogen atmosphere at 50° C. for 4 hours. After the reaction solution was cooled to room temperature, the solvent was distilled off under reduced pressure, and the resulting residue was purified by silica gel column chromatography (hexane:ethyl acetate=100:0 to 95:5 (v/v)), whereby the objective title compound was obtained as a colorless oily substance (125 mg, yield: 75%).

$^1$H NMR (CDCl$_3$, 400 MHz): δ1.14 (3H, t, J=7.1 Hz), 1.23 (3H, t, J=7.1 Hz), 2.56 (1H, dd, J=5.5, 15.3 Hz), 2.80 (1H, dd, J=9.0, 15.3 Hz), 3.31-3.39 (2H, m), 4.14 (2H, q, J=7.0 Hz), 4.69 (1H, dd, J=5.1, 8.6 Hz), 5.02 (2H, s), 6.92 (2H, d, J=8.6 Hz), 7.26 (3H, t, J=4.3 Hz), 7.36 (3H, s)

(7B) 3-Ethoxy-3-(4-{[4-(trifluoromethyl)benzyl]oxy}phenyl)propionic acid

Ethyl 3-ethoxy-3-(4-{[4-(trifluoromethyl)benzyl]oxy}phenyl)propionate (125 mg, 0.315 mmol) produced in (7A) was dissolved in tetrahydrofuran (3 mL) and ethanol (3 mL), and a 1 N aqueous solution of sodium hydroxide (2 mL) was added thereto at room temperature, and then, the resulting mixture was stirred at room temperature for 4 hours. The solvent was distilled off from the reaction solution under reduced pressure, and to the resulting residue, 1 N hydrochloric acid was added, and the organic matter was extracted with ethyl acetate. The organic layer was washed with a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 70:30 (v/v)), whereby the objective title compound was obtained as a white solid (103 mg, yield: 78%).

$^1$H NMR (CDCl$_3$, 400 MHz): δ1.17 (3H, t, J=7.1 Hz), 2.64 (1H, dd, J=4.7, 15.7 Hz), 2.85 (1H, dd, J=9.3, 15.6 Hz), 3.33-3.43 (2H, m), 4.69 (1H, dd, J=4.3, 9.4 Hz), 5.12 (2H, s), 6.94 (2H, d, J=8.6 Hz), 7.26 (2H, d, J=8.6 Hz), 7.54 (2H, d, J=7.8 Hz), 7.64 (2H, d, J=8.2 Hz)

Example 8

3-(4-{[3-(Dimethylamino)benzyl]oxy}phenyl)-3-ethoxypropionic acid (Illustrative Compound No: 1-64)

(8A) Ethyl 3-(4-{[3-(dimethylamino)benzyl]oxy}phenyl)-3-ethoxypropionate

Ethyl 3-ethoxy-3-(4-hydroxyphenyl)propionate (100 mg, 0.420 mmol) produced in Example 1 (1C) and [3-(dimethylamino)phenyl]methanol (95 mg, 0.630 mmol) were dissolved in tetrahydrofuran (10 mL), and triphenylphosphine (178 mg, 0.680 mmol) and a 40% diethyl azodicarboxylate toluene solution (309 µL, 0.680 mmol) were added thereto at room temperature, and then, the resulting mixture was stirred under a nitrogen atmosphere at 50° C. for 4 hours. After the reaction solution was cooled to room temperature, the solvent was distilled off under reduced pressure, and the resulting residue was purified by silica gel column chromatography (hexane:ethyl acetate=100:0 to 95:5 (v/v)), whereby the objective title compound was obtained as a white solid (119 mg, yield: 76%).

$^1$H NMR (CDCl$_3$, 400 MHz): δ1.14 (3H, t, J=7.0 Hz), 1.23 (3H, t, J=7.4 Hz), 2.56 (1H, dd, J=5.1, 14.9 Hz), 2.80 (1H, dd, J=9.0, 15.3 Hz), 2.96 (6H, s), 3.30-3.34 (2H, m), 4.14 (2H, q, J=7.1 Hz), 4.69 (1H, dd, J=5.1, 9.4 Hz), 5.01 (2H, s), 6.71 (1H, d, J=8.6 Hz), 6.78 (2H, d, J=7.0 Hz), 6.96 (2H, d, J=8.6 Hz), 7.23-7.26 (3H, m)

(8B) 3-(4-{[3-(Dimethylamino) benzyl]oxy}phenyl)-3-ethoxypropionic acid

Ethyl 3-(4-{[3-(dimethylamino) benzyl]oxy}phenyl)-3-ethoxypropionate (119 mg, 0.320 mmol) produced in (8A) was dissolved in tetrahydrofuran (3 mL) and ethanol (3 mL), and a 1 N aqueous solution of sodium hydroxide (2 mL) was added thereto at room temperature, and then, the resulting mixture was stirred at room temperature for 4 hours. The solvent was distilled off under reduced pressure, and to the resulting residue, 1 N hydrochloric acid was added, and the organic matter was extracted with ethyl acetate. The organic layer was washed with a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 70:30 (v/v)), whereby the objective title compound was obtained as a white solid (58 mg, yield: 53%).

$^1$H NMR (CDCl$_3$, 400 MHz): δ1.15 (3H, t, J=7.0 Hz), 2.62 (1H, dd, J=4.3, 15.6 Hz), 2.84 (1H, dd, J=9.4, 15.6 Hz), 2.95 (6H, s), 3.33-3.42 (2H, m), 4.69 (1H, dd, J=4.3, 9.0 Hz), 5.01 (2H, s), 6.70 (1H, d, J=8.2 Hz), 6.77 (2H, d, J=7.9 Hz), 6.96 (2H, d, J=8.6 Hz), 7.22-7.26 (3H, m)

Example 9

3-{4-[2-(4-Chlorophenyl)ethoxy]phenyl}-3-ethoxypropionic acid (Illustrative Compound No: 1-37)

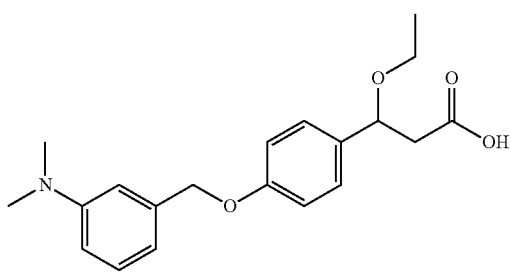

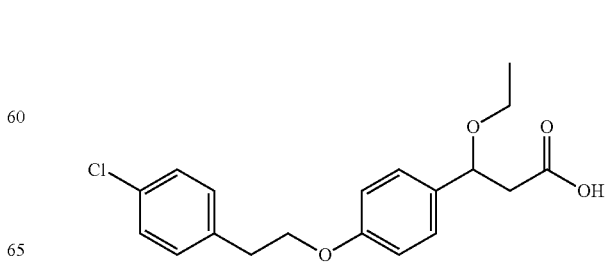

(9A) Ethyl 3-{4-[2-(4-chlorophenyl)ethoxy]phenyl}-3-ethoxypropionate

Ethyl 3-ethoxy-3-(4-hydroxyphenyl)propionate (100 mg, 0.420 mmol) produced in Example 1 (1C) and 2-(4-chlorophenyl)ethanol (99 mg, 0.630 mmol) were dissolved in tetrahydrofuran (10 mL), and triphenylphosphine (178 mg, 0.680 mmol) and a 40% diethyl azodicarboxylate toluene solution (309 μL, 0.680 mmol) were added thereto at room temperature, and then, the resulting mixture was stirred under a nitrogen atmosphere at 50° C. for 4 hours. After the reaction solution was cooled to room temperature, the solvent was distilled off under reduced pressure, and the resulting residue was purified by silica gel column chromatography (hexane:ethyl acetate=100:0 to 95:5 (v/v)), whereby the objective title compound was obtained as a yellow oily substance (151 mg, yield: 95%).

$^1$H NMR (CDCl$_3$, 400 MHz): δ1.13 (3H, t, J=7.0 Hz), 1.23 (3H, t, J=7.0 Hz), 2.55 (1H, dd, J=5.0, 15.2 Hz), 2.79 (1H, dd, J=9.0, 15.2 Hz), 3.06 (2H, t, J=7.0 Hz), 3.30-3.38 (2H, m), 4.14 (4H, t, J=7.3 Hz), 4.68 (1H, dd, J=5.0, 8.9 Hz), 6.86 (2H, d, J=8.6 Hz), 7.22 (2H, d, J=8.3 Hz), 7.24 (2H, d, J=8.6 Hz), 7.28 (2H, d, J=8.6 Hz)

(9B) 3-{4-[2-(4-Chlorophenyl)ethoxy]phenyl}-3-ethoxypropionic acid

Ethyl 3-{4-[2-(4-chlorophenyl)ethoxy]phenyl}-3-ethoxypropionate (151 mg, 0.400 mmol) produced in (9A) was dissolved in tetrahydrofuran (4 mL) and ethanol (4 mL), and a 1 N aqueous solution of sodium hydroxide (3 mL) was added thereto at room temperature, and then, the resulting mixture was stirred at room temperature for 4 hours. The solvent was distilled off under reduced pressure, and to the resulting residue, 1 N hydrochloric acid was added, and the organic matter was extracted with ethyl acetate. The organic layer was washed with a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 70:30 (v/v)), whereby the objective title compound was obtained as a white solid (131 mg, yield: 94%).

$^1$H NMR (CDCl$_3$, 400 MHz): δ1.23 (3H, t, J=7.0 Hz), 2.63 (1H, dd, J=3.9, 15.6 Hz), 2.83 (1H, dd, J=9.4, 15.6 Hz), 3.06 (2H, t, J=6.6 Hz), 3.35-3.44 (2H, m), 4.15 (2H, t, J=6.7 Hz), 4.67 (1H, dd, J=4.3, 9.8 Hz), 6.87 (2H, d, J=8.6 Hz), 7.22 (2H, d, J=8.2 Hz), 7.23 (2H, d, J=8.6 Hz), 7.28 (2H, d, J=8.6 Hz)

Example 10

3-{4-[(1R)-1-(3-Chlorophenyl)ethoxy]phenyl}-3-ethoxypropionic acid (Illustrative Compound No: 1-35)

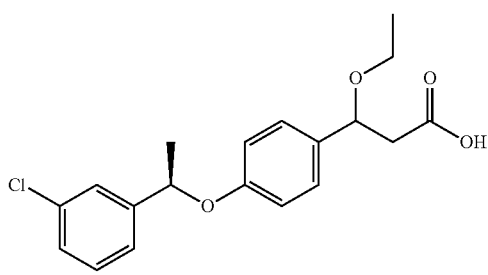

(10A) Ethyl 3-{4-[(1R)-1-(3-chlorophenyl)ethoxy]phenyl}-3-ethoxypropionate

Ethyl 3-ethoxy-3-(4-hydroxyphenyl)propionate (100 mg, 0.420 mmol) produced in Example 1 (1C) and (1S)-1-(3-chlorophenyl)ethanol (99 mg, 0.630 mmol) were dissolved in tetrahydrofuran (10 mL), and triphenylphosphine (178 mg, 0.680 mmol) and a 40% diethyl azodicarboxylate toluene solution (309 μL, 0.680 mmol) were added thereto at room temperature, and then, the resulting mixture was stirred under a nitrogen atmosphere at 50° C. for 4 hours. After the reaction solution was cooled to room temperature, the solvent was distilled off under reduced pressure, and the resulting residue was purified by silica gel column chromatography (hexane:ethyl acetate=100:0 to 95:5 (v/v)), whereby the objective title compound was obtained as a yellow oily substance (142 mg, yield: 90%).

$^1$H NMR (CDCl$_3$, 400 MHz): δ1.12 (3H, t, J=7.1 Hz), 1.21 (3H, td, J=4.6, 7.3 Hz), 1.61 (3H, d, J=6.3 Hz), 2.52 (1H, dd, J=5.0, 15.2 Hz), 2.76 (1H, dd, J=8.9, 14.4 Hz), 3.27-3.37 (2H, m), 4.11 (2H, qd, J=2.8, 7.1 Hz), 4.62-4.66 (1H, m), 5.25 (1H, q, J=6.6 Hz), 6.81 (2H, d, J=9.0 Hz), 7.17 (2H, d, J=9.0 Hz), 7.22-7.30 (3H, m), 7.37 (1H, s)

(10B) 3-{4-[(1R)-1-(3-Chlorophenyl)ethoxy]phenyl}-3-ethoxypropionic acid

Ethyl 3-{4-[(1R)-1-(3-chlorophenyl)ethoxy]phenyl}-3-ethoxypropionate (142 mg, 0.377 mmol) produced in (10A) was dissolved in tetrahydrofuran (4 mL) and ethanol (4 mL), and a 1 N aqueous solution of sodium hydroxide (3 mL) was added thereto at room temperature, and then, the resulting mixture was stirred at room temperature for 4 hours. The solvent was distilled off under reduced pressure, and to the resulting residue, 1 N hydrochloric acid was added, and the organic matter was extracted with ethyl acetate. The organic layer was washed with a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 70:30 (v/v)), whereby the objective title compound was obtained as a colorless oily substance (130 mg, yield: 100%).

$^1$H NMR (CDCl$_3$, 400 MHz): δ1.15 (3H, t, J=7.1 Hz), 1.61 (3H, d, J=6.6 Hz), 2.59 (1H, dd, J=4.3, 16.1 Hz), 2.79 (1H, dd, J=9.4, 15.6 Hz), 3.32-3.41 (2H, m), 4.61-4.65 (1H, m), 5.25 (1H, q, J=6.5 Hz), 6.82 (2H, d, J=8.6 Hz), 7.17 (2H, d, J=9.0 Hz), 7.22-7.30 (3H, m), 7.37 (1H, s)

Example 11

3-{4-[3-(3,4-Dichlorophenyl)propoxy]phenyl}-3-ethoxypropionic acid (Illustrative Compound No: 1-40)

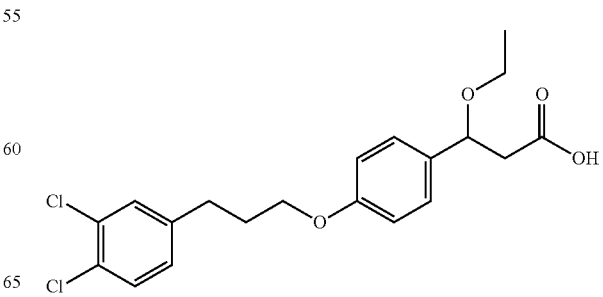

(11A) 3-(3,4-Dichlorophenyl)propanol (2E)-3-(3,4-Dichlorophenyl)acrylic acid (800 mg, 3.69 mmol) was dissolved in tetrahydrofuran (80 mL), and the resulting solution was cooled to 0° C. Then, lithium aluminum hydride (280 mg, 7.38 mmol) was added thereto, and the temperature of the resulting mixture was raised to room temperature, and the mixture was stirred for 8 hours. Water was added to the reaction solution, and the organic matter was extracted with ethyl acetate. The organic layer was washed with water and a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 70:30 (v/v)), whereby the objective title compound was obtained as a yellow oily substance (229 mg, yield: 30%).

$^1$H NMR (CDCl$_3$, 400 MHz): δ1.31 (1H, brs), 1.83-1.90 (2H, m), 2.68 (2H, t, J=7.5 Hz), 3.67 (2H, t, J=6.2 Hz), 7.04 (1H, dd, J=2.4, 8.2 Hz), 7.30 (1H, d, J=2.3 Hz), 7.32 (1H, d, J=8.2 Hz)

(11B) Ethyl 3-{4-[3-(3,4-dichlorophenyl)propoxy]phenyl}-3-ethoxypropionate

Ethyl 3-ethoxy-3-(4-hydroxyphenyl)propionate (100 mg, 0.420 mmol) produced in Example 1 (1C) and 3-(3,4-dichlorophenyl)propanol (129 mg, 0.630 mmol) synthesized in (11A) were dissolved in tetrahydrofuran (10 mL), and triphenylphosphine (178 mg, 0.680 mmol) and a 40% diethyl azodicarboxylate toluene solution (309 μL, 0.680 mmol) were added thereto at room temperature, and then, the resulting mixture was stirred under a nitrogen atmosphere at 50° C. for 4 hours. After the reaction solution was cooled to room temperature, the solvent was distilled off under reduced pressure, and the resulting residue was purified by silica gel column chromatography (hexane:ethyl acetate=100:0 to 95:5 (v/v)), whereby the objective title compound was obtained as a colorless oily substance (130 mg, yield: 73%).

$^1$H NMR (CDCl$_3$, 400 MHz): δ1.14 (3H, t, J=7.0 Hz), 1.24 (3H, t, J=7.1 Hz), 2.03-2.10 (2H, m), 2.56 (1H, dd, J=5.1, 15.2 Hz), 2.76-2.83 (3H, m), 3.29-3.41 (2H, m), 3.94 (2H, t, J=6.1 Hz), 4.14 (2H, q, J=7.2 Hz), 4.70 (1H, dd, J=4.1, 9.0 Hz), 6.86 (2H, d, J=8.6 Hz), 7.05 (1H, dd, J=2.4, 8.2 Hz), 7.26 (2H, d, J=8.6 Hz), 7.31 (1H, d, J=1.9 Hz), 7.34 (1H, d, J=8.2 Hz)

(11C) 3-{4-[3-(3,4-Dichlorophenyl)propoxy]phenyl}-3-ethoxypropionic acid

Ethyl 3-{4-[3-(3,4-dichlorophenyl)propoxy]phenyl}-3-ethoxypropionate (130 mg, 0.306 mmol) produced in (11B) was dissolved in tetrahydrofuran (3 mL) and ethanol (3 mL), and a 1 N aqueous solution of sodium hydroxide (2 mL) was added thereto at room temperature, and then, the resulting mixture was stirred at room temperature for 4 hours. The solvent was distilled off under reduced pressure, and to the resulting residue, 1 N hydrochloric acid was added, and the organic matter was extracted with ethyl acetate. The organic layer was washed with a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 70:30 (v/v)), whereby the objective title compound was obtained as a white solid (70 mg, yield: 58%).

$^1$H NMR (CDCl$_3$, 400 MHz): δ1.18 (3H, t, J=7.1 Hz), 2.06-2.11 (2H, m), 2.64 (1H, dd, J=4.3, 15.6 Hz), 2.78 (2H, t, J=7.1 Hz), 2.85 (1H, dd, J=9.8, 16 Hz), 3.34-3.45 (2H, m), 3.95 (2H, t, J=6.3 Hz), 4.68 (1H, dd, J=3.9, 9.3 Hz), 6.88 (2H, d, J=9.0 Hz), 7.06 (1H, dd, J=2.0, 8.2 Hz), 7.25 (2H, d, J=8.6 Hz), 7.31 (1H, d, J=2.0 Hz), 7.34 (1H, d, J=8.3 Hz)

Example 12

3-[4-({3-[(Dimethylamino)sulfonyl]benzyl}oxy)phenyl]-3-ethoxypropionic acid (Illustrative Compound No: 1-65)

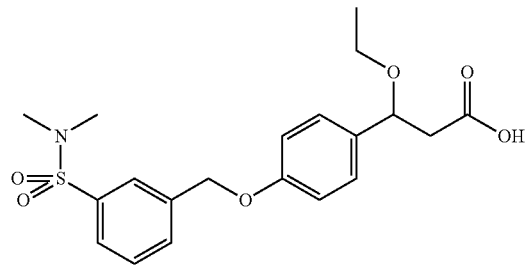

(12A) N,N-3-trimethylbenzenesulfonamide

3-Methyl sulfonyl chloride (600 mg, 3.15 mmol) was dissolved in tetrahydrofuran (40 mL), and the resulting solution was cooled to 0° C. Then, a 2 M dimethylamine tetrahydrofuran solution (2.36 mL, 4.73 mmol) and pyridine (3 mL) were added thereto, and the temperature of the resulting mixture was raised to room temperature, and the mixture was stirred for 3 hours. Water was added to the reaction solution, and the organic matter was extracted with ethyl acetate. The organic layer was washed with water and a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 70:30 (v/v)), whereby the objective title compound was obtained as a white solid (565 mg, yield: 90%).

$^1$H NMR (CDCl$_3$, 400 MHz): δ2.45 (3H, s), 2.71 (6H, s), 7.40-7.45 (2H, m), 7.57-7.59 (2H, m)

(12B) 3-(Bromomethyl)-N,N-dimethylbenzenesulfonamide

N,N-3-trimethylbenzenesulfonamide (560 mg, 2.81 mmol) synthesized in (12A), N-bromosuccinimide (500 mg, 2.81 mmol), and α,α'-azobisisobutyronitrile (23 mg, 0.141 mmol) were dissolved in carbon tetrachloride (50 mL), and the resulting solution was heated to reflux for 3 hours. After the temperature of the reaction solution was raised to room temperature, water was added thereto, and the organic matter was extracted with methylene chloride. The organic layer was washed with a 10% aqueous solution of hydrochloric acid, a saturated aqueous solution of sodium carbonate, and a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 90:10 (v/v)), whereby the objective title compound was obtained as a colorless oily substance (270 mg, yield: 35%).

$^1$H NMR (CDCl$_3$, 400 MHz): δ2.73 (6H, s), 4.53 (2H, s), 7.54 (1H, t, J=7.4 Hz), 7.64 (1H, d, J=7.8 Hz), 7.71 (1H, d, J=7.8 Hz), 7.80 (1H, s)

(12C) Ethyl 3-[4-({3-[(dimethylamino)sulfonyl]benzyl}oxy)phenyl]-3-ethoxypropionate Ethyl 3-ethoxy-3-(4-hydroxyphenyl)propionate (130 mg, 0.546 mmol) produced in Example 1 (1C) was dissolved in acetone (6 mL), and 3-(bromomethyl)-N,N-dimethylbenzenesulfonamide (182 mg, 0.655 mmol) produced in (12B) and potassium carbonate (113 mg, 0.819 mmol) were added thereto at room temperature, and then, the resulting mixture was stirred under a nitrogen atmosphere at 60° C. for 4 hours. After cooling to room temperature, the reaction solution was filtered, and the solvent was distilled off under reduced pressure, whereby a crude product was obtained. This crude product was purified by silica gel column chromatography (hexane:ethyl acetate=100:0 to 75:25 (v/v)), whereby the objective title compound was obtained as a colorless oily substance (154 mg, yield: 65%).

$^1$H NMR (CDCl$_3$, 400 MHz): δ1.14 (3H, t, J=7.0 Hz), 1.24 (3H, t, J=7.0 Hz), 2.56 (1H, dd, J=5.1, 15.3 Hz), 2.70 (6H, s), 2.80 (1H, dd, J=9.0, 15.2 Hz), 3.31-3.39 (2H, m), 4.14 (2H, q, J=7.0 Hz), 4.70 (1H, dd, J=5.1, 9.0 Hz), 5.14 (2H, s), 6.95 (2H, d, J=8.3 Hz), 7.28 (2H, d, J=9.4 Hz), 7.58 (1H, t, J=7.8 Hz), 7.69 (1H, d, J=7.8 Hz), 7.74 (1H, d, J=7.8 Hz), 7.84 (1H, s)

(12D) 3-[4-({3-[(Dimethylamino)sulfonyl]benzyl}oxy)phenyl]-3-ethoxypropionic acid Ethyl 3-[4-({3-[(dimethylamino)sulfonyl]benzyl}oxy)phenyl]-3-ethoxypropionate (150 mg, 0.344 mmol) produced in (12C) was dissolved in tetrahydrofuran (3 mL) and ethanol (3 mL), and a 1 N aqueous solution of sodium hydroxide (2 mL) was added thereto at room temperature, and then, the resulting mixture was stirred at room temperature for 4 hours. The solvent was distilled off under reduced pressure, and to the resulting residue, 1 N hydrochloric acid was added, and the organic matter was extracted with ethyl acetate. The organic layer was washed with a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 50:50 (v/v)), whereby the objective title compound was obtained as a white solid (126 mg, yield: 90%).

$^1$H NMR (CDCl$_3$, 400 MHz): δ1.14 (3H, t, J=7.1 Hz), 2.61 (1H, dd, J=4.7, 15.6 Hz), 2.67 (6H, s), 2.83 (1H, dd, J=4.3, 9.0 Hz), 3.32-3.39 (2H, m), 4.69 (1H, dd, J=4.7, 9.4 Hz), 5.13 (2H, s), 6.94 (2H, d, J=8.6 Hz), 7.27 (2H, d, J=8.6 Hz), 7.56 (1H, t, J=7.8 Hz), 7.68 (1H, d, J=7.8 Hz), 7.72 (1H, d, J=7.8 Hz), 7.83 (1H, s)

Example 13

3-Ethoxy-3-(4-{[3-(methylsulfonyl)benzyl]oxy}phenyl)propionic acid (Illustrative Compound No: 1-66)

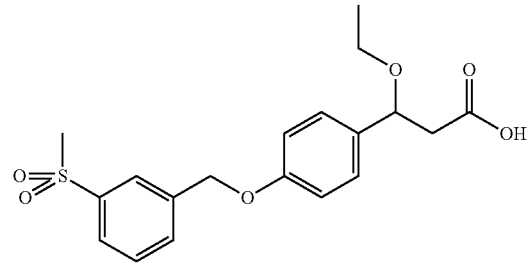

(13A) [3-(Methylsulfonyl)phenyl]methanol 3-(Methylsulfonyl)benzoic acid (540 mg, 2.70 mmol) was dissolved in tetrahydrofuran (40 mL), and the resulting solution was cooled to 0° C. Then, lithium aluminum hydride (102 mg, 2.70 mmol) was added thereto, and the temperature of the resulting mixture was raised to room temperature, and the mixture was stirred for 3 hours. Water was added to the reaction solution, and the organic matter was extracted with ethyl acetate. The organic layer was washed with water and a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 70:30 (v/v)), whereby the objective title compound was obtained as a colorless oily substance (257 mg, yield: 51%).

$^1$H NMR (CDCl$_3$, 400 MHz): δ1.26 (1H, brs), 3.06 (3H, s), 4.81 (2H, d, J=5.5 Hz), 7.57 (1H, t, J=7.8 Hz), 7.67 (1H, d, J=7.5 Hz), 7.86 (1H, d, J=7.5 Hz), 7.96 (1H, s)

(13B) Ethyl 3-ethoxy-3-(4-{[3-(methylsulfonyl)benzyl]oxy}phenyl)propionate

Ethyl 3-ethoxy-3-(4-hydroxyphenyl)propionate (100 mg, 0.420 mmol) produced in Example 1 (1C) and [3-(methylsulfonyl)phenyl]methanol (117 mg, 0.630 mmol) produced in (13A) were dissolved in tetrahydrofuran (10 mL), and triphenylphosphine (178 mg, 0.680 mmol) and a 40% diethyl azodicarboxylate toluene solution (309 μL, 0.680 mmol) were added thereto at room temperature, and then, the resulting mixture was stirred under a nitrogen atmosphere at 50° C. for 4 hours. After the reaction solution was cooled to room temperature, the solvent was distilled off under reduced pressure, and the resulting residue was purified by silica gel column chromatography (hexane:ethyl acetate=100:0 to 95:5 (v/v)), whereby the objective title compound was obtained as a white solid (199 mg, yield: 99%).

$^1$H NMR (CDCl$_3$, 400 MHz): δ1.15 (3H, t, J=7.0 Hz), 1.23 (3H, t, J=7.4 Hz), 2.57 (1H, dd, J=5.1, 15.3 Hz), 2.81 (1H, dd, J=9.0, 15.3 Hz), 3.08 (3H, s), 3.30-3.40 (2H, m), 4.23 (2H, q, J=7.3 Hz), 4.71 (1H, dd, J=5.1, 9.0 Hz), 5.14 (2H, s), 6.96

(2H, d, J=9.0 Hz), 7.29 (2H, d, J=8.6 Hz), 7.61 (1H, t, J=7.9 Hz), 7.74 (1H, d, J=8.2 Hz), 7.92 (1H, d, J=8.2 Hz), 8.04 (1H, s)

(13C) 3-Ethoxy-3-(4-{[3-(methylsulfonyl)benzyl]oxy}phenyl)propionic acid

Ethyl 3-ethoxy-3-(4-{[3-(methylsulfonyl)benzyl]oxy}phenyl)propionate (190 mg, 0.436 mmol) produced in (13B) was dissolved in tetrahydrofuran (4 mL) and ethanol (4 mL), and a 1 N aqueous solution of sodium hydroxide (3 mL) was added thereto at room temperature, and then, the resulting mixture was stirred at room temperature for 4 hours. The solvent was distilled off under reduced pressure, and to the resulting residue, 1 N hydrochloric acid was added, and the organic matter was extracted with ethyl acetate. The organic layer was washed with a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 50:50 (v/v)), whereby the objective title compound was obtained as a white solid (105 mg, yield: 64%).

$^1$H NMR (CDCl$_3$, 400 MHz): δ1.16 (3H, t, J=7.0 Hz), 2.64 (1H, dd, J=4.7, 15.6 Hz), 2.85 (1H, dd, J=9.4, 15.7 Hz), 3.08 (3H, s), 3.33-3.44 (2H, m), 4.71 (1H, dd, J=4.7, 9.0 Hz), 5.14 (2H, s), 6.97 (2H, d, J=9.0 Hz), 7.30 (2H, d, J=8.6 Hz), 7.61 (1H, t, J=7.9 Hz), 7.74 (1H, d, J=7.9 Hz), 7.92 (1H, d, J=7.8 Hz), 8.04 (1H, s)

Example 14

3-Ethoxy-3-{4-[(3-phenoxybenzyl)oxy]phenyl}propionic acid (Illustrative Compound No: 1-60)

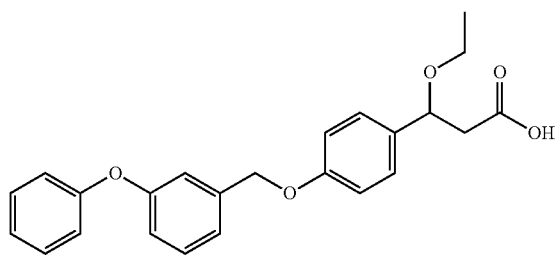

(14A) Ethyl 3-ethoxy-3-{4-[(3-phenoxybenzyl)oxy]phenyl}propionate

Ethyl 3-ethoxy-3-(4-hydroxyphenyl)propionate (100 mg, 0.420 mmol) produced in Example 1 (1C) was dissolved in dimethylformamide (2.0 mL), and 3-phenoxybenzyl chloride (116 μL, 0.63 mmol), potassium carbonate (174 mg, 1.26 mmol), and potassium iodide (catalytic amount, about 5 mg) were sequentially added thereto at room temperature, and then, the resulting mixture was stirred under a nitrogen atmosphere at 40° C. for 4 hours. To the reaction solution, a saturated aqueous solution of ammonium chloride was added, and the organic matter was extracted with ethyl acetate. The organic layer was washed with water and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=100:0 to 80:20 (v/v)), whereby the objective title compound was obtained (165 mg, yield: 93%).

$^1$H NMR (CDCl$_3$, 400 MHz): δ1.14 (3H, t, J=7.1 Hz), 1.23 (3H, t, J=7.1 Hz), 2.55 (1H, dd, J=5.1, 15.3 Hz), 2.79 (1H, dd, J=9.0, 15.3 Hz), 3.29-3.42 (2H, m), 4.13 (2H, q, J=7.1 Hz), 4.69 (1H, dd, J=5.1, 9.0 Hz), 5.03 (2H, s), 6.91-6.98 (3H, m), 7.00-7.05 (2H, m), 7.09-7.19 (3H, m), 7.24-7.29 (2H, m), 7.32-7.38 (3H, m)

(14B) 3-Ethoxy-3-{4-[(3-phenoxybenzyl)oxy]phenyl}propionic acid

Ethyl 3-ethoxy-3-{4-[(3-phenoxybenzyl)oxy]phenyl}propionate (165 mg, 0.392 mmol) produced in (14A) was dissolved in tetrahydrofuran (1.5 mL) and ethanol (1.5 mL), and a 2 N aqueous solution of sodium hydroxide (0.60 mL) was added thereto at room temperature, and then, the resulting mixture was stirred at room temperature for 18 hours. After water was added to the reaction solution, 2 N hydrochloric acid (0.60 mL) was added thereto, and the organic matter was extracted with ethyl acetate. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=90:10 to 50:50 (v/v)), whereby the objective title compound was obtained as a white solid (165 mg, yield: 93%).

$^1$H NMR (CDCl$_3$, 400 MHz): δ1.19 (3H, t, J=7.1 Hz), 2.63 (1H, dd, J=16.0 Hz, 3.8 Hz), 2.84 (1H, dd, J=16.0 Hz, 9.6 Hz), 3.35-3.48 (2H, m), 4.68 (1H, dd, J=9.6 Hz, 3.8 Hz), 5.04 (2H, s), 6.93-6.99 (3H, m), 7.00-7.05 (2H, m), 7.08-7.19 (3H, m), 7.23-7.30 (2H, m), 7.32-7.39 (3H, m)

MS (FAB) m/z: 431 (M+K)$^+$

Example 15

3-{4-[(3,4-Dichlorobenzyl)amino]phenyl}-3-ethoxypropionic acid (Illustrative Compound No: 1-84)

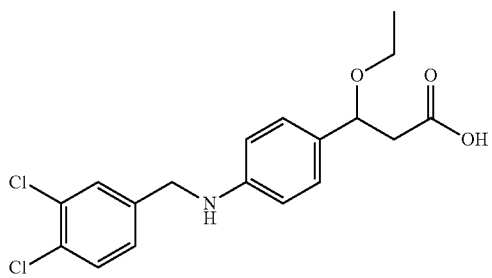

(15A) Ethyl 3-hydroxy-3-(4-nitrophenyl)propionate

Ethyl acetate (3.55 g, 40.3 mmol) was dissolved in tetrahydrofuran (100 mL), and a 1 M lithium bis(trimethylsilyl)amide hexane solution (40.0 mL, 40.0 mmol) was added thereto at −78° C., and then, the resulting mixture was stirred under a nitrogen atmosphere at −78° C. for 20 minutes. Thereafter, a tetrahydrofuran solution of 4-nitrobenzaldehyde (5.08 g, 33.6 mmol) was added thereto at −78° C., and the resulting mixture was stirred under a nitrogen atmosphere at −78° C. for 30 minutes. To the reaction solution, a saturated aqueous solution of ammonium chloride was added at −78° C., and the organic matter was extracted with ethyl acetate. The organic layer was washed with water and a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 20:80 (v/v)), whereby the objective title compound was obtained as a colorless oily substance (4.31 g, yield: 54%).

$^1$H NMR (CDCl$_3$, 400 MHz): δ1.28 (3H, t, J=7.0 Hz), 2.68-2.79 (2H, m), 3.65 (1H, d, J=3.5 Hz), 4.21 (2H, q, J=7.0 Hz), 5.24 (1H, dt, J=3.5, 8.6 Hz), 7.57 (2H, d, J=8.6 Hz), 8.23 (2H, d, J=8.6 Hz)

(15B) Ethyl 3-ethoxy-3-(4-nitrophenyl)propionate

Ethyl 3-hydroxy-3-(4-nitrophenyl)propionate (4.31 g, 18.0 mmol) produced in (15A) was dissolved in toluene (150 mL), and ethyl iodide (4.32 mL, 54.1 mmol) and silver oxide (I) (12.5 g, 54.1 mmol) were added thereto at room temperature, and then, the resulting mixture was stirred under a nitrogen atmosphere at 100° C. for 4 hours. After cooling to room temperature, the reaction solution was filtered, and the solvent was distilled off under reduced pressure, whereby a crude product was obtained. This crude product was purified by silica gel column chromatography (hexane:ethyl acetate=100:0 to 30:70 (v/v)), whereby the objective title compound was obtained as a colorless oily substance (2.20 g, yield: 46%).

$^1$H NMR (CDCl$_3$, 500 MHz): δ1.18 (3H, t, J=7.3 Hz), 1.24 (3H, t, J=7.3 Hz), 2.57 (1H, dd, J=5.4, 15.6 Hz), 2.80 (1H, dd, J=8.8, 15.6 Hz), 3.36-3.45 (2H, m), 4.12-4.17 (2H, m), 4.85 (1H, dd, J=5.3, 8.8 Hz), 7.53 (2H, d, J=8.8 Hz), 8.22 (2H, d, J=8.8 Hz)

(15C) Ethyl 3-(4-aminophenyl)-3-ethoxypropionate

Ethyl 3-ethoxy-3-(4-nitrophenyl)propionate (300 mg, 1.12 mmol) produced in (15B) was dissolved in ethyl acetate (10 mL), and 10% palladium carbon (100 mg) was added thereto at room temperature, and then, the resulting mixture was stirred under a hydrogen atmosphere at room temperature for 2 hours. Then, the reaction solution was filtered through a Celite filter, and the solvent was distilled off under reduced pressure, whereby a crude product was obtained as a colorless oily substance (310 mg).

$^1$H NMR (CDCl$_3$, 500 MHz): δ1.13 (3H, t, J=7.3 Hz), 1.23 (3H, t, J=7.3 Hz), 2.54 (1H, dd, J=5.4, 15.1 Hz), 2.78 (1H, dd, J=8.8, 15.1 Hz), 3.28-3.40 (2H, m), 3.66 (2H, br s), 4.11-4.15 (2H, m), 4.63 (1H, dd, J=5.4, 8.8 Hz), 6.66 (2H, d, J=8.3 Hz), 7.12 (2H, d, J=8.3 Hz)

(15D) Ethyl 3-{4-[(3,4-dichlorobenzyl)amino]phenyl}-3-ethoxypropionate

Ethyl 3-(4-aminophenyl)-3-ethoxypropionate (310 mg, 1.30 mmol) produced in (15C) was dissolved in acetone (10 mL), and 3,4-dichlorobenzyl bromide (313 mg, 1.30 mmol) and potassium carbonate (180 mg, 1.30 mmol) were added thereto at room temperature, and then, the resulting mixture was stirred under a nitrogen atmosphere at room temperature for 4 hours. Water was added to the reaction solution, and the organic matter was extracted with ethyl acetate. The organic layer was dried over anhydrous magnesium sulfate and filtered. Then, the solvent was distilled off under reduced pressure, whereby a crude product was obtained. This crude product was purified by silica gel column chromatography (hexane:ethyl acetate=100:0 to 60:40 (v/v)), whereby the objective title compound was obtained as a colorless oily substance (235 mg, yield: 45%).

$^1$H NMR (CDCl$_3$, 400 MHz): δ1.13 (3H, t, J=7.0 Hz), 1.23 (3H, t, J=7.0 Hz), 2.53 (1H, dd, J=5.1, 14.9 Hz), 2.78 (1H, dd, J=9.0, 14.9 Hz), 3.27-3.41 (2H, m), 4.09-4.15 (2H, m), 4.31 (2H, s), 4.62 (1H, dd, J=5.1, 9.0 Hz), 6.56 (2H, d, J=8.6 Hz), 7.14 (2H, d, J=8.6 Hz), 7.21 (1H, dd, J=2.0, 8.2 Hz), 7.41 (1H, d, J=8.2 Hz), 7.47 (1H, d, J=2.0 Hz)

(15E) 3-{4-[(3,4-Dichlorobenzyl)amino]phenyl}-3-ethoxypropionic acid

Ethyl 3-{4-[(3,4-dichlorobenzyl)amino]phenyl}-3-ethoxypropionate (235 mg, 0.593 mmol) produced in (15D) was dissolved in tetrahydrofuran (5 mL) and ethanol (5 mL), and a 1 N aqueous solution of sodium hydroxide (3 mL) was added thereto at room temperature, and then, the resulting mixture was stirred at room temperature for 4 hours. The solvent was distilled off under reduced pressure, and to the resulting residue, 1 N hydrochloric acid was added, and then, the organic matter was extracted with ethyl acetate. The organic layer was washed with a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 0:100 (v/v)), whereby the objective title compound was obtained as a yellow solid (43 mg, yield: 20%).

$^1$H NMR (CDCl$_3$, 400 MHz): δ1.18 (3H, t, J=7.0 Hz), 2.60 (1H, dd, J=4.0, 15.6 Hz), 2.82 (1H, dd, J=9.8, 15.6 Hz), 3.32-3.47 (2H, m), 4.31 (2H, s), 4.61 (1H, dd, J=4.0, 9.8 Hz), 6.57 (2H, d, J=8.6 Hz), 7.12 (2H, d, J=8.6 Hz), 7.21 (1H, dd, J=2.0, 8.2 Hz), 7.41 (1H, d, J=8.2 Hz), 7.47 (1H, d, J=2.0 Hz)
MS (ESI) m/z: 366 (M−H)$^−$

Example 16

(3S)-3-{4-[(3,4-Dichlorobenzyl)oxy]phenyl}-3-ethoxypropionic acid (Illustrative Compound No: 1-80)

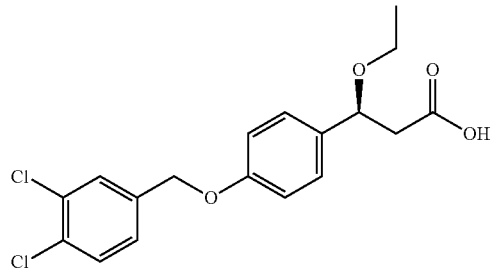

3-{4-[(3,4-Dichlorobenzyl)oxy]phenyl}-3-ethoxypropionic acid (150 mg) produced in Example 1 (1E) was dissolved in hexane (6 mL) and isopropanol (3 mL), and the resulting solution was subjected to optical resolution by high-performance liquid chromatography using a Chiralpak AS semi-preparative column (2.0 cm×25.0 cm, manufactured by Daicel Chemical Industries, Ltd.) (conditions: flow rate: 20 mL/min, solvent: hexane/isopropanol/trifluoroacetic acid=95/5/0.1 (v/v), detection wavelength: 220 nm).

The solvent in the solution having been subjected to optical resolution was distilled off under reduced pressure, and a compound with a retention time of 17 minutes was obtained as (3R)-3-{4-[(3,4-dichlorobenzyl)oxy]phenyl}-3-ethoxypropionic acid (a white solid, 37 mg, yield: 25%), and a compound with a retention time of 25 minutes was obtained as (3S)-3-{4-[(3,4-dichlorobenzyl)oxy]phenyl}-3-ethoxypropionic acid (a white solid, 39 mg, yield: 26%).

Example 17

3-Ethoxy-3-(6-{[4-(trifluoromethyl)benzyl]oxy}pyridin-3-yl)propionic acid (Illustrative Compound No: 2-5)

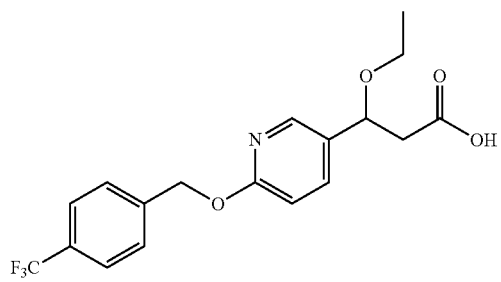

(17A) 1-(6-Bromopyridin-3-yl)-3,3-diethoxypropan-1-ol 2,5-Dibromopyridine (15.7 g, 66.3 mmol) was dissolved in diethyl ether (500 mL), and a 1.6 M n-butyllithium hexane solution (42.0 mL, 67.2 mmol) was added thereto at −78° C., and then, the resulting mixture was stirred under a nitrogen atmosphere at −78° C. for 45 minutes. Thereafter, a diethyl ether solution of 3,3-diethoxypropionaldehyde (7.57 g, 51.8 mmol) produced in accordance with the description of Tetrahedron 1992, vol. 48, No. 10, pp. 1895-1910 was added thereto at −78° C., and the resulting mixture was stirred under a nitrogen atmosphere at −78° C. for 1 hour. To the reaction solution, water was added at −78° C., and the organic matter was extracted with ethyl acetate. The organic layer was washed with a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 30:70 (v/v)), whereby the objective title compound was obtained as a colorless oily substance (4.33 g, yield: 27%).

$^1$H NMR (CDCl$_3$, 400 MHz): δ1.23 (3H, t, J=7.0 Hz), 1.27 (3H, t, J=7.0 Hz), 1.94-2.09 (2H, m), 3.51-3.60 (2H, m), 3.65-3.82 (2H, m), 3.93 (1H, d, J=2.2 Hz), 4.73 (1H, dd, J=4.3, 5.9 Hz), 4.98 (1H, dt, J=2.2, 9.4 Hz), 7.47 (1H, d, J=8.2 Hz), 7.60 (1H, dd, J=2.4, 8.2 Hz), 8.36 (1H, d, J=2.4 Hz)

(17B) 2-Bromo-5-(1,3,3-triethoxypropyl)pyridine 1-(6-Bromopyridin-3-yl)-3,3-diethoxypropan-1-ol (4.33 g, 14.2 mmol) produced in (17A) was dissolved in tetrahydrofuran (30 mL) and dimethylformamide (300 mL), and ethyl iodide (2.3 mL, 28.5 mmol) was added thereto at room temperature. Subsequently, 60% sodium hydride (813 mg, 21.3 mmol) was added thereto at 0° C., and the resulting mixture was stirred under a nitrogen atmosphere at room temperature for 1 hour. Water was added to the reaction solution, and the organic matter was extracted with diethyl ether. The organic layer was washed with a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 50:50 (v/v)), whereby the objective title compound was obtained as a colorless oily substance (3.63 g, yield: 79%).

$^1$H NMR (CDCl$_3$, 400 MHz): δ1.16 (3H, t, J=7.0 Hz), 1.19 (3H, t, J=7.0 Hz), 1.22 (3H, t, J=7.0 Hz), 1.81-1.88 (1H, m), 2.05-2.13 (1H, m), 3.30-3.36 (2H, m), 3.44-3.56 (2H, m), 3.59-3.72 (2H, m), 4.40 (1H, dd, J=4.7, 9.0 Hz), 4.61 (1H, dd, J=4.3, 7.0 Hz), 7.47 (1H, d, J=8.2 Hz), 7.54 (1H, dd, J=2.4, 8.2 Hz), 8.30 (1H, d, J=2.4 Hz)

(17C) 5-(1,3,3-Triethoxypropyl)-2-{[4-(trifluoromethyl)benzyl]oxy}pyridine

4-Trifluoromethylbenzyl alcohol (318 mg, 1.81 mmol) was dissolved in dimethylformamide (10 mL), and 60% sodium hydride (86 mg, 2.3 mmol) was added thereto at 0° C., and then, the resulting mixture was stirred under a nitrogen atmosphere at room temperature for 30 minutes. Subsequently, a dimethylformamide solution of 2-bromo-5-(1,3,3-triethoxy propyl)pyridine (500 mg, 1.50 mmol) produced in (17B) was added thereto at 0° C., and the resulting mixture was stirred under a nitrogen atmosphere at 60° C. for 1 hour. Water was added to the reaction solution, and the organic matter was extracted with ethyl acetate. The organic layer was washed with water and a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 60:40 (v/v)), whereby the objective title compound was obtained as a colorless oily substance (325 mg, yield: 51%).

$^1$H NMR (CDCl$_3$, 400 MHz): δ1.15 (3H, t, J=6.6 Hz), 1.20 (3H, t, J=6.6 Hz), 1.22 (3H, t, J=6.6 Hz), 1.82-1.89 (1H, m), 2.10-2.17 (1H, m), 3.27-3.36 (2H, m), 3.44-3.56 (2H, m), 3.60-3.71 (2H, m), 4.36 (1H, dd, J=5.1, 9.0 Hz), 4.60 (1H, dd, J=4.7, 7.4 Hz), 5.44 (2H, s), 6.83 (1H, d, J=8.6 Hz), 7.57 (2H, d, J=7.8 Hz), 7.60 (1H, dd, J=2.4, 8.6 Hz), 7.63 (2H, d, J=7.8 Hz), 8.06 (1H, d, J=2.4 Hz)

(17D) 3-Ethoxy-3-(6-{[4-(trifluoromethyl)benzyl]oxy}pyridin-3-yl)propionic acid 5-(1,3,3-Triethoxypropyl)-2-{[4-(trifluoromethyl)benzyl]oxy}pyridine (325 mg, 0.760 mmol) produced in (17C) was dissolved in acetone (10 mL) and water (5 mL), and a catalytic amount of p-toluenesulfonic acid was added thereto, and then, the resulting mixture was stirred at 60° C. for 2 hours. Then, the solvent was distilled off under reduced pressure, and to the resulting residue, a saturated aqueous solution of sodium hydrogen carbonate was added, and then, the organic matter was extracted with ethyl acetate. The organic layer was washed with a saturated sodium chloride solution, then dried over anhydrous magnesium sulfate and filtered. Then, the solvent was distilled off under reduced pressure, whereby a crude product (260 mg) was obtained. This crude product was dissolved in a mixed solvent (15 mL) of tetrahydrofuran/water/tert-butanol/2-methyl-2-butene (3/1/3/0.5 (v/v)), and sodium dihydrogen phosphate dihydrate (300 mg) was added thereto. Then, an aqueous solution obtained by dissolving sodium chlorite (300 mg) in water (1 mL) was added dropwise thereto at 0° C., and the resulting mixture was stirred at 0° C. for 30 minutes. To the reaction solution, an aqueous solution of sodium thiosulfate was added at 0° C., and then, the organic matter was extracted with ethyl acetate. The organic layer was washed with a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 0:100 (v/v)), whereby the objective title compound was obtained as a white solid (205 mg, yield: 76%).

$^1$H NMR (CDCl$_3$, 500 MHz): δ1.19 (3H, t, J=6.8 Hz), 2.63 (1H, dd, J=4.9, 16.1 Hz), 2.88 (1H, dd, J=8.8, 16.1 Hz), 3.41 (2H, q, J=6.8 Hz), 4.71 (1H, dd, J=4.9, 8.8 Hz), 5.44 (2H, s), 6.86 (1H, d, J=8.3 Hz), 7.56 (2H, d, J=8.3 Hz), 7.62-7.64 (3H, m), 8.11 (1H, d, J=2.4 Hz)

MS (ESI) m/z: 368 (M−H)$^−$

Example 18

(3S)-3-Ethoxy-3-(6-{[4-(trifluoromethyl)benzyl]oxy}pyridin-3-yl)propionic acid (Illustrative Compound No: 2-5)

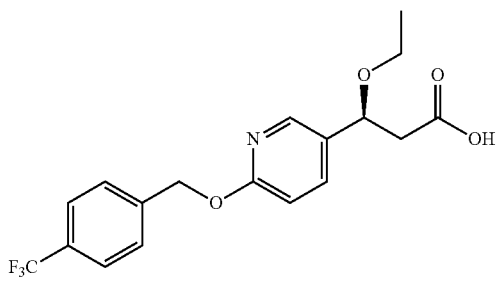

3-Ethoxy-3-(6-{[4-(trifluoromethyl)benzyl]oxy}pyridin-3-yl)propionic acid (200 mg) produced in Example 17 (17D) was dissolved in hexane (6 mL) and isopropanol (3 mL) and the resulting solution was subjected to optical resolution by high-performance liquid chromatography using a Chiralpak AD semi-preparative column (2.0 cm×25.0 cm, manufactured by Daicel Chemical Industries, Ltd.) (conditions: flow rate: 20 mL/min, solvent: hexane/isopropanol/trifluoroacetic acid=90/10/0.1 (v/v), detection wavelength: 220 nm). The solvent in the solution having been subjected to optical resolution was distilled off under reduced pressure, and a compound with a retention time of 7 minutes was obtained as (3S)-3-ethoxy-3-(6-{[4-(trifluoromethyl)benzyl]oxy}pyridin-3-yl)propionic acid (a white solid, 45 mg, yield: 23%), and a compound with a retention time of 10 minutes was obtained as (3R)-3-ethoxy-3-(6-{[4-(trifluoromethyl)benzyl]oxy}pyridin-3-yl)propionic acid (a white solid, 47 mg, yield: 24%).

Example 19

3-Ethoxy-3-(6-{[4-(trifluoromethyl)benzyl]amino}pyridin-3-yl)propionic acid (Illustrative Compound No: 2-21)

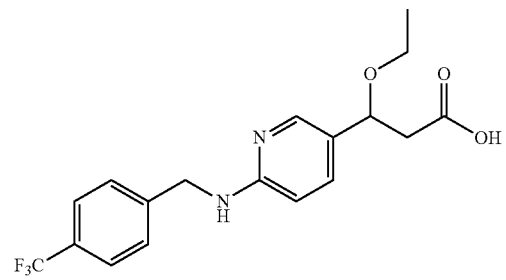

(19A) 5-(1,3,3-Triethoxypropyl)-N-[4-(trifluoromethyl)benzyl]pyridin-2-amine

2-Bromo-5-(1,3,3-triethoxypropyl)pyridine (328 mg, 0.987 mmol) produced in Example 17 (17B) and 4-trifluoromethylbenzylamine (346 mg, 1.98 mmol) were dissolved in 1,2-dimethoxyethane (10 mL), and potassium tert-butoxide (346 mg, 1.98 mmol) and [1,3-bis(2,6-diisopropylphenyl)imidazol-2-ylidene](3-chloropyridyl)palladium(II) (34 mg, 5 mol %) were added thereto, and then, the resulting mixture was stirred under a nitrogen atmosphere at 100° C. for 3 hours. After the reaction solution was cooled to room temperature, water was added thereto, and the organic matter was extracted with ethyl acetate. The organic layer was washed with a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 50:50 (v/v)), whereby the objective title compound was obtained as a colorless oily substance (25 mg, yield: 6%).

$^1$H NMR (CDCl$_3$, 400 MHz): δ1.14 (3H, t, J=6.8 Hz), 1.19 (3H, t, J=6.8 Hz), 1.21 (3H, t, J=6.8 Hz), 1.82-1.87 (1H, m), 2.10-2.16 (1H, m), 3.24-3.37 (2H, m), 3.44-3.55 (2H, m), 3.61-3.68 (2H, m), 4.26 (1H, dd, J=5.4, 8.8 Hz), 4.58-4.61 (3H, m), 4.91 (1H, br s), 6.37 (1H, d, J=8.8 Hz), 7.41 (1H, dd, J=2.4, 8.8 Hz), 7.48 (2H, d, J=8.8 Hz), 7.59 (1H, d, J=8.8 Hz), 8.01 (1H, d, J=2.4 Hz)

(19B) 3-Ethoxy-3-(6-{[4-(trifluoromethyl)benzyl]amino}pyridin-3-yl)propionic acid 5-(1,3,3-Triethoxypropyl)-N-[4-(trifluoromethyl)-benzyl]pyridin-2-amine (25 mg, 0.059 mmol) produced in (19A) was dissolved in acetone (5 mL) and water (2 mL), and a catalytic amount of p-toluenesulfonic acid was added thereto, and then, the resulting mixture was stirred at 60° C. for 3 hours. Then, the solvent was distilled off under reduced pressure, and to the resulting residue, a saturated aqueous solution of sodium hydrogen carbonate was added, and then, the organic matter was extracted with ethyl acetate. The organic layer was washed with a saturated sodium chloride solution, then dried over anhydrous magnesium sulfate and filtered. Then, the solvent was distilled off under reduced pressure, whereby a crude product (20 mg) was obtained. This crude product was dissolved in a mixed solvent (3 mL) of tetrahydrofuran/water/tert-butanol/2-methyl-2-butene (3/1/3/0.5 (v/v)), and sodium dihydrogen phosphate dihydrate (20 mg) was added thereto. Then, an aqueous solution obtained by dissolving sodium chlorite (20 mg) in water (1 mL) was added dropwise thereto at 0° C., and the resulting mixture was stirred at 0° C. for 30 minutes. To the reaction solution, ethyl acetate was added, then dried over anhydrous magnesium sulfate and filtered. Then, the solvent was distilled off under reduced pressure, whereby a crude product was obtained. This crude product was purified by silica gel column chromatography (hexane:ethyl acetate:methanol=100:0:0 to 0:100:0 to 0:90:10 (v/v)), whereby the objective title compound was obtained as a colorless oily substance (5.8 mg, yield: 27%).

$^1$H NMR (CDCl$_3$, 400 MHz): δ1.18 (3H, t, J=7.0 Hz), 2.50 (1H, dd, J=8.6, 14.9 Hz), 3.00 (1H, dd, J=6.3, 14.9 Hz), 3.35-3.42 (2H, m), 4.43-4.54 (2H, m), 4.68 (1H, dd, J=7.0, 7.8 Hz), 6.42 (1H, d, J=9.0 Hz), 7.45 (2H, d, J=8.2 Hz), 7.59 (2H, d, J=8.2 Hz), 7.64 (1H, d, J=9.0 Hz), 7.94 (1H, s)

MS (ESI) m/z: 367 (M−H)$^−$

Example 20

3-Ethoxy-3-{4-[(2-methylbenzyl)oxy]phenyl}propionic acid (Illustrative Compound No: 1-67)

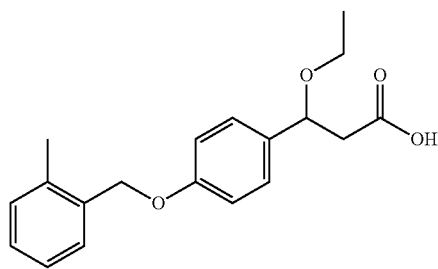

(20A) 4-[(2-Methylbenzyl)oxy]benzaldehyde

4-Hydroxybenzaldehyde (10.0 g, 81.9 mmol) and 2-methyl benzyl bromide (40.0 g, 98.3 mmol) were dissolved in dimethylformamide (100 mL), and cesium carbonate (18.2 g, 123 mmol) was added thereto, and then, the resulting mixture was stirred under a nitrogen atmosphere at room temperature for 1 hour. Water was added to the reaction solution, and the organic matter was extracted with diethyl ether. The organic layer was washed with water and a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 60:40 (v/v)), whereby the objective title compound was obtained as a colorless oily substance (19.2 g, yield: 103%).

$^1$H NMR (CDCl$_3$, 400 MHz): δ2.39 (3H, s), 5.13 (2H, s), 7.10 (2H, d, J=8.6 Hz), 7.21-7.31 (3H, m), 7.39 (1H, d, J=7.4 Hz), 7.86 (2H, d, J=8.6 Hz), 9.90 (1H, s)

(20B) Ethyl 3-hydroxy-3-{4-[(2-methylbenzyl)oxy]phenyl}propionate

Ethyl acetate (9.00 g, 102 mmol) was dissolved in tetrahydrofuran (200 mL), and a 1 M lithium bis(trimethylsilyl)amide hexane solution (102 mL, 102 mmol) was added thereto at −78° C., and then, the resulting mixture was stirred under a nitrogen atmosphere at −78° C. for 20 minutes. Thereafter, a tetrahydrofuran solution of 4-[(2-methylbenzyl)oxy]benzaldehyde (19.2 g, 84.9 mmol) produced in (20A) was added thereto at −78° C., and the resulting mixture was stirred under a nitrogen atmosphere at −78° C. for 30 minutes. To the reaction solution, a saturated aqueous solution of ammonium chloride was added at −78° C., and the organic matter was extracted with ethyl acetate. The organic layer was washed with water and a saturated sodium chloride solution, then dried over anhydrous magnesium sulfate and filtered. Then, the solvent was distilled off under reduced pressure, whereby a crude product was obtained. This crude product was washed with hexane/ethyl acetate (34/1 (v/v)), whereby the objective title compound was obtained as a white solid (22.4 g, yield: 84%).

$^1$H NMR (CDCl$_3$, 400 MHz): δ1.27 (3H, t, J=7.0 Hz), 2.37 (3H, s), 2.68 (1H, dd, J=3.9, 16.4 Hz), 2.76 (1H, dd, J=9.4, 16.4 Hz), 3.16 (1H, d, J=3.5 Hz), 4.19 (2H, q, J=7.0 Hz), 5.03 (2H, s), 5.10 (1H, dt, J=3.5, 9.0 Hz), 6.98 (2H, d, J=9.0 Hz), 7.19-7.28 (3H, m), 7.32 (2H, d, J=9.0 Hz), 7.40 (1H, d, J=7.0 Hz)

(20C) Ethyl 3-ethoxy-3-{4-[(2-methylbenzyl)oxy]phenyl}propionate

Ethyl 3-hydroxy-3-{4-[(2-methylbenzyl)oxy]phenyl}propionate (392 mg, 1.25 mmol) produced in (20B) was dissolved in toluene (10 mL), and ethyl iodide (140 μL, 1.75 mmol) and silver oxide(I) (347 mg, 1.50 mmol) were added thereto at room temperature, and then, the resulting mixture was stirred under a nitrogen atmosphere at 100° C. for 10 hours. After cooling to room temperature, the reaction solution was filtered, and the solvent was distilled off under reduced pressure, whereby a crude product was obtained. This crude product was purified by silica gel column chromatography (hexane:ethyl acetate=100:0 to 60:40 (v/v)), whereby the objective title compound was obtained as a colorless oily substance (120 mg, yield: 28%).

$^1$H NMR (CDCl$_3$, 500 MHz): δ1.14 (3H, t, J=6.8 Hz), 1.23 (3H, t, J=7.3 Hz), 2.38 (3H, s), 2.56 (1H, dd, J=4.9, 15.1 Hz), 2.80 (1H, dd, J=8.8, 15.1 Hz), 3.31-3.42 (2H, m), 4.14 (2H, q, J=7.3 Hz), 4.70 (1H, dd, J=4.9, 8.8 Hz), 5.03 (2H, s), 6.97 (2H, d, J=8.3 Hz), 7.20-7.29 (5H, m), 7.40 (1H, d, J=7.3 Hz)

(20D) 3-Ethoxy-3-{4-[(2-methylbenzyl)oxy]phenyl}propionic acid

Ethyl 3-ethoxy-3-{4-[(2-methylbenzyl)oxy]phenyl}propionate (120 mg, 0.350 mmol) produced in (20C) was dissolved in ethanol (5 mL), and a 1 N aqueous solution of sodium hydroxide (3 mL) was added thereto at room temperature, and then, the resulting mixture was stirred at room temperature for 4 hours.

The solvent was distilled off under reduced pressure, and to the resulting residue, 1 N hydrochloric acid was added, and the organic matter was extracted with ethyl acetate. The organic layer was washed with a saturated sodium chloride solution, then dried over anhydrous magnesium sulfate and filtered. Then, the solvent was distilled off under reduced pressure, whereby a crude product was obtained. This crude product was washed with hexane/diethyl ether (3/1 (v/v)), whereby the objective title compound was obtained as a white solid (71 mg, yield: 64%).

$^1$H NMR (CDCl$_3$, 400 MHz): δ1.20 (3H, t, J=7.0 Hz), 2.38 (3H, s), 2.63 (1H, dd, J=4.3, 16.0 Hz), 2.84 (1H, dd, J=9.4, 16.0 Hz), 3.36-3.49 (2H, m), 4.68 (1H, dd, J=4.3, 9.4 Hz), 5.03 (2H, s), 6.99 (2H, d, J=8.6 Hz), 7.20-7.28 (5H, m), 7.40 (1H, d, J=7.4 Hz)

MS (ESI) m/z: 313 (M−H)$^-$

Example 21

3-{4-[1-(4-Chlorophenyl)-2,2,2-trifluoroethoxy] phenyl}-3-ethoxypropionic acid (Illustrative Compound No: 1-41)

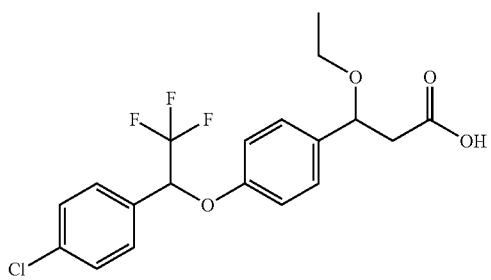

(21A) 1-(4-Chlorophenyl)-2,2,2-trifluoroethyl trifluoromethanesulfonate 1-(4-Chlorophenyl)-2,2,2-trifluoroethanol (1.20 g, 5.70 mmol) was dissolved in diethyl ether (80 mL), and the resulting solution was cooled to 0° C. Then, 63% sodium hydride (217 mg, 5.70 mmol) was added thereto, and the resulting mixture was stirred for 1 hour. Thereafter, trifluoromethanesulfonyl chloride (0.910 mL, 8.55 mmol) was added dropwise thereto. Then, the temperature of the reaction solution was raised to room temperature, and the reaction solution was stirred for 2 hours. Water was added to the reaction solution, and the organic matter was extracted with ethyl acetate. The organic layer was washed with water and a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 93:7 (v/v)), whereby the objective title compound was obtained as a colorless oily substance (495 mg, yield: 25%).

$^1$H NMR (CDCl$_3$, 400 MHz): δ5.83 (1H, q, J=5.7 Hz), 7.45 (2H, d, J=8.2 Hz), 7.49 (2H, d, J=9.0 Hz)

(21B) 4-[1-(4-Chlorophenyl)-2,2,2-trifluoroethoxy] benzaldehyde 1-(4-Chlorophenyl)-2,2,2-trifluoroethyl trifluoromethanesulfonate (337 mg, 0.983 mmol) obtained in (21A), 4-hydroxybenzaldehyde (120 mg, 0.983 mmol), and cesium carbonate (320 mg, 0.983 mmol) were dissolved in N,N-dimethylformamide (2 mL), and the resulting mixture was stirred at room temperature for 5 hours. Water was added to the reaction solution, and the organic matter was extracted with ethyl acetate. The organic layer was washed with water and a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 95:5 (v/v)), whereby the objective title compound was obtained as a yellow oily substance (101 mg, yield: 33%).

$^1$H NMR (CDCl$_3$, 400 MHz): δ5.50 (1H, q, J=6.1 Hz), 6.99 (2H, d, J=9.0 Hz), 7.42 (2H, d, J=8.9 Hz), 7.46 (2H, d, J=8.6 Hz), 7.80 (2H, d, J=9.0 Hz), 9.87 (1H, s)

(21C) Ethyl 3-{4-[1-(4-chlorophenyl)-2,2,2-trifluoroethoxy]phenyl}-3-hydroxypropionate Ethyl acetate (0.0378 mL, 0.381 mmol) was dissolved in tetrahydrofuran (1.50 mL), and a 1 M lithium bis(trimethylsilyl)amide hexane solution (0.0378 mL, 0.381 mmol) was added thereto at −78° C., and then, the resulting mixture was stirred under a nitrogen atmosphere at −78° C. for 20 minutes. Thereafter, a tetrahydrofuran solution of 4-[1-(4-chlorophenyl)-2,2,2-trifluoroethoxy]benzaldehyde (100 mg, 0.318 mmol) produced in (21B) was added thereto at −78° C., and the resulting mixture was stirred under a nitrogen atmosphere at −78° C. for 30 minutes. To the reaction solution, a saturated aqueous solution of ammonium chloride was added at −78° C., and the organic matter was extracted with ethyl acetate. The organic layer was washed with water and a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 20:80 (v/v)), whereby the objective title compound was obtained as a colorless oily substance (88 mg, yield: 69%).

$^1$H NMR (CDCl$_3$, 400 MHz): δ1.25 (3H, t, J=7.1 Hz), 2.65 (1H, dd, J=3.9, 16.4 Hz), 2.70 (1H, dd, J=9.0, 16.4 Hz), 3.23 (1H, t, J=2.7 Hz), 4.18 (2H, q, J=7.2 Hz), 5.05 (1H, d, J=8.6 Hz), 5.37 (1H, q, J=6.3 Hz), 6.87 (2H, d, J=8.6 Hz), 7.25 (2H, d, J=8.2 Hz), 7.39 (2H, d, J=8.6 Hz), 7.45 (2H, d, J=8.6 Hz)

(21D) Ethyl 3-{4-[1-(4-chlorophenyl)-2,2,2-trifluoroethoxy]phenyl}-3-ethoxypropionate Ethyl 3-{4-[1-(4-chlorophenyl)-2,2,2-trifluoroethoxy] phenyl}-3-hydroxypropionate (88 mg, 0.218 mmol) produced in (21C) was dissolved in toluene (5 mL), and ethyl iodide (0.870 mL, 1.09 mmol) and silver oxide(I) (253 mg, 1.09 mmol) were added thereto at room temperature, and then, the resulting mixture was stirred under a nitrogen atmosphere at 100° C. for 4 hours. After cooling to room temperature, the reaction solution was filtered, and the solvent was distilled off under reduced pressure, whereby a crude product was obtained. This crude product was purified by silica gel column chromatography (hexane:ethyl acetate=100:0 to 95:5 (v/v)), whereby the objective title compound was obtained as a colorless oily substance (77 mg, yield: 82%).

$^1$H NMR (CDCl$_3$, 400 MHz): δ1.12 (3H, t, J=7.1 Hz), 1.21 (3H, td, J=3.9, 7.0 Hz), 2.50 (1H, dd, J=5.1, 15.3 Hz), 2.74 (1H, dd, J=8.6, 15.2 Hz), 3.27-3.35 (2H, m), 4.11 (2H, qd, J=2.4, 7.1 Hz), 4.63-4.67 (1H, m), 5.36 (1H, q, J=6.3 Hz), 6.84 (2H, d, J=8.6 Hz), 7.21 (2H, d, J=8.6 Hz), 7.40 (2H, d, J=8.6 Hz), 7.46 (2H, d, J=8.6 Hz)

(21E) 3-{4-[1-(4-Chlorophenyl)-2,2,2-trifluoroethoxy]phenyl}-3-ethoxypropionic acid Ethyl 3-{4-[1-(4-chlorophenyl)-2,2,2-trifluoroethoxy] phenyl}-3-ethoxypropionate (77 mg, 0.179 mmol) produced in (21D) was dissolved in tetrahydrofuran (2 mL) and ethanol (2 mL), and a 1 N aqueous solution of sodium hydroxide (1.5 mL) was added thereto at room temperature, and then, the resulting mixture was stirred at room temperature for 4 hours. The solvent was distilled off under reduced pressure, and to the resulting residue, 1 N hydrochloric acid was added, and the organic matter was extracted with ethyl acetate. The organic layer was washed with a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 70:30 (v/v)), whereby the objective title compound was obtained as a white solid (70 mg, yield: 97%).

$^1$H NMR (CDCl$_3$, 400 MHz): δ1.15 (3H, t, J=7.0 Hz), 2.58 (1H, dd, J=3.9, 16.0 Hz), 2.78 (1H, dd, J=9.3, 15.2 Hz), 3.31-3.38 (2H, m), 4.62-4.65 (1H, m), 5.37 (1H, q, J=5.9 Hz), 6.86 (2H, d, J=8.6 Hz), 7.21 (2H, d, J=9.0 Hz), 7.40 (2H, d, J=8.6 Hz), 7.46 (2H, d, J=8.6 Hz)

Example 22

3-Ethoxy-3-(4{[8-(trifluoromethyl)quinolin-4-yl]oxy}phenyl)propionic acid (Illustrative Compound No: 1-160)

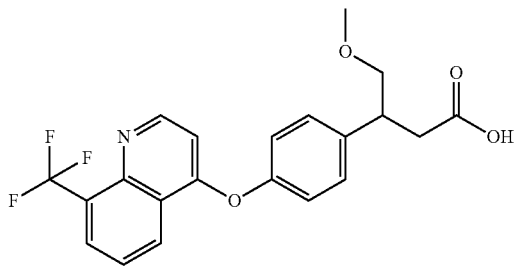

(22A) 4-{[8-(Trifluoromethyl)quinolin-4-yl]oxy}benzaldehyde

4-Chloro-8-(trifluoromethyl)quinoline (500 mg, 2.16 mmol), 4-hydroxybenzaldehyde (264 mg, 2.16 mmol), and cesium carbonate (845 mg, 2.59 mmol) were dissolved in N,N-dimethylformamide (20 mL), and the resulting mixture was stirred at 100° C. for 5 hours. Water was added to the reaction solution, and the organic matter was extracted with ethyl acetate. The organic layer was washed with water and a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 70:30 (v/v)), whereby the objective title compound was obtained as a white solid (680 mg, yield: 99%).

$^1$H NMR (CDCl$_3$, 400 MHz): δ6.82 (1H, d, J=5.1 Hz), 7.34 (2H, d, J=11 Hz), 7.66 (1H, t, J=7.8 Hz), 8.01 (2H, d, J=8.6 Hz), 8.17 (1H, d, J=7.5 Hz), 8.53 (1H, d, J=7.4 Hz), 8.53 (1H, d, J=5.1 Hz), 10.05 (1H, s)

(22B) Ethyl 3-hydroxy-3-(4{[8-(trifluoromethyl)quinolin-4-yl]oxy}phenyl)propionate Ethyl acetate (0.255 mL, 2.57 mmol) was dissolved in tetrahydrofuran (10 mL), and a 1 M lithium bis(trimethylsilyl)amide hexane solution (2.57 mL, 2.57 mmol) was added thereto at −78° C., and then, the resulting mixture was stirred under a nitrogen atmosphere at −78° C. for 1 hour. Thereafter, a tetrahydrofuran solution of 4-{[8-(trifluoromethyl)quinolin-4-yl]oxy}benzaldehyde (680 mg, 2.14 mmol) synthesized in (22A) was added thereto at −78° C., and the resulting mixture was stirred under a nitrogen atmosphere at −78° C. for 2 hours. To the reaction solution, a saturated aqueous solution of ammonium chloride was added at −78° C., and the organic matter was extracted with ethyl acetate. The organic layer was washed with water and a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 30:70 (v/v)), whereby the objective title compound was obtained as a white solid (730 mg, yield: 84%).

$^1$H NMR (CDCl$_3$, 400 MHz): δ1.30 (3H, t, J=7.4 Hz), 2.77 (1H, s), 2.79 (1H, d, J=2.7 Hz), 3.49 (1H, d, J=3.5 Hz), 4.24 (2H, q, J=7.0 Hz), 5.19-5.23 (1H, m), 6.65 (1H, d, J=5.5 Hz), 7.19 (2H, d, J=8.6 Hz), 7.52 (2H, d, J=8.6 Hz), 7.64 (1H, t, J=8.2 Hz), 8.14 (1H, d, J=7.0 Hz), 8.61 (1H, d, J=8.6 Hz), 8.84 (1H, d, J=5.1 Hz)

(22C) Ethyl 3-ethoxy-3-(4{[8-(trifluoromethyl)quinolin-4-yl]oxy}phenyl)propionate Ethyl 3-hydroxy-3-(4{[8-(trifluoromethyl)quinolin-4-yl]oxy}phenyl)propionate (730 mg, 1.80 mmol) produced in (22B) was dissolved in toluene (10 mL), and ethyl iodide (0.72 mL, 9.00 mmol) and silver oxide(I) (2.09 g, 9.00 mmol) were added thereto at room temperature, and then, the resulting mixture was stirred under a nitrogen atmosphere at 100° C. for 4 hours. After cooling to room temperature, the reaction solution was filtered, and the solvent was distilled off under reduced pressure, whereby a crude product was obtained. This crude product was purified by silica gel column chromatography (hexane:ethyl acetate=100:0 to 70:30 (v/v)), whereby the objective title compound was obtained as a colorless oily substance (384 mg, yield: 49%).

$^1$H NMR (CDCl$_3$, 400 MHz): δ1.20 (3H, t, J=7.1 Hz), 1.27 (3H, t, J=7.1 Hz), 2.63 (1H, dd, J=5.1, 15.2 Hz), 2.66 (1H, dd, J=8.9, 15.2 Hz), 3.40-3.48 (2H, m), 4.18 (2H, q, J=7.1 Hz), 4.81 (1H, dd, J=5.1, 9.0 Hz), 6.65 (1H, d, J=5.5 Hz), 7.19 (2H, d, J=8.6 Hz), 7.52 (2H, d, J=8.6 Hz), 7.64 (1H, t, J=8.2 Hz), 8.14 (1H, d, J=7.0 Hz), 8.61 (1H, d, J=8.6 Hz), 8.84 (1H, d, J=5.1 Hz)

(22D) 3-Ethoxy-3-(4 {[8-(trifluoromethyl)quinolin-4-yl]oxy}phenyl)propionic acid Ethyl 3-ethoxy-3-(4 {[8-(trifluoromethyl)quinolin-4-yl]oxy}phenyl)propionate (380 mg, 0.877 mmol) produced in (22C) was dissolved in tetrahydrofuran (4 mL) and ethanol (4 mL), and a 1 N aqueous solution of sodium hydroxide (3 mL) was added thereto at room temperature, and then, the resulting mixture was stirred at room temperature for 4 hours. The solvent was distilled off under reduced pressure, and to the resulting residue, 1 N hydrochloric acid was added, and the organic matter was extracted with ethyl acetate. The organic layer was washed with a saturated sodium chloride solution, then dried over anhydrous magnesium sulfate and filtered. Then, the solvent was distilled off under reduced pressure, whereby a crude product was obtained. This crude product was purified by silica gel column chromatography (ethyl acetate:methanol=100:0 to 90:10 (v/v)), whereby the objective title compound was obtained as a colorless amorphous substance (340 mg, yield: 96%).

¹H NMR (CDCl₃, 400 MHz): δ1.24 (3H, t, J=7.1 Hz), 2.72 (1H, dd, J=4.3, 15.7 Hz), 2.91 (1H, dd, J=9.0, 15.6 Hz), 3.43-3.52 (2H, m), 4.82 (1H, dd, J=4.7, 9.4 Hz), 6.68 (1H, d, J=5.1 Hz), 7.21 (2H, d, J=8.6 Hz), 7.48 (2H, d, J=8.6 Hz), 7.64 (1H, t, J=7.9 Hz), 8.14 (1H, d, J=7.5 Hz), 8.60 (1H, d, J=8.6 Hz), 8.87 (1H, d, J=5.1 Hz)

Example 23

3-{4-[(4-Cyano-1-naphthyl)oxy]phenyl}-3-ethoxypropionic acid (Illustrative Compound No: 1-151)

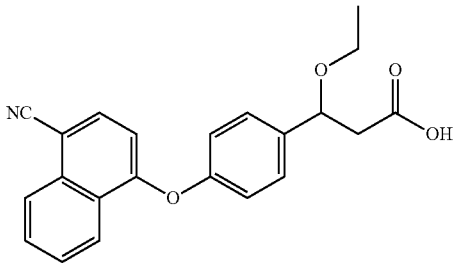

(23A) 4-(4-Formylphenoxy)-1-naphthonitrile

4-Hydroxybenzaldehyde (300 mg, 2.46 mmol) was dissolved in dimethylacetoamide (8.0 mL), and 4-fluoro-naphthalene-1-carbonitrile (463 mg, 0.420 mmol) and cesium carbonate (1.20 g, 3.69 mmol) were sequentially added thereto at room temperature, and then, the resulting mixture was stirred under a nitrogen atmosphere at 120° C. for 2 hours. After the temperature of the reaction solution was returned to room temperature, water was added thereto, and the organic matter was extracted with ethyl acetate. The organic layer was washed with water and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=95:5 to 70:30 (v/v)), whereby the objective title compound was obtained (515 mg, yield: 77%).

¹H NMR (CDCl₃, 400 MHz): δ7.00 (1H, d, J=7.8 Hz), 7.24 (2H, d, J=8.6 Hz), 7.72-7.66 (1H, m), 7.83-7.78 (1H, m), 7.89 (1H, d, J=8.2 Hz), 7.97 (2H, d, J=8.6 Hz), 8.31 (2H, d, J=9.4 Hz), 10.0 (1H, s)

(23B) Ethyl 3-{4-[(4-cyano-1-naphthyl)oxy]phenyl}-3-hydroxypropionate

Ethyl acetate (0.370 mL, 3.76 mmol) was dissolved in tetrahydrofuran (5 mL), and a 1.0 M lithium bis(trimethylsilyl)amide tetrahydrofuran solution (3.4 mL, 3.39 mmol) was added thereto at −78° C., and then, the resulting mixture was stirred under a nitrogen atmosphere at −78° C. for 30 minutes. Thereafter, a solution obtained by dissolving 4-(4-formylphenoxy)-1-naphthonitrile (515 mg, 1.88 mmol) produced in (23A) in tetrahydrofuran (5.0 mL) was added thereto at −78° C., and the resulting mixture was stirred under a nitrogen atmosphere at −78° C. for 1 hour. To the reaction solution, a saturated aqueous solution of ammonium chloride was added at −78° C., and the organic matter was extracted with ethyl acetate. The organic layer was washed with water and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=90:10 to 60:40 (v/v)), whereby the objective title compound was obtained (669 mg, yield: 98%).

¹H NMR (CDCl₃, 400 MHz): δ1.30 (3H, t, J=7.2 Hz), 2.76-2.80 (2H, m), 3.44 (1H, d, J=3.5 Hz), 4.23 (3H, q, J=7.2 Hz), 5.15-5.22 (1H, m), 6.74 (1H, d, J=8.2 Hz), 7.15 (2H, d, J=8.6 Hz), 7.48 (2H, d, J=8.6 Hz), 7.64-7.70 (1H, m), 7.78 (1H, d, J=8.2 Hz), 7.74-7.81 (1H, m), 8.25 (1H, d, J=8.2 Hz), 8.45 (1H, d, J=8.2 Hz)

(23C) Ethyl 3-{4-[(4-cyano-1-naphthyl)oxy]phenyl}-3-ethoxypropionate

Ethyl 3-{4-[(4-cyano-1-naphthyl)oxy]phenyl}-3-hydroxypropionate (669 mg, 1.85 mmol) produced in (23B) was dissolved in toluene (8.0 mL), and ethyl iodide (0.745 mL, 9.26 mmol) and silver oxide (I) (2.15 g, 9.26 mmol) were added thereto at room temperature, and then, the resulting mixture was stirred under a nitrogen atmosphere at 100° C. for 2 hours. After cooling to room temperature, the reaction solution was filtered, and the solvent was distilled off under reduced pressure, whereby a crude product was obtained. This crude product was purified by silica gel column chromatography (hexane:ethyl acetate=95:5 to 60:40 (v/v)), whereby the objective title compound was obtained as a colorless solid (560 mg, yield: 78%).

¹H NMR (CDCl₃, 400 MHz): δ1.19 (3H, t, J=7.1 Hz), 1.27 (3H, t, J=7.2 Hz), 2.61 (1H, dd, J=15.1 Hz, 5.1 Hz), 2.84 (1H, dd, J=15.1 Hz, 9.0 Hz), 3.37-3.49 (2H, m), 4.17 (2H, q, J=7.1 Hz), 4.80 (1H, dd, J=9.0 Hz, 5.1 Hz), 6.76 (1H, d, J=7.8 Hz), 7.14 (2H, d, J=8.6 Hz), 7.44 (2H, d, J=8.6 Hz), 7.65-7.71 (1H, m), 7.75-7.80 (1H, m), 7.79 (1H, d, J=8.3 Hz), 8.25 (1H, d, J=8.6 Hz), 8.45 (1H, d, J=9.0 Hz)

(23D) 3-{4-[(4-Cyano-1-naphthyl)oxy]phenyl}-3-ethoxypropionic acid

Ethyl 3-{4-[(4-cyano-1-naphthyl)oxy]phenyl}-3-ethoxypropionate (250 mg, 0.642 mmol) produced in (23C) was dissolved in tetrahydrofuran (1.5 mL) and ethanol (1.5 mL), and a 2 N aqueous solution of sodium hydroxide (0.355 mL, 0.706 mmol) was added thereto at room temperature, and then, the resulting mixture was stirred at room temperature for 18 hours. After water was added to the reaction solution, 2 N hydrochloric acid (0.355 mL, 0.706 mmol) was added thereto, and the organic matter was extracted with ethyl acetate. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=90:10 to 45:55 (v/v)), whereby the objective title compound was obtained as a white solid (188 mg, yield: 81%).

¹H NMR (CDCl₃, 500 MHz): δ1.23 (3H, t, J=7.1 Hz), 2.70 (1H, dd, J=4.3, 15.8 Hz), 2.89 (1H, dd, J=9.2, 15.8 Hz), 3.42-3.54 (2H, m), 4.79 (1H, dd, J=4.3, 9.2 Hz), 6.77 (1H, d, J=8.3 Hz), 7.15 (2H, d, J=8.3 Hz), 7.43 (2H, d, J=8.8 Hz), 7.67 (2H, dd, J=7.6, 7.6 Hz), 7.74-7.82 (2H, m), 8.25 (1H, d, J=8.3 Hz), 8.43 (1H, d, J=8.3 Hz)

MS (FAB) m/z: 384 (M+Na)⁺

Example 24

3-[4-(3,5-Dichlorophenoxy)phenyl]-3-ethoxypropionic acid (Illustrative Compound No: 1-15)

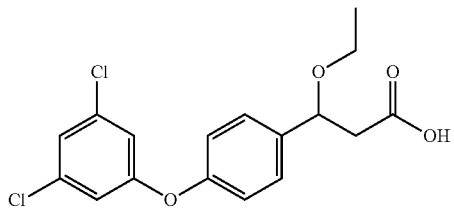

(24A) 4-(3,5-Dichlorophenoxy)benzaldehyde 3,5-Dichlorophenol (500 mg, 3.07 mmol) was dissolved in dimethylacetamide (8.0 mL), and 4-fluorobenzaldehyde (0.390 mL, 0.368 mmol) and cesium carbonate (1.50 g, 3.69 mmol) were sequentially added thereto at room temperature, and then, the resulting mixture was stirred under a nitrogen atmosphere at 150° C. for 3 hours. After the temperature of the reaction solution was returned to room temperature, water was added thereto, and the organic matter was extracted with ethyl acetate. The organic layer was washed with a saturated aqueous solution of ammonium chloride and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=100:0 to 85:15 (v/v)), whereby the objective title compound was obtained as a white solid (364 mg, yield: 44%).

$^1$H NMR (CDCl$_3$, 400 MHz): δ6.98 (2H, d, J=1.9 Hz), 7.13 (2H, d, J=8.8 Hz), 7.21 (1H, t like, J=1.9 Hz), 7.92 (2H, d, J=8.8 Hz), 9.98 (1H, s)

(24B) Ethyl 3-[4-(3,5-dichlorophenoxy)phenyl]-3-hydroxypropionate

Ethyl acetate (0.270 mL, 2.72 mmol) was dissolved in tetrahydrofuran (4.0 mL), and a 1.0 M lithium bis(trimethylsilyl)amide tetrahydrofuran solution (2.5 mL, 2.45 mmol) was added thereto at −78° C., and then, the resulting mixture was stirred under a nitrogen atmosphere at −78° C. for 30 minutes. Thereafter, a solution obtained by dissolving 4-(3,5-dichlorophenoxy)benzaldehyde (364 mg, 1.36 mmol) produced in (24A) in tetrahydrofuran (4.0 mL) was added thereto at −78° C., and the resulting mixture was stirred under a nitrogen atmosphere at −78° C. for 1 hour. To the reaction solution, a saturated aqueous solution of ammonium chloride was added at −78° C., and the organic matter was extracted with ethyl acetate. The organic layer was washed with water and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=95:5 to 70:30 (v/v)), whereby the objective title compound was obtained as a white solid (419 mg, yield: 87%).

$^1$H NMR (CDCl$_3$, 500 MHz): δ1.28 (3H, t, J=7.1 Hz), 2.80-2.71 (2H, m), 3.39 (1H, d, J=3.4 Hz), 4.21 (2H, q, J=7.1 Hz), 5.18-5.13 (1H, m), 6.85 (2H, brs), 7.03 (2H, d, J=8.5 Hz), 7.07 (1H, brs), 7.41 (2H, d, J=8.5 Hz)

(24C) Ethyl 3-[4-(3,5-dichlorophenoxy)phenyl]-3-ethoxypropionate

Ethyl 3-[4-(3,5-dichlorophenoxy)phenyl]-3-hydroxypropionate (210 mg, 0.591 mmol) produced in (24B) was dissolved in toluene (5.0 mL), and ethyl iodide (0.335 mL, 4.14 mmol) and silver oxide(I) (959 mg, 4.14 mmol) were added thereto at room temperature, and then, the resulting mixture was stirred under a nitrogen atmosphere at 100° C. for 90 minutes. After cooling to room temperature, the reaction solution was filtered, and the solvent was distilled off under reduced pressure, whereby a crude product was obtained. This crude product was purified by silica gel column chromatography (hexane:ethyl acetate=100:0 to 70:30 (v/v)), whereby the objective title compound was obtained as a colorless solid (93 mg, yield: 41%).

$^1$H NMR (CDCl$_3$, 400 MHz): δ1.18 (3H, t, J=7.0 Hz), 1.25 (3H, t, J=7.3 Hz), 2.59 (1H, dd, J=15.1 Hz, 5.0 Hz), 2.82 (1H, dd, J=15.1 Hz, 8.8 Hz), 3.35-3.47 (2H, m), 4.16 (2H, q, J=7.0 Hz), 4.76 (1H, dd, J=8.8 Hz, 5.0 Hz), 6.88 (2H, d, J=1.9 Hz), 7.02 (2H, d, J=8.2 Hz), 7.09 (1H, t like, J=1.9 Hz), 7.37 (2H, d, J=8.2 Hz)

(24D) 3-[4-(3,5-Dichlorophenoxy)phenyl]-3-ethoxypropionic acid

Ethyl 3-[4-(3,5-dichlorophenoxy)phenyl]-3-ethoxypropionate (93 mg, 0.243 mmol) produced in (24C) was dissolved in tetrahydrofuran (1.5 mL) and ethanol (1.5 mL), and a 2 N aqueous solution of sodium hydroxide (0.185 mL, 0.364 mmol) was added thereto at room temperature, and then, the resulting mixture was stirred at room temperature for 18 hours. After water was added to the reaction solution, 2 N hydrochloric acid (0.185 mL, 0.364 mmol) was added thereto, and the organic matter was extracted with ethyl acetate. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=90:10 to 50:50 (v/v)), whereby the objective title compound was obtained as a white solid (44 mg, yield: 51%).

$^1$H NMR (CDCl$_3$, 400 MHz): δ1.22 (3H, t, J=7.1 Hz), 2.67 (1H, dd, J=4.1, 15.6 Hz), 2.87 (1H, dd, J=9.4, 15.6 Hz), 3.40-3.52 (2H, m), 4.76 (1H, dd, J=4.1, 9.4 Hz), 6.90 (2H, d, J=1.7 Hz), 7.04 (2H, d, J=8.6 Hz), 7.11 (1H, t like, J=1.7 Hz), 7.37 (2H, d, J=8.6 Hz)

MS (FAB) m/z: 377 (M+Na)$^+$

Example 25

3-[4-(2,5-Dichlorophenoxy)phenyl]-3-ethoxypropionic acid (Illustrative Compound No: 1-16)

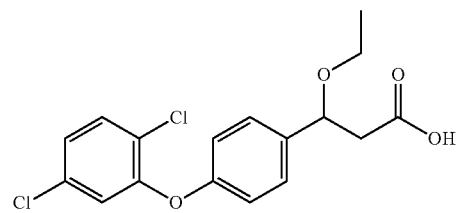

(25A) 4-(2,5-Dichlorophenoxy)benzaldehyde 2,5-Dichlorophenol (500 mg, 3.07 mmol) was dissolved in dimethylacetamide (8.0 mL), and 4-fluorobenzaldehyde (0.390 mL, 0.368 mmol) and cesium carbonate (1.50 g, 3.69 mmol) were sequentially added thereto at room temperature, and then, the resulting mixture was stirred under a nitrogen atmosphere at 150° C. for 3 hours.

After the temperature of the reaction solution was returned to room temperature, water was added thereto, and the organic matter was extracted with ethyl acetate. The organic layer was washed with a saturated aqueous solution of ammonium chloride and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=100:0 to 85:15 (v/v)), whereby the objective title compound was obtained as a colorless oily substance (354 mg, yield: 43%).

$^1$H NMR (CDCl$_3$, 400 MHz): δ7.05 (2H, d, J=8.6 Hz), 7.14 (1H, d, J=2.3 Hz), 7.21 (1H, dd, J=2.3, 8.6 Hz), 7.45 (1H, d, J=8.6 Hz), 7.90 (2H, d, J=8.6 Hz), 9.96 (1H, s)

(25B) Ethyl 3-[4-(2,5-dichlorophenoxy)phenyl]-3-hydroxypropionate

Ethyl acetate (0.260 mL, 2.66 mmol) was dissolved in tetrahydrofuran (4.0 mL), and a 1.0 M lithium bis(trimethylsilyl)amide tetrahydrofuran solution (2.4 mL, 2.39 mmol) was added thereto at −78° C., and then, the resulting mixture was stirred under a nitrogen atmosphere at −78° C. for 30 minutes. Thereafter, a solution obtained by dissolving 4-(2, 5-dichlorophenoxy)benzaldehyde (354 mg, 1.33 mmol) produced in (25A) in tetrahydrofuran (4.0 mL) was added thereto at −78° C., and the resulting mixture was stirred under a nitrogen atmosphere at −78° C. for 1 hour.

To the reaction solution, a saturated aqueous solution of ammonium chloride was added at −78° C., and the organic matter was extracted with ethyl acetate. The organic layer was washed with water and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=95:5 to 70:30 (v/v)), whereby the objective title compound was obtained (343 mg, yield: 73%).

$^1$H NMR (CDCl$_3$, 400 MHz): δ1.28 (3H, t, J=7.1 Hz), 2.81-2.69 (2H, m), 3.36 (1H, d, J=3.1 Hz), 4.21 (2H, q, J=7.1 Hz), 5.18-5.12 (1H, m), 6.92 (1H, d, J=2.3 Hz), 7.00 (2H, d, J=8.6 Hz), 7.06 (1H, dd, J=2.3, 8.6 Hz), 7.37-7.43 (3H, m)

(25C) Ethyl 3-[4-(2,5-dichlorophenoxy)phenyl]-3-ethoxypropionate

Ethyl 3-[4-(2,5-dichlorophenoxy)phenyl]-3-hydroxypropionate (183 mg, 0.515 mmol) produced in (25B) was dissolved in toluene (4.0 mL), and ethyl iodide (0.290 mL, 3.61 mmol) and silver oxide(I) (836 mg, 3.61 mmol) were added thereto at room temperature, and then, the resulting mixture was stirred under a nitrogen atmosphere at 100° C. for 4 hours. After cooling to room temperature, the reaction solution was filtered, and the solvent was distilled off under reduced pressure, whereby a crude product was obtained. This crude product was purified by silica gel column chromatography (hexane:ethyl acetate=100:0 to 70:30 (v/v)), whereby the objective title compound was obtained as a colorless solid (128 mg, yield: 65%).

$^1$H NMR (CDCl$_3$, 400 MHz): δ1.17 (3H, t, J=7.1 Hz), 1.24 (3H, t, J=7.1 Hz), 2.58 (1H, dd, J=5.1, 15.2 Hz), 2.81 (1H, dd, J=9.0, 15.2 Hz), 3.46-3.33 (2H, m), 4.15 (2H, q, J=7.1 Hz), 4.75 (1H, dd, J=5.1, 9.0 Hz), 6.94 (1H, d, J=2.4 Hz), 6.98 (2H, d, J=8.6 Hz), 7.07 (1H, dd, J=2.4, 8.6 Hz), 7.35 (2H, d, J=8.6 Hz), 7.39 (1H, d, J=8.6 Hz)

(25D) 3-[4-(2,5-Dichlorophenoxy)phenyl]-3-ethoxypropionic acid

Ethyl 3-[4-(2,5-dichlorophenoxy)phenyl]-3-ethoxypropionate (128 mg, 0.334 mmol) produced in (25C) was dissolved in tetrahydrofuran (1.5 mL) and ethanol (1.5 mL), and a 2 N aqueous solution of sodium hydroxide (0.200 mL, 0.400 mmol) was added thereto at room temperature, and then, the resulting mixture was stirred at room temperature for 18 hours. After water was added to the reaction solution, 2 N hydrochloric acid (0.200 mL, 0.400 mmol) was added thereto, and the organic matter was extracted with ethyl acetate. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=90:10 to 55:45 (v/v)), whereby the objective title compound was obtained as a white solid (79 mg, yield: 67%).

$^1$H NMR (CDCl$_3$, 400 MHz): δ1.21 (3H, t, J=7.0 Hz), 2.66 (1H, dd, J=4.0, 15.6 Hz), 2.86 (1H, dd, J=9.4, 15.6 Hz), 3.51-3.39 (2H, m), 4.74 (1H, dd, J=4.0, 9.4 Hz), 7.02-6.96 (3H, m), 7.09 (1H, dd, J=2.4, 8.6 Hz), 7.34 (2H, d, J=8.6 Hz), 7.40 (1H, d, J=8.6 Hz)

MS (FAB) m/z: 393 (M+K)$^+$

Example 26

6-[(2',6'-Dimethylbiphenyl-3-yl)methoxy]-1,3-dihydrofuro[3,4-c]pyridin-3-yl-acetic acid (Illustrative Compound No: 2-14)

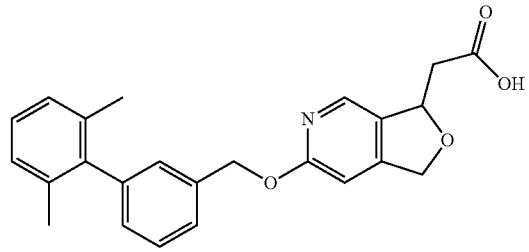

(26A) 5-Bromo-2-[(2',6'-dimethylbiphenyl-3-yl)methoxy]pyridine (2',6'-Dimethylbiphenyl-3-yl)methanol (46.8 g, 0.220 mol) produced in accordance with the description of European Patent Publication No. 1559422 was dissolved in dimethylformamide (500 mL), and sodium hydride (about 63%, oily, 12.6 g, 0.331 mol) was added thereto at 0° C., and then, the resulting mixture was stirred under a nitrogen atmosphere at 0° C. for 30 minutes. Thereafter, 2,5-dibromopyridine (52.1 g, 0.220 mol) was added to the reaction solution, and the resulting mixture was stirred under a nitrogen atmosphere at 60° C. for 3 hours. Water was added to the reaction solution, and the organic matter was extracted with diethyl ether. The organic layer was washed with water and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=100:0 to 25:1 (v/v)), whereby the objective title compound was obtained as a white solid (49.9 g, yield: 62%).

$^1$H NMR (CDCl$_3$, 400 MHz): δ2.03 (6H, s), 5.39 (2H, s), 6.74 (1H, d, J=8.6 Hz), 7.09-7.14 (3H, m), 7.18 (1H, dd, J=6.2, 8.6 Hz), 7.24 (1H, brs), 7.39-7.47 (2H, m), 7.66 (1H, dd, J=2.9, 9.2 Hz), 8.21 (1H, d, J=2.3 Hz)

(26B) 5-Bromo-2-[(2',6'-dimethylbiphenyl-3-yl)methoxy]isonicotinealdehyde

Diisopropylamine (1.00 mL, 7.08 mmol) was dissolved in tetrahydrofuran (20 mL), and under a nitrogen atmosphere, an n-butyllithium hexane solution (1.61 M, 4.30 mL, 6.92 mmol) was added thereto at 0° C., and then, the resulting mixture was stirred at 0° C. for 20 minutes. Thereafter, a tetrahydrofuran solution of 5-bromo-2-[(2',6'-dimethylbiphenyl-3-yl)methoxy]pyridine (2.25 g, 6.11 mmol) produced in (26A) was added thereto at −78° C., and the resulting mixture was stirred at −78° C. for 2 hours. Thereafter, dimethylformamide (0.600 mL, 7.75 mmol) was added dropwise thereto at −78° C., and the temperature of the resulting mixture was raised to room temperature. To the reaction solution, a saturated aqueous solution of ammonium chloride was added, and the organic matter was extracted with diethyl ether. The organic layer was washed with water, then dried over anhydrous sodium sulfate and filtered. Then, the solvent was distilled off under reduced pressure, whereby a crude product was obtained. This crude product was purified by silica gel column chromatography (hexane:ethyl acetate=99:1 (v/v)), whereby the objective title compound was obtained as a white solid (1.01 mg, yield: 25%).

$^1$H NMR (CDCl$_3$, 400 MHz): δ2.00 (6H, s), 5.40 (2H, s), 7.07-7.11 (3H, m), 7.15 (1H, dd, J=6.3, 8.6 Hz), 7.19-7.22 (2H, m), 7.36-7.45 (2H, m), 8.39 (1H, s), 10.3 (1H, s)

(26C) 5-Bromo-2-[(2',6'-dimethylbiphenyl-3-yl)methoxy]-pyridin-4-yl-methanol 5-Bromo-2-[(2',6'-dimethylbiphenyl-3-yl)methoxy]isonicotinealdehyde (351 mg, 0.886 mmol) produced in (26B) was dissolved in methanol (3 mL) and tetrahydrofuran (3 mL), and sodium borohydride (42 mg, 1.11 mmol) was added thereto at 0° C., and then, the resulting mixture was stirred at 0° C. for 10 minutes. To the reaction solution, a saturated aqueous solution of ammonium chloride was added, and the organic matter was extracted with ethyl acetate. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=80:20 (v/v)), whereby the objective title compound was obtained as a white solid (339 mg, yield: 98%).

$^1$H NMR (CDCl$_3$, 500 MHz): δ2.01 (1H, t, J=6.3 Hz), 2.05 (6H, s), 4.72 (2H, d, J=6.3 Hz), 5.43 (2H, s), 7.05 (1H, s), 7.11-7.15 (3H, m), 7.19 (1H, dd, J=6.3, 8.6 Hz), 7.25-7.26 (2H, m), 7.42-7.48 (2H, m), 8.20 (1H, s)

(26D) Ethyl 3-({5-bromo-2-[(2',6'-dimethylbiphenyl-3-yl)methoxy]pyridin-4-yl}methoxy)acrylate 5-Bromo-2-[(2',6'-dimethylbiphenyl-3-yl)methoxy]-pyridin-4-yl-methanol (155 mg, 0.389 mmol) produced in (26C) and ethyl propionate (71 mg, 0.72 mmol) were dissolved in dichloromethane (3 mL), and tributylphosphine (15 mg, 0.074 mmol) was added thereto at room temperature, and then, the resulting mixture was stirred at room temperature for 1 hour. The solvent was distilled off under reduced pressure, and the resulting residue was purified by silica gel column chromatography (hexane:ethyl acetate=90:10 (v/v)), whereby the objective title compound was obtained as a colorless oily substance (192 mg, yield: 99%).

$^1$H NMR (CDCl$_3$, 400 MHz): δ1.26 (3H, t, J=7.0 Hz), 2.00 (6H, s), 4.16 (2H, q, J=7.0 Hz), 4.87 (2H, s), 5.32 (1H, d, J=12.9 Hz), 5.37 (2H, s), 7.07-7.11 (3H, m), 7.14 (1H, dd, J=6.3, 8.6 Hz), 7.20-7.22 (2H, m), 7.36-7.44 (2H, m), 7.64 (1H, d, J=12.9 Hz), 8.20 (1H, s)

(26E) Ethyl 6-[(2',6'-dimethylbiphenyl-3-yl)methoxy]-1,3-dihydrofuro[3,4-c]pyridin-3-yl-acetate Ethyl 3-({5-bromo-2-[(2',6'-dimethylbiphenyl-3-yl)methoxy]pyridin-4-yl}methoxy)acrylate (188 mg, 0.379 mmol) produced in (26D) and α,α'-azobisisobutyronitrile (10 mg, 0.061 mmol) were dissolved in toluene (13 mL), and the temperature of the resulting solution was raised to 110° C. A toluene solution of tributyltin hydride (143 mg, 0.491 mmol) was added dropwise thereto over 1 hour while heating to reflux, and then, the resulting mixture was heated to reflux for 5 hours. After the reaction solution was cooled to room temperature, water (0.05 mL) and 1,8-diazabicyclo[2.2.2]undeca-7-ene (0.05 mL) were added thereto, and the resulting mixture was stirred at room temperature for 15 minutes. The reaction solution was filtered, and the solvent was distilled off under reduced pressure, whereby a crude product was obtained. This crude product was purified by silica gel column chromatography (hexane:ethyl acetate=95:5 to 80:20 (v/v)), whereby the objective title compound was obtained as a colorless oily substance (50 mg, yield: 32%).

$^1$H NMR (CDCl$_3$, 400 MHz): δ1.26 (3H, t, J=7.0 Hz), 2.01 (6H, s), 4.18 (2H, q, J=7.0 Hz), 4.95 (1H, m), 5.04 (1H, m), 5.41 (2H, s), 5.61 (1H, dd, J=6.3, 6.6 Hz), 6.64 (1H, s), 7.06-7.10 (3H, m), 7.14 (1H, dd, J=6.3, 8.6 Hz), 7.21 (1H, m), 7.38-7.44 (2H, m), 7.99 (1H, s)

(26F) 6-[(2',6'-Dimethylbiphenyl-3-yl)methoxy]-1,3-dihydrofuro[3,4-c]pyridin-3-yl-acetic acid Ethyl 6-[(2',6'-dimethylbiphenyl-3-yl)methoxy]-1,3-dihydrofuro[3,4-c]pyridin-3-yl-acetate (40 mg, 0.096 mmol) produced in (26E) was dissolved in ethanol (1.5 mL), and a 1 N aqueous solution of sodium hydroxide (0.5 mL) was added thereto at room temperature, and then, the resulting mixture was stirred at room temperature for 2 hours. 1 N Hydrochloric acid was added to the reaction solution, and the organic matter was extracted with ethyl acetate. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=80:20 to 70:30 (v/v)), whereby the objective title compound was obtained as a colorless oily substance (12 mg, yield: 31%).

$^1$H NMR (CDCl$_3$, 400 MHz): δ2.01 (6H, s), 4.98 (1H, m), 5.06 (1H, m), 5.41 (2H, s), 5.61 (1H, dd, J=6.3, 6.6 Hz), 6.66

(1H, s), 7.07-7.11 (3H, m), 7.14 (1H, dd, J=6.3, 8.6 Hz), 7.22 (1H, m), 7.38-7.45 (2H, m), 8.05 (1H, s)

Example 27

3-[4-(3,4-Dichlorobenzyloxy)phenyl]-3-(2,2,2-trifluoroethoxy)propionic acid (Illustrative Compound No: 1-68)

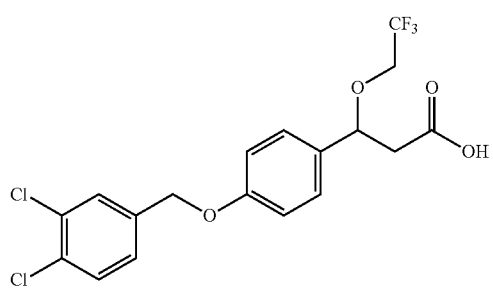

(27A)
4-[(4-Bromophenoxy)methyl]-1,2-dichlorobenzene

4-Bromophenol (1.07 g, 6.18 mmol), 3,4-dichlorobenzyl alcohol (1.42 g, 8.02 mmol), and triphenylphosphine (2.10 g, 8.01 mmol) were dissolved in tetrahydrofuran (30 mL), and a diethyl azodicarboxylate toluene solution (2.2M, 3.65 mL, 8.03 mmol) was slowly added dropwise thereto at room temperature, and then, the resulting mixture was stirred under a nitrogen atmosphere at room temperature for 2 hours. The solvent was distilled off under reduced pressure, and the resulting residue was purified by silica gel column chromatography (hexane:ethyl acetate=100:0 to 95:5 (v/v)), whereby the objective title compound was obtained as a white solid (2.25 g, quantitative).

$^1$H NMR (CDCl$_3$, 400 MHz): δ4.98 (2H, s), 6.83 (2H, d, J=9.0 Hz), 7.24 (1H, m), 7.39 (2H, d, J=9.0 Hz), 7.45 (1H, d, J=8.2 Hz), 7.52 (1H, d, J=2.0 Hz)

(27B) 3-(tert-Butyldimethylsilyloxy)-1-[4-(3,4-dichlorobenzyloxy)phenyl]propan-1-ol 4-[(4-Bromophenoxy)methyl]-1,2-dichlorobenzene (2.25 g, 6.18 mmol) produced in (27A) was dissolved in tetrahydrofuran (25 mL), and under a nitrogen atmosphere, an n-butyllithium hexane solution (1.61 M, 3.80 mL, 6.12 mmol) was added thereto at −78° C., and then, the resulting mixture was stirred at −78° C. for 1 hour. Thereafter, 3-(tert-butyldimethylsilyloxy)propionaldehyde (1.20 g, 6.37 mmol) was added thereto at −78° C., and the resulting mixture was stirred at −78° C. for 5 minutes. Then, the temperature of the reaction solution was raised to room temperature, and a saturated aqueous solution of ammonium chloride was added thereto, and the organic matter was extracted with ethyl acetate. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=95:5 to 80:20 (v/v)), whereby the objective title compound was obtained as a colorless oily substance (1.22 g, yield: 45%).

$^1$H NMR (CDCl$_3$, 500 MHz): δ0.09 (6H, s), 0.93 (9H, s), 1.88 (1H, m), 1.95 (1H, m), 3.77 (1H, m), 3.81-3.89 (2H, m), 4.91 (1H, m), 5.01 (2H, s), 6.92 (2H, d, J=8.3 Hz), 7.26 (1H, m), 7.30 (2H, d, J=8.3 Hz), 7.45 (1H, d, J=8.3 Hz), 7.54 (1H, m)

(27C) tert-Butyl {3-[4-(3,4-dichlorobenzyloxy)phenyl]-3-(2,2,2-trifluoroethoxy)propoxy}dimethylsilane 3-(tert-Butyldimethylsilyloxy)-1-[4-(3,4-dichlorobenzyloxy)phenyl]propan-1-ol (300 mg, 0.680 mmol) produced in (27B), 1,1'-(azodicarbonyl)dipiperidine (343 mg, 1.36 mmol), and tributylphosphine (0.34 mL, 1.36 mmol) were dissolved in toluene (20 mL), and the resulting solution was stirred under a nitrogen atmosphere at room temperature for 10 minutes. Thereafter, to the reaction solution, 2,2,2-trifluoroethanol (0.10 mL, 1.37 mmol) was added dropwise, and the resulting mixture was vigorously stirred at room temperature for 3 hours. The reaction solution was filtered, and the solvent was distilled off under reduced pressure. The resulting crude product was purified by silica gel column chromatography (hexane:ethyl acetate=95:5 (v/v)), whereby the objective title compound was obtained as a colorless oily substance (245 mg, yield: 69%).

$^1$H NMR (CDCl$_3$, 400 MHz): δ0.03 (3H, s), 0.05 (3H, s), 0.90 (9H, s), 1.79 (1H, m), 2.06 (1H, m), 3.52-3.70 (3H, m), 3.76 (1H, m), 4.55 (1H, dd, J=5.1, 8.2 Hz), 5.02 (2H, s), 6.94 (2H, d, J=8.6 Hz), 7.23 (2H, d, J=8.6 Hz), 7.27 (1H, m), 7.46 (1H, d, J=8.2 Hz), 7.55 (1H, d, J=2.0 Hz)

(27D) 3-[4-(3,4-Dichlorobenzyloxy)phenyl]-3-(2,2,2-trifluoroethoxy)propionaldehyde tert-Butyl {3-[4-(3,4-dichlorobenzyloxy)phenyl]-3-(2,2,2-trifluoroethoxy)propoxy}dimethylsilane (240 mg, 0.458 mmol) produced in (27C) was dissolved in tetrahydrofuran (5 mL). To the reaction solution, a tetrabutyl ammonium fluoride tetrahydrofuran solution (1.0 M, 0.60 mL, 0.60 mmol) was added dropwise at room temperature, and the resulting mixture was stirred at room temperature for 1 hour.

To the reaction solution, a saturated aqueous solution of ammonium chloride was added, and the organic matter was extracted with ethyl acetate. The organic layer was washed with a saturated sodium chloride solution, then dried over anhydrous sodium sulfate and filtered. Then, the solvent was distilled off under reduced pressure, and the resulting crude product was dissolved in dichloromethane (5 mL). To the reaction solution, sodium hydrogen carbonate (228 mg, 2.71 mmol) and Dess-Martin periodinane (255 mg, 0.601 mmol) were added at room temperature, and the resulting mixture was stirred at room temperature for 1 hour.

To the reaction solution, diethyl ether, a saturated aqueous solution of sodium hydrogen carbonate, and a saturated aqueous solution of sodium thiosulfate were added. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=100:0 to 95:5 (v/v)), whereby the objective title compound was obtained as a colorless oily substance (95 mg, yield: 51%).

$^1$H NMR (CDCl$_3$, 400 MHz): δ2.69 (1H, ddd, J=1.6, 4.3, 16.8 Hz), 3.02 (1H, ddd, J=2.0, 8.6, 16.8 Hz), 3.60-3.71 (2H, m), 4.94 (1H, dd, J=4.3, 8.6 Hz), 5.02 (2H, s), 6.97 (2H, d, J=9.0 Hz), 7.24-7.29 (3H, m), 7.46 (1H, d, J=8.2 Hz), 7.54 (1H, d, J=2.0 Hz), 9.79 (1H, dd, J=1.6, 2.0 Hz)

(27E) 3-[4-(3,4-Dichlorobenzyloxy)phenyl]-3-(2,2,2-trifluoroethoxy) propionic acid 3-[4-(3,4-Dichlorobenzyloxy)phenyl]-3-(2,2,2-trifluoroethoxy)propionaldehyde (95 mg, 0.233 mmol) produced in (27D) and sodium dihydrogen phosphate (250 mg, 1.60 mmol) were dissolved in a mixed solvent of tetrahydrofuran/t-butanol/water/2-methyl-2-butene (6/6/2/1, 5 mL), and sodium chlorite (80%, 68 mg, 0.602 mmol) was added thereto at room temperature, and then, the resulting mixture was stirred at room temperature for 3 hours. To the reaction solution, a saturated aqueous solution of ammonium chloride was added, and the organic matter was extracted with ethyl acetate. The organic layer was washed with a saturated sodium chloride solution, then dried over anhydrous sodium sulfate and filtered. Then, the solvent was distilled off under reduced pressure, and the resulting residue was purified by silica gel column chromatography (hexane:ethyl acetate=80:20 to 50:50 (v/v)), whereby the objective title compound was obtained as a white solid (89 mg, yield: 900).

$^1$H NMR (CDCl$_3$, 500 MHz): δ2.68 (1H, dd, J=4.9, 16.1 Hz), 2.94 (1H, dd, J=8.8, 16.1 Hz), 3.63-3.70 (2H, m), 4.86 (1H, dd, J=4.9, 8.8 Hz), 5.02 (2H, s), 6.96 (2H, d, J=8.3 Hz), 7.25-7.30 (3H, m), 7.46 (1H, d, J=8.3 Hz), 7.54 (1H, m)

Example 28

3-Cyclopropyloxy-3-[4-(3,4-dichlorobenzyloxy)phenyl]propionic acid (Illustrative Compound No: 1-69)

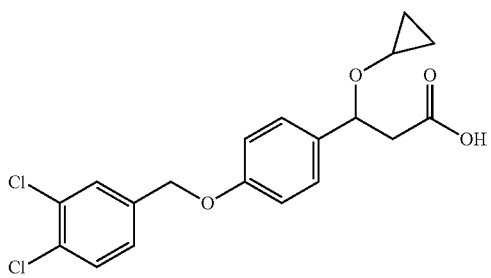

(28A) tert-Butyl {3-[4-(3,4-dichlorobenzyloxy)phenyl]-3-vinyloxypropoxy}dimethylsilane 3-(tert-Butyldimethylsilyloxy)-1-[4-(3,4-dichlorobenzyloxy)phenyl]propan-1-ol (300 mg, 0.680 mmol) produced in Example 27 (27B), palladium(II) trifluoroacetate (12 mg, 0.036 mmol), and 4,7-diphenyl-1,10-phenanthroline (12 mg, 0.036 mmol) were dissolved in butyl vinyl ether (5 mL), and triethylamine (20 μL, 0.14 mmol) was added thereto, and the resulting mixture was stirred under a nitrogen atmosphere at 80° C. for 4 hours. After cooling to room temperature, the reaction solution was filtered, and the solvent was distilled off under reduced pressure, whereby a crude product was obtained. This crude product was purified by silica gel column chromatography (hexane:ethyl acetate=100:0 to 96:4 (v/v)), whereby the objective title compound was obtained as a colorless oily substance (275 mg, yield: 87%).

$^1$H NMR (CDCl$_3$, 400 MHz): δ0.04 (3H, s), 0.05 (3H, s), 0.91 (9H, s), 1.85 (1H, m), 2.07 (1H, m), 3.41 (1H, m), 3.57 (1H, m), 3.95 (1H, dd, J=1.6, 6.6 Hz), 4.23 (1H, dd, J=1.6, 14.1 Hz), 4.90 (1H, dd, J=5.1, 8.2 Hz), 5.00 (2H, s), 6.29 (1H, dd, J=6.6, 14.1 Hz), 6.92 (2H, d, J=9.0 Hz), 7.22 (2H, d, J=9.0 Hz), 7.24-7.28 (2H, m), 7.45 (1H, d, J=8.6 Hz), 7.54 (1H, d, J=2.0 Hz)

(28B) tert-Butyl {3-cyclopropyloxy-3-[4-(3,4-dichlorobenzyloxy)phenyl]propoxy}dimethylsilane tert-Butyl {3-[4-(3,4-dichlorobenzyloxy)phenyl]-3-vinyloxypropoxy}dimethylsilane (250 mg, 0.535 mmol) produced in (28A) and diiodomethane (0.43 mL, 5.4 mmol) were dissolved in dichloromethane (10 mL). To the reaction solution, a diethylzinc hexane solution (1.0 M, 2.6 mL, 2.6 mmol) was slowly added dropwise under a nitrogen atmosphere at room temperature, and the resulting mixture was stirred at room temperature for 15 minutes. To the reaction solution, a saturated aqueous solution of sodium hydrogen carbonate was added, and the organic matter was extracted with diethyl ether. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=100:0 to 96:4 (v/v)), whereby the objective title compound was obtained as a colorless oily substance (113 mg, yield: 44%).

$^1$H NMR (CDCl$_3$, 400 MHz): δ0.02 (3H, s), 0.04 (3H, s), 0.29-0.63 (4H, m), 0.90 (9H, s), 1.74 (1H, m), 1.95 (1H, m), 3.11 (1H, m), 3.51 (1H, m), 3.64 (1H, m), 4.50 (1H, dd, J=5.1, 8.6 Hz), 5.01 (2H, s), 6.93 (2H, d, J=8.6 Hz), 7.25-7.30 (3H, m), 7.45 (1H, d, J=8.2 Hz), 7.55 (1H, d, J=2.0 Hz)

(28C) 3-Cyclopropyloxy-3-[4-(3,4-dichlorobenzyloxy)phenyl]propionaldehyde tert-Butyl {3-cyclopropyloxy-3-[4-(3,4-dichlorobenzyloxy)phenyl]propoxy}dimethylsilane (110 mg, 0.228 mmol) produced in (28B) was dissolved in tetrahydrofuran (3 mL). To the reaction solution, a tetrabutyl ammonium fluoride tetrahydrofuran solution (1.0 M, 0.30 mL, 0.30 mmol) was added dropwise at room temperature, and the resulting mixture was stirred at room temperature for 1 hour. To the reaction solution, a saturated aqueous solution of ammonium chloride was added, and the organic matter was extracted with ethyl acetate. The organic layer was washed with a saturated sodium chloride solution, then dried over anhydrous sodium sulfate and filtered. Then, the solvent was distilled off under reduced pressure.

The resulting crude product was dissolved in dichloromethane (3 mL). To the reaction solution, sodium hydrogen carbonate (111 mg, 1.32 mmol) and Dess-Martin periodinane (125 mg, 0.295 mmol) were added at room temperature, and the resulting mixture was stirred at room temperature for 1 hour. To the reaction solution, diethyl ether, a saturated aqueous solution of sodium hydrogen carbonate, and a saturated aqueous solution of sodium thiosulfate were added. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=100:0 to 95:5 (v/v)), whereby the objective title compound was obtained as a colorless oily substance (74 mg, 89%).

¹H NMR (CDCl₃, 400 MHz): δ0.34-0.47 (2H, m), 0.53-0.64 (2H, m), 2.60 (1H, ddd, J=1.6, 4.3, 16.4 Hz), 2.91 (1H, ddd, J=2.3, 9.0, 16.4 Hz), 3.14 (1H, m), 4.87 (1H, dd, J=4.3, 9.0 Hz), 5.02 (2H, s), 6.95 (2H, d, J=8.6 Hz), 7.27 (1H, dd, J=2.0, 8.2 Hz), 7.32 (2H, d, J=8.6 Hz), 7.46 (1H, d, J=8.2 Hz), 7.54 (1H, d, J=2.0 Hz), 9.72 (1H, dd, J=1.6, 2.3 Hz)

(28D) 3-Cyclopropyloxy-3-[4-(3,4-dichlorobenzyloxy)phenyl]propionic acid

3-Cyclopropyloxy-3-[4-(3,4-dichlorobenzyloxy)phenyl]propionaldehyde (74 mg, 0.20 mmol) produced in (28C) and sodium dihydrogen phosphate (240 mg, 1.54 mmol) were dissolved in a mixed solvent of tetrahydrofuran/t-butanol/water/2-methyl-2-butene (6/6/2/1, 5 mL), and sodium chlorite (80%, 65 mg, 0.57 mmol) was added thereto at room temperature, and then, the resulting mixture was stirred at room temperature for 3 hours. To the reaction solution, a saturated aqueous solution of ammonium chloride was added, and the organic matter was extracted with ethyl acetate. The organic layer was washed with a saturated sodium chloride solution, then dried over anhydrous sodium sulfate and filtered. Then, the solvent was distilled off under reduced pressure, and the resulting residue was purified by silica gel column chromatography (hexane:ethyl acetate=80:20 to 50:50 (v/v)), whereby the objective title compound was obtained as a white solid (62 mg, 800).

¹H NMR (CDCl₃, 400 MHz): δ0.31-0.50 (2H, m), 0.55-0.66 (2H, m), 2.61 (1H, dd, J=4.3, 15.6 Hz), 2.82 (1H, ddd, J=9.4, 15.6 Hz), 3.16 (1H, m), 4.79 (1H, dd, J=4.3, 9.4 Hz), 5.02 (2H, s), 6.95 (2H, d, J=8.6 Hz), 7.27 (1H, dd, J=2.0, 8.2 Hz), 7.32 (2H, d, J=8.6 Hz), 7.46 (1H, d, J=8.2 Hz), 7.54 (1H, d, J=2.0 Hz)

Example 29

3-[4-(3,4-Dichlorobenzyloxy)phenyl]-3-phenoxy propionic acid (Illustrative Compound No: 1-70)

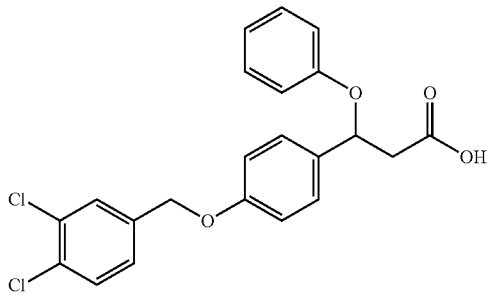

(29A) tert-Butyl {3-[4-(3,4-dichlorobenzyloxy)phenyl]-phenoxypropoxy}dimethylsilane 3-(tert-Butyldimethylsilyloxy)-1-[4-(3,4-dichlorobenzyloxy)phenyl]propan-1-ol (200 mg, 0.453 mmol) produced in Example 27 (27B) and phenol (56 mg, 0.60 mmol) were dissolved in tetrahydrofuran (5 mL), and triphenylphosphine (120 mg, 0.458 mmol) and a diethyl azodicarboxylate toluene solution (2.2M, 230 μL, 0.506 mmol) were added thereto at room temperature, and then, the resulting mixture was stirred under a nitrogen atmosphere at room temperature for 5 hours. The solvent was distilled off under reduced pressure and the resulting residue was purified by silica gel column chromatography (hexane:ethyl acetate=100:0 to 95:5 (v/v)), whereby the objective title compound was obtained as a colorless oily substance (68 mg, yield: 29%).

¹H NMR (CDCl₃, 400 MHz): δ−0.01 (3H, s), 0.02 (3H, s), 0.88 (9H, s), 1.95 (1H, m), 2.19 (1H, m), 3.65 (1H, m), 3.82 (1H, m), 4.97 (2H, s), 5.31 (1H, dd, J=5.1, 8.6 Hz), 6.83-6.86 (3H, m), 6.90 (2H, d, J=8.6 Hz), 7.15-7.19 (2H, m), 7.24 (1H, dd, J=2.0, 8.2 Hz), 7.29 (2H, d, J=8.6 Hz), 7.44 (1H, d, J=8.2 Hz), 7.52 (1H, d, J=2.0 Hz)

(29B) 3-[4-(3,4-Dichlorobenzyloxy)phenyl]-3-phenoxypropionaldehyde tert-Butyl {3-[4-(3,4-dichlorobenzyloxy)phenyl]-3-phenoxypropoxy}dimethylsilane (68 mg, 0.13 mmol) produced in (29A) was dissolved in tetrahydrofuran (3 mL). To the reaction solution, a tetrabutyl ammonium fluoride tetrahydrofuran solution (1.0 M, 0.20 mL, 0.20 mmol) was added dropwise at room temperature, and the resulting mixture was stirred at room temperature for 1 hour. To the reaction solution, a saturated aqueous solution of ammonium chloride was added, and the organic matter was extracted with ethyl acetate. The organic layer was washed with a saturated sodium chloride solution, then dried over anhydrous sodium sulfate and filtered. Then, the solvent was distilled off under reduced pressure. The resulting crude product was dissolved in dichloromethane (3 mL). To the reaction solution, sodium hydrogen carbonate (54 mg, 0.64 mmol) and Dess-Martin periodinane (70 mg, 0.17 mmol) were added at room temperature, and the resulting mixture was stirred at room temperature for 1 hour.

To the reaction solution, diethyl ether, a saturated aqueous solution of sodium hydrogen carbonate, and a saturated aqueous solution of sodium thiosulfate were added. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=100:0 to 95:5 (v/v)), whereby the objective title compound was obtained as a colorless oily substance (42 mg, yield: 80%).

¹H NMR (CDCl₃, 400 MHz): δ2.84 (1H, ddd, J=1.6, 4.3, 16.8 Hz), 3.13 (1H, ddd, J=2.3, 8.6, 16.8 Hz), 4.98 (2H, s), 5.66 (1H, dd, J=4.3, 8.6 Hz), 6.82-6.93 (5H, m), 7.17-7.22 (2H, m), 7.24 (1H, dd, J=2.0, 8.2 Hz), 7.32 (2H, d, J=8.6 Hz), 7.44 (1H, d, J=8.2 Hz), 7.52 (1H, d, J=2.0 Hz), 9.85 (1H, dd, J=1.6, 2.3 Hz)

(29C) 3-[4-(3,4-Dichlorobenzyloxy)phenyl]-3-phenoxy propionic acid

3-[4-(3,4-Dichlorobenzyloxy)phenyl]-3-phenoxypropionaldehyde (42 mg, 0.11 mmol) produced in (29B) and sodium dihydrogen phosphate (123 mg, 0.788 mmol) were dissolved in a mixed solvent of tetrahydrofuran/t-butanol/water/2-methyl-2-butene (6/6/2/1, 4 mL), and sodium chlorite (80%, 33 mg, 0.29 mmol) was added thereto at room temperature, and then, the resulting mixture was stirred at room temperature for 4 hours. To the reaction solution, a saturated aqueous solution of ammonium chloride was added, and the organic matter was extracted with ethyl acetate. The organic layer was washed with a saturated sodium chloride solution, then dried over anhydrous sodium sulfate and filtered. Then, the solvent was distilled off under reduced pressure, and the resulting residue was purified by silica gel column chromatography (hexane:ethyl acetate=80:20 to 50:50 (v/v)), whereby the objective title compound was obtained as a white solid (39 mg, yield: 89%).

$^1$H NMR (CDCl$_3$, 400 MHz): δ2.80 (1H, dd, J=4.7, 16.0 Hz), 3.07 (1H, dd, J=8.6, 16.0 Hz), 4.97 (2H, s), 5.58 (1H, dd, J=4.7, 8.6 Hz), 6.86 (2H, d, J=8.6 Hz), 6.88-6.93 (3H, m), 7.16-7.20 (2H, m), 7.23 (1H, dd, J=2.0, 8.2 Hz), 7.33 (2H, d, J=8.6 Hz), 7.44 (1H, d, J=8.2 Hz), 7.51 (1H, d, J=2.0 Hz)

Example 30

3-{4-[Difluoro(4-trifluoromethylphenyl)methoxy]phenyl}-3-ethoxypropionic acid (Illustrative Compound No: 1-34)

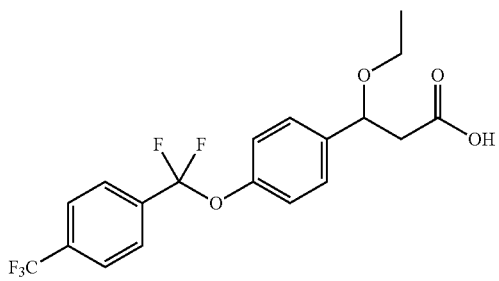

(30A) 1-Bromo-4-[difluoro(4-trifluoromethylphenyl)methoxy]benzene

4-Bromophenol (470 mg, 2.72 mmol) and 1-chlorodifluoromethyl-4-trifluoromethylbenzene (1.07 g, 4.64 mmol) were dissolved in dimethylformamide (50 mL), and sodium hydride (63%, 156 mg, 4.10 mmol) was added thereto at 0° C., and then, the resulting mixture was stirred under a nitrogen atmosphere at 60° C. for 4 hours. After the reaction solution was cooled to room temperature, a saturated aqueous solution of ammonium chloride was added thereto, and the organic matter was extracted with diethyl ether. The organic layer was washed with water, then dried over anhydrous sodium sulfate and filtered. Then, the solvent was distilled off under reduced pressure, whereby a crude product was obtained. This crude product was purified by silica gel column chromatography (hexane:ethyl acetate=95:5 (v/v)), whereby the objective title compound was obtained as a white solid (690 mg, yield: 69%).

$^1$H NMR (CDCl$_3$, 400 MHz): δ7.14 (2H, d, J=9.0 Hz), 7.48 (2H, d, J=9.0 Hz), 7.74 (2H, d, J=8.6 Hz), 7.84 (2H, d, J=8.6 Hz)

(30B) 3-(tert-Butyldimethylsilyloxy)-1-{4-[difluoro(4-trifluoromethylphenyl)methoxy]phenyl}propan-1-ol 1-Bromo-4-[difluoro(4-trifluoromethylphenyl)methoxy]benzene (174 mg, 0.474 mmol) produced in (30A) was dissolved in tetrahydrofuran (5 mL), and under a nitrogen atmosphere, an n-butyllithium hexane solution (1.61 M, 0.35 mL, 0.56 mmol) was added thereto at −78° C., and the resulting mixture was stirred at −78° C. for 1 hour. Thereafter, 3-(tert-butyldimethylsilyloxy)propionaldehyde (130 mg, 0.690 mmol) was added thereto at −78° C., and the resulting mixture was stirred at −78° C. for 5 minutes. Then, the temperature of the reaction solution was raised to room temperature, and a saturated aqueous solution of ammonium chloride was added thereto, and the organic matter was extracted with diethyl ether. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=97:3 to 90:10 (v/v)), whereby the objective title compound was obtained as a colorless oily substance (199 mg, yield: 88%).

$^1$H NMR (CDCl$_3$, 400 MHz): δ0.10 (3H, s), 0.11 (3H, s), 0.93 (9H, s), 1.88-2.01 (2H, m), 3.88 (2H, dd, J=5.0, 6.4 Hz), 3.94 (1H, d, J=2.7 Hz), 4.98 (1H, m), 7.24 (2H, d, J=8.6 Hz), 7.39 (2H, d, J=8.6 Hz), 7.75 (2H, d, J=8.2 Hz), 7.87 (2H, d, J=8.2 Hz)

(30C) tert-Butyl[3-{4-[difluoro (4-trifluoromethylphenyl)methoxy]phenyl}-3-ethoxypropoxy]dimethylsilane 3-(tert-Butyldimethylsilyloxy)-1-{4-[difluoro-(4-trifluoromethylphenyl)methoxy]phenyl}propan-1-ol (190 mg, 0.399 mmol) produced in (30B) and ethyl iodide (0.10 mL, 1.25 mmol) were dissolved in tetrahydrofuran (5 mL) and dimethylformamide (1 mL), and sodium hydride (63%, 23 mg, 0.60 mmol) was added thereto at room temperature, and then, the resulting mixture was stirred under a nitrogen atmosphere at 60° C. for 3 hours. After the reaction solution was cooled to room temperature, a saturated aqueous solution of ammonium chloride was added thereto, and the organic matter was extracted with diethyl ether. The organic layer was washed with water, then dried over anhydrous sodium sulfate and filtered. Then, the solvent was distilled off under reduced pressure, whereby a crude product was obtained. This crude product was purified by silica gel column chromatography (hexane:ethyl acetate=100:0 to 90:10 (v/v)), whereby the objective title compound was obtained as a white solid (168 mg, yield: 83%).

$^1$H NMR (CDCl$_3$, 500 MHz): δ0.05 (3H, s), 0.06 (3H, s), 0.92 (9H, s), 1.18 (3H, t, J=7.0 Hz), 1.77 (1H, ddd, J=5.4, 7.8, 13.7 Hz), 1.97 (1H, ddd, J=4.9, 5.4, 13.7 Hz), 3.28-3.42 (2H, m), 3.56 (1H, ddd, J=5.4, 5.4, 10.3 Hz), 3.77 (1H, ddd, J=4.9, 7.8, 10.3 Hz), 4.45 (1H, dd, J=5.5, 8.8 Hz), 7.24 (2H, d, J=8.8 Hz), 7.32 (2H, d, J=8.8 Hz), 7.75 (2H, d, J=8.3 Hz), 7.88 (2H, d, J=8.3 Hz)

(30D) 3-{4-[Difluoro(4-trifluoromethylphenyl)methoxy]phenyl}-3-ethoxypropionaldehyde tert-Butyl[3-{4-[difluoro(4-trifluoromethylphenyl)-methoxy]phenyl}-3-ethoxypropoxy]dimethylsilane (100 mg, 0.198 mmol) produced in (30C) was dissolved in tetrahydrofuran (3 mL). To the reaction solution, a tetrabutyl ammonium fluoride tetrahydrofuran solution (1.0 M, 0.30 mL, 0.30 mmol) was added dropwise at room temperature, and the resulting mixture was stirred at room temperature for 1 hour. To the reaction solution, a saturated aqueous solution of ammonium chloride was added, and the organic matter was extracted with ethyl acetate. The organic layer was washed with a saturated sodium chloride solution, then dried over anhydrous sodium sulfate and filtered. Then, the solvent was distilled off under reduced pressure.

The resulting crude product was dissolved in dichloromethane (3 mL). To the reaction solution, sodium hydrogen carbonate (83 mg, 0.99 mmol) and Dess-Martin periodinane (131 mg, 0.309 mmol) were added at room temperature, and the resulting mixture was stirred at room temperature for 30 minutes. To the reaction solution, diethyl ether, a saturated aqueous solution of sodium hydrogen carbonate, and a saturated aqueous solution of sodium thiosulfate were added. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=100:0 to 96:4 (v/v)), whereby the objective title compound was obtained as a colorless oily substance (25 mg, yield: 33%).

$^1$H NMR (CDCl$_3$, 400 MHz): δ1.16 (3H, t, J=7.0 Hz), 2.62 (1H, ddd, J=1.6, 4.3, 16.6 Hz), 2.90 (1H, ddd, J=2.3, 9.0, 16.6 Hz), 3.31-3.44 (2H, m), 4.81 (1H, dd, J=4.3, 9.0 Hz), 7.26 (2H, d, J=8.6 Hz), 7.34 (2H, d, J=8.6 Hz), 7.74 (2H, d, J=8.2 Hz), 7.86 (2H, d, J=8.2 Hz), 9.79 (1H, dd, J=1.6, 2.3 Hz)

(30E) 3-{4-[Difluoro(4-trifluoromethylphenyl)methoxy]phenyl}-3-ethoxypropionic acid 3-{4-[Difluoro(4-trifluoromethylphenyl)methoxy]-phenyl}-3-ethoxypropionaldehyde (25 mg, 0.065 mmol) produced in (30D) and sodium dihydrogen phosphate (84 mg, 0.54 mmol) were dissolved in a mixed solvent of tetrahydrofuran/t-butanol/water/2-methyl-2-butene (6/6/2/1, 3 mL), and sodium chlorite (80%, 22 mg, 0.19 mmol) was added thereto at room temperature, and then, the resulting mixture was stirred at room temperature for 3 hours. To the reaction solution, a saturated aqueous solution of ammonium chloride was added, and the organic matter was extracted with ethyl acetate. The organic layer was washed with a saturated sodium chloride solution, then dried over anhydrous sodium sulfate and filtered. Then, the solvent was distilled off under reduced pressure, and the resulting residue was purified by silica gel column chromatography (hexane:ethyl acetate=80:20 to 60:40 (v/v)), whereby the objective title compound was obtained as a white solid (10 mg, yield: 38%).

$^1$H NMR (CDCl$_3$, 400 MHz): δ1.21 (3H, t, J=7.0 Hz), 2.66 (1H, dd, J=4.3, 16.0 Hz), 2.84 (1H, dd, J=9.4, 16.0 Hz), 3.37-3.50 (2H, m), 4.76 (1H, dd, J=4.3, 9.4 Hz), 7.28 (2H, d, J=8.6 Hz), 7.37 (2H, d, J=8.6 Hz), 7.76 (2H, d, J=8.2 Hz), 7.88 (2H, d, J=8.2 Hz)

Example 31

3-{6-[(2',6'-Dimethylbiphenyl-3-yl)methoxy]pyridin-3-yl}-3-(prop-2-in-1-yloxy)propionic acid (Illustrative Compound No: 2-8)

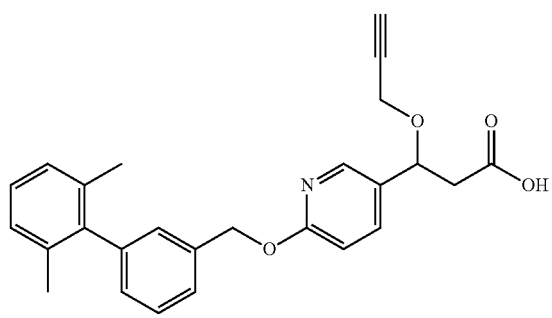

(31A) 6-[(2',6'-Dimethylbiphenyl-3-yl)methoxy] nicotinaldehyde

5-Bromo-2-[(2',6'-dimethylbiphenyl-3-yl)methoxy]-pyridine (49.9 g, 0.135 mol) produced in Example 26 (26A) was dissolved in diethyl ether (500 mL), and a 2.7 M n-butyl-lithium hexane solution (59 mL, 0.163 mol) was added thereto at −78° C., and then, the resulting mixture was stirred under a nitrogen atmosphere at −78° C. for 50 minutes. Thereafter, dimethylformamide (21 mL, 0.271 mol) was added thereto at −78° C., and while stirring the resulting mixture under a nitrogen atmosphere, the temperature of the mixture was raised to 0° C. over 1 hour.

To the reaction solution, a saturated aqueous solution of ammonium chloride was added at 0° C., and the organic matter was extracted with ethyl acetate. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=100:0 to 5:1 (v/v)), whereby the objective title compound was obtained as a white solid (38.3 g, yield: 89%).

$^1$H NMR (CDCl$_3$, 400 MHz): δ2.03 (6H, s), 5.54 (2H, s), 6.92 (1H, d, J=8.6 Hz), 7.10-7.20 (4H, m), 7.25-7.28 (1H, m), 7.42-7.49 (2H, m), 8.09 (1H, dd, J=2.2, 8.6 Hz), 8.65 (1H, d, J=2.2 Hz), 9.98 (1H, s)

(31B) Ethyl 3-{6-[(2',6'-dimethylbiphenyl-3-yl) methoxy]pyridin-3-yl}-3-hydroxypropionate Ethyl acetate (23.5 mL, 0.242 mol) was dissolved in tetrahydrofuran (200 mL), and a 1.0 M lithium bis(trimethylsilyl)amide tetrahydrofuran solution (205 mL, 0.205 mol) was added thereto at −78° C., and then, the resulting mixture was stirred under a nitrogen atmosphere at −78° C. for 15 minutes. Thereafter, a solution obtained by dissolving 6-[(2',6'-dimethylbiphenyl-3-yl)methoxy]nicotinaldehyde (38.3 g, 0.121 mol) produced in (31A) in tetrahydrofuran (300 mL) was added thereto at −78° C., and the resulting mixture was stirred under a nitrogen atmosphere at −78° C. for 90 minutes.

To the reaction solution, a saturated aqueous solution of ammonium chloride was added at −78° C., and the organic matter was extracted with ethyl acetate. The organic layer was washed with water and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=10:1 to 1:1 (v/v)), whereby the objective title compound was obtained as a white solid (48.4 g, yield: 99%).

$^1$H NMR (CDCl$_3$, 400 MHz): δ1.28 (3H, t, J=7.0 Hz), 2.03 (6H, s), 2.65-2.82 (2H, m), 3.33 (1H, d, J=3.5 Hz), 4.20 (2H, q, J=7.0 Hz), 5.12 (1H, dt, J=3.5, 9.4 Hz), 5.42 (2H, s), 6.83 (1H, d, J=8.6 Hz), 7.09-7.14 (3H, m), 7.17 (1H, dd, J=6.3, 8.6 Hz), 7.25 (1H, brs), 7.41-7.45 (2H, m), 7.66 (1H, dd, J=2.6, 8.6 Hz), 8.16 (1H, d, J=2.6 Hz)

(31C) 1-{6-[(2',6'-Dimethylbiphenyl-3-yl)methoxy] pyridin-3-yl}-3-(trityloxy)propan-1-ol Tetrahydrofuran (250 mL) was added to lithium aluminum hydride (9.2 g, 0.242 mol), and the resulting mixture was stirred under a nitrogen atmosphere at 0° C. Then, a tetrahydrofuran (350 mL) solution of ethyl 3-{6-[(2',6'-dimethylbiphenyl-3-yl)methoxy]pyridin-3-yl}-3-hydroxypropionate (48.4 g, 0.119 mol) produced in (31B) was added dropwise thereto at 0° C., and the resulting mixture was stirred at room temperature for 1 hour.

To the reaction solution, water (9.2 mL), a 15% aqueous solution of sodium hydroxide (9.2 mL), and water (27.6 mL) were sequentially added at 0° C., and the resulting mixture was appropriately stirred. Then, the mixture was filtered through a Celite filter, and the solvent was distilled off under reduced pressure, whereby a crude product was obtained. This crude product was used in the subsequent reaction step without performing further purification procedures.

The crude product was dissolved in dichloromethane (450 mL), and pyridine (29 mL, 0.348 mol) and triphenylmethyl chloride (33.9 g, 0.122 mol) were sequentially added thereto, and the resulting mixture was stirred under a nitrogen atmosphere at room temperature for 12 hours. To the reaction solution, water was added and the organic matter was extracted with dichloromethane. The organic layer was washed with water, a saturated sodium bicarbonate solution, and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=100:0 to 60:40 (v/v)), whereby the objective title compound was obtained as a white solid (51.7 g, yield: 72%).

$^1$H NMR (CDCl$_3$, 400 MHz): δ1.85-1.97 (1H, m), 2.03 (6H, s), 2.04-2.14 (1H, m), 3.23-3.31 (2H, m), 3.36-3.42 (1H, m), 4.90 (1H, dt, J=3.3, 8.3 Hz), 5.41 (2H, s), 6.76 (1H, d, J=8.6 Hz), 7.08-7.14 (3H, m), 7.17 (1H, dd, J=6.1, 8.8 Hz), 7.23-7.28 (4H, m), 7.29-7.35 (6H, m), 7.41-7.47 (8H, m), 7.58 (1H, dd, J=2.4, 8.6 Hz), 8.08 (1H, d, J=2.4 Hz)

(31D) 2-[(2',6'-Dimethylbiphenyl-3-yl)methoxy]-5-[1-(prop-2-in-1-yloxy)-3-(trityloxy)propyl]pyridine 1-{6-[(2',6'-Dimethylbiphenyl-3-yl)methoxy]pyridin-3-yl}-3-(trityloxy)propan-1-ol (350 mg, 0.578 mmol) produced in (31C) was dissolved in dimethylformamide (3.0 mL), and sodium hydride (about 63%, oily, 44 mg, 1.16 mmol) was added thereto at 0° C., and then, the resulting mixture was stirred under a nitrogen atmosphere at 0° C. for 30 minutes. Thereafter, propargyl bromide (0.087 mL, 1.16 mmol) was added thereto at 0° C., and the resulting mixture was stirred under a nitrogen atmosphere at 40° C. for 3 hours.

To the reaction solution, a saturated aqueous solution of ammonium chloride was added at 0° C., and the organic matter was extracted with ethyl acetate. The organic layer was washed with water, a saturated sodium bicarbonate solution, and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=100:0 to 75:25 (v/v)), whereby the objective title compound was obtained (312 mg, yield: 99%).

$^1$H NMR (CDCl$_3$, 400 MHz): δ1.82-1.91 (1H, m), 2.03 (6H, s), 2.13-2.23 (1H, m), 2.36 (1H, t, J=2.4 Hz), 2.94-3.01 (1H, m), 3.23-3.31 (1H, m), 3.84 (1H, dd, J=2.4, 15.6 Hz), 4.04 (1H, dd, J=2.4, 15.6 Hz), 4.79 (1H, t, J=6.8 Hz), 5.41 (2H, s), 6.76 (1H, d, J=8.6 Hz), 7.09-7.14 (3H, m), 7.15-7.24 (4H, m), 7.26-7.32 (7H, m), 7.40-7.47 (8H, m), 7.50 (1H, dd, J=2.2, 8.6 Hz), 8.06 (1H, d, J=2.2 Hz)

(31E) 3-{6-[(2',6'-Dimethylbiphenyl-3-yl)methoxy]pyridin-3-yl}-3-(prop-2-in-1-yloxy)propan-1-ol 80% Acetic acid (10 mL) was added to 2-[(2',6'-dimethylbiphenyl-3-yl)methoxy]-5-[1-(prop-2-in-1-yloxy)-3-(trityloxy)propyl]pyridine (312 mg, 0.485 mmol) produced in (31D), and the resulting mixture was stirred at 70° C. for 4 hours. After the reaction solution was distilled off under reduced pressure, a saturated aqueous solution of sodium bicarbonate was added to the resulting residue, and the organic matter was extracted with ethyl acetate. The organic layer was washed with water, a saturated sodium bicarbonate solution, and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=90:10 to 60:40 (v/v)), whereby the objective title compound was obtained (138 mg, yield: 71%).

$^1$H NMR (CDCl$_3$, 400 MHz): δ1.82-1.91 (1H, m), 2.03 (6H, s), 2.16-2.06 (2H, m), 2.44 (1H, t, J=2.4 Hz), 3.72-3.88 (2H, m), 3.85 (1H, dd, J=2.4, 15.6 Hz), 4.12 (1H, dd, J=2.4, 15.6 Hz), 4.75 (1H, dd, J=4.5, 9.2 Hz), 5.43 (2H, s), 6.84 (1H, d, J=8.6 Hz), 7.09-7.13 (3H, m), 7.17 (1H, dd, J=6.1, 8.8 Hz), 7.23-7.26 (1H, m), 7.41-7.46 (2H, m), 7.61 (1H, dd, J=2.3, 8.6 Hz), 8.11 (1H, d, J=2.3 Hz)

(31F) 3-{6-[(2',6'-Dimethylbiphenyl-3-yl)methoxy]pyridin-3-yl}-3-(prop-2-in-1-yloxy)propionic acid 3-{6-[(2',6'-Dimethylbiphenyl-3-yl)methoxy]pyridin-3-yl}-3-(prop-2-in-1-yloxy)propan-1-ol (138 mg, 0.344 mmol) produced in (31E) was dissolved in dichloromethane (4.0 mL), and Dess-Martin periodinane (219 mg, 0.516 mmol) was added thereto at 0° C., and then, the resulting mixture was stirred under a nitrogen atmosphere at room temperature for 3 hours.

To the reaction solution, a saturated aqueous solution of sodium bicarbonate and a saturated aqueous solution of sodium thiosulfate were added, and the organic matter was extracted with diethyl ether. The organic layer was washed with water and a saturated sodium chloride solution, then dried over anhydrous sodium sulfate and filtered. Then, the solvent was distilled off under reduced pressure, whereby a crude product was obtained. This crude product was used in the subsequent reaction step without performing further purification procedures.

The crude product was dissolved in a mixed solvent of tert-butyl alcohol/tetrahydrofuran/water (5/2/2, 4.5 mL), and 2-methyl-2-butene (0.37 mL, 3.44 mmol), sodium dihydrogen phosphate dihydrate (268 mg, 1.72 mmol), and sodium chlorite (80%, 194 mg, 1.72 mmol) were sequentially added thereto, and then, the resulting mixture was stirred at room temperature for 90 minutes.

To the reaction solution, water was added and the organic matter was extracted with ethyl acetate. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=90:10 to 55:45 (v/v)), whereby the objective title compound was obtained as a colorless oily substance (118 mg, yield: 83%).

$^1$H NMR (CDCl$_3$, 400 MHz): δ2.02 (6H, s), 2.43 (1H, t, J=2.6 Hz), 2.68 (1H, dd, J=5.3, 15.8 Hz), 2.96 (1H, dd, J=8.4, 15.8 Hz), 3.89 (1H, dd, J=2.3, 15.6 Hz), 4.12 (1H, dd, J=2.3, 15.6 Hz), 4.99 (1H, dd, J=5.3, 8.4 Hz), 5.43 (2H, s), 6.85 (1H, d, J=8.6 Hz), 7.09-7.13 (3H, m), 7.17 (1H, dd, J=6.3, 8.6 Hz), 7.24 (1H, brs), 7.41-7.47 (2H, m), 7.62 (1H, dd, J=2.4, 8.6 Hz), 8.16 (1H, d, J=2.4 Hz)

MS (FAB) m/z: 416 (M+H)$^+$

Example 32

3-(Allyloxy)-3-{6-[(2',6'-dimethylbiphenyl-3-yl)methoxy]pyridin-3-yl}propionic acid (Illustrative Compound No: 2-9)

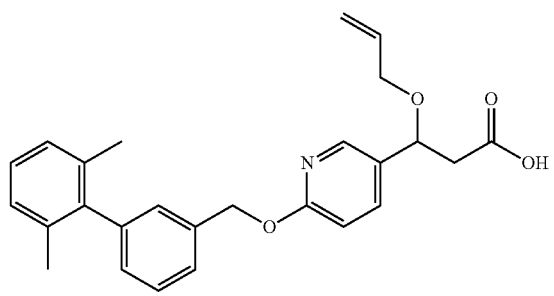

(32A) 5-[1-(Allyloxy)-3-(trityloxy)propyl]-2-[(2',6'-dimethylbiphenyl-3-yl)methoxy]pyridine 1-{6-[(2',6'-Dimethylbiphenyl-3-yl)methoxy]pyridin-3-yl}-3-(trityloxy)propan-1-ol (250 mg, 0.413 mmol) produced in Example 31 (31C) was dissolved in dimethylformamide (2.5 mL), and sodium hydride (about 63%, oily, 32 mg, 0.825 mmol) was added thereto at 0° C., and then, the resulting mixture was stirred under a nitrogen atmosphere at 0° C. for 50 minutes. Thereafter, allyl bromide (0.070 mL, 0.825 mmol) was added thereto at 0° C., and the resulting mixture was stirred under a nitrogen atmosphere at 45° C. for 4 hours.

To the reaction solution, a saturated aqueous solution of ammonium chloride was added at 0° C., and the organic matter was extracted with ethyl acetate. The organic layer was washed with water, a saturated sodium bicarbonate solution, and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=100:0 to 75:25 (v/v)), whereby the objective title compound was obtained (263 mg, yield: 99%).

$^1$H NMR (CDCl$_3$, 400 MHz): δ1.81-1.91 (1H, m), 2.03 (6H, s), 2.06-2.22 (1H, m), 2.96-3.04 (1H, m), 3.23-3.30 (1H, m), 3.70-3.78 (1H, m), 3.81-3.87 (1H, m), 4.59 (1H, dd, J=5.6, 8.0 Hz), 5.10-5.22 (2H, m), 5.41 (2H, s), 5.75-5.86 (1H, m), 6.76 (1H, d, J=8.5 Hz), 7.10-7.14 (3H, m), 7.15-7.25 (4H, m), 7.25-7.32 (7H, m), 7.40-7.46 (8H, m), 7.50 (1H, dd, J=2.4, 8.5 Hz), 8.03 (1H, d, J=2.4 Hz)

(32B) 3-(Allyloxy)-3-{6-[(2',6'-dimethylbiphenyl-3-yl)methoxy]pyridin-3-yl}propan-1-ol 80% acetic acid (10 mL) was added to 5-[1-(allyloxy)-3-(trityloxy)propyl]-2-[(2',6'-dimethylbiphenyl-3-yl)methoxy]pyridine (263 mg, 0.407 mmol) produced in (32A), and the resulting mixture was stirred at 70° C. for 90 minutes.

After the reaction solution was distilled off under reduced pressure, a saturated aqueous solution of sodium bicarbonate was added to the resulting residue, and the organic matter was extracted with ethyl acetate. The organic layer was washed with water, a saturated sodium bicarbonate solution, and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=90:10 to 55:45 (v/v)), whereby the objective title compound was obtained (126 mg, yield: 77%).

$^1$H NMR (CDCl$_3$, 400 MHz): δ1.80-1.89 (1H, m), 2.03 (6H, s), 2.05-2.14 (1H, m), 2.41 (1H, dd, J=4.1, 6.5 Hz), 3.74-3.84 (3H, m), 3.88-3.94 (1H, m), 4.55 (1H, dd, J=4.3, 9.4 Hz), 5.16-5.27 (2H, m), 5.43 (2H, s), 5.82-5.93 (1H, m), 6.84 (1H, d, J=8.2 Hz), 7.09-7.13 (3H, m), 7.17 (1H, dd, J=6.3, 8.6 Hz), 7.24-7.27 (1H, m), 7.41-7.47 (2H, m), 7.60 (1H, dd, J=2.4, 8.6 Hz), 8.07 (1H, d, J=2.4 Hz)

(32C) 3-(Allyloxy)-3-{6-[(2',6'-dimethylbiphenyl-3-yl)methoxy]pyridin-3-yl}propionic acid 3-(Allyloxy)-3-{6-[(2',6'-dimethylbiphenyl-3-yl)-methoxy]pyridin-3-yl}propan-1-ol (126 mg, 0.312 mmol) produced in (32B) was dissolved in dichloromethane (4.0 mL), and Dess-Martin periodinane (200 mg, 0.468 mmol) was added thereto at 0° C., and then, the resulting mixture was stirred under a nitrogen atmosphere at room temperature for 3 hours.

To the reaction solution, a saturated aqueous solution of sodium bicarbonate and a saturated aqueous solution of sodium thiosulfate were added, and the organic matter was extracted with diethyl ether. The organic layer was washed with water and a saturated sodium chloride solution, then dried over anhydrous sodium sulfate and filtered. Then, the solvent was distilled off under reduced pressure, whereby a crude product was obtained. This crude product was used in the subsequent reaction step without performing further purification procedures.

The crude product was dissolved in a mixed solvent of tert-butyl alcohol/tetrahydrofuran/water (5/2/2, 4.5 mL), and 2-methyl-2-butene (0.27 mL, 2.50 mmol), sodium dihydrogen phosphate dihydrate (243 mg, 1.56 mmol), and sodium chlorite (80%, 176 mg, 1.56 mmol) were sequentially added thereto, and then, the resulting mixture was stirred at room temperature for 90 minutes.

To the reaction solution, water was added and the organic matter was extracted with ethyl acetate. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=90:10 to 55:45 (v/v)), whereby the objective title compound was obtained as a colorless oily substance (106 mg, yield: 81%).

$^1$H NMR (CDCl$_3$, 500 MHz): δ2.02 (6H, s), 2.64 (1H, dd, J=4.9, 15.6 Hz), 2.91 (1H, dd, J=8.9, 15.6 Hz), 3.81 (1H, dd, J=6.4, 12.7 Hz), 3.89-3.99 (1H, m), 4.78 (1H, dd, J=4.9, 8.9 Hz), 5.15-5.26 (2H, m), 5.42 (2H, s), 5.81-5.90 (1H, m), 6.84 (1H, d, J=8.8 Hz), 7.07-7.13 (2H, m), 7.16 (1H, dd, J=6.4, 8.3 Hz), 7.23-7.28 (2H, m), 7.40-7.46 (2H, m), 7.60 (1H, dd, J=2.4, 8.8 Hz), 8.11 (1H, d, J=2.4 Hz)

MS (FAB) m/z: 418 (M+H)$^+$

Example 33

3-{6-[(2',6'-Dimethylbiphenyl-3-yl)methoxy]pyridin-3-yl}-3-(methoxymethoxy)propionic acid (Illustrative Compound No: 2-10)

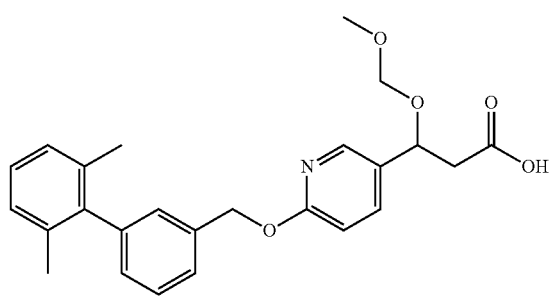

(33A) 2-[(2',6'-Dimethylbiphenyl-3-yl)methoxy]-5-[1-(methoxymethoxy)-3-(trityloxy)propyl]pyridine 1-{6-[(2',6'-Dimethylbiphenyl-3-yl)methoxy]pyridin-3-yl}-3-(trityloxy)propan-1-ol (250 mg, 0.413 mmol) produced in Example 31 (31C) was dissolved in dimethylformamide (2.5 mL), and sodium hydride (about 63%, oily, 32 mg, 0.83 mmol) was added thereto at 0° C., and then, the resulting mixture was stirred under a nitrogen atmosphere at 0° C. for 50 minutes. Thereafter, chloromethyl methyl ether (0.063 mL, 0.825 mmol) and tetra-n-butyl ammonium iodide (8.0 mg, 0.021 mmol) were sequentially added thereto at 0° C., and the resulting mixture was stirred under a nitrogen atmosphere at 50° C. for 5 hours. To the reaction solution, a saturated aqueous solution of ammonium chloride was added at 0° C., and the organic matter was extracted with ethyl acetate. The organic layer was washed with water, a saturated sodium bicarbonate solution, and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=100:0 to 75:25 (v/v)), whereby the objective title compound was obtained (85 mg, yield: 32%).

$^1$H NMR (CDCl$_3$, 500 MHz): δ1.86-1.97 (1H, m), 2.03 (6H, s), 2.11-2.23 (1H, m), 3.06-3.14 (1H, m), 3.18 (3H, s), 3.15-3.25 (1H, m), 4.44 (2H, s), 4.78 (1H, dd, J=5.8, 8.2 Hz), 5.41 (2H, s), 6.75 (1H, d, J=8.2 Hz), 7.09-7.15 (3H, m), 7.15-7.35 (11H, m), 7.38-7.48 (8H, m), 7.50 (1H, dd, J=2.4, 8.6 Hz), 8.06 (1H, d, J=2.4 Hz)

(33B) 3-{6-[(2',6'-Dimethylbiphenyl-3-yl)methoxy]pyridin-3-yl}-3-(methoxymethoxy)propan-1-ol 80% acetic acid (5.0 mL) was added to 2-[(2',6'-dimethylbiphenyl-3-yl)methoxy]-5-[1-(methoxymethoxy)-3-(trityloxy)propyl]pyridine (85 mg, 0.131 mmol) produced in (33A), and the resulting mixture was stirred at 70° C. for 90 minutes. After the reaction solution was distilled off under reduced pressure, a saturated aqueous solution of sodium bicarbonate was added to the resulting residue, and the organic matter was extracted with ethyl acetate. The organic layer was washed with water, a saturated sodium bicarbonate solution, and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=85:15 to 45:55 (v/v)), whereby the objective title compound was obtained (39 mg, yield: 73%).

$^1$H NMR (CDCl$_3$, 400 MHz): δ1.86-1.95 (1H, m), 2.02 (6H, s), 2.05-2.15 (1H, m), 2.17 (1H, dd, J=5.1, 6.2 Hz), 3.39 (3H, s), 3.72-3.88 (2H, m), 4.53 (2H, s), 4.82 (1H, dd, J=4.5, 9.2 Hz), 5.43 (2H, s), 6.83 (1H, d, J=8.6 Hz), 7.09-7.14 (3H, m), 7.17 (1H, dd, J=6.5, 8.8 Hz), 7.23-7.26 (1H, m), 7.42-7.46 (2H, m), 7.60 (1H, dd, J=2.6, 8.6 Hz), 8.10 (1H, d, J=2.6 Hz)

(33C) 3-{6-[(2',6'-Dimethylbiphenyl-3-yl)methoxy]pyridin-3-yl}-3-(methoxymethoxy)propionic acid 3-{6-[(2',6'-Dimethylbiphenyl-3-yl)methoxy]pyridin-3-yl}-3-(methoxymethoxy)propan-1-ol (39 mg, 0.096 mmol) produced in (33B) was dissolved in dichloromethane (1.0 mL), and Dess-Martin periodinane (60 mg, 0.14 mmol) was added thereto at 0° C., and then, the resulting mixture was stirred under a nitrogen atmosphere at room temperature for 3 hours.

To the reaction solution, a saturated aqueous solution of sodium bicarbonate and a saturated aqueous solution of sodium thiosulfate were added, and the organic matter was extracted with diethyl ether. The organic layer was washed with water and a saturated sodium chloride solution, then dried over anhydrous sodium sulfate and filtered. Then, the solvent was distilled off under reduced pressure, whereby a crude product was obtained. This crude product was used in the subsequent reaction step without performing further purification procedures.

The crude product was dissolved in a mixed solvent of tert-butyl alcohol/tetrahydrofuran/water (5/2/2, 1.8 mL), and 2-methyl-2-butene (0.10 mL, 0.96 mmol), sodium dihydrogen phosphate dihydrate (75 mg, 0.48 mmol), and sodium chlorite (80%, 54 mg, 0.48 mmol) were sequentially added thereto, and then, the resulting mixture was stirred at room temperature for 2 hours. To the reaction solution, water was added and the organic matter was extracted with ethyl acetate. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=90:10 to 50:50 (v/v)), whereby the objective title compound was obtained as a colorless oily substance (35 mg, yield: 89%).

$^1$H NMR (CDCl$_3$, 400 MHz): δ2.02 (6H, s), 2.68 (1H, dd, J=5.2, 16.2 Hz), 2.94 (1H, dd, J=9.0, 16.2 Hz), 3.33 (3H, s), 4.51 (1H, d, J=6.8 Hz), 4.55 (1H, d, J=6.8 Hz), 5.07 (1H, dd, J=5.2, 9.0 Hz), 5.42 (2H, s), 6.83 (1H, d, J=8.6 Hz), 7.13-7.08 (3H, m), 7.17 (1H, dd, J=6.0, 8.8 Hz), 7.26-7.22 (1H, m), 7.47-7.40 (2H, m), 7.62 (1H, dd, J=2.7, 8.6 Hz), 8.15 (1H, d, J=2.3 Hz)

MS (FAB) m/z: 422 (M+H)$^+$

Example 34

3-Acetoxy-3-{6-[(2',6'-dimethylbiphenyl-3-yl)methoxy]pyridin-3-yl}propionic acid (Illustrative Compound No: 2-11)

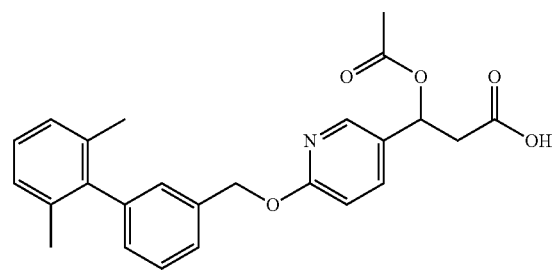

(34A) 1-{6-[(2',6'-Dimethylbiphenyl-3-yl)methoxy]pyridin-3-yl}-3-(trityloxy)propyl acetate 1-{6-[(2',6'-Dimethylbiphenyl-3-yl)methoxy]pyridin-3-yl}-3-(trityloxy)propan-1-ol (250 mg, 0.413 mmol) produced in Example 31 (31C) was dissolved in pyridine (3.0 mL), and acetic anhydride (0.116 mL, 1.24 mmol) was added thereto at 0° C., and then, the resulting mixture was stirred under a nitrogen atmosphere at 65° C. for 4 hours. To the reaction solution, a saturated sodium bicarbonate chloride solution was added, and the organic matter was extracted with ethyl acetate. The organic layer was washed with a saturated sodium bicarbonate solution and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=100:0 to 80:20 (v/v)), whereby the objective title compound was obtained (212 mg, yield: 79%).

$^1$H NMR (CDCl$_3$, 400 MHz): δ1.95 (3H, s), 2.03 (6H, s), 1.97-2.06 (1H, m), 2.17-2.28 (1H, m), 2.97-3.04 (1H, m), 3.14-3.22 (1H, m), 5.40 (2H, s), 5.97 (1H, dd, J=6.2, 8.2 Hz), 6.73 (1H, d, J=8.8 Hz), 7.09-7.13 (3H, m), 7.15-7.32 (11H, m), 7.38-7.47 (8H, m), 7.51 (1H, dd, J=2.3, 8.8 Hz), 8.12 (1H, d, J=2.3 Hz)

(34B) 1-{6-[(2',6'-Dimethylbiphenyl-3-yl)methoxy]pyridin-3-yl}-3-hydroxypropyl acetate 80% acetic acid (10 mL) was added to 1-{6-[(2',6'-dimethylbiphenyl-3-yl)methoxy]pyridin-3-yl}-3-(trityloxy)-propyl acetate (209 mg, 0.323 mmol) produced in (34A), and the resulting mixture was stirred at 70° C. for 90 minutes.

After the reaction solution was distilled off under reduced pressure, a saturated aqueous solution of sodium bicarbonate was added to the resulting residue, and the organic matter was extracted with ethyl acetate. The organic layer was washed with water, a saturated sodium bicarbonate solution, and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=85:15 to 45:55 (v/v)), whereby the objective title compound was obtained as a colorless oily substance (77 mg, yield: 59%).

$^1$H NMR (CDCl$_3$, 400 MHz): δ1.89 (1H, t, J=5.7 Hz), 2.03 (6H, s), 1.96-2.05 (1H, m), 2.09 (3H, s), 2.10-2.19 (1H, m), 3.63-3.70 (2H, m), 5.42 (2H, s), 5.96 (1H, dd, J=4.9, 9.2 Hz), 6.82 (1H, d, J=8.6 Hz), 7.09-7.13 (3H, m), 7.17 (1H, dd, J=6.3, 8.6 Hz), 7.24 (1H, brs), 7.40-7.47 (2H, m), 7.61 (1H, dd, J=2.3, 8.6 Hz), 8.18 (1H, d, J=2.3 Hz)

(34C) 3-Acetoxy-3-{6-[(2',6'-dimethylbiphenyl-3-yl)methoxy]pyridin-3-yl}propionic acid 1-{6-[(2',6'-Dimethylbiphenyl-3-yl)methoxy]pyridin-3-yl}-3-hydroxypropyl acetate (75 mg, 0.185 mmol) produced in (34B) was dissolved in dichloromethane (1.5 mL), and Dess-Martin periodinane (118 mg, 0.277 mmol) was added thereto at 0° C., and then, the resulting mixture was stirred under a nitrogen atmosphere at room temperature for 1 hour.

To the reaction solution, a saturated aqueous solution of sodium bicarbonate and a saturated aqueous solution of sodium thiosulfate were added, and the organic matter was extracted with diethyl ether. The organic layer was washed with water and a saturated sodium chloride solution, then dried over anhydrous sodium sulfate and filtered. Then, the solvent was distilled off under reduced pressure, whereby a crude product was obtained. This crude product was used in the subsequent reaction step without performing further purification procedures.

The crude product was dissolved in a mixed solvent of tert-butyl alcohol/tetrahydrofuran/water (5/2/2, 2.7 mL), and 2-methyl-2-butene (0.195 mL, 1.85 mmol), sodium dihydrogen phosphate dihydrate (144 mg, 0.925 mmol), and sodium chlorite (80%, 105 mg, 0.925 mmol) were sequentially added thereto, and then, the resulting mixture was stirred at room temperature for 2.5 hours.

To the reaction solution, water was added and the organic matter was extracted with ethyl acetate. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=90:10 to 45:55 (v/v)), whereby the objective title compound was obtained as a white solid (56 mg, yield: 72%).

$^1$H NMR (CDCl$_3$, 400 MHz): δ2.02 (6H, s), 2.05 (3H, s), 2.80 (1H, dd, J=5.7, 16.2 Hz), 3.06 (1H, dd, J=8.4, 16.2 Hz), 5.41 (2H, s), 6.14 (1H, dd, J=5.7, 8.4 Hz), 6.81 (1H, d, J=8.6 Hz), 7.08-7.13 (3H, m), 7.17 (1H, dd, J=6.2, 8.6 Hz), 7.23 (1H, brs), 7.39-7.47 (2H, m), 7.62 (1H, dd, J=2.4, 8.6 Hz), 8.22 (1H, d, J=2.4 Hz)

MS (FAB) m/z: 420 (M+H)$^+$

Example 35

3-{4-[(3,4-Dichlorobenzyl)oxy]-2-fluorophenyl}-3-ethoxypropionic acid (Illustrative Compound No: 1-81)

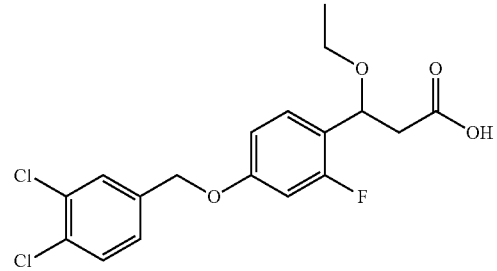

(35A) 4-[(3,4-Dichlorobenzyl)oxy]-2-fluorobenzonitrile

2-Fluoro-4-hydroxybenzonitrile (350 mg, 2.55 mmol) and 3,4-dichlorobenzyl alcohol (542 mg, 3.06 mmol) were dissolved in tetrahydrofuran (7.0 mL), and triphenylphosphine (803 mg, 3.06 mmol) and a 40% diethyl azodicarboxylate toluene solution (1.40 mL, 3.06 mmol) were added thereto at room temperature, and then, the resulting mixture was stirred under a nitrogen atmosphere at 50° C. for 5 hours. After the reaction solution was cooled to room temperature, the solvent was distilled off under reduced pressure, and the resulting residue was purified by silica gel column chromatography (hexane:ethyl acetate=100:0 to 65:35 (v/v)), whereby the objective title compound was obtained as a white solid (676 mg, yield: 89%).

$^1$H NMR (CDCl$_3$, 400 MHz): δ5.06 (2H, s), 6.76-6.85 (2H, m), 7.23-7.28 (1H, m), 7.48-7.59 (3H, m)

(35B) 4-[(3,4-Dichlorobenzyl)oxy]-2-fluorobenzaldehyde

4-[(3,4-Dichlorobenzyl)oxy]-2-fluorobenzonitrile (676 mg, 2.28 mmol) produced in (35A) was dissolved in dichloromethane (12 mL), and a 0.99 M diisobutylaluminum hydride toluene solution (4.6 mL, 4.57 mmol) was added thereto under a nitrogen atmosphere at −78° C., and then, the resulting mixture was stirred for 12 hours while gradually raising the temperature of the mixture to room temperature.

To the reaction solution, a saturated aqueous solution of ammonium chloride was added at 0° C., and the organic matter was extracted with ethyl acetate. The organic layer was washed with 1 N hydrochloric acid and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=100:0 to 50:50 (v/v)), whereby the objective title compound was obtained as a colorless solid (411 mg, yield: 60%).

$^1$H NMR (CDCl$_3$, 400 MHz): δ5.08 (2H, s), 6.71 (1H, dd, J=2.3, 12.1 Hz), 6.85 (1H, dd, J=2.3, 8.4 Hz), 7.24-7.28 (1H, m), 7.50 (1H, d, J=8.4 Hz), 7.54 (1H, d, J=2.3 Hz), 7.86 (1H, t like, J=8.4 Hz), 10.2 (1H, s)

(35C) Ethyl 3-{4-[(3,4-dichlorobenzyl)oxy]-2-fluorophenyl}-3-hydroxypropionate Ethyl acetate (0.270 mL, 2.75 mmol) was dissolved in tetrahydrofuran (4.0 mL), and a 1.0 M lithium bis(trimethylsilyl)amide tetrahydrofuran solution (2.5 mL, 2.47 mmol) was added thereto at −78° C., and then, the resulting mixture was stirred under a nitrogen atmosphere at −78° C. for 30 minutes. Thereafter, a solution obtained by dissolving 4-[(3,4-dichlorobenzyl)oxy]-2-fluorobenzaldehyde (411 mg, 1.37 mmol) produced in (35B) in tetrahydrofuran (4.0 mL) was added thereto at −78° C., and the resulting mixture was stirred under a nitrogen atmosphere at −78° C. for 1 hour.

To the reaction solution, a saturated aqueous solution of ammonium chloride was added at −78° C., and the organic matter was extracted with ethyl acetate. The organic layer was washed with water and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=95:5 to 70:30 (v/v)), whereby the objective title compound was obtained (491 mg, yield: 92%).

$^1$H NMR (CDCl$_3$, 400 MHz): δ1.27 (3H, t, J=7.0 Hz), 2.69-2.80 (2H, m), 3.43 (1H, d, J=3.9 Hz), 4.20 (2H, q, J=7.0 Hz), 5.00 (2H, s), 5.32-5.38 (1H, m), 6.65 (1H, dd, J=2.4, 12.1 Hz), 6.77 (1H, dd, J=2.4, 9.0 Hz), 7.23-7.29 (1H, m), 7.41-7.49 (2H, m), 7.53 (1H, d, J=1.1 Hz)

(35D) Ethyl 3-{4-[(3,4-dichlorobenzyl)oxy]-2-fluorophenyl}-3-ethoxypropionate Ethyl 3-{4-[(3,4-dichlorobenzyl)oxy]-2-fluorophenyl}-3-hydroxypropionate (245 mg, 0.633 mmol) produced in (35C) was dissolved in toluene (5.0 mL), and ethyl iodide (0.355 mL, 4.43 mmol) and silver oxide(I) (1.02 g, 4.43 mmol) were added thereto at room temperature, and then, the resulting mixture was stirred under a nitrogen atmosphere at 100° C. for 2 hours.

After cooling to room temperature, the reaction solution was filtered, and the solvent was distilled off under reduced pressure, whereby a crude product was obtained. This crude product was purified by silica gel column chromatography (hexane:ethyl acetate=100:0 to 75:25 (v/v)), whereby the objective title compound was obtained as a colorless oily substance (223 mg, yield: 85%).

$^1$H NMR (CDCl$_3$, 400 MHz): δ1.16 (3H, t, J=7.0 Hz), 1.25 (3H, t, J=7.0 Hz), 2.63 (1H, dd, J=4.7, 15.3 Hz), 2.77 (1H, dd, J=9.1, 15.3 Hz), 3.41 (2H, q, J=7.0 Hz), 4.15 (2H, q, J=7.0 Hz), 5.00 (2H, s), 5.03 (1H, dd, J=4.7, 9.1 Hz), 6.65 (1H, dd, J=2.7, 11.7 Hz), 6.76 (1H, dd, J=2.4, 8.4 Hz), 7.24-7.28 (1H, m), 7.35 (1H, t like, J=8.4 Hz), 7.48 (1H, d, J=8.4 Hz), 7.53 (1H, d, J=2.4 Hz)

(35E) 3-{4-[(3,4-Dichlorobenzyl)oxy]-2-fluorophenyl}-3-ethoxypropionic acid

Ethyl 3-{4-[(3,4-dichlorobenzyl)oxy]-2-fluorophenyl}-3-ethoxypropionate (223 mg, 0.537 mmol) produced in (35D) was dissolved in tetrahydrofuran (2.0 mL) and ethanol (2.0 mL), and a 2 N aqueous solution of sodium hydroxide (0.405 mL, 0.805 mmol) was added thereto at room temperature, and then, the resulting mixture was stirred at room temperature for 4 hours.

After water was added to the reaction solution, 2 N hydrochloric acid (0.405 mL, 0.805 mmol) was added thereto, and the organic matter was extracted with ethyl acetate. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=90:10 to 50:50 (v/v)), whereby the objective title compound was obtained as a white solid (150 mg, yield: 72%).

$^1$H NMR (CDCl$_3$, 400 MHz): δ1.21 (3H, t, J=7.1 Hz), 2.70 (1H, dd, J=4.0, 15.9 Hz), 2.83 (1H, dd, J=9.4, 15.9 Hz), 3.42-3.50 (2H, m), 5.00 (2H, s), 5.03 (1H, dd, J=4.0, 9.4 Hz), 6.66 (1H, dd, J=2.2, 11.8 Hz), 6.78 (1H, dd, J=2.2, 8.6 Hz), 7.24-7.29 (1H, m), 7.33 (1H, t like, J=8.6 Hz), 7.48 (1H, d, J=8.6 Hz), 7.53 (1H, d, J=2.2 Hz)

MS (FAB) m/z: 409 (M+Na)$^+$

Example 36

3-[4-(3,4-Dichlorobenzyloxy)-2-methoxyphenyl]-3-ethoxypropionic acid (Illustrative Compound No: 1-71)

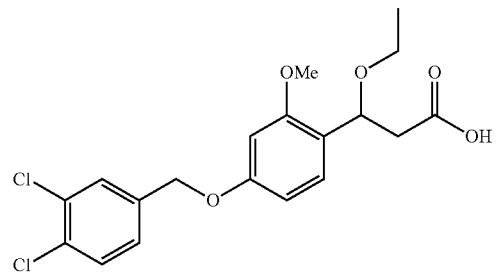

(36A) 4-(3,4-Dichlorobenzyloxy)-2-methoxybenzaldehyde

4-Hydroxy-2-methoxybenzaldehyde (408 mg, 2.68 mmol), 3,4-dichlorobenzyl alcohol (665 mg, 3.76 mmol), and triphenylphosphine (980 mg, 3.74 mmol) were dissolved in tetrahydrofuran (8 mL), and a diethyl azodicarboxylate toluene solution (2.2 M, 1.71 mL, 3.76 mmol) was slowly added dropwise thereto at room temperature, and then, the resulting mixture was stirred under a nitrogen atmosphere at room temperature for 2 hours. The solvent in the reaction solution was distilled off under reduced pressure, and the resulting residue was purified by silica gel column chromatography (hexane:ethyl acetate=100:0 to 90:10 (v/v)), whereby the objective title compound was obtained as a white solid (801 mg, yield: 96%).

$^1$H NMR (CDCl$_3$, 400 MHz): δ3.91 (3H, s), 5.08 (2H, s), 6.53 (1H, m), 6.58 (1H, m), 7.42 (1H, m), 7.48 (1H, d, J=8.2 Hz), 7.55 (1H, m), 7.82 (1H, d, J=8.6 Hz), 10.3 (1H, s)

(36B) Ethyl 3-[4-(3,4-dichlorobenzyloxy)-2-methoxyphenyl]-3-hydroxypropionate

Ethyl acetate (0.50 mL, 5.1 mmol) was dissolved in tetrahydrofuran (15 mL), and a lithium diisopropylamide tetrahydrofuran solution (1.01 M, 5.0 mL, 5.1 mmol) was added thereto at −78° C., and then, the resulting mixture was stirred under a nitrogen atmosphere at −78° C. for 1 hour. Thereafter, a tetrahydrofuran solution of 4-(3,4-dichlorobenzyloxy)-2-methoxybenzaldehyde (801 mg, 2.57 mmol) produced in (36A) was added thereto at −78° C., and the resulting mixture was stirred under a nitrogen atmosphere at −78° C. for 30 minutes.

To the reaction solution, a saturated aqueous solution of ammonium chloride was added at −78° C., and the organic matter was extracted with diethyl ether. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=80:20 to 50:50 (v/v)), whereby the objective title compound was obtained as a white solid (1.01 g, yield: 98%).

$^1$H NMR (CDCl$_3$, 400 MHz): δ1.23 (3H, t, J=7.0 Hz), 2.67 (1H, dd, J=9.1, 16.0 Hz), 2.76 (1H, dd, J=3.9, 16.0 Hz), 3.40 (1H, br), 3.79 (3H, s), 4.14 (2H, q, J=7.0 Hz), 4.97 (2H, s), 5.26 (1H, m), 6.46-6.50 (2H, m), 7.23 (1H, dd, J=2.0, 8.2 Hz), 7.29 (1H, d, J=8.2 Hz), 7.42 (1H, d, J=8.2 Hz), 7.51 (1H, d, J=2.0 Hz)

(36C) Ethyl 3-[4-(3,4-dichlorobenzyloxy)-2-methoxyphenyl]-3-ethoxypropionate

Ethyl 3-[4-(3,4-dichlorobenzyloxy)-2-methoxyphenyl]-3-hydroxypropionate (400 mg, 1.00 mmol) produced in (36B) was dissolved in toluene (8 mL), and ethyl iodide (0.32 mL, 4.00 mmol) and silver oxide (I) (703 mg, 3.03 mmol) were added thereto at room temperature, and then, the resulting mixture was stirred under a nitrogen atmosphere at 110° C. for 2 hours.

After cooling to room temperature, the reaction solution was filtered, and the solvent was distilled off under reduced pressure, whereby a crude product was obtained. This crude product was purified by silica gel column chromatography (hexane:ethyl acetate=97:3 to 90:10 (v/v)), whereby the objective title compound was obtained as a colorless oily substance (324 mg, yield: 77%).

$^1$H NMR (CDCl$_3$, 400 MHz): δ1.14 (3H, t, J=7.0 Hz), 1.24 (3H, t, J=7.0 Hz), 2.56 (1H, dd, J=9.4, 15.2 Hz), 2.63 (1H, dd, J=3.9, 15.2 Hz), 3.32-3.46 (2H, m), 3.78 (3H, s), 4.11-4.18 (2H, m), 4.98 (2H, s), 5.05 (1H, dd, J=3.9, 9.4 Hz), 6.48-6.52 (2H, m), 7.24 (1H, dd, J=2.0, 8.2 Hz), 7.29 (1H, d, J=8.2 Hz), 7.44 (1H, d, J=8.2 Hz), 7.53 (1H, d, J=2.0 Hz)

(36D) 3-[4-(3,4-Dichlorobenzyloxy)-2-methoxyphenyl]-3-ethoxypropionic acid

Ethyl 3-[4-(3,4-dichlorobenzyloxy)-2-methoxyphenyl]-3-ethoxypropionate (320 mg, 0.313 mmol) produced in (36C) was dissolved in tetrahydrofuran (3 mL) and ethanol (3 mL), and a 2 N aqueous solution of sodium hydroxide (1 mL) was added thereto at room temperature, and then, the resulting mixture was stirred at room temperature for 6 hours.

2 N Hydrochloric acid was added to the reaction solution, and the organic matter was extracted with ethyl acetate. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=80:20 to 60:40 (v/v)), whereby the objective title compound was obtained as a white solid (279 mg, yield: 84%).

$^1$H NMR (CDCl$_3$, 400 MHz): δ1.20 (3H, t, J=7.0 Hz), 2.64 (1H, dd, J=3.9, 15.6 Hz), 2.70 (1H, dd, J=9.4, 15.6 Hz), 3.38-3.54 (2H, m), 3.79 (3H, s), 4.99 (2H, s), 5.07 (1H, dd, J=3.9, 9.4 Hz), 6.49-6.54 (2H, m), 7.24 (1H, m), 7.27 (1H, d, J=8.2 Hz), 7.45 (1H, d, J=8.2 Hz), 7.53 (1H, d, J=2.0 Hz)

Example 37

3-[4-(3,4-Dichlorobenzyloxy)-3-methylphenyl]-3-ethoxypropionic acid (Illustrative Compound No: 1-72)

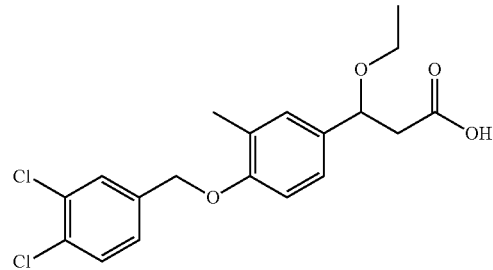

(37A) 4-(3,4-Dichlorobenzyloxy)-3-methylbenzaldehyde

4-Hydroxy-3-methylbenzaldehyde (365 mg, 2.68 mmol), 3,4-dichlorobenzyl alcohol (665 mg, 3.76 mmol), and triphenylphosphine (980 mg, 3.74 mmol) were dissolved in tetrahydrofuran (8 mL), and a diethyl azodicarboxylate toluene solution (2.2 M, 1.71 mL, 3.76 mmol) was slowly added dropwise thereto at room temperature, and then, the resulting mixture was stirred under a nitrogen atmosphere at room temperature for 2 hours. The solvent was distilled off under reduced pressure, and the resulting residue was purified by silica gel column chromatography (hexane:ethyl acetate=100:0 to 95:5 (v/v)), whereby the objective title compound was obtained as a white solid (542 mg, yield: 69%).

$^1$H NMR (CDCl$_3$, 400 MHz): δ2.31 (3H, s), 5.10 (2H, s), 6.92 (1H, d, J=8.2 Hz), 7.26 (1H, m), 7.46 (1H, d, J=8.2 Hz), 7.52 (1H, m), 7.68 (1H, m), 7.71 (1H, s), 9.85 (1H, s)

(37B) Ethyl 3-[4-(3,4-dichlorobenzyloxy)-3-methylphenyl]-3-hydroxypropionate Ethyl acetate (0.36 mL, 3.7 mmol) was dissolved in tetrahydrofuran (15 mL), and a lithium diisopropylamide tetrahydrofuran solution (1.01 M, 3.7 mL, 3.7 mmol) was added thereto at −78° C., and then, the resulting mixture was stirred under a nitrogen atmosphere at −78° C. for 1 hour. Thereafter, a tetrahydrofuran solution of 4-(3,4-dichlorobenzyloxy)-3-methylbenzaldehyde (542 mg, 1.84 mmol) produced in (37A) was added thereto at −78° C., and the resulting mixture was stirred under a nitrogen atmosphere at −78° C. for 30 minutes.

To the reaction solution, a saturated aqueous solution of ammonium chloride was added at −78° C., and the organic matter was extracted with diethyl ether. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=80:20 to 60:40 (v/v)), whereby the objective title compound was obtained as a white solid (610 mg, yield: 83%).

$^1$H NMR (CDCl$_3$, 400 MHz): δ1.27 (3H, t, J=7.0 Hz), 2.28 (3H, s), 2.68 (1H, dd, J=3.5, 16.4 Hz), 2.75 (1H, dd, J=9.4, 16.4 Hz), 3.17 (1H, d, J=3.5 Hz), 4.19 (2H, q, J=7.0 Hz), 5.02 (2H, s), 5.06 (1H, ddd, J=3.5, 3.5, 9.4 Hz), 6.79 (1H, d, J=8.2 Hz), 7.15 (1H, m), 7.20 (1H, m), 7.27 (1H, m), 7.45 (1H, d, J=8.2 Hz), 7.53 (1H, d, J=2.0 Hz)

(37C) Ethyl 3-[4-(3,4-dichlorobenzyloxy)-3-methylphenyl]-3-ethoxypropionate

Ethyl 3-[4-(3,4-dichlorobenzyloxy)-3-methylphenyl]-3-hydroxypropionate (610 mg, 1.59 mmol) produced in (37B) was dissolved in toluene (8 mL), and ethyl iodide (0.50 mL, 6.3 mmol) and silver oxide (I) (1.11 g, 4.79 mmol) were added thereto at room temperature, and then, the resulting mixture was stirred under a nitrogen atmosphere at 110° C. for 2 hours. After cooling to room temperature, the reaction solution was filtered, and the solvent was distilled off under reduced pressure, whereby a crude product was obtained. This crude product was purified by silica gel column chromatography (hexane:ethyl acetate=95:5 (v/v)), whereby the objective title compound was obtained as a colorless oily substance (533 mg, yield: 82%).

$^1$H NMR (CDCl$_3$, 400 MHz): δ1.14 (3H, t, J=7.0 Hz), 1.23 (3H, t, J=7.0 Hz), 2.28 (3H, s), 2.54 (1H, dd, J=5.1, 14.9 Hz), 2.78 (1H, dd, J=9.0, 14.9 Hz), 3.29-3.42 (2H, m), 4.13 (2H, q, J=7.0 Hz), 4.66 (1H, dd, J=5.1, 9.0 Hz), 5.02 (2H, s), 6.78 (1H, d, J=8.2 Hz), 7.11 (1H, m), 7.15 (1H, m), 7.27 (1H, m), 7.46 (1H, d, J=8.2 Hz), 7.53 (1H, d, J=2.0 Hz)

(37D) 3-[4-(3,4-Dichlorobenzyloxy)-3-methylphenyl]-3-ethoxypropionic acid

Ethyl 3-[4-(3,4-dichlorobenzyloxy)-3-methylphenyl]-3-ethoxypropionate (530 mg, 1.44 mmol) produced in (37C) was dissolved in tetrahydrofuran (6 mL) and ethanol (6 mL), and a 2 N aqueous solution of sodium hydroxide (2 mL) was added thereto at room temperature, and then, the resulting mixture was stirred at room temperature for 6 hours.

2 N Hydrochloric acid was added to the reaction solution, and the organic matter was extracted with ethyl acetate. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=80:20 to 60:40 (v/v)), whereby the objective title compound was obtained as a white solid (431 mg, yield: 78%).

$^1$H NMR (CDCl$_3$, 400 MHz): δ1.16 (3H, t, J=7.0 Hz), 2.27 (3H, s), 2.60 (1H, dd, J=4.3, 15.6 Hz), 2.81 (1H, dd, J=9.4, 15.6 Hz), 3.30-3.45 (2H, m), 4.63 (1H, dd, J=4.3, 9.4 Hz), 5.00 (2H, s), 6.78 (1H, d, J=8.2 Hz), 7.09 (1H, m), 7.12 (1H, m), 7.25 (1H, m), 7.44 (1H, d, J=8.2 Hz), 7.52 (1H, d, J=2.0 Hz)

Example 38

3-[4-(3,4-Dichlorobenzyloxy)-3-nitrophenyl]-3-ethoxypropionic acid (Illustrative Compound No: 1-73)

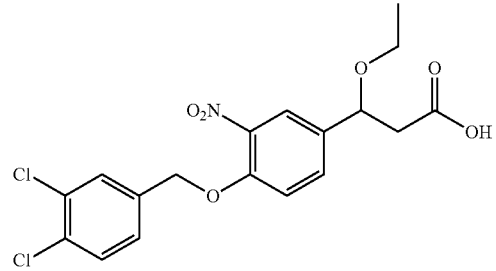

(38A) 4-(3,4-Dichlorobenzyloxy)-3-nitrobenzaldehyde

4-Hydroxy-3-nitrobenzaldehyde (448 mg, 2.68 mmol), 3,4-dichlorobenzyl alcohol (665 mg, 3.76 mmol), and triphenylphosphine (980 mg, 3.74 mmol) were dissolved in tetrahydrofuran (8 mL), and a diethyl azodicarboxylate toluene solution (2.2 M, 1.71 mL, 3.76 mmol) was slowly added dropwise thereto at room temperature, and then, the resulting mixture was stirred under a nitrogen atmosphere at room temperature for 2 hours. The solvent was distilled off under reduced pressure, and the resulting residue was washed with hexane/dichloromethane (6/1 (v/v)), whereby the objective title compound was obtained as a yellow solid (351 mg, yield: 40%).

$^1$H NMR (CDCl$_3$, 400 MHz): δ5.26 (2H, s), 7.22 (1H, d, J=8.6 Hz), 7.31 (1H, dd, J=2.0, 8.6 Hz), 7.48 (1H, d, J=8.6 Hz), 7.55 (1H, d, J=2.0 Hz), 8.06 (1H, dd, J=2.0, 8.6 Hz), 8.38 (1H, d, J=2.0 Hz), 9.93 (1H, s)

(38B) Ethyl 3-[4-(3,4-dichlorobenzyloxy)-3-nitrophenyl]-3-hydroxypropionate

Ethyl acetate (0.21 mL, 2.1 mmol) was dissolved in tetrahydrofuran (10 mL), and a lithium diisopropylamide tetrahydrofuran solution (1.01 M, 2.1 mL, 2.1 mmol) was added thereto at −78° C., and then, the resulting mixture was stirred under a nitrogen atmosphere at −78° C. for 1 hour. Thereafter, a tetrahydrofuran solution of 4-(3,4-dichlorobenzyloxy)-3-nitrobenzaldehyde (351 mg, 1.08 mmol) produced in (38A) was added thereto at −78° C., and the resulting mixture was stirred under a nitrogen atmosphere at −78° C. for 30 minutes.

To the reaction solution, a saturated aqueous solution of ammonium chloride was added at −78° C., and the organic matter was extracted with diethyl ether. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=70: 30 to 50:50 (v/v)), whereby the objective title compound was obtained as a light yellow solid (390 mg, yield: 87%).

¹H NMR (CDCl₃, 400 MHz): δ1.28 (3H, t, J=7.0 Hz), 2.70-2.74 (2H, m), 3.55 (1H, d, J=3.5 Hz), 4.20 (2H, q, J=7.0 Hz), 5.13 (1H, m), 5.17 (2H, s), 7.07 (1H, d, J=8.2 Hz), 7.32 (1H, dd, J=2.0, 8.2 Hz), 7.47 (1H, d, J=8.2 Hz), 7.54-7.58 (2H, m), 7.92 (1H, d, J=2.0 Hz)

(38C) Ethyl 3-[4-(3,4-dichlorobenzyloxy)-3-nitrophenyl]-3-ethoxypropionate

Ethyl 3-[4-(3,4-dichlorobenzyloxy)-3-nitrophenyl]-3-hydroxypropionate (390 mg, 0.941 mmol) produced in (38B) was dissolved in toluene (8 mL), and ethyl iodide (0.30 mL, 3.8 mmol) and silver oxide (I) (662 mg, 2.86 mmol) were added thereto at room temperature, and then, the resulting mixture was stirred under a nitrogen atmosphere at 110° C. for 2 hours.

After cooling to room temperature, the reaction solution was filtered, and the solvent was distilled off under reduced pressure, whereby a crude product was obtained. This crude product was purified by silica gel column chromatography (hexane:ethyl acetate=90:10 to 80:20 (v/v)), whereby the objective title compound was obtained as a yellow oily substance (232 mg, yield: 56%).

¹H NMR (CDCl₃, 400 MHz): δ1.15 (3H, t, J=7.0 Hz), 1.22 (3H, t, J=7.0 Hz), 2.54 (1H, dd, J=5.5, 15.6 Hz), 2.78 (1H, dd, J=8.6, 15.6 Hz), 3.36 (2H, q, J=7.0 Hz), 4.12 (2H, q, J=7.0 Hz), 4.72 (1H, dd, J=5.5, 8.6 Hz), 5.15 (2H, s), 7.05 (1H, d, J=8.6 Hz), 7.31 (1H, dd, J=2.0, 8.6 Hz), 7.46 (1H, d, J=8.6 Hz), 7.50 (1H, dd, J=2.0, 8.6 Hz), 7.54 (1H, d, J=2.0 Hz), 7.85 (1H, d, J=2.0 Hz)

(38D) 3-[4-(3,4-Dichlorobenzyloxy)-3-nitrophenyl]-3-ethoxypropionic acid

Ethyl 3-[4-(3,4-dichlorobenzyloxy)-3-nitrophenyl]-3-ethoxypropionate (70 mg, 0.18 mmol) produced in (38C) was dissolved in tetrahydrofuran (2 mL) and ethanol (2 mL), and a 2 N aqueous solution of sodium hydroxide (1 mL) was added thereto at room temperature, and then, the resulting mixture was stirred at room temperature for 6 hours.

2 N Hydrochloric acid was added to the reaction solution, and the organic matter was extracted with ethyl acetate. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=60:40 to 30:70 (v/v)), whereby the objective title compound was obtained as a light yellow solid (51 mg, yield: 70%).

¹H NMR (CDCl₃, 400 MHz): δ1.19 (3H, t, J=7.0 Hz), 2.64 (1H, dd, J=5.1, 16.0 Hz), 2.85 (1H, dd, J=9.0, 16.0 Hz), 3.41 (2H, q, J=7.0 Hz), 4.74 (1H, dd, J=5.1, 9.0 Hz), 5.18 (2H, s), 7.09 (1H, d, J=8.2 Hz), 7.33 (1H, dd, J=2.0, 8.6 Hz), 7.48 (1H, d, J=8.2 Hz), 7.52 (1H, dd, J=2.0, 8.6 Hz), 7.56 (1H, d, J=2.0 Hz), 7.88 (1H, d, J=2.0 Hz)

Example 39

3-[2-Chloro-4-(3,4-dichlorobenzyloxy)phenyl]-3-ethoxypropionic acid (Illustrative Compound No: 1-74)

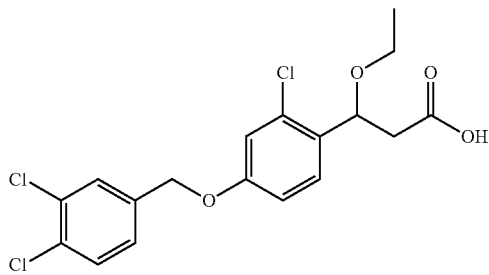

(39A) 2-Chloro-4-(3,4-dichlorobenzyloxy)benzaldehyde

2-Chloro-4-hydroxybenzaldehyde (324 mg, 2.07 mmol), 3,4-dichlorobenzyl alcohol (513 mg, 2.90 mmol), and triphenylphosphine (760 mg, 2.90 mmol) were dissolved in tetrahydrofuran (8 mL), and a diethyl azodicarboxylate toluene solution (2.2 M, 1.32 mL, 2.90 mmol) was slowly added dropwise thereto at room temperature, and then, the resulting mixture was stirred under a nitrogen atmosphere at room temperature for 2 hours. The solvent in the reaction solution was distilled off under reduced pressure, and the resulting residue was washed with hexane/dichloromethane (6/1 (v/v)), whereby the objective title compound was obtained as a white solid (244 mg, yield: 37%).

¹H NMR (CDCl₃, 400 MHz): δ5.06 (2H, s), 6.93 (1H, dd, J=2.3, 8.6 Hz), 6.99 (1H, d, J=2.3 Hz), 7.24 (1H, m), 7.47 (1H, d, J=8.6 Hz), 7.52 (1H, d, J=2.3 Hz), 7.90 (1H, d, J=8.6 Hz), 10.3 (1H, s)

(39B) Ethyl 3-[2-chloro-4-(3,4-dichlorobenzyloxy)phenyl]-3-hydroxypropionate Ethyl acetate (0.15 mL, 1.5 mmol) was dissolved in tetrahydrofuran (15 mL), and a lithium diisopropylamide tetrahydrofuran solution (1.01 M, 1.5 mL, 1.5 mmol) was added thereto at −78° C., and then, the resulting mixture was stirred under a nitrogen atmosphere at −78° C. for 1 hour. Thereafter, a tetrahydrofuran solution of 2-chloro-4-(3,4-dichlorobenzyloxy)benzaldehyde (244 mg, 0.773 mmol) produced in (39A) was added thereto at −78° C., and the resulting mixture was stirred under a nitrogen atmosphere at −78° C. for 30 minutes.

To the reaction solution, a saturated aqueous solution of ammonium chloride was added at −78° C., and the organic matter was extracted with diethyl ether. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=80: 20 to 60:40 (v/v)), whereby the objective title compound was obtained as a white solid (280 mg, yield: 90%).

¹H NMR (CDCl₃, 400 MHz): δ1.26 (3H, t, J=7.0 Hz), 2.56 (1H, dd, J=9.8, 16.8 Hz), 2.79 (1H, dd, J=2.7, 16.8 Hz), 3.50 (1H, d, J=3.5 Hz), 4.18 (2H, q, J=7.0 Hz), 4.97 (2H, s), 5.41 (1H, ddd, J=2.7, 3.5, 9.8 Hz), 6.87 (1H, dd, J=2.3, 8.6 Hz), 6.92 (1H, d, J=2.3 Hz), 7.22 (1H, dd, J=2.3, 8.6 Hz), 7.44 (1H, d, J=8.6 Hz), 7.50 (1H, m), 7.51 (1H, d, J=8.6 Hz)

(39C) Ethyl 3-[2-chloro-4-(3,4-dichlorobenzyloxy)phenyl]-3-ethoxypropionate

Ethyl 3-[2-chloro-4-(3,4-dichlorobenzyloxy)phenyl]-3-hydroxypropionate (280 mg, 0.694 mmol) produced in (39B) was dissolved in toluene (8 mL), and ethyl iodide (0.23 mL, 2.9 mmol) and silver oxide (I) (488 mg, 2.11 mmol) were added thereto at room temperature, and then, the resulting mixture was stirred under a nitrogen atmosphere at 110° C. for 2 hours. After cooling to room temperature, the reaction solution was filtered, and the solvent was distilled off under reduced pressure, whereby a crude product was obtained. This crude product was purified by silica gel column chromatography (hexane:ethyl acetate=95:5 (v/v)), whereby the objective title compound was obtained as a colorless oily substance (248 mg, yield: 83%).

¹H NMR (CDCl₃, 400 MHz): δ1.14 (3H, t, J=7.0 Hz), 1.24 (3H, t, J=7.0 Hz), 2.57 (1H, dd, J=9.4, 15.2 Hz), 2.63 (1H, dd, J=3.9, 15.2 Hz), 3.38 (2H, q, J=7.0 Hz), 4.10-4.20 (2H, m), 4.97 (2H, s), 5.12 (1H, dd, J=3.9, 9.4 Hz), 6.87 (1H, dd, J=2.3, 8.6 Hz), 6.92 (1H, d, J=2.3 Hz), 7.23 (1H, m), 7.40 (1H, d, J=8.6 Hz), 7.44 (1H, d, J=8.6 Hz), 7.50 (1H, d, J=2.3 Hz)

(39D) 3-[2-Chloro-4-(3,4-dichlorobenzyloxy)phenyl]-3-ethoxypropionic acid

Ethyl 3-[2-chloro-4-(3,4-dichlorobenzyloxy)phenyl]-3-ethoxypropionate (240 mg, 0.619 mmol) produced in (39C) was dissolved in tetrahydrofuran (3 mL) and ethanol (3 mL), and a 2 N aqueous solution of sodium hydroxide (1 mL) was added thereto at room temperature, and then, the resulting mixture was stirred at room temperature for 6 hours.

2 N Hydrochloric acid was added to the reaction solution, and the organic matter was extracted with ethyl acetate. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=80:20 to 60:40 (v/v)), whereby the objective title compound was obtained as a white solid (203 mg, yield: 81%).

¹H NMR (CDCl₃, 400 MHz): δ1.20 (3H, t, J=7.0 Hz), 2.64 (1H, dd, J=9.8, 16.0 Hz), 2.73 (1H, dd, J=3.5, 16.0 Hz), 3.44 (2H, q, J=7.0 Hz), 5.00 (2H, s), 5.15 (1H, dd, J=3.5, 9.8 Hz), 6.91 (1H, dd, J=2.3, 8.6 Hz), 6.96 (1H, d, J=2.3 Hz), 7.25 (1H, m), 7.43 (1H, d, J=8.6 Hz), 7.47 (1H, d, J=8.6 Hz), 7.53 (1H, d, J=2.3 Hz)

Example 40

3-[4-(3,4-Dichlorobenzyloxy)-3-fluorophenyl]-3-ethoxypropionic acid (Illustrative Compound No: 1-75)

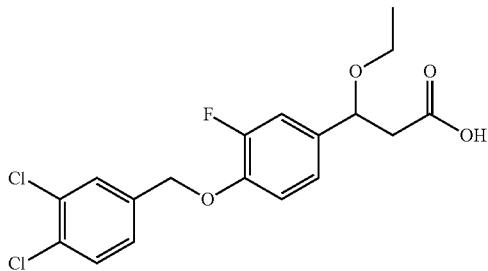

(40A)
4-(3,4-Dichlorobenzyloxy)-3-fluorobenzaldehyde

3-Fluoro-4-hydroxybenzaldehyde (400 mg, 2.85 mmol), 3,4-dichlorobenzyl alcohol (665 mg, 3.76 mmol), and triphenylphosphine (980 mg, 3.74 mmol) were dissolved in tetrahydrofuran (8 mL), and a diethyl azodicarboxylate toluene solution (2.2 M, 1.71 mL, 3.76 mmol) was slowly added dropwise thereto at room temperature, and then, the resulting mixture was stirred under a nitrogen atmosphere at room temperature for 2 hours. The solvent in the reaction solution was distilled off under reduced pressure, and the resulting residue was purified by silica gel column chromatography (hexane:ethyl acetate=100:0 to 95:5 (v/v)), whereby the objective title compound was obtained as a colorless oily substance (680 mg, yield: 80%).

¹H NMR (CDCl₃, 400 MHz): δ5.16 (2H, s), 7.08 (1H, d, J=8.2 Hz), 7.18 (1H, dd, J=8.2, 2.0 Hz), 7.27 (1H, dd, J=8.2, 2.0 Hz), 7.41 (1H, d, J=8.2 Hz), 7.47 (1H, m), 7.54 (1H, d, J=2.0 Hz), 9.85 (1H, s)

(40B) Ethyl 3-[4-(3,4-dichlorobenzyloxy)-3-fluorophenyl]-3-hydroxypropionate

Ethyl acetate (0.15 mL, 1.5 mmol) was dissolved in tetrahydrofuran (5 mL), and a lithium diisopropylamide tetrahydrofuran solution (1.01 M, 1.5 mL, 1.5 mmol) was added thereto at −78° C., and then, the resulting mixture was stirred under a nitrogen atmosphere at −78° C. for 1 hour. Thereafter, a tetrahydrofuran solution of 4-(3,4-dichlorobenzyloxy)-3-fluorobenzaldehyde (208 mg, 0.740 mmol) produced in (40A) was added thereto at −78° C., and the resulting mixture was stirred under a nitrogen atmosphere at −78° C. for 30 minutes.

To the reaction solution, a saturated aqueous solution of ammonium chloride was added at −78° C., and the organic matter was extracted with diethyl ether. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=80:20 to 70:30 (v/v)), whereby the objective title compound was obtained as a colorless oily substance (251 mg, yield: 84%).

¹H NMR (CDCl₃, 400 MHz): δ1.26 (3H, t, J=7.0 Hz), 2.63-2.73 (2H, m), 3.38 (1H, d, J=3.1 Hz), 4.18 (2H, q, J=7.0 Hz), 5.05 (1H, m), 5.07 (2H, s), 6.92 (1H, dd, J=8.2, 8.2 Hz), 7.04 (1H, m), 7.16 (1H, dd, J=2.0, 12.1 Hz), 7.27 (1H, dd, J=2.0, 8.2 Hz), 7.45 (1H, d, J=8.2 Hz), 7.53 (1H, d, J=2.0 Hz)

(40C) Ethyl 3-[4-(3,4-dichlorobenzyloxy)-3-fluorophenyl]-3-ethoxypropionate

Ethyl 3-[4-(3,4-dichlorobenzyloxy)-3-fluorophenyl]-3-hydroxypropionate (251 mg, 0.622 mmol) produced in (40B) was dissolved in toluene (8 mL), and ethyl iodide (0.50 mL, 6.3 mmol) and silver oxide (I) (1.11 g, 4.79 mmol) were added thereto at room temperature, and then, the resulting mixture was stirred under a nitrogen atmosphere at 110° C. for 2 hours.

After cooling to room temperature, the reaction solution was filtered, and the solvent was distilled off under reduced pressure. The resulting residue was dissolved in toluene (8 mL) again, and ethyl iodide (4.92 mL, 61.5 mmol) and silver oxide(I) (12.0 g, 61.5 mmol) were added thereto at room temperature, and then, the resulting mixture was stirred under a nitrogen atmosphere at 110° C. for 2 hours. After cooling to room temperature, the reaction solution was filtered, and the solvent was distilled off under reduced pressure. The resulting residue was purified by silica gel column chromatography (hexane:ethyl acetate=100:0 to 95:5 (v/v)), whereby the objective title compound was obtained as a colorless oily substance (125 mg, yield: 48%).

$^1$H NMR (CDCl$_3$, 400 MHz): δ1.15 (3H, t, J=7.0 Hz), 1.23 (3H, t, J=7.0 Hz), 2.53 (1H, dd, J=5.1, 15.2 Hz), 2.76 (1H, dd, J=8.6, 15.2 Hz), 3.30-3.42 (2H, m), 4.13 (2H, q, J=7.0 Hz), 4.67 (1H, dd, J=5.1, 8.6 Hz), 5.07 (2H, s), 6.92 (1H, dd, J=8.2, 8.2 Hz), 7.01 (1H, m), 7.12 (1H, dd, J=2.0, 11.7 Hz), 7.28 (1H, dd, J=2.0, 8.2 Hz), 7.46 (1H, d, J=8.2 Hz), 7.54 (1H, d, J=2.0 Hz)

(40D) 3-[4-(3,4-Dichlorobenzyloxy)-3-fluorophenyl]-3-ethoxypropionic acid

Ethyl 3-[4-(3,4-dichlorobenzyloxy)-3-fluorophenyl]-3-ethoxypropionate (125 mg, 0.301 mmol) produced in (40C) was dissolved in tetrahydrofuran (1 mL) and ethanol (1 mL), and a 2 N aqueous solution of sodium hydroxide (0.5 mL) was added thereto at room temperature, and then, the resulting mixture was stirred at room temperature for 6 hours. 2 N Hydrochloric acid was added to the reaction solution, and the organic matter was extracted with ethyl acetate. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=80:20 to 50:50 (v/v)), whereby the objective title compound was obtained as a white solid (93 mg, yield: 80%).

$^1$H NMR (CDCl$_3$, 400 MHz): δ1.18 (3H, t, J=7.0 Hz), 2.61 (1H, dd, J=4.3, 15.6 Hz), 2.80 (1H, dd, J=9.0, 15.6 Hz), 3.33-3.45 (2H, m), 4.66 (1H, dd, J=4.3, 9.0 Hz), 5.08 (2H, s), 6.93 (1H, dd, J=8.2, 8.2 Hz), 7.01 (1H, m), 7.12 (1H, dd, J=2.0, 11.7 Hz), 7.28 (1H, dd, J=2.0, 8.2 Hz), 7.46 (1H, d, J=8.2 Hz), 7.54 (1H, d, J=2.0 Hz)

Example 41

(3S)-3-[4-(2,3-Dihydro-1H-inden-2-yloxy)phenyl]-3-ethoxypropionic acid (Illustrative Compound No: 1-178)

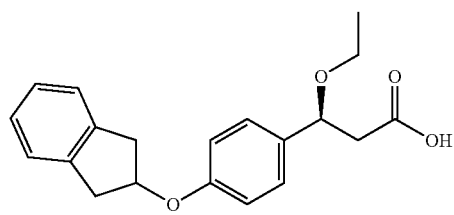

(41A) Methyl (3S)-3-[4-(tert-butyldimethylsilyloxy)phenyl]-3-hydroxypropionate

Triethylamine (21.6 g, 213 mmol) was cooled to 0° C., and formic acid (11.5 g, 250 mmol) was slowly added dropwise thereto. Methyl 3-[4-(tert-butyldimethylsilyloxy)phenyl]-3-oxopropionate (22.0 g, 71.3 mmol) produced in accordance with the description of WO 2003020690 (A1) and chloro[(1S, 2S)—N-(p-toluenesulfonyl)-1,2-diphenylethanediamine](p-cymene)-ruthenium(II) (0.90 g, 1.61 mmol) were added thereto at room temperature, and then, the resulting mixture was stirred under a nitrogen atmosphere at 35° C. for 8 hours. The reaction solution was distilled off under reduced pressure, and the resulting residue was purified by silica gel column chromatography (hexane:ethyl acetate=90:10 to 80:20 (v/v)), whereby the objective title compound was obtained as a light yellow oily substance (12.8 g, yield: 58%).

Incidentally, the absolute configuration was confirmed according to the method described in Journal of the American Chemical Society, 1991, vol. 113 (11), pp. 4092-4096.

$^1$H NMR (CDCl$_3$, 400 MHz): δ0.19 (6H, s), 0.98 (9H, s), 2.68 (1H, dd, J=3.5, 16.4 Hz), 2.76 (1H, dd, J=9.4, 16.4 Hz), 3.08 (1H, d, J=3.1 Hz), 3.72 (3H, s), 5.08 (1H, ddd, J=3.1, 3.5, 9.4 Hz), 6.82 (2H, d, J=8.6 Hz), 7.23 (2H, d, J=8.6 Hz)

(41B) Methyl (3S)-3-[4-(tert-butyldimethylsilyloxy)phenyl]-3-ethoxypropionate

Methyl (3S)-3-[4-(tert-butyldimethylsilyloxy)phenyl]-3-hydroxypropionate (12.7 g, 40.9 mmol) produced in (41A) was dissolved in toluene (150 mL), and ethyl iodide (11.5 mL, 144 mmol) and silver oxide(I) (28.5 g, 123 mmol) were added thereto at room temperature, and then, the resulting mixture was stirred under a nitrogen atmosphere at 110° C. for 1.5 hours.

After cooling to room temperature, the reaction solution was filtered, and the solvent was distilled off under reduced pressure. The resulting residue was dissolved in toluene (150 mL) again, and ethyl iodide (11.5 mL, 144 mmol) and silver oxide(I) (28.5 g, 123 mmol) were added thereto at room temperature, and then, the resulting mixture was stirred under a nitrogen atmosphere at 110° C. for 1.5 hours. After cooling to room temperature, the reaction solution was filtered, and the solvent was distilled off under reduced pressure. The resulting residue was purified by silica gel column chromatography (hexane:ethyl acetate=100:0 to 90:10 (v/v)), whereby the objective title compound was obtained as a colorless oily substance (10.2 g, yield: 74%).

$^1$H NMR (CDCl$_3$, 400 MHz): δ0.20 (6H, s), 0.98 (9H, s), 1.13 (3H, t, J=7.0 Hz), 2.56 (1H, dd, J=4.7, 15.2 Hz), 2.80 (1H, dd, J=9.0, 15.2 Hz), 3.28-3.41 (2H, m), 3.67 (3H, s), 4.68 (1H, dd, J=4.7, 9.0 Hz), 6.80 (2H, d, J=8.6 Hz), 7.18 (2H, d, J=8.6 Hz)

(41C) Methyl (3S)-3-ethoxy-3-(4-hydroxyphenyl)propionate

Methyl (3S)-3-[4-(tert-butyldimethylsilyloxy)phenyl]-3-ethoxypropionate (10.2 g, 30.1 mmol) produced in (41B) was dissolved in tetrahydrofuran (150 mL). The reaction solution was cooled to 0° C., and a tetrabutyl ammonium fluoride tetrahydrofuran solution (1.0 M, 36.0 mL, 36.0 mmol) was added dropwise thereto, and then, the resulting mixture was stirred at 0° C. for 1.5 hours. To the reaction solution, a saturated aqueous solution of ammonium chloride was added, and the organic matter was extracted with diethyl ether. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=80:20 to 60:40 (v/v)), whereby the objective title compound was obtained as a white solid (6.7 g, yield: 100%).

$^1$H NMR (CDCl$_3$, 500 MHz): δ1.16 (3H, t, J=7.0 Hz), 2.59 (1H, dd, J=4.9, 15.1 Hz), 2.84 (1H, dd, J=8.8, 15.1 Hz), 3.32-3.44 (2H, m), 3.70 (3H, s), 4.71 (1H, dd, J=4.9, 8.8 Hz), 5.01 (1H, br), 6.84 (2H, d, J=8.8 Hz), 7.24 (2H, d, J=8.8 Hz)

(41D) Methyl (3S)-3-[4-(2,3-dihydro-1H-inden-2-yloxy)phenyl]-3-ethoxypropionate

Methyl (3S)-3-ethoxy-3-(4-hydroxyphenyl)propionate (100 mg, 0.446 mmol) produced in (41C) and indan-2-ol (90 mg, 0.669 mmol) were dissolved in tetrahydrofuran (10 mL), and triphenylphosphine (178 mg, 0.680 mmol) and a 40% diethyl azodicarboxylate toluene solution (309 μL, 0.680 mmol) were added thereto at room temperature, and then, the resulting mixture was stirred under a nitrogen atmosphere at 50° C. for 4 hours. After the reaction solution was cooled to room temperature, the solvent was distilled off under reduced pressure, and the resulting residue was purified by silica gel column chromatography (hexane:ethyl acetate=100:0 to 95:5 (v/v)), whereby the objective title compound was obtained as a yellow oily substance (103 mg, yield: 68%).

$^1$H NMR (CDCl$_3$, 400 MHz): δ1.14 (3H, t, J=7.0 Hz), 2.58 (1H, dd, J=4.7, 15.3 Hz), 2.82 (1H, dd, J=8.9, 15.2 Hz), 3.20 (2H, dd, J=2.7, 16.4 Hz), 3.31-3.41 (4H, m), 3.68 (3H, s), 4.70 (1H, dd, J=5.1, 9.0 Hz), 5.14-5.19 (1H, m), 6.88 (2H, d, J=8.6 Hz), 7.19 (1H, d, J=5.9 Hz), 7.20 (1H, t, J=5.5 Hz), 7.24-7.26 (4H, m)

(41E) (3S)-3-[4-(2,3-Dihydro-1H-inden-2-yloxy)phenyl]-3-ethoxypropionic acid

Methyl (3S)-3-[4-(2,3-dihydro-1H-inden-2-yloxy)phenyl]-3-ethoxypropionate (103 mg, 0.303 mmol) produced in (41D) was dissolved in tetrahydrofuran (3 mL) and ethanol (3 mL), and a 1 N aqueous solution of sodium hydroxide (2 mL) was added thereto at room temperature, and then, the resulting mixture was stirred at room temperature for 4 hours. The solvent was distilled off under reduced pressure, and to the resulting residue, 1 N hydrochloric acid was added, and the organic matter was extracted with ethyl acetate. The organic layer was washed with a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 70:30 (v/v)), whereby the objective title compound was obtained as a white solid (88 mg, yield: 92%).

$^1$H NMR (CDCl$_3$, 400 MHz): δ1.18 (3H, t, J=7.0 Hz), 2.64 (1H, dd, J=4.3, 15.6 Hz), 2.85 (1H, dd, J=9.4, 15.6 Hz), 3.21 (2H, dd, J=2.7, 16.8 Hz), 3.33-3.44 (4H, m), 4.69 (1H, dd, J=4.3, 9.4 Hz), 5.14-5.19 (1H, m), 6.89 (2H, d, J=8.6 Hz), 7.18-7.26 (6H, m)

Example 42

(3S)-3-Ethoxy-3-{4-[(4-methoxy-2,3-dihydro-1H-inden-1-yl)oxy]phenyl}-propionic acid (Illustrative Compound No: 1-194)

(42A) Methyl (3S)-3-ethoxy-3-{4-[(4-methoxy-2,3-dihydro-1H-inden-1-yl)oxy]phenyl}-propionate Methyl (3S)-3-ethoxy-3-(4-hydroxyphenyl)propionate (100 mg, 0.446 mmol) produced in Example 41 (41C) and 4-methoxy-1-indanol (110 mg, 0.669 mmol) were dissolved in tetrahydrofuran (10 mL), and triphenylphosphine (178 mg, 0.680 mmol) and a 40% diethyl azodicarboxylate toluene solution (309 μL, 0.680 mmol) were added thereto at room temperature, and then, the resulting mixture was stirred under a nitrogen atmosphere at 50° C. for 4 hours. After the reaction solution was cooled to room temperature, the solvent was distilled off under reduced pressure, and the resulting residue was purified by silica gel column chromatography (hexane:ethyl acetate=100:0 to 95:5 (v/v)), whereby the objective title compound was obtained as a yellow oily substance (87 mg, yield: 53%).

$^1$H NMR (CDCl$_3$, 400 MHz): δ1.15 (3H, t, J=7.0 Hz), 2.21 (1H, ddd, J=4.6, 8.9, 18.3 Hz), 2.53-2.61 (2H, m), 2.82 (1H, dd, J=9.4, 15.2 Hz), 2.84-2.91 (1H, m), 3.08 (1H, ddd, J=5.1, 8.6, 16.4 Hz), 3.31-3.44 (2H, m), 3.69 (3H, s), 3.86 (3H, s), 4.72 (1H, dd, J=5.1, 9.4 Hz), 5.76 (1H, dd, J=4.3, 6.3 Hz), 6.82 (1H, d, J=7.8 Hz), 6.98 (2H, d, J=9.0 Hz), 7.05 (1H, d, J=7.4 Hz), 7.23-7.29 (3H, m)

(42B) (3S)-3-Ethoxy-3-{4-[(4-methoxy-2,3-dihydro-1H-inden-1-yl)oxy]phenyl}-propionic acid Methyl (3S)-3-ethoxy-3-{4-[(4-methoxy-2,3-dihydro-1H-inden-1-yl)oxy]phenyl}-propionate (87 mg, 0.235 mmol) produced in (42A) was dissolved in tetrahydrofuran (3 mL) and ethanol (3 mL), and a 1 N aqueous solution of sodium hydroxide (2 mL) was added thereto at room temperature, and then, the resulting mixture was stirred at room temperature for 4 hours. The solvent was distilled off under reduced pressure, and to the resulting residue, 1 N hydrochloric acid was added, and the organic matter was extracted with ethyl acetate. The organic layer was washed with a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 70:30 (v/v)), whereby the objective title compound was obtained as a white solid (67 mg, yield: 79%).

$^1$H NMR (CDCl$_3$, 400 MHz): δ1.19 (3H, t, J=7.1 Hz), 2.21 (1H, ddd, J=4.6, 8.9, 17.9 Hz), 2.53-2.60 (1H, m), 2.66 (1H, dd, J=4.3, 15.7 Hz), 2.83-2.91 (2H, m), 3.09 (1H, ddd, J=5.5, 9.0, 16.5 Hz), 3.35-3.48 (2H, m), 3.86 (3H, s), 4.71 (1H, dd, J=4.0, 9.4 Hz), 5.76 (1H, t, J=4.6 Hz), 6.82 (1H, d, J=7.8 Hz), 6.99 (2H, d, J=8.6 Hz), 7.05 (1H, d, J=7.9 Hz), 7.23-7.29 (3H, m)

Example 43

(3S)-3-{4-[(3,3-Dimethyl-2,3-dihydro-1H-inden-1-yl)oxy]phenyl}-3-ethoxypropionic acid (Illustrative Compound No: 1-186)

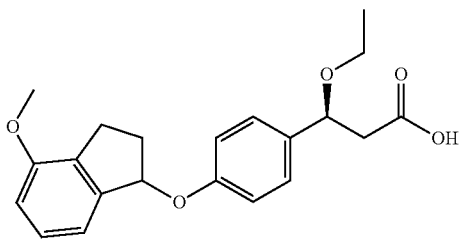

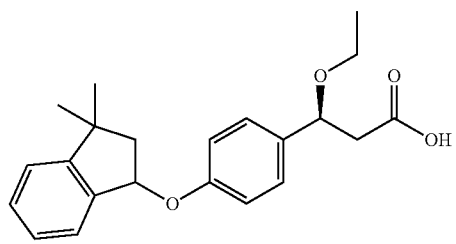

(43A) Methyl (3S)-3-{4-[(3,3-dimethyl-2,3-dihydro-1H-inden-1-yl)oxy]phenyl}-3-ethoxypropionate Methyl (3S)-3-ethoxy-3-(4-hydroxyphenyl)propionate (100 mg, 0.446 mmol) produced in Example 41 (41C) and 3,3-dimethylindan-1-ol (110 mg, 0.669 mmol) were dissolved in tetrahydrofuran (10 mL), and triphenylphosphine (178 mg, 0.680 mmol) and a 40% diethyl azodicarboxylate toluene solution (309 µL, 0.680 mmol) were added thereto at room temperature, and then, the resulting mixture was stirred under a nitrogen atmosphere at 50° C. for 4 hours. After the reaction solution was cooled to room temperature, the solvent was distilled off under reduced pressure, and the resulting residue was purified by silica gel column chromatography (hexane:ethyl acetate=100:0 to 95:5 (v/v)), whereby the objective title compound was obtained as a yellow oily substance (101 mg, yield: 62%).

$^1$H NMR (CDCl$_3$, 400 MHz): δ1.16 (3H, t, J=7.0 Hz), 1.32 (3H, s), 1.39 (3H, s), 2.12 (1H, dd, J=4.7, 13.7 Hz), 2.45 (1H, dd, J=7.0, 13.7 Hz), 2.61 (1H, dd, J=5.1, 15.3 Hz), 2.84 (1H, dd, J=9.0, 15.3 Hz), 3.31-3.43 (2H, m), 3.69 (3H, s), 4.72 (1H, dd, J=4.7, 9.0 Hz), 5.74 (1H, t, J=5.8 Hz), 6.99 (2H, d, J=8.6 Hz), 7.24-7.30 (4H, m), 7.36 (1H, t, J=7.5 Hz), 7.41 (1H, d, J=7.1 Hz)

(43B) (3S)-3-{4-[(3,3-Dimethyl-2,3-dihydro-1H-inden-1-yl)oxy]phenyl}-3-ethoxypropionic acid Methyl (3S)-3-{4-[(3,3-dimethyl-2,3-dihydro-1H-inden-1-yl)oxy]phenyl}-3-ethoxypropionate (101 mg, 0.274 mmol) produced in (43A) was dissolved in tetrahydrofuran (3 mL) and ethanol (3 mL), and a 1 N aqueous solution of sodium hydroxide (2 mL) was added thereto at room temperature, and then, the resulting mixture was stirred at room temperature for 4 hours. The solvent was distilled off under reduced pressure, and to the resulting residue, 1 N hydrochloric acid was added, and the organic matter was extracted with ethyl acetate. The organic layer was washed with a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 70:30 (v/v)), whereby the objective title compound was obtained as a colorless oily substance (44 mg, yield: 44%).

$^1$H NMR (CDCl$_3$, 400 MHz): δ1.21 (3H, t, J=7.0 Hz), 1.32 (3H, s), 1.40 (3H, s), 2.12 (1H, dd, J=4.7, 13.7 Hz), 2.46 (1H, dd, J=6.7, 13.3 Hz), 2.67 (1H, dd, J=4.3, 15.7 Hz), 2.87 (1H, dd, J=9.8, 16.0 Hz), 3.37-3.49 (2H, m), 4.71 (1H, dd, J=4.3, 9.7 Hz), 5.75 (1H, t, J=5.4 Hz), 7.01 (2H, d, J=9.0 Hz), 7.24-7.30 (4H, m), 7.37 (1H, t, J=7.4 Hz), 7.41 (1H, d, J=7.5 Hz)

Example 44

(3S)-3-Ethoxy-3-{4-[(4-ethyl-2,3-dihydro-1H-inden-1-yl)oxy]phenyl}-propionic acid (Illustrative Compound No: 1-187)

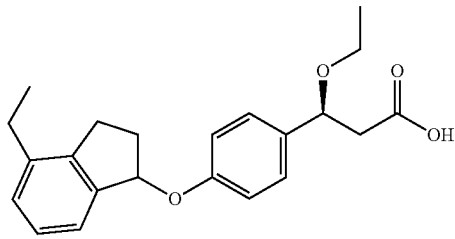

(44A) 4-Ethylindan-1-one

4-Bromoindan-1-one (600 mg, 2.84 mmol) was dissolved in toluene (10 mL), and ethyl boronate (105 mg, 8.52 mmol), silver oxide (I) (274 mg, 7.10 mmol), potassium carbonate (196 mg, 8.52 mmol), and [1,1'-bis(diphenylphosphino)ferrocene]palladium (II) dichloride dichloromethane complex (46 mg, 0.0568 mmol) were added thereto, and then, the resulting mixture was stirred under a nitrogen atmosphere at 100° C. for 4 hours. After cooling to room temperature, the reaction solution was filtered, and the solvent was distilled off under reduced pressure, whereby a crude product was obtained. This crude product was purified by silica gel column chromatography (hexane:ethyl acetate=100:0 to 80:20 (v/v)), whereby the objective title compound was obtained as a colorless oily substance (421 mg, yield: 92%).

$^1$H NMR (CDCl$_3$, 400 MHz): δ1.28 (3H, t, J=7.4 Hz), 2.70-2.75 (4H, m), 3.08 (2H, t, J=5.9 Hz), 7.34 (1H, t, J=7.4 Hz), 7.44 (1H, d, J=7.0 Hz), 7.62 (1H, d, J=7.4 Hz)

(44B) 4-Ethylindan-1-ol

4-Ethylindan-1-one (160 mg, 0.998 mmol) synthesized in (44A) was dissolved in tetrahydrofuran (5 mL), and the resulting solution was cooled to 0° C. Thereafter, sodium borohydride (57 mg, 1.50 mmol) was added thereto, and methanol (2 mL) was added dropwise thereto, and then, the resulting mixture was stirred at room temperature for 8 hours. Water was added to the reaction solution, and the organic matter was extracted with ethyl acetate. The organic layer was washed with water and a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 70:30 (v/v)), whereby the objective title compound was obtained as a yellow oily substance (162 mg, yield: 100%).

$^1$H NMR (CDCl$_3$, 400 MHz): δ1.22 (3H, t, J=7.4 Hz), 1.69 (1H, d, J=6.6 Hz), 1.92-2.00 (1H, m), 2.46-2.54 (1H, m), 2.63 (2H, q, J=7.4 Hz), 2.77 (1H, ddd, J=6.3, 8.6, 14.9 Hz), 3.04 (1H, ddd, J=5.1, 8.6, 16.0 Hz), 5.26 (1H, dd, J=6.2, 11.6 Hz), 7.12 (1H, d, J=7.4 Hz), 7.22 (1H, t, J=7.5 Hz), 7.27 (1H, d, J=8.6 Hz)

(44C) Methyl (3S)-3-ethoxy-3-{4-[(4-ethyl-2,3-dihydro-1H-inden-1-yl)oxy]phenyl}-propionate Methyl (3S)-3-ethoxy-3-(4-hydroxyphenyl)propionate (100 mg, 0.446 mmol) produced in Example 41 (41C) and 4-ethylindan-1-ol (109 mg, 0.669 mmol) synthesized in (44B) were dissolved in tetrahydrofuran (10 mL), and triphenylphosphine (178 mg, 0.680 mmol) and a 40% diethyl azodicarboxylate toluene solution (309 µL, 0.680 mmol) were added thereto at room temperature, and then, the resulting mixture was stirred under a nitrogen atmosphere at 50° C. for 4 hours.

After the reaction solution was cooled to room temperature, the solvent was distilled off under reduced pressure, and the resulting residue was purified by silica gel column chromatography (hexane:ethyl acetate=100:0 to 95:5 (v/v)), whereby the objective title compound was obtained as a colorless oily substance (93 mg, yield: 56%).

$^1$H NMR (CDCl$_3$, 400 MHz): δ1.15 (3H, t, J=7.0 Hz), 1.24 (3H, t, J=7.8 Hz), 2.23 (1H, ddd, J=4.3, 9.0, 18.3 Hz), 2.52-2.61 (2H, m), 2.66 (2H, q, J=7.4 Hz), 2.84 (1H, dd, J=9.0, 15.2 Hz), 2.85 (1H, m), 3.10 (1H, ddd, J=5.5, 8.6, 16.0 Hz), 3.31-3.41 (2H, m), 3.69 (3H, s), 4.72 (1H, dd, J=5.1, 9.4 Hz), 5.76 (1H, dd, J=4.3, 6.7 Hz), 6.99 (2H, d, J=8.6 Hz), 7.17 (1H, d, J=7.4 Hz), 7.23 (1H, t, J=7.4 Hz), 7.26-7.32 (5H, m)

(44D) (3S)-3-Ethoxy-3-{4-[(4-ethyl-2,3-dihydro-1H-inden-1-yl)oxy]phenyl}-propionic acid Methyl (3S)-3-ethoxy-3-{4-[(4-ethyl-2,3-dihydro-1H-inden-1-yl)oxy]phenyl}-propionate (92 mg, 0.250 mmol) produced in (44C) was dissolved in tetrahydrofuran (3 mL) and ethanol (3 mL), and a 1 N aqueous solution of sodium hydroxide (2 mL) was added thereto at room temperature, and then, the resulting mixture was stirred at room temperature for 4 hours. The solvent was distilled off under reduced pressure, and to the resulting residue, 1 N hydrochloric acid was added, and the organic matter was extracted with ethyl acetate. The organic layer was washed with a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 70:30 (v/v)), whereby the objective title compound was obtained as a white solid (80 mg, yield: 90%).

$^1$H NMR (CDCl$_3$, 400 MHz): δ1.19 (3H, t, J=7.1 Hz), 1.24 (3H, t, J=7.4 Hz), 2.23 (1H, ddd, J=5.5, 9.0, 18.0 Hz), 2.53-2.60 (2H, m), 2.66 (2H, q, J=7.9 Hz), 2.85 (1H, dd, J=9.4, 15.6 Hz), 2.86-2.92 (1H, m), 3.11 (1H, ddd, J=5.5, 8.6, 16.1 Hz), 3.35-3.47 (2H, m), 4.71 (1H, dd, J=4.3, 9.8 Hz), 5.76 (1H, dd, J=4.3, 6.6 Hz), 7.00 (2H, d, J=9.0 Hz), 7.17 (1H, d, J=7.4 Hz), 7.23 (1H, t, J=7.4 Hz), 7.25-7.29 (5H, m)

Example 45

(3S)-3-Ethoxy-3-(4-{[trans-4-(trifluoromethyl)cyclohexyl]methoxy}phenyl)propionic acid (Illustrative Compound No: 1-174)

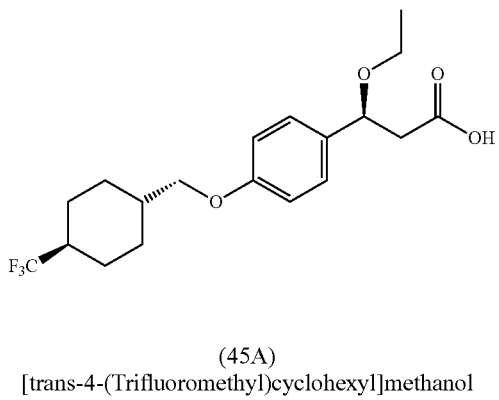

(45A) [trans-4-(Trifluoromethyl)cyclohexyl]methanol trans-4-(Trifluoromethyl)cyclohexanecarboxylic acid (1.5 g, 7.65 mmol) was dissolved in tetrahydrofuran (20 mL). The reaction solution was cooled to 0° C., and lithium aluminum hydride (435 mg, 11.5 mmol) was added thereto, and then, the resulting mixture was stirred at room temperature for 3 hours. The reaction solution was cooled to 0° C., and water (0.4 mL), a 5 N aqueous solution of sodium hydroxide (0.4 mL), and water (1.2 mL) were added thereto, followed by filtration. To the filtrate, ethyl acetate was added, and the organic layer was washed with a saturated aqueous solution of sodium hydrogen carbonate and a saturated sodium chloride solution, then dried over anhydrous magnesium sulfate and filtered. Then, the solvent was distilled off under reduced pressure, whereby a crude product was obtained as a colorless oily substance (1.18 g).

$^1$H NMR (CDCl$_3$, 400 MHz): δ1.00 (2H, dq, J=3.1, 12.5 Hz), 1.28-1.38 (2H, m), 1.44-1.55 (1H, m), 1.90-2.02 (5H, m), 3.48 (2H, d, J=6.3 Hz)

(45B) Methyl (3S)-3-ethoxy-3-(4-{[trans-4-(trifluoromethyl)cyclohexyl]methoxy}phenyl)propionate Methyl (3S)-3-ethoxy-3-(4-hydroxyphenyl)propionate (150 mg, 0.669 mmol) produced in Example 41 (41C) and [trans-4-(trifluoromethyl)cyclohexyl]methanol (183 mg, 1.00 mmol) produced in (45A) were dissolved in tetrahydrofuran (5 mL), and triphenylphosphine (350 mg, 1.34 mmol) and a 40% diethyl azodicarboxylate toluene solution (600 µL, 1.34 mmol) were added thereto at room temperature, and then, the resulting mixture was stirred under a nitrogen atmosphere at 50° C. for 3 hours.

After the reaction solution was cooled to room temperature, the solvent was distilled off under reduced pressure, and the resulting residue was purified by silica gel column chromatography (hexane:ethyl acetate=100:0 to 80:20 (v/v)), whereby the objective title compound was obtained as a colorless oily substance (103 mg, yield: 40%).

$^1$H NMR (CDCl$_3$, 400 MHz): δ1.07-1.17 (2H, m), 1.14 (3H, t, J=7.0 Hz), 1.30-1.43 (2H, m), 1.74-1.86 (1H, m), 1.95-2.05 (5H, m), 2.56 (1H, dd, J=5.1, 15.3 Hz), 2.81 (1H, dd, J=9.0, 15.3 Hz), 3.30-3.39 (2H, m), 3.67 (3H, s), 3.77 (2H, d, J=6.3 Hz), 4.68 (1H, dd, J=5.1, 9.0 Hz), 6.86 (2H, d, J=9.0 Hz), 7.25 (2H, d, J=9.0 Hz)

(45C) (3S)-3-Ethoxy-3-(4-{[trans-4-(trifluoromethyl)cyclohexyl]methoxy}phenyl)propionic acid Methyl (3S)-3-ethoxy-3-(4-{[trans-4-(trifluoromethyl)cyclohexyl]methoxy}phenyl)propionate (100 mg, 0.257 mmol) produced in (45B) was dissolved in tetrahydrofuran (3 mL) and methanol (3 mL), and a 1 N aqueous solution of sodium hydroxide (2 mL) was added thereto at room temperature, and then, the resulting mixture was stirred at room temperature for 4 hours. To the reaction solution, 1 N hydrochloric acid was added, and the organic matter was extracted with ethyl acetate. The organic layer was washed with a saturated sodium chloride solution, then dried over anhydrous magnesium sulfate and filtered. Then, the solvent was distilled off under reduced pressure, whereby a crude product was obtained. This crude product was purified by preparative thin-layer chromatography (ethyl acetate), whereby the objective title compound was obtained as a white solid (40 mg, yield: 41%).

$^1$H NMR (CDCl$_3$, 400 MHz): δ1.07-1.18 (2H, m), 1.18 (3H, t, J=7.0 Hz), 1.31-1.43 (2H, m), 1.74-1.86 (1H, m), 1.91-2.03 (5H, m), 2.62 (1H, dd, J=4.3, 16.0 Hz), 2.83 (1H, dd, J=9.8, 16.0 Hz), 3.33-3.46 (2H, m), 3.77 (2H, d, J=6.3 Hz), 4.68 (1H, dd, J=4.3, 9.8 Hz), 6.87 (2H, d, J=8.6 Hz), 7.24 (2H, d, J=8.6 Hz)

Example 46

(3S)-3-Ethoxy-3-(4-{[cis-4-(trifluoromethyl)cyclohexyl]methoxy}phenyl)propionic acid (Illustrative Compound No: 1-174)

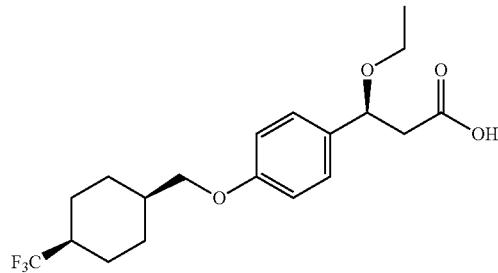

(46A) [cis-4-(Trifluoromethyl)cyclohexyl]methanol cis-4-(Trifluoromethyl)cyclohexanecarboxylic acid (1.5 g, 7.65 mmol) was dissolved in tetrahydrofuran (20 mL). The reaction solution was cooled to 0° C., and lithium aluminum hydride (435 mg, 11.5 mmol) was added thereto, and then, the resulting mixture was stirred at room temperature for 3 hours. The reaction solution was cooled to 0° C., and water (0.4 mL), a 5 N aqueous solution of sodium hydroxide (0.4 mL), and water (1.2 mL) were added thereto, followed by filtration. To the filtrate, ethyl acetate was added, and the organic layer was washed with a saturated aqueous solution of sodium hydrogen carbonate and a saturated sodium chloride solution, then dried over anhydrous magnesium sulfate and filtered. Then, the solvent was distilled off under reduced pressure, whereby a crude product was obtained as a colorless oily substance (1.26 g).

$^1$H NMR (CDCl$_3$, 400 MHz): δ1.51-1.62 (4H, m), 1.65-1.73 (4H, m), 1.76-1.86 (1H, m), 2.07-2.15 (1H, m), 3.62 (2H, d, J=7.4 Hz)

(46B) Methyl (3S)-3-ethoxy-3-(4-{[cis-4-(trifluoromethyl)cyclohexyl]methoxy}phenyl)propionate Methyl (3S)-3-ethoxy-3-(4-hydroxyphenyl)propionate (150 mg, 0.669 mmol) produced in Example 41 (41C) and [cis-4-(trifluoromethyl)cyclohexyl]methanol (183 mg, 1.00 mmol) produced in (46A) were dissolved in tetrahydrofuran (5 mL), and triphenylphosphine (350 mg, 1.34 mmol) and a 40% diethyl azodicarboxylate toluene solution (600 μL, 1.34 mmol) were added thereto at room temperature, and then, the resulting mixture was stirred under a nitrogen atmosphere at 50° C. for 3 hours.

After the reaction solution was cooled to room temperature, the solvent was distilled off under reduced pressure, and the resulting residue was purified by silica gel column chromatography (hexane:ethyl acetate=100:0 to 80:20 (v/v)), whereby the objective title compound was obtained as a colorless oily substance (73 mg, yield: 28%).

$^1$H NMR (CDCl$_3$, 400 MHz): δ1.14 (3H, t, J=7.0 Hz), 1.58-1.84 (8H, m), 2.09-2.18 (2H, m), 2.56 (1H, dd, J=5.1, 15.3 Hz), 2.81 (1H, dd, J=9.0, 15.3 Hz), 3.31-3.39 (2H, m), 3.67 (3H, s), 3.90 (2H, d, J=7.4 Hz), 4.70 (1H, dd, J=5.1, 9.0 Hz), 6.88 (2H, d, J=8.6 Hz), 7.25 (2H, d, J=8.6 Hz)

(46C) (3S)-3-Ethoxy-3-(4-{[cis-4-(trifluoromethyl)cyclohexyl]methoxy}phenyl)propionic acid Methyl (3S)-3-ethoxy-3-(4-{[cis-4-(trifluoromethyl)cyclohexyl]methoxy}phenyl)propionate (73 mg, 0.188 mmol) produced in (46B) was dissolved in tetrahydrofuran (3 mL) and methanol (3 mL), and a 1 N aqueous solution of sodium hydroxide (2 mL) was added thereto at room temperature, and then, the resulting mixture was stirred at room temperature for 4 hours.

To the reaction solution, 1 N hydrochloric acid was added, and the organic matter was extracted with ethyl acetate. The organic layer was washed with a saturated sodium chloride solution, then dried over anhydrous magnesium sulfate and filtered. Then, the solvent was distilled off under reduced pressure, whereby a crude product was obtained. This crude product was purified by preparative thin-layer chromatography (ethyl acetate), whereby the objective title compound was obtained as a white solid (24 mg, yield: 34%).

$^1$H NMR (CDCl$_3$, 400 MHz): δ1.19 (3H, t, J=7.0 Hz), 1.58-1.83 (8H, m), 2.07-2.20 (2H, m), 2.62 (1H, dd, J=3.9, 15.6 Hz), 2.84 (1H, dd, J=9.8, 15.6 Hz), 3.34-3.47 (2H, m), 3.91 (2H, d, J=7.0 Hz), 4.67 (1H, dd, J=3.9, 9.8 Hz), 6.90 (2H, d, J=8.6 Hz), 7.25 (2H, d, J=8.6 Hz)

Example 47

(3S)-3-Ethoxy-3-(4-{[7-(trifluoromethyl)-2,3-dihydro-1-benzofuran-3-yl]oxy}phenyl)propionic acid (Illustrative Compound No: 1-170)

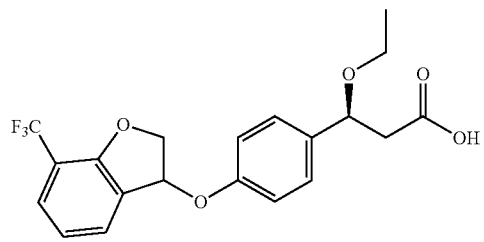

(47A) Methyl 2-hydroxy-3-(trifluoromethyl)benzoate

2-Hydroxy-3-(trifluoromethyl)benzoic acid (9.64 g, 46.8 mmol) produced in accordance with the description of European Journal of Organic Chemistry, 2001, vol. 2001, pp. 2911-2915 was dissolved in methanol (100 mL), and concentrated sulfuric acid (8 mL) was added thereto, and then, the resulting mixture was heated to reflux under a nitrogen atmosphere at 80° C. for 15 hours.

After the reaction solution was cooled to room temperature, the solvent was distilled off under reduced pressure, and water was added to the resulting residue. Then, the organic matter was extracted with ethyl acetate, and the organic layer was washed with a saturated aqueous solution of sodium carbonate and a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 70:30 (v/v)), whereby the objective title compound was obtained as a colorless oily substance (5.80 g, yield: 56%).

$^1$H NMR (CDCl$_3$, 500 MHz): δ3.99 (3H, s), 6.96 (1H, t, J=7.8 Hz), 7.76 (1H, d, J=7.8 Hz), 8.03 (1H, d, J=7.8 Hz), 11.54 (1H, s)

(47B) Methyl 2-(2-ethoxy-2-oxoethoxy)-3-(trifluoromethyl)benzoate

Methyl 2-hydroxy-3-(trifluoromethyl)benzoate (5.80 g, 26.3 mmol) produced in (47A) was dissolved in dimethylformamide (100 mL), and ethyl bromoacetate (5.28 g, 31.6 mmol) and potassium carbonate (7.28 g, 52.6 mmol) were added thereto at room temperature, and then, the resulting mixture was stirred under a nitrogen atmosphere at room temperature for 1 hour.

Water was added to the reaction solution, and the organic matter was extracted with diethyl ether. The organic layer was washed with a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 60:40 (v/v)), whereby the objective title compound was obtained as a colorless oily substance (7.83 g, yield: 97%).

¹H NMR (CDCl₃, 500 MHz): δ1.34 (3H, t, J=7.3 Hz), 3.91 (3H, s), 4.32 (2H, q, J=7.3 Hz), 4.66 (2H, s), 7.32 (1H, t, J=7.8 Hz), 7.80 (1H, d, J=7.8 Hz), 8.08 (1H, d, J=7.8 Hz)

(47C) 2-(Carboxymethoxy)-3-(trifluoromethyl)benzoic acid

Methyl 2-(2-ethoxy-2-oxoethoxy)-3-(trifluoromethyl)benzoate (4.83 g, 15.8 mmol) produced in (47B) was dissolved in methanol (100 mL), and a 1 N aqueous solution of sodium hydroxide (50 mL) was added thereto at room temperature, and then, the resulting mixture was stirred at 70° C. for 4 hours. The solvent was distilled off under reduced pressure, and to the resulting residue, 1 N hydrochloric acid was added, and the deposited solid was filtered, whereby the objective title compound was obtained as a white solid (2.96 g, yield: 71%).

¹H NMR (D₂O, 400 MHz): δ4.42 (2H, s), 7.30 (1H, t, J=7.8 Hz), 7.61 (1H, d, J=7.8 Hz), 7.71 (1H, d, J=7.8 Hz)

(47D) 7-(Trifluoromethyl)-1-benzofuran-3-yl-acetic acid

To 2-(carboxymethoxy)-3-(trifluoromethyl)benzoic acid (2.96 g, 11.2 mmol) produced in (47C), sodium acetate (1.38 g, 16.8 mmol), acetic anhydride (12 mL), and acetic acid (1.8 mL) were added, and then, the resulting mixture was stirred under a nitrogen atmosphere at 130° C. for 2 hours. After the reaction solution was cooled to room temperature, water was added thereto, and the organic matter was extracted with ethyl acetate. The organic layer was washed with water, a saturated aqueous solution of sodium hydrogen carbonate, and a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 60:40 (v/v)), whereby the objective title compound was obtained as a white solid (470 mg, yield: 17%).

¹H NMR (CDCl₃, 400 MHz): δ2.40 (3H, s), 7.36 (1H, t, J=7.8 Hz), 7.60 (1H, d, J=7.8 Hz), 7.77 (1H, d, J=7.8 Hz), 8.14 (1H, s)

(47E) 7-(Trifluoromethyl)-1-benzofuran-3-one 7-(Trifluoromethyl)-1-benzofuran-3-yl-acetic acid (470 mg, 1.92 mmol) produced in (47D) was dissolved in methanol (20 mL), and 1 N hydrochloric acid (5 mL) was added thereto at room temperature, and then, the resulting mixture was stirred at 70° C. for 6 hours. The solvent was distilled off under reduced pressure, and to the resulting residue, ethyl acetate was added, and the mixture was dried over anhydrous magnesium sulfate and filtered. Then, the solvent was distilled off under reduced pressure, whereby a crude product was obtained. This crude product was purified by silica gel column chromatography (hexane:ethyl acetate=100:0 to 60:40 (v/v)), whereby the objective title compound was obtained as a white solid (197 mg, yield: 51%).

¹H NMR (CDCl₃, 500 MHz): 4.77 (2H, s), 7.21 (1H, t, J=7.8 Hz), 7.86 (1H, d, J=7.8 Hz), 7.87 (1H, d, J=7.8 Hz)

(47F) 7-(Trifluoromethyl)-2,3-dihydro-1-benzofuran-3-ol 7-(Trifluoromethyl)-1-benzofuran-3-one (197 mg, 0.975 mmol) produced in (47E) was dissolved in methanol (10 mL), and sodium borohydride (100 mg, 2.64 mmol) was added thereto at room temperature, and then, the resulting mixture was stirred at room temperature for 2 hours. The solvent was distilled off under reduced pressure, and to the resulting residue, 2 N hydrochloric acid was added, and the organic matter was extracted with ethyl acetate. The organic layer was washed with a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 60:40 (v/v)), whereby the objective title compound was obtained as a colorless oily substance (151 mg, yield: 76%).

¹H NMR (CDCl₃, 400 MHz): 4.59 (1H, dd, J=2.7, 11.0 Hz), 4.69 (1H, dd, J=6.7, 11.0 Hz), 5.42 (1H, dd, J=2.7, 6.7 Hz), 7.03 (1H, t, J=7.4 Hz), 7.51 (1H, d, J=7.4 Hz), 7.60 (1H, d, J=7.4 Hz)

(47G) Methyl (3S)-3-ethoxy-3-(4-{[7-(trifluoromethyl)-2,3-dihydro-1-benzofuran-3-yl]oxy}phenyl)propionate Methyl (3S)-3-ethoxy-3-(4-hydroxyphenyl)propionate (166 mg, 0.740 mmol) produced in Example 41 (41C) and 7-(trifluoromethyl)-2,3-dihydro-1-benzofuran-3-ol (151 mg, 0.740 mmol) produced in (47F) were dissolved in tetrahydrofuran (5 mL), and triphenylphosphine (291 mg, 1.11 mmol) and a 40% diethyl azodicarboxylate toluene solution (500 µL, 1.11 mmol) were added thereto at room temperature, and then, the resulting mixture was stirred under a nitrogen atmosphere at 50° C. for 3 hours. After the reaction solution was cooled to room temperature, the solvent was distilled off under reduced pressure, and the resulting residue was purified by silica gel column chromatography (hexane:ethyl acetate=100:0 to 60:40 (v/v)), whereby the objective title compound was obtained as a colorless oily substance (115 mg, yield: 38%).

¹H NMR (CDCl₃, 500 MHz): δ1.16 (3H, t, J=7.3 Hz), 2.58 (1H, dd, J=5.4, 15.6 Hz), 2.82 (1H, dd, J=8.8, 15.6 Hz), 3.32-3.42 (2H, m), 3.68 (3H, s), 4.71 (1H, dd, J=5.4, 8.8 Hz), 4.76 (1H, dd, J=2.4, 10.7 Hz), 4.83 (1H, dd, J=6.6, 10.7 Hz), 5.91-5.93 (1H, m), 6.89 (2H, d, J=8.8 Hz), 7.02 (1H, t, J=7.8 Hz), 7.30 (2H, d, J=8.8 Hz), 7.55 (1H, t, J=7.8 Hz), 7.57 (1H, t, J=7.8 Hz)

(47H) (3S)-3-Ethoxy-3-(4-{[7-(trifluoromethyl)-2,3-dihydro-1-benzofuran-3-yl]oxy}phenyl)propionic acid Methyl (3S)-3-ethoxy-3-(4-{[7-(trifluoromethyl)-2,3-dihydro-1-benzofuran-3-yl]oxy}phenyl)propionate (115 mg, 0.280 mmol) produced in (47G) was dissolved in methanol (5 mL), and a 1 N aqueous solution of sodium hydroxide (2 mL) was added thereto at room temperature, and then, the resulting mixture was stirred at room temperature for 3 hours.

The solvent was distilled off under reduced pressure, and to the resulting residue, 1 N hydrochloric acid was added, and the organic matter was extracted with ethyl acetate. The organic layer was washed with a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 0:100 (v/v)), whereby the objective title compound was obtained as a colorless oily substance (97 mg, yield: 87%).

¹H NMR (CDCl₃, 500 MHz): δ1.20 (3H, t, J=7.3 Hz), 2.63 (1H, dd, J=4.4, 15.6 Hz), 2.85 (1H, dd, J=9.3, 15.6 Hz), 3.37-3.47 (2H, m), 4.70 (1H, dd, J=4.4, 9.3 Hz), 4.75 (1H, dd, J=2.9, 10.7 Hz), 4.83 (1H, dd, J=6.4, 10.7 Hz), 5.92-5.94 (1H, m), 6.91 (2H, d, J=8.8 Hz), 7.03 (1H, t, J=7.3 Hz), 7.30 (2H, d, J=8.8 Hz), 7.55 (1H, t, J=7.3 Hz), 7.57 (1H, t, J=7.3 Hz)
MS (ESI) m/z: 395 (M−H)⁻

Example 48

(3S)-3-Ethoxy-3-(4-{[5-(trifluoromethyl)-1,2,3,4-tetrahydronaphthalen-1-yl]oxy}phenyl)propionic acid (Illustrative Compound No: 1-159)

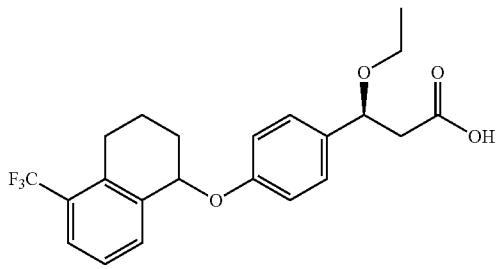

(48A) 4-[2-(Trifluoromethyl)phenyl]butanal

4-[2-(Trifluoromethyl)phenyl]butanenitrile (5.76 g, 27.0 mmol) produced in accordance with the description of Journal of Photochemistry and Photobiology, A: Chemistry (1997), 102 (2-3), 179-188 was dissolved in dichloromethane (100 mL), and a diisobutylaluminum hydride dichloromethane solution (1 M, 31.8 mL, 31.8 mmol) was added thereto at −78° C., and then, the temperature of the resulting mixture was raised to room temperature and the mixture was stirred for 1 hour. To the reaction solution, 1 N hydrochloric acid was added, and the organic matter was extracted with dichloromethane. The organic layer was washed with a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 60:40 (v/v)), whereby the objective title compound was obtained as a colorless oily substance (5.08 g, yield: 87%).
¹H NMR (CDCl₃, 500 MHz): δ1.94-2.00 (2H, m), 2.53 (2H, dt, J=1.5, 7.3 Hz), 2.82 (2H, t, J=7.8 Hz), 7.31 (1H, t, J=7.8 Hz), 7.35 (1H, d, J=7.8 Hz), 7.48 (1H, t, J=7.8 Hz), 7.62 (1H, d, J=7.8 Hz), 9.80 (1H, t, J=1.5 Hz)

(48B) 4-[2-(Trifluoromethyl)phenyl]butanoic acid

4-[2-(Trifluoromethyl)phenyl]butanal (5.08 g, 23.5 mmol) produced in (48A) was dissolved in a mixed solvent (80 mL) of tetrahydrofuran/water/tert-butanol/2-methyl-2-butene (3/1/3/0.5 (v/v)), and sodium dihydrogen phosphate dihydrate (5.0 g) was added thereto. Then, an aqueous solution obtained by dissolving sodium chlorite (4.0 g) in water (10 mL) was added dropwise thereto at 0° C., and the resulting mixture was stirred at 0° C. for 1 hour.
To the reaction solution, an aqueous solution of sodium sulfite was added at 0° C., and 2 N hydrochloric acid was added thereto, and then, the organic matter was extracted with ethyl acetate. The organic layer was washed with a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 0:100 (v/v)), and the resulting solid was washed with hexane, whereby the objective title compound was obtained as a white solid (4.14 g, yield: 76%).
¹H NMR (CDCl₃, 500 MHz): δ1.95-2.01 (2H, m), 2.45 (2H, t, J=7.3 Hz), 2.85 (2H, t, J=7.8 Hz), 7.30 (1H, t, J=7.8 Hz), 7.35 (1H, d, J=7.8 Hz), 7.48 (1H, t, J=7.8 Hz), 7.62 (1H, d, J=7.8 Hz)

(48C) 5-(Trifluoromethyl)-3,4-dihydronaphthalen-1(2H)-one

To 4-[2-(trifluoromethyl)phenyl]butanoic acid (246 mg, 1.06 mmol) produced in (48B), chlorosulfonic acid (2 mL) was added at 0° C., and the resulting mixture was stirred at 0° C. for 1 hour.
The reaction solution was added to ice water to stop the reaction. The organic matter was extracted with ethyl acetate, and the organic layer was washed with a saturated aqueous solution of sodium hydrogen carbonate and a saturated sodium chloride solution, then dried over anhydrous magnesium sulfate and filtered. Then, the solvent was distilled off under reduced pressure, whereby the objective title compound was obtained as a colorless oily substance (160 mg, yield: 70%).
¹H NMR (CDCl₃, 500 MHz): δ2.16-2.21 (2H, m), 2.70 (2H, dd, J=6.4, 6.8 Hz), 3.14 (2H, t, J=6.4 Hz), 7.43 (1H, t, J=7.8 Hz), 7.83 (1H, d, J=7.8 Hz), 8.27 (1H, d, J=7.8 Hz)

(48D) 5-(Trifluoromethyl)-1,2,3,4-tetrahydronaphthalen-1-ol 5-(Trifluoromethyl)-3,4-dihydronaphthalen-1(2H)-one (160 mg, 0.747 mmol) produced in (48C) was dissolved in methanol (5 mL), and sodium borohydride (20 mg, 0.53 mmol) was added thereto at 0° C., and then, the resulting mixture was stirred at 0° C. for 30 minutes. To the reaction solution, 1 N hydrochloric acid was added, and the organic matter was extracted with ethyl acetate. The organic layer was washed with a saturated sodium chloride solution, then dried over anhydrous magnesium sulfate and filtered. Then, the solvent was distilled off under reduced pressure, whereby the objective title compound was obtained as a colorless oily substance (149 mg, yield: 93%).
¹H NMR (CDCl₃, 500 MHz): δ1.78-1.93 (2H, m), 1.96-2.07 (2H, m), 2.82-2.88 (1H, m), 3.00-3.05 (1H, m), 4.82 (1H, dd, J=4.9, 5.4 Hz), 7.30 (1H, t, J=7.8 Hz), 7.56 (1H, d, J=7.8 Hz), 7.66 (1H, d, J=7.8 Hz)

(48E) Methyl (3S)-3-ethoxy-3-(4-{[5-(trifluoromethyl)-1,2,3,4-tetrahydronaphthalen-1-yl]oxy}phenyl)propionate Methyl (3S)-3-ethoxy-3-(4-hydroxyphenyl)propionate (154 mg, 0.689 mmol) produced in Example 41 (41C) and 5-(trifluoromethyl)-1,2,3,4-tetrahydronaphthalen-1-ol (149 mg, 0.689 mmol) produced in (48D) were dissolved in tetrahydrofuran (5 mL), and triphenylphosphine (271 mg, 1.03 mmol) and a 40% diethyl azodicarboxylate toluene solution (470 μL, 1.03 mmol) were added thereto at room temperature, and then, the resulting mixture was stirred under a nitrogen atmosphere at 60° C. for 2 hours. After the reaction solution was cooled to room temperature, the solvent was distilled off under reduced pressure, and the resulting residue was purified by silica gel column chromatography (hexane:ethyl acetate=100:0 to 70:30 (v/v)), whereby the objective title compound was obtained as a colorless oily substance (30 mg, yield: 10%).

$^1$H NMR (CDCl$_3$, 500 MHz): δ1.16 (3H, t, J=6.8 Hz), 1.79-1.88 (1H, m), 1.98-2.06 (2H, m), 2.12-2.19 (1H, m), 2.58 (1H, dd, J=4.9, 15.6 Hz), 2.82 (1H, dd, J=9.3, 15.6 Hz), 3.08-3.14 (1H, m), 3.33-3.44 (2H, m), 3.69 (3H, s), 4.71 (1H, dd, J=4.9, 9.3 Hz), 5.38 (1H, t, J=4.4 Hz), 6.99 (2H, d, J=8.3 Hz), 7.28-7.31 (3H, m), 7.57 (1H, d, J=7.8 Hz), 7.61 (1H, d, J=7.8 Hz)

(48F) (3S)-3-Ethoxy-3-(4-{[5-(trifluoromethyl)-1, 2, 3,4-tetrahydronaphthalen-1-yl]oxy}phenyl)propionic acid Methyl (3S)-3-ethoxy-3-(4-{[5-(trifluoromethyl)-1,2,3,4-tetrahydronaphthalen-1-yl]oxy}phenyl)propionate (30 mg, 0.071 mmol) produced in (48E) was dissolved in methanol (5 mL), and a 1 N aqueous solution of sodium hydroxide (2 mL) was added thereto at room temperature, and then, the resulting mixture was stirred at room temperature for 3 hours. The solvent was distilled off under reduced pressure, and to the resulting residue, 1 N hydrochloric acid was added, and the organic matter was extracted with ethyl acetate. The organic layer was washed with a saturated sodium chloride solution, then dried over anhydrous magnesium sulfate and filtered. Then, the solvent was distilled off under reduced pressure, whereby a crude product was obtained as a solid. This crude product was washed with hexane, whereby the objective title compound was obtained as a white solid (17 mg, yield: 59%).

$^1$H NMR (CDCl$_3$, 500 MHz): δ1.22 (3H, t, J=6.8 Hz), 1.81-1.87 (1H, m), 1.98-2.07 (2H, m), 2.12-2.19 (1H, m), 2.66 (1H, dd, J=3.9, 15.7 Hz), 2.83-2.91 (2H, m), 3.09-3.14 (1H, m), 3.39-3.51 (2H, m), 4.70 (1H, dd, J=3.9, 9.8 Hz), 5.39 (1H, t, J=4.4 Hz), 7.01 (2H, d, J=8.8 Hz), 7.28-7.32 (3H, m), 7.56 (1H, d, J=7.8 Hz), 7.61 (1H, d, J=7.8 Hz)

MS (ESI) m/z: 407 (M–H)$^-$

Example 49

(3S)-3-Ethoxy-3-(4-{[4-(trifluoromethyl)benzyl]oxy}phenyl)propionic acid (Illustrative Compound No: 1-48)

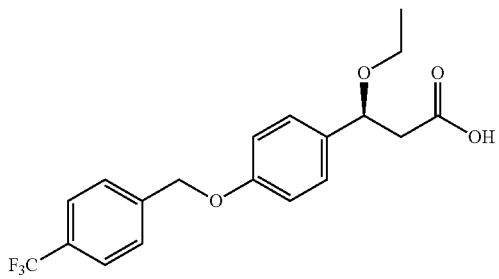

Methyl (3S)-3-ethoxy-3-(4-hydroxyphenyl)propionate (1.50 g, 6.69 mmol) produced in Example 41 (41C), 4-trifluoromethylbenzyl alcohol (1.65 g, 9.37 mmol), and triphenylphosphine (2.46 g, 9.38 mmol) were dissolved in tetrahydrofuran (40 mL), and a diethyl azodicarboxylate toluene solution (2.2 M, 4.26 mL, 9.37 mmol) was slowly added dropwise thereto at room temperature, and then, the resulting mixture was stirred under a nitrogen atmosphere at room temperature for 2 hours.

After the solvent in the reaction solution was distilled off under reduced pressure, the resulting residue was passed through a silica gel pad (hexane:ethyl acetate=80:20 (v/v)), and then, the solvent was distilled off under reduced pressure. The resulting crude product was dissolved in tetrahydrofuran (25 mL) and ethanol (25 mL), and a 2 N aqueous solution of sodium hydroxide (12 mL) was added thereto at room temperature, and then, the resulting mixture was stirred at room temperature for 5 hours.

To the reaction solution, 2 N hydrochloric acid was added, and the organic matter was extracted with ethyl acetate. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=80:20 to 60:40 (v/v)), whereby the objective title compound was obtained as a white solid (2.17 g, yield: 88%).

$^1$H NMR (CDCl$_3$, 500 MHz): δ1.19 (3H, t, J=7.3 Hz), 2.63 (1H, dd, J=4.4, 16.1 Hz), 2.83 (1H, dd, J=9.8, 16.1 Hz), 3.36-3.47 (2H, m), 4.68 (1H, dd, J=4.4, 9.8 Hz), 5.13 (2H, s), 6.96 (1H, d, J=8.8 Hz), 7.27 (2H, d, J=8.8 Hz), 7.56 (2H, d, J=8.3 Hz), 7.65 (2H, d, J=8.3 Hz)

MS (ESI) m/z: 367 (M–H)$^-$

Example 50

(3S)-3-(4-{[(1R)-4-Chloro-2,3-dihydro-1H-inden-1-yl]oxy}phenyl)-3-ethoxypropionic acid (Illustrative Compound No: 1-200)

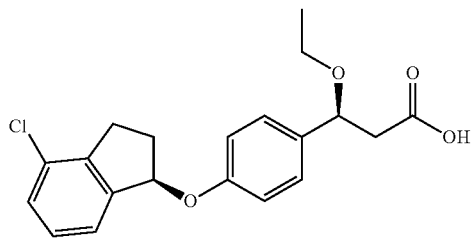

(50A) Methyl (3S)-3-(4-benzyloxyphenyl)-3-hydroxypropionate

Triethylamine (21.2 g, 210 mmol) was cooled to 0° C., and formic acid (11.3 g, 245 mmol) was slowly added dropwise thereto. Methyl 3-[4-(benzyloxy)phenyl]-3-oxopropionate (18.3 g, 64.4 mmol) produced in accordance with the description of WO 2004050632 (A1) was added thereto at room temperature, and the resulting mixture was stirred under a nitrogen atmosphere at 35° C. for 15 minutes to form a uniform solution. Then, chloro[(1S,2S)—N-(p-toluenesulfonyl)-1,2-diphenylethanediamine](mesitylene)ruthenium(II) (1.00 g, 1.61 mmol) was added thereto, and the resulting mixture was stirred under a nitrogen atmosphere at 35° C. for 2 hours.

The reaction solution was distilled off under reduced pressure, and the resulting residue was purified by silica gel column chromatography (hexane:ethyl acetate=80:20 to 50:50 (v/v)), whereby the objective title compound was obtained as a yellow solid (16.2 g, yield: 90%).

Incidentally, the absolute configuration was determined according to the method described in Journal of the American Chemical Society, 1991, vol. 113 (11), pp. 4092-4096.

$^1$H NMR (CDCl$_3$, 400 MHz): δ2.51 (1H, dd, J=3.9, 16.4 Hz), 2.58 (1H, dd, J=9.4, 16.4 Hz), 2.90 (1H, d, J=3.1 Hz), 3.54 (3H, s), 4.88 (2H, s), 4.91 (1H, ddd, J=3.1, 3.9, 9.4 Hz), 6.78 (2H, d, J=9.0 Hz), 7.12 (2H, d, J=9.0 Hz), 7.14-7.26 (5H, m)

(50B) (1S)-1-(4-Benzyloxyphenyl)propan-1,3-diol

Lithium aluminum hydride (3.67 g, 96.7 mmol) was suspended in tetrahydrofuran (200 mL), and a tetrahydrofuran solution of methyl (3S)-3-(4-benzyloxyphenyl)-3-hydroxypropionate (16.2 g, 56.6 mmol) produced in (50A) was slowly added dropwise thereto at 0° C., and then, the resulting mixture was stirred under a nitrogen atmosphere at 0° C. for 1 hour.

To the reaction solution, water and a 5 N aqueous solution of sodium hydroxide were slowly added at 0° C. The reaction solution was filtered, and the solvent was distilled off under reduced pressure, whereby a crude product was obtained. This crude product was washed with hexane/diethyl ether/ethyl acetate (10/2/1 (v/v/v)) and then recrystallized from hexane/ethyl acetate (1/1 (v/v)), whereby the objective title compound was obtained as a white solid (10.2 g, yield: 70%).

$^1$H NMR (CDCl$_3$, 500 MHz): δ1.92 (1H, m), 2.04 (1H, m), 2.54 (1H, m), 2.86 (1H, m), 3.83-3.90 (2H, m), 4.93 (1H, m), 5.09 (2H, s), 6.99 (2H, d, J=8.8 Hz), 7.29-7.47 (7H, m)

(50C) (1S)-1-(4-Benzyloxyphenyl)-3-(triisopropylsilyloxy)propan-1-ol (1S)-1-(4-Benzyloxyphenyl)propan-1,3-diol (10.0 g, 38.7 mmol) produced in (50B) was dissolved in dimethylformamide (90 mL), and imidazole (3.20 g, 47.0 mmol) was added thereto. The reaction solution was cooled to 0° C., and triisopropylsilyl chloride (8.70 mL, 40.7 mmol) was added thereto, and then, the resulting mixture was stirred at room temperature for 3 hours.

To the reaction solution, a saturated aqueous solution of ammonium chloride was added, and the organic matter was extracted with diethyl ether. The organic layer was washed with water, then dried over anhydrous sodium sulfate and filtered. Then, the solvent was distilled off under reduced pressure, whereby a crude product was obtained. This crude product was purified by silica gel column chromatography (hexane:ethyl acetate=100:0 to 80:20 (v/v)), whereby the objective title compound was obtained as a colorless oily substance (15.5 g, yield: 97%).

$^1$H NMR (CDCl$_3$, 400 MHz): δ1.02-1.16 (21H, m), 1.87 (1H, m), 1.96 (1H, m), 3.87-3.98 (3H, m), 4.93 (1H, ddd, J=2.5, 2.9, 8.6 Hz), 5.05 (2H, s), 6.94 (2H, d, J=9.0 Hz), 7.29 (2H, d, J=9.0 Hz), 7.30-7.44 (5H, m)

(50D) (3S)-3-(4-Benzyloxyphenyl)-3-ethoxypropyloxy triisopropylsilane (1S)-1-(4-Benzyloxyphenyl)-3-(triisopropylsilyloxy)-propan-1-ol (15.2 g, 36.7 mmol) produced in (50C) was dissolved in dimethylformamide (100 mL), and ethyl iodide (5.80 mL, 72.5 mmol) was added thereto. The reaction solution was cooled to 0° C., and sodium hydride (63%, 2.2 g, 57.8 mmol) was added thereto, and then, the resulting mixture was stirred at room temperature for 3 hours.

To the reaction solution, a saturated aqueous solution of ammonium chloride was added, and the organic matter was extracted with diethyl ether. The organic layer was washed with water, then dried over anhydrous sodium sulfate and filtered. Then, the solvent was distilled off under reduced pressure, whereby a crude product was obtained. This crude product was purified by silica gel column chromatography (hexane:ethyl acetate=100:0 to 90:10 (v/v)), whereby the objective title compound was obtained as a colorless oily substance (14.3 g, yield: 88%).

$^1$H NMR (CDCl$_3$, 400 MHz): δ1.01-1.09 (21H, m), 1.15 (3H, t, J=7.0 Hz), 1.76 (1H, m), 1.99 (1H, m), 3.24-3.40 (2H, m), 3.61 (1H, ddd, J=5.5, 5.9, 10.2 Hz), 3.82 (1H, ddd, J=5.1, 7.8, 10.2 Hz), 4.43 (1H, dd, J=5.1, 8.2 Hz), 5.05 (2H, s), 6.94 (2H, d, J=8.6 Hz), 7.22 (2H, d, J=8.6 Hz), 7.29-7.46 (5H, m)

(50E) 4-{(1S)-1-Ethoxy-3-[(triisopropylsilyl)oxy]propyl}phenol (3S)-3-(4-Benzyloxyphenyl)-3-ethoxypropyloxytriisopropylsilane (14.1 g, 31.9 mmol) produced in (50D) was dissolved in tetrahydrofuran (120 mL), and a suspension (24 mL) of Raney nickel (2800, manufactured by W.R. Grace) was added thereto at room temperature, and then, the resulting mixture was stirred under a hydrogen atmosphere at room temperature for 14 hours. The reaction solution was filtered, and the solvent was distilled off under reduced pressure. The resulting residue was purified by silica gel column chromatography (hexane:ethyl acetate=90:10 to 80:20 (v/v)), whereby the objective title compound was obtained as a white solid (11.2 g, yield: 100%).

$^1$H NMR (CDCl$_3$, 400 MHz): δ1.01-1.07 (21H, m), 1.14 (3H, t, J=7.0 Hz), 1.76 (1H, m), 1.99 (1H, m), 3.25-3.42 (2H, m), 3.60 (1H, ddd, J=5.5, 5.9, 9.8 Hz), 3.81 (1H, ddd, J=5.1, 7.8, 9.8 Hz), 4.42 (1H, dd, J=5.1, 8.2 Hz), 4.99 (1H, m), 6.78 (2H, d, J=8.6 Hz), 7.16 (2H, d, J=8.6 Hz)

(50F) (1S)-4-Chloroindan-1-ol

To a mixture of formic acid (1.35 mL, 35.3 mmol) and triethylamine (4.2 mL, 30.3 mmol), a dichloromethane (6.0 mL) solution of 4-chloroindan-1-one (1.68 g, 10.1 mmol) produced in accordance with the description of Journal of Medicinal Chemistry, 2003, vol. 46 (3), pp. 399-408 was added, and chloro[(1S,2S)—N-(p-toluenesulfonyl)-1,2-diphenylethanediamine](mesitylene)ruthenium(II) (314 mg, 0.504 mmol) was added thereto at room temperature, and then, the resulting mixture was stirred under a nitrogen atmosphere at room temperature for 2 hours. Water was added to the reaction solution, and the organic matter was extracted with ethyl acetate. The organic layer was washed with a saturated sodium bicarbonate solution and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=95:5 to 65:35 (v/v)), whereby the objective title compound was obtained as a white solid (1.63 g, yield: 96%).

The absolute configuration (S) of the objective title compound was confirmed by converting the compound into an α-methoxy-α-(trifluoromethyl)phenyl acetate ester and according to the method described in Journal of the American Chemical Society, 1991, vol. 113 (11), pp. 4092-4096.

$^1$H NMR (CDCl$_3$, 500 MHz): δ1.76 (1H, d, J=7.0 Hz), 1.93-2.02 (1H, m), 2.49-2.57 (1H, m), 2.81-2.89 (1H, m), 3.07-3.15 (1H, m), 5.29 (1H, dt, J=6.3, 6.5 Hz), 7.20 (1H, t like, J=7.3 Hz), 7.26 (1H, d, J=7.3 Hz), 7.31 (1H, d, J=7.3 Hz)

(50G) (3S)-3-(4-{[(1R)-4-Chloro-2,3-dihydro-1H-inden-1-yl]oxy}phenyl)-3-ethoxypropan-1-ol (1S)-4-Chloroindan-1-ol (1.63 g, 9.67 mmol) produced in (50F) and 4-{(1S)-1-ethoxy-3-[(triisopropylsilyl)oxy]propyl}phenol (2.84 g, 8.05 mmol) produced in (50E) were dissolved in tetrahydrofuran (40 mL), and triphenylphosphine (2.54 g, 9.67 mmol) and a 40% diethyl azodicarboxylate toluene solution (4.4 mL, 9.67 mmol) were added thereto at room temperature, and then, the resulting mixture was stirred under a nitrogen atmosphere at 50° C. for 8 hours.

After the reaction solution was cooled to room temperature, the solvent was distilled off under reduced pressure, and the resulting residue was roughly purified by silica gel column chromatography (hexane:ethyl acetate=100:0 to 65:35 (v/v)), whereby a crude product was obtained. This crude product was dissolved in tetrahydrofuran (30 mL), and a 1.0 M tetra-n-butylammonium fluoride tetrahydrofuran solution (12.5 mL, 12.5 mmol) was added thereto at 0° C., and then, the resulting mixture was stirred under a nitrogen atmosphere at 40° C. for 2 hours. To the reaction solution, a saturated aqueous solution of ammonium chloride was added, and the organic matter was extracted with ethyl acetate. The organic layer was washed with water and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=90:10 to 60:40 (v/v)), whereby the objective title compound was obtained as a colorless solid (1.81 g, yield: 65%).

$^1$H NMR (CDCl$_3$, 400 MHz): δ1.20 (3H, t, J=7.0 Hz), 1.80-1.89 (1H, m), 2.00-2.11 (1H, m), 2.19-2.29 (1H, m), 2.56-2.66 (1H, m), 2.89 (1H, dd, J=4.3, 6.6 Hz), 2.93-3.02 (1H, m), 3.13-3.23 (1H, m), 3.30-3.47 (2H, m), 3.75-3.86 (2H, m), 4.49 (1H, dd, J=3.9, 9.4 Hz), 5.79 (1H, dd, J=4.5, 6.8 Hz), 6.98 (2H, d, J=8.5 Hz), 7.22 (1H, t like, J=8.0 Hz), 7.27 (2H, d, J=8.5 Hz), 7.31-7.35 (2H, m)

(50H) (3S)-3-(4-{[(1R)-4-Chloro-2,3-dihydro-1H-inden-1-yl]oxy}phenyl)-3-ethoxypropionic acid (3S)-3-(4-{[(1R)-4-Chloro-2,3-dihydro-1H-inden-1-yl]oxy}phenyl)-3-ethoxypropan-1-ol (1.50 g, 4.32 mmol) produced in (50G) was dissolved in acetonitrile (50 mL), and a phosphate buffer (pH 6.8, 50 mL), 2,2,6,6-tetramethylpiperidine-N-oxyl (135 mg, 0.865 mmol), sodium chlorite (80%, 2.44 g, 21.6 mmol), and an aqueous solution of sodium hypochlorite (effective chlorine concentration: 5%) (1.70 mL, 0.865 mmol) were sequentially added thereto at 0° C., and then, the resulting mixture was stirred at 0° C. for 2 hours. To the reaction solution, ethyl acetate was added, and the organic layer was washed with 1 N hydrochloric acid, water, and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=90:10 to 55:45 (v/v)), whereby the objective title compound was obtained as a white solid (1.32 g, yield: 85%).

$^1$H NMR (CDCl$_3$, 500 MHz): δ1.21 (3H, t, J=7.1 Hz), 2.19-2.27 (1H, m), 2.56-2.65 (1H, m), 2.65 (1H, dd, J=3.9, 15.6 Hz), 2.86 (1H, dd, J=9.5, 15.6 Hz), 2.94-3.01 (1H, m), 3.14-3.21 (1H, m), 3.37-3.50 (2H, m), 4.70 (1H, dd, J=3.9, 9.5 Hz), 5.78 (1H, dd, J=4.1, 6.6 Hz), 6.98 (2H, d, J=8.8 Hz), 7.21 (1H, t like, J=7.6 Hz), 7.25-7.34 (4H, m).

MS (FAB) m/z: 399 (M+K)$^+$

Example 51

(3S)-3-Ethoxy-3-(4-{[(1R)-4-(trifluoromethyl)-2,3-dihydro-1H-inden-1-yl]oxy}phenyl)propionic acid (Illustrative Compound No: 1-202)

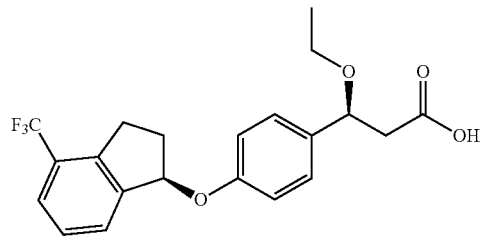

(51A) (1S)-4-(Trifluoromethyl)indan-1-ol

To a mixture of formic acid (0.995 mL, 26.2 mmol) and triethylamine (3.10 mL, 22.5 mmol), a dichloromethane (4.0 mL) solution of 4-(trifluoromethyl)indan-1-one (1.50 g, 7.49 mmol) was added, and chloro[(1S,2S)—N-(p-toluenesulfonyl)-1,2-diphenylethanediamine](mesitylene)ruthenium (II) (233 mg, 0.375 mmol) was added thereto at room temperature, and then, the resulting mixture was stirred under a nitrogen atmosphere at room temperature for 4 hours.

Water was added to the reaction solution, and the organic matter was extracted with ethyl acetate. The organic layer was washed with a saturated sodium bicarbonate solution and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=95:5 to 65:35 (v/v)), whereby the objective title compound was obtained as a white solid (1.49 g, yield: 98%).

The absolute configuration (S) of the objective title compound was confirmed by converting the compound into an α-methoxy-α-(trifluoromethyl)phenyl acetate ester and according to the method described in Journal of the American Chemical Society, 1991, vol. 113 (11), pp. 4092-4096.

$^1$H NMR (CDCl$_3$, 400 MHz): δ1.78-1.79 (1H, d, J=6.7 Hz), 1.95-2.05 (1H, m), 2.51-2.62 (1H, m), 2.93-3.05 (1H, m), 3.20-3.30 (1H, m), 5.29 (1H, dt, J=6.7, 6.7 Hz), 7.37 (1H, t, J=7.6 Hz), 7.55 (1H, d, J=7.6 Hz), 7.61 (1H, d, J=7.6 Hz)

(51B) (3S)-3-Ethoxy-3-(4-{[(1R)-4-(trifluoromethyl)-2,3-dihydro-1H-inden-1-yl]oxy}phenyl)propan-1-ol (1S)-4-(Trifluoromethyl)indan-1-ol (1.48 g, 7.33 mmol) produced in (51A) and 4-{(1S)-1-ethoxy-3-[(triisopropylsilyl)oxy]propyl}phenol (2.34 g, 6.65 mmol) produced in Example 50 (50E) were dissolved in tetrahydrofuran (35 mL), and triphenylphosphine (1.93 g, 7.33 mmol) and a 40% diethyl azodicarboxylate toluene solution (3.35 mL, 7.33 mmol) were added thereto at room temperature, and then, the resulting mixture was stirred under a nitrogen atmosphere at 50° C. for 10 hours. After the reaction solution was cooled to room temperature, the solvent was distilled off under reduced pressure, and the resulting residue was roughly purified by silica gel column chromatography (hexane:ethyl acetate=100:0 to 90:10 (v/v)), whereby a crude product was obtained. This crude product was used in the subsequent reaction step without performing further purification procedures.

The crude product was dissolved in tetrahydrofuran (30 mL), and a 1.0 M tetra-n-butylammonium fluoride tetrahydrofuran solution (10.0 mL, 10.0 mmol) was added thereto at 0° C., and then, the resulting mixture was stirred under a nitrogen atmosphere at room temperature for 4 hours.

To the reaction solution, a saturated aqueous solution of ammonium chloride was added, and the organic matter was extracted with ethyl acetate. The organic layer was washed with water and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=85:15 to 60:40 (v/v)), whereby the objective title compound was obtained (1.59 g, yield: 63%).

$^1$H NMR (CDCl$_3$, 400 MHz): δ1.20 (3H, t, J=7.0 Hz), 1.81-1.90 (1H, m), 2.01-2.11 (1H, m), 2.22-2.32 (1H, m), 2.59-2.69 (1H, m), 2.88 (1H, dd, J=4.3, 6.7 Hz), 3.06-3.16 (1H, m), 3.27-3.47 (3H, m), 3.75-3.86 (2H, m), 4.49 (1H, dd, J=3.9, 9.0 Hz), 5.77 (1H, dd, J=4.7, 6.6 Hz), 6.99 (2H, d, J=8.6 Hz), 7.28 (2H, d, J=8.6 Hz), 7.38 (1H, t, J=7.0 Hz), 7.60 (1H, d, J=7.0 Hz), 7.62 (1H, d, J=7.0 Hz)

(51C) (3S)-3-Ethoxy-3-(4-{[(1R)-4-(trifluoromethyl)-2,3-dihydro-1H-inden-1-yl]oxy}phenyl)propionic acid (3S)-3-Ethoxy-3-(4-{[(1R)-4-(trifluoromethyl)-2,3-dihydro-1H-inden-1-yl}oxy]phenyl)propan-1-ol (1.59 g, 4.18 mmol) produced in (51B) was dissolved in acetonitrile (50 mL), and a phosphate buffer (pH 6.8, 50 mL), 2,2,6,6-tetramethyl piperidine-N-oxyl (131 mg, 0.836 mmol), sodium chlorite (80%, 2.36 g, 20.9 mmol), and an aqueous solution of sodium hypochlorite (effective chlorine concentration: 5%) (1.65 mL, 0.836 mmol) were sequentially added thereto at 0° C., and then, the resulting mixture was stirred at 0° C. for 2.5 hours. To the reaction solution, ethyl acetate was added, and the organic layer was washed with a saturated aqueous solution of sodium thiosulfate, 1 N hydrochloric acid, water, and a saturated sodium chloride solution, then dried over anhydrous sodium sulfate and filtered. Then, the solvent was distilled off under reduced pressure, whereby a crude product was obtained. This crude product was purified by silica gel column chromatography (dichloromethane:methanol=100:0 to 95:5 (v/v)), whereby the objective title compound was obtained as a white solid (1.30 g, yield: 79%).

$^1$H NMR (CDCl$_3$, 400 MHz): δ1.22 (3H, t, J=7.1 Hz), 2.22-2.31 (1H, m), 2.59-2.70 (1H, m), 2.66 (1H, dd, J=4.1, 15.8 Hz), 2.86 (1H, dd, J=9.7, 15.8 Hz), 3.07-3.17 (1H, m), 3.27-3.37 (1H, m), 3.38-3.53 (2H, m), 4.71 (1H, dd, J=4.1, 9.7 Hz), 5.77 (1H, dd, J=4.5, 6.9 Hz), 7.00 (2H, d, J=9.0 Hz), 7.30 (2H, d, J=9.0 Hz), 7.38 (1H, t, J=7.8 Hz), 7.61 (1H, d, J=7.8 Hz), 7.61 (1H, d, J=7.8 Hz)

MS (FAB) m/z: 433 (M+K)$^+$

Example 52

(3S)-3-(4-{[(1S)-4-Chloro-2,3-dihydro-1H-inden-1-yl]oxy}phenyl)-3-ethoxypropionic acid (Illustrative Compound No: 1-200)

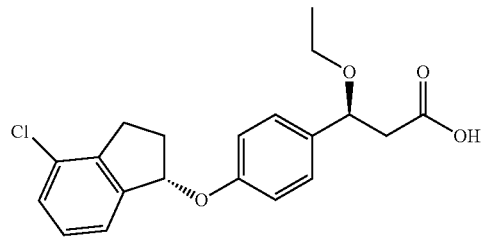

(52A) (1R)-4-Chloroindan-1-ol

To a mixture of formic acid (0.240 mL, 6.30 mmol) and triethylamine (0.750 mL, 5.40 mmol), a dichloromethane (1.0 mL) solution of 4-chloroindan-1-one (300 mg, 1.80 mmol) produced in accordance with the description of Journal of Medicinal Chemistry, 2003, vol. 46 (3), pp. 399-408 was added, and chloro[(1R,2R)—N-(p-toluenesulfonyl)-1,2-diphenyl ethanediamine](mesitylene)ruthenium(II) (55 mg, 0.090 mmol) was added thereto at room temperature, and then, the resulting mixture was stirred under a nitrogen atmosphere at room temperature for 2 hours. The solvent in the reaction solution was distilled off under reduced pressure, and the resulting residue was purified by silica gel column chromatography (hexane:ethyl acetate=95:5 to 65:35 (v/v)), whereby the objective title compound was obtained as a white solid (270 mg, yield: 89%).

The absolute configuration (R) of the objective title compound was confirmed by converting the compound into an α-methoxy-α-(trifluoromethyl)phenyl acetate ester and according to the method described in Journal of the American Chemical Society, 1991, vol. 113 (11), pp. 4092-4096.

$^1$H NMR (CDCl$_3$, 400 MHz): δ1.76 (1H, d, J=7.0 Hz), 1.93-2.02 (1H, m), 2.48-2.59 (1H, m), 2.80-2.90 (1H, m), 3.07-3.16 (1H, m), 5.30 (1H, dt, J=6.2, 6.4 Hz), 7.21 (1H, t like, J=7.3 Hz), 7.27 (1H, d, J=7.3 Hz), 7.32 (1H, d, J=7.3 Hz)

(52B) Methyl (3S)-3-(4-{[(1S)-4-chloro-2,3-dihydro-1H-inden-1-yl]oxy}phenyl)-3-ethoxypropionate (1R)-4-Chloroindan-1-ol (169 mg, 1.00 mmol) produced in (52A) and methyl (3S)-3-ethoxy-3-(4-hydroxyphenyl)propionate (150 mg, 0.669 mmol) produced in Example 41 (41C) were dissolved in tetrahydrofuran (4.0 mL), and triphenylphosphine (260 mg, 1.00 mmol) and a 40% diethyl azodicarboxylate toluene solution (0.450 mL, 1.00 mmol) were added thereto at room temperature, and then, the resulting mixture was stirred under a nitrogen atmosphere at 50° C. for 3 hours. After the reaction solution was cooled to room temperature, the solvent was distilled off under reduced pressure, and the resulting residue was purified by silica gel column chromatography (hexane:ethyl acetate=95:5 to 80:20 (v/v)), whereby the objective title compound was obtained (176 mg, yield: 70%).

$^1$H NMR (CDCl$_3$, 400 MHz): δ1.16 (3H, t, J=7.1 Hz), 2.18-2.28 (1H, m), 2.58 (1H, dd, J=5.0, 15.2 Hz), 2.55-2.66

(1H, m), 2.83 (1H, dd, J=9.0, 15.2 Hz,), 2.92-3.02 (1H, m), 3.13-3.22 (1H, m), 3.31-3.45 (2H, m), 3.69 (3H, s), 4.72 (1H, dd, J=5.0, 9.0 Hz), 5.78 (1H, dd, J=4.3, 7.1 Hz), 6.97 (2H, d, J=8.6 Hz), 7.21 (1H, t like, J=7.8 Hz), 7.25-7.35 (4H, m)

(52C) (3S)-3-(4-{[(1S)-4-Chloro-2,3-dihydro-1H-inden-1-yl]oxy}phenyl)-3-ethoxypropionic acid Methyl (3S)-3-(4-{[(1S)-4-chloro-2,3-dihydro-1H-inden-1-yl]oxy}phenyl)-3-ethoxypropionate (174 mg, 0.464 mmol) produced in (52B) was dissolved in tetrahydrofuran (2.0 mL) and methanol (2.0 mL), and a 2N aqueous solution of sodium hydroxide (0.700 mL, 1.39 mmol) was added thereto at room temperature, and then, the resulting mixture was stirred at room temperature for 2 hours.

Water was added to the reaction solution, and 2 N hydrochloric acid (0.700 mL, 1.39 mmol) was added thereto, and the organic matter was extracted with ethyl acetate. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=90:10 to 55:45 (v/v)), whereby the objective title compound was obtained as a white solid (150 mg, yield: 90%).

$^1$H NMR (CDCl$_3$, 400 MHz): δ1.21 (3H, t, J=7.0 Hz), 2.18-2.28 (1H, m), 2.56-2.66 (1H, m), 2.66 (1H, dd, J=3.9, 16.1 Hz), 2.86 (1H, dd, J=9.6, 15.8 Hz), 2.93-3.02 (1H, m), 3.13-3.23 (1H, m), 3.37-3.53 (2H, m), 4.70 (1H, dd, J=4.1, 9.6 Hz), 5.79 (1H, dd, J=4.3, 6.7 Hz), 6.99 (2H, d, J=8.6 Hz), 7.22 (1H, dd, J=7.2, 8.0 Hz), 7.26-7.35 (4H, m).

MS (FAB) m/z: 399 (M+K)$^+$

Example 53

(3S)-3-Ethoxy-3-(4-{[4-(trifluoromethyl)-2,3-dihydro-1H-inden-1-yl]oxy}phenyl)propionic acid (Illustrative Compound No: 1-202)

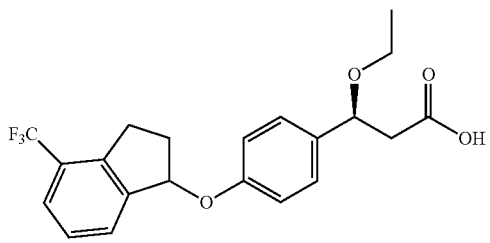

(53A) 4-(Trifluoromethyl)indan-1-ol 4-(Trifluoromethyl)indan-1-one (300 mg, 1.50 mmol) was dissolved in methanol (2.5 mL) and tetrahydrofuran (2.5 mL), and sodium borohydride (85 mg, 2.25 mmol) was added thereto at 0° C., and then, the resulting mixture was stirred at room temperature for 2 hours. To the reaction solution, a saturated aqueous solution of ammonium chloride was added, and the organic matter was extracted with ethyl acetate. The organic layer was washed with a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=95:5 to 67:33 (v/v)), whereby the objective title compound was obtained as a white solid (291 mg, yield: 96%).

$^1$H NMR (CDCl$_3$, 400 MHz): δ1.78-1.79 (1H, d, J=6.7 Hz), 1.95-2.05 (1H, m), 2.62-2.51 (1H, m), 3.05-2.93 (1H, m), 3.30-3.20 (1H, m), 5.29 (1H, dt, J=6.7, 6.7 Hz), 7.37 (1H, t like, J=7.6 Hz), 7.55 (1H, d, J=7.6 Hz), 7.61 (1H, d, J=7.6 Hz)

(53B) Methyl (3S)-3-ethoxy-3-(4-{[4-(trifluoromethyl)-2,3-dihydro-1H-inden-1-yl]oxy}phenyl)propionate 4-(Trifluoromethyl)indan-1-ol (200 mg, 0.986 mmol) produced in (53A) and methyl (3S)-3-ethoxy-3-(4-hydroxyphenyl)propionate (150 mg, 0.657 mmol) produced in Example 41 (41C) were dissolved in tetrahydrofuran (4.0 mL), and triphenylphosphine (260 mg, 0.986 mmol) and a 40% diethyl azodicarboxylate toluene solution (0.450 mL, 0.986 mmol) were added thereto at room temperature, and then, the resulting mixture was stirred under a nitrogen atmosphere at 50° C. for 5 hours. After the reaction solution was cooled to room temperature, the solvent was distilled off under reduced pressure, and the resulting residue was purified by silica gel column chromatography (hexane:ethyl acetate=95:5 to 80:20 (v/v)), whereby the objective title compound was obtained (181 mg, yield: 66%).

$^1$H NMR (CDCl$_3$, 400 MHz): δ1.16 (3H, t, J=7.0 Hz), 2.22-2.32 (1H, m), 2.59 (1H, dd, J=4.7, 15.3 Hz), 2.56-2.69 (1H, m), 2.84 (1H, dd, J=9.0, 15.3 Hz), 3.06-3.17 (1H, m), 3.27-3.46 (3H, m), 3.70 (3H, s), 4.73 (1H, dd, J=4.7, 9.0 Hz), 5.77 (1H, brt, J=5.5 Hz), 6.99 (2H, d, J=8.8 Hz), 7.31 (2H, d, J=8.8 Hz), 7.38 (1H, t like, J=7.5 Hz), 7.58-7.64 (2H, m)

(53C) (3S)-3-Ethoxy-3-(4-{[4-(trifluoromethyl)-2,3-dihydro-1H-inden-1-yl]oxy}phenyl)propionic acid Methyl (3S)-3-ethoxy-3-(4-{[4-(trifluoromethyl)-2,3-dihydro-1H-inden-1-yl]oxy}phenyl)propionate (181 mg, 0.443 mmol) produced in (53B) was dissolved in tetrahydrofuran (2.0 mL) and methanol (2.0 mL), and a 2N aqueous solution of sodium hydroxide (0.665 mL, 1.33 mmol) was added thereto at room temperature, and then, the resulting mixture was stirred at room temperature for 2 hours.

Water was added to the reaction solution, and 2 N hydrochloric acid (0.665 mL, 1.33 mmol) was added thereto, and the organic matter was extracted with ethyl acetate. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=90:10 to 55:45 (v/v)), whereby the objective title compound was obtained as a white solid (135 mg, yield: 77%).

$^1$H NMR (CDCl$_3$, 400 MHz): δ1.22 (3H, t, J=7.0 Hz), 2.22-2.31 (1H, m), 2.66 (1H, dd, J=4.0, 15.7 Hz), 2.70-2.58 (1H, m), 2.86 (1H, dd, J=9.6, 15.7 Hz), 3.07-3.17 (1H, m), 3.27-3.37 (1H, m), 3.37-3.52 (2H, m), 4.71 (1H, dd, J=4.0, 9.6 Hz), 5.77 (1H, dd, J=4.9, 6.1 Hz), 7.01 (2H, d, J=8.6 Hz), 7.30 (2H, d, J=8.6 Hz), 7.38 (1H, t like, J=7.6 Hz), 7.63-7.58 (2H, m).

MS (FAB) m/z: 433 (M+K)$^+$

In accordance with the above-mentioned methods of Examples 1 to 53, compounds of Examples shown below were produced.

Example 54-1

3-Isopropoxy-3-{4-[(2-methylbenzyl)oxy]phenyl}propionic acid (Illustrative Compound No: 1-53)

MS (ESI) m/z: 327 (M−H)⁻

Example 54-2

(3S)-3-(4-{[2-Chloro-3-(trifluoromethyl)benzyl]oxy}phenyl)-3-ethoxypropionic acid (Illustrative Compound No: 1-85)

MS (ESI) m/z: 401 (M−H)⁻

Example 54-3

3-(4-{[4-(Difluoromethyl)benzyl]oxy}phenyl)-3-ethoxypropionic acid (Illustrative Compound No: 1-104)

MS (ESI) m/z: 349 (M−H)⁻

Example 54-4

(3S)-3-{4-[(2,3-Difluorobenzyl)oxy]phenyl}-3-ethoxypropionic acid (Illustrative Compound No: 1-108)

MS (ESI) m/z: 335 (M−H)⁻

Example 54-5

3-Ethoxy-3-(4-{[(3R)-1-phenylpiperidin-3-yl]methoxy}phenyl)propionic acid (Illustrative Compound No: 1-146)

$^1$H NMR (CDCl$_3$, 400 MHz): δ1.16 (3H, t, J=7.0 Hz), 1.26-1.36 (1H, m), 1.71-1.92 (3H, m), 2.21-2.29 (1H, m), 2.63 (1H, dd, J=4.7, 15.6 Hz), 2.68 (1H, dd, J=9.8, 11.1 Hz), 2.76-2.87 (2H, m), 3.32-3.44 (2H, m), 3.57 (1H, d, J=11.7 Hz), 3.76 (1H, dd, J=3.1, 12.1 Hz), 3.85-3.96 (2H, m), 4.69 (1H, dd, J=4.3, 9.4 Hz), 6.84 (1H, t, J=7.4 Hz), 6.90 (2H, d, J=9.8 Hz), 6.97 (2H, d, J=7.8 Hz), 7.23-7.27 (4H, m)

Example 54-6

3-Ethoxy-3-(4-{[(3S)-1-phenylpiperidin-3-yl]methoxy}phenyl)propionic acid (Illustrative Compound No: 1-146)

$^1$H NMR (CDCl$_3$, 400 MHz): δ1.18 (3H, t, J=7.0 Hz), 1.26-1.37 (1H, m), 1.71-1.92 (3H, m), 2.21-2.27 (1H, m), 2.64 (1H, dd, J=4.3, 16.0 Hz), 2.69 (1H, dd, J=9.8, 11.8 Hz), 2.77-2.87 (2H, m), 3.34-3.46 (2H, m), 3.57 (1H, d, J=12.1 Hz), 3.76 (1H, dd, J=3.1, 12.1 Hz), 3.86-3.95 (2H, m), 4.68 (1H, dd, J=3.9, 9.4 Hz), 6.84 (1H, t, J=7.4 Hz), 6.91 (2H, d, J=8.6 Hz), 6.97 (2H, d, J=8.7 Hz), 7.24-7.28 (4H, m)

Example 54-7

3-Ethoxy-3-{4-[(1-phenylpiperidin-4-yl)methoxy]phenyl}propionic acid (Illustrative Compound No: 1-147)

$^1$H NMR (CDCl$_3$, 400 MHz): δ1.19 (3H, t, J=7.0 Hz), 1.52 (1H, dd, J=4.3, 13.0 Hz), 1.58 (1H, dd, J=3.1, 12.7 Hz), 1.95-1.98 (3H, m), 2.64 (1H, dd, J=4.3, 16.0 Hz), 2.76 (2H, td, J=2.3, 12.5 Hz), 2.85 (1H, dd, J=9.4, 15.7 Hz), 3.36-3.36 (2H, m), 3.74 (2H, d, J=12.1 Hz), 3.87 (2H, d, J=5.8 Hz), 4.68 (1H, dd, J=4.3, 9.8 Hz), 6.85 (1H, t, J=7.0 Hz), 6.90 (2H, d, J=8.5 Hz), 6.98 (2H, d, J=8.6 Hz), 7.24-7.29 (4H, m)

Example 54-8

3-Ethoxy-3-(4-{[4-(trifluoromethoxy)benzyl]oxy}phenyl)propionic acid (Illustrative Compound No: 1-46)

$^1$H NMR (CDCl$_3$, 400 MHz): δ1.20 (3H, t, J=7.0 Hz), 2.65 (1H, dd, J=3.9, 15.7 Hz), 2.85 (1H, dd, J=9.8, 16.0 Hz), 3.35-3.49 (2H, m), 4.69 (1H, dd, J=4.3, 9.8 Hz), 5.06 (2H, s), 6.97 (2H, d, J=8.6 Hz), 7.23-7.28 (4H, m), 7.47 (2H, d, J=8.6 Hz)

Example 54-9

3-(4-{[2-Chloro-3-(trifluoromethyl)benzyl]oxy}phenyl)-3-ethoxypropionic acid (Illustrative Compound No: 1-96)

$^1$H NMR (CDCl$_3$, 400 MHz): δ1.19 (3H, t, J=7.0 Hz), 2.45 (1H, dd, J=4.3, 15.6 Hz), 2.86 (1H, dd, J=9.3, 15.6 Hz), 3.37-3.46 (2H, m), 4.71 (1H, dd, J=4.3, 9.4 Hz), 5.22 (2H, s), 6.99 (2H, d, J=8.6 Hz), 7.29 (2H, d, J=8.7 Hz), 7.42 (1H, t, J=7.4 Hz), 7.69 (1H, d, J=7.0 Hz), 7.79 (1H, d, J=7.9 Hz)

Example 54-10

3-(4-{[4-Chloro-3-(trifluoromethoxy)benzyl]oxy}phenyl)-3-ethoxypropionic acid (Illustrative Compound No: 1-101)

$^1$H NMR (CDCl$_3$, 400 MHz): δ1.17 (3H, t, J=7.0 Hz), 2.64 (1H, dd, J=4.3, 15.7 Hz), 2.85 (1H, dd, J=9.4, 15.6 Hz), 3.33-3.42 (2H, m), 4.70 (1H, dd, J=4.7, 9.4 Hz), 5.04 (2H, s), 6.94 (2H, d, J=8.6 Hz), 7.26-7.33 (3H, m), 7.40 (1H, s), 7.49 (1H, d, J=8.2 Hz)

Example 54-11

3-(4-{[3-Chloro-5-(trifluoromethoxy)benzyl]oxy}phenyl)-3-ethoxypropionic acid (Illustrative Compound No: 1-102)

$^1$H NMR (CDCl$_3$, 400 MHz): δ1.18 (3H, t, J=7.0 Hz), 2.64 (1H, dd, J=3.9, 15.6 Hz), 2.85 (1H, dd, J=9.4, 15.6 Hz), 3.36-3.44 (2H, m), 4.70 (1H, dd, J=3.9, 9.3 Hz), 5.05 (2H, s), 6.95 (2H, d, J=8.6 Hz), 7.20 (2H, s), 7.28 (2H, d, J=8.6 Hz), 7.38 (1H, s)

Example 54-12

3-Ethoxy-3-{4-[(4-fluoro-1-naphthyl)methoxy]phenyl}propionic acid (Illustrative Compound No: 1-152)

$^1$H NMR (CDCl$_3$, 400 MHz): δ1.19 (3H, t, J=7.0 Hz), 2.66 (1H, dd, J=4.3, 15.6 Hz), 2.87 (1H, dd, J=9.4, 15.6 Hz), 3.35-3.46 (2H, m), 4.71 (1H, dd, J=4.3, 9.4 Hz), 5.43 (2H, s), 7.04 (2H, d, J=8.6 Hz), 7.13 (1H, dd, J=7.8, 10.1 Hz), 7.30 (2H, d, J=8.6 Hz), 7.52 (1H, dd, J=5.4, 7.4 Hz), 7.60 (2H, t, J=4.5 Hz), 8.04-8.06 (1H, m), 8.17 (1H, t, J=4.7 Hz)

Example 54-13

3-(4-{[4-Chloro-3-(trifluoromethyl)benzyl] oxy}phenyl)-3-ethoxypropionic acid (Illustrative Compound No: 1-103)

$^1$H NMR (CDCl$_3$, 400 MHz): δ1.18 (3H, t, J=7.0 Hz), 2.64 (1H, dd, J=4.3, 15.6 Hz), 2.85 (1H, dd, J=9.4, 15.6 Hz), 3.34-3.44 (2H, m), 4.70 (1H, dd, J=4.3, 9.4 Hz), 5.07 (2H, s), 6.95 (2H, d, J=8.6 Hz), 7.28 (2H, d, J=8.6 Hz), 7.53-7.55 (2H, m), 7.76 (1H, s)

Example 54-14

3-{4-[(7-Chloroquinolin-4-yl)oxy]phenyl}-3-ethoxypropionic acid (Illustrative Compound No: 1-161)

$^1$H NMR (CDCl$_3$, 400 MHz): δ1.24 (3H, t, J=7.1 Hz), 2.73 (1H, dd, J=5.1, 15.3 Hz), 2.95 (1H, dd, J=8.6, 15.2 Hz), 3.45-3.52 (2H, m), 4.83 (1H, dd, J=5.5, 9.0 Hz), 6.56 (1H, d, J=5.1 Hz), 7.19 (2H, d, J=8.6 Hz), 7.49 (2H, d, J=8.6 Hz), 7.56 (1H, dd, J=2.0, 9.0 Hz), 8.12 (1H, d, J=2.3 Hz), 8.31 (1H, d, J=9.0 Hz), 8.67 (1H, d, J=5.1 Hz)

Example 54-15

(3S)-3-(4-{[3,4-Bis(trifluoromethyl)benzyl] oxy}phenyl)-3-ethoxypropionic acid (Illustrative Compound No: 1-118)

$^1$H NMR (CDCl$_3$, 400 MHz): δ1.19 (3H, t, J=7.0 Hz), 2.65 (1H, dd, J=4.3, 16.0 Hz), 2.85 (1H, dd, J=9.4, 15.7 Hz), 3.37-3.46 (2H, m), 4.70 (1H, dd, J=4.3, 9.4 Hz), 5.17 (2H, s), 6.99 (2H, d, J=8.6 Hz), 7.29 (2H, d, J=8.6 Hz), 7.76 (1H, d, J=8.2 Hz), 7.89 (1H, d, J=8.2 Hz), 7.92 (1H, s)

Example 54-16

(3S)-3-(4-{[3-Chloro-4-(trifluoromethyl)benzyl] oxy}phenyl)-3-ethoxypropionic acid (Illustrative Compound No: 1-120)

$^1$H NMR (CDCl$_3$, 400 MHz): δ1.17 (3H, t, J=7.0 Hz), 2.64 (1H, dd, J=4.3, 15.6 Hz), 2.85 (1H, dd, J=9.0, 15.6 Hz), 3.35-3.43 (2H, m), 4.70 (1H, dd, J=4.7, 9.4 Hz), 5.09 (2H, s), 6.95 (2H, d, J=8.6 Hz), 7.29 (2H, d, J=8.2 Hz), 7.42 (1H, d, J=8.2 Hz), 7.60 (1H, s), 7.71 (1H, d, J=8.3 Hz)

Example 54-17

(3S)-3-{4-[(3-Chloro-4-fluorobenzyl)oxy]phenyl}-3-ethoxypropionic acid (Illustrative Compound No: 1-122)

$^1$H NMR (CDCl$_3$, 400 MHz): δ1.16 (3H, t, J=7.0 Hz), 2.63 (1H, dd, J=4.3, 15.3 Hz), 2.85 (1H, dd, J=9.4, 15.6 Hz), 3.34-3.42 (2H, m), 4.70 (1H, dd, J=4.7, 9.4 Hz), 4.99 (2H, s), 6.94 (2H, d, J=8.2 Hz), 7.15 (1H, t, J=8.6 Hz), 7.27-7.31 (3H, m), 7.49 (1H, d, J=7.0 Hz)

Example 54-18

(3S)-3-{4-[(4-Chloro-3-fluorobenzyl)oxy]phenyl}-3-ethoxypropionic acid (Illustrative Compound No: 1-123)

$^1$H NMR (CDCl$_3$, 400 MHz): δ1.18 (3H, t, J=7.0 Hz), 2.64 (1H, dd, J=4.3, 16.0 Hz), 2.84 (1H, dd, J=9.3, 15.6 Hz), 3.34-3.44 (2H, m), 4.69 (1H, dd, J=4.3, 9.8 Hz), 5.03 (2H, s), 6.94 (2H, d, J=8.6 Hz), 7.15 (1H, t, J=8.2 Hz), 7.23-7.28 (3H, m), 7.41 (1H, d, J=7.8 Hz)

Example 54-19

(3S)-3-Ethoxy-3-{4-[(2,3,5-trifluorobenzyl] oxy}phenyl}propionic acid (Illustrative Compound No: 1-127)

$^1$H NMR (CDCl$_3$, 400 MHz): δ1.18 (3H, t, J=7.0 Hz), 2.64 (1H, dd, J=3.9, 15.6 Hz), 2.85 (1H, dd, J=9.4, 15.6 Hz), 3.34-3.46 (2H, m), 4.70 (1H, dd, J=4.7, 9.8 Hz), 5.06 (2H, s), 6.95-7.00 (3H, m), 7.28 (2H, d, J=8.6 Hz), 7.32-7.39 (1H, m)

Example 54-20

(3S)-3-Ethoxy-3-(4-{[3-fluoro-4-(trifluoromethoxy) benzyl]oxy}phenyl)propionic acid (Illustrative Compound No: 1-130)

$^1$H NMR (CDCl$_3$, 400 MHz): δ1.19 (3H, t, J=7.1 Hz), 2.65 (1H, dd, J=3.9, 15.6 Hz), 2.85 (1H, dd, J=9.4, 15.6 Hz), 3.37-3.45 (2H, m), 4.69 (1H, dd, J=4.3, 9.8 Hz), 5.05 (2H, s), 6.95 (2H, d, J=9.0 Hz), 7.22 (1H, d, J=8.2 Hz), 7.26-7.35 (4H, m)

Example 54-21

(3S)-3-Ethoxy-3-(4-{[4-fluoro-3-(trifluoromethoxy) benzyl]oxy}phenyl)propionic acid (Illustrative Compound No: 1-131)

$^1$H NMR (CDCl$_3$, 400 MHz): δ1.18 (3H, t, J=7.1 Hz), 2.64 (1H, dd, J=4.3, 15.6 Hz), 2.85 (1H, dd, J=9.4, 15.6 Hz), 3.38-3.43 (2H, m), 4.70 (1H, dd, J=4.3, 9.3 Hz), 5.03 (2H, s), 6.97 (2H, d, J=8.6 Hz), 7.24 (1H, dd, J=8.6, 10.8 Hz), 7.28 (2H, d, J=8.6 Hz), 7.33-7.37 (1H, m), 7.49 (1H, d, J=7.1 Hz)

Example 54-22

(3S)-3-Ethoxy-3-{4-[(4-methyl-2,3-dihydro-1H-inden-1-yl)oxy]phenyl}propionic acid (Illustrative Compound No: 1-183)

$^1$H NMR (CDCl$_3$, 400 MHz): δ1.19 (3H, t, J=7.1 Hz), 2.18-2.26 (1H, m), 2.30 (3H, s), 2.52-2.61 (1H, m), 2.66 (1H, dd, J=4.3, 15.6 Hz), 2.87 (2H, dd, J=9.4, 15.6 Hz), 3.02-3.10 (1H, m), 3.35-3.46 (2H, m), 4.71 (1H, dd, J=4.3, 9.8 Hz), 5.77 (1H, dd, J=4.3, 6.6 Hz), 6.99 (2H, d, J=8.2 Hz), 7.15 (1H, t, J=7.4 Hz), 7.19 (1H, d, J=7.0 Hz), 7.26-7.29 (3H, m)

Example 54-23

(3S)-3-Ethoxy-3-{4-[(6-methyl-2,3-dihydro-1H-inden-1-yl)oxy]phenyl}propionic acid (Illustrative Compound No: 1-184)

$^1$H NMR (CDCl$_3$, 400 MHz): δ1.21 (3H, t, J=7.1 Hz), 2.16-2.24 (1H, m), 2.36 (3H, s), 2.52-2.61 (1H, m), 2.67 (1H, dd, J=3.9, 16.1 Hz), 2.85 (1H, dd, J=9.8, 16.0 Hz), 2.86-2.92 (1H, m), 3.06-3.14 (1H, m), 3.39-3.47 (2H, m), 4.70 (1H, dd, J=3.9, 9.8 Hz), 5.72 (1H, dd, J=4.3, 6.6 Hz), 7.01 (2H, d, J=8.6 Hz), 7.15 (1H, d, J=8.6 Hz), 7.20 (1H, d, J=7.9 Hz), 7.24-7.29 (3H, m)

Example 54-24

(3S)-3-Ethoxy-3-{4-[(5-methoxy-2,3-dihydro-1H-inden-1-yl)oxy]phenyl}propionic acid (Illustrative Compound No: 1-192)

$^1$H NMR (CDCl$_3$, 400 MHz): δ1.18 (3H, t, J=7.0 Hz), 2.20-2.28 (1H, m), 2.51-2.58 (1H, m), 2.66 (1H, dd, J=4.3, 15.1 Hz), 2.85-2.94 (2H, m), 3.10-3.18 (1H, m), 3.34-3.48 (72H, m), 3.82 (3H, s), 4.70 (1H, dd, J=4.3, 9.4 Hz), 5.71 (1H, dd, J=3.6, 6.7 Hz), 6.83 (2H, d, J=8.6 Hz), 6.98 (1H, d, J=9.0 Hz), 7.21 (1H, d, J=8.6 Hz), 7.26-7.28 (2H, m), 7.33 (1H, d, J=8.2 Hz)

Example 54-25

(3S)-3-Ethoxy-3-{4-[(6-methoxy-2,3-dihydro-1H-inden-1-yl)oxy]phenyl}propionic acid (Illustrative Compound No: 1-193)

$^1$H NMR (CDCl$_3$, 400 MHz): δ1.21 (3H, t, J=7.1 Hz), 2.17-2.25 (1H, m), 2.56-2.62 (1H, m), 2.67 (1H, dd, J=3.9, 15.6 Hz), 2.84-2.90 (1H, m), 2.87 (1H, dd, J=9.4, 15.6 Hz), 3.03-3.11 (1H, m), 3.37-3.49 (2H, m), 3.80 (3H, s), 4.70 (1H, dd, J=3.9, 9.8 Hz), 5.72 (1H, dd, J=4.7, 6.7 Hz), 6.89 (1H, dd, J=2.8, 8.2 Hz), 6.96 (1H, d, J=2.4 Hz), 7.01 (2H, d, J=9.0 Hz), 7.20 (1H, d, J=8.2 Hz), 7.28 (2H, m)

Example 54-26

(3S)-3-{4-[(4-Chloro-5-methoxy-2,3-dihydro-1H-inden-1-yl)oxy]phenyl}-3-ethoxypropionic acid (Illustrative Compound No: 1-195)

$^1$H NMR (CDCl$_3$, 400 MHz): δ1.18 (3H, t, J=7.0 Hz), 2.23-2.30 (1H, m), 2.53-2.64 (1H, m), 2.66 (1H, dd, J=4.7, 15.7 Hz), 2.87 (1H, dd, J=9.0, 15.6 Hz), 2.93-3.01 (1H, m), 3.13-3.21 (1H, m), 3.34-3.45 (2H, m), 3.91 (3H, s), 4.72 (1H, dd, J=4.6, 9.3 Hz), 5.74 (1H, dd, J=3.9, 6.6 Hz), 6.85 (1H, d, J=8.6 Hz), 6.97 (2H, d, J=8.1 Hz), 7.26-7.29 (3H, m)

Example 54-27

(3S)-3-Ethoxy-3-{4-[(5-methyl-2,3-dihydro-1H-inden-1-yl)oxy]phenyl}propionic acid (Illustrative Compound No: 1-185)

$^1$H NMR (CDCl$_3$, 400 MHz): δ1.18 (3H, t, J=7.0 Hz), 2.17-2.25 (1H, m), 2.36 (3H, s), 2.50-2.58 (1H, m), 2.66 (1H, dd, J=4.3, 15.7 Hz), 2.85 (1H, dd, J=9.4, 15.7 Hz), 2.86-2.92 (1H, m), 3.07-3.15 (1H, m), 3.35-3.46 (2H, m), 4.71 (1H, dd, J=4.3, 9.7 Hz), 5.72 (1H, dd, J=3.9, 6.6 Hz), 6.99 (2H, d, J=8.6 Hz), 7.07 (1H, d, J=7.5 Hz), 7.13 (1H, s), 7.27 (2H, d, J=8.6 Hz), 7.31 (1H, d, J=7.8 Hz)

Example 54-28

3-[4-(2,4-Dichloro-3,5-dimethylphenoxy)phenyl]-3-propoxypropionic acid (Illustrative Compound No: 1-33)

$^1$H NMR (CDCl$_3$, 400 MHz): δ0.90 (3H, t, J=7.4 Hz), 1.54-1.65 (2H, m), 2.33 (3H, s), 2.54 (3H, s), 2.65 (1H, dd, J=3.9, 15.7 Hz), 2.84 (1H, dd, J=9.8, 15.7 Hz), 3.26-3.40 (2H, m), 4.70 (1H, dd, J=3.9, 9.8 Hz), 6.82 (1H, s), 6.91 (2H, d, J=8.6 Hz), 7.28 (2H, d, J=8.6 Hz)
MS (FAB) m/z: 419 (M+Na)$^+$

Example 54-29

(3S)-3-{4-[(5-Chloro-2,3-dihydro-1H-inden-1-yl)oxy]phenyl}-3-ethoxypropionic acid (Illustrative Compound No: 1-197)

$^1$H NMR (CDCl$_3$, 400 MHz): δ1.21 (3H, t, J=7.0 Hz), 2.18-2.28 (1H, m), 2.54-2.65 (1H, m), 2.66 (1H, dd, J=4.0, 15.7 Hz), 2.86 (1H, dd, J=9.5, 15.7 Hz), 2.87-2.97 (1H, m), 3.09-3.19 (1H, m), 3.37-3.52 (2H, m), 4.70 (1H, dd, J=4.0, 9.5 Hz), 5.71 (1H, dd, J=3.9, 6.6 Hz), 6.99 (2H, d, J=8.6 Hz), 7.23 (1H, dd, J=1.6, 8.3 Hz), 7.25-7.32 (3H, m), 7.35 (1H, d, J=8.3 Hz)
MS (FAB) m/z: 399 (M+K)$^+$

Example 54-30

(3S)-3-{4-[(6-Chloro-2,3-dihydro-1H-inden-1-yl)oxy]phenyl}-3-ethoxypropionic acid (Illustrative Compound No: 1-198)

$^1$H NMR (CDCl$_3$, 400 MHz): δ1.21 (3H, t, J=7.1 Hz), 2.18-2.27 (1H, m), 2.55-2.66 (1H, m), 2.66 (1H, dd, J=3.9, 15.6 Hz), 2.86 (1H, dd, J=9.8, 15.6 Hz), 2.85-2.95 (1H, m), 3.05-3.15 (1H, m), 3.37-3.53 (2H, m), 4.71 (1H, dd, J=3.9, 9.8 Hz), 5.72 (1H, dd, J=4.7, 6.7 Hz), 7.00 (2H, d, J=9.0 Hz), 7.23 (1H, d, J=8.2 Hz), 7.29 (2H, d, J=9.0 Hz), 7.26-7.31 (1H, m), 7.40 (1H, d, J=2.0 Hz)
MS (FAB) m/z: 399 (M+K)$^+$

Example 54-31

(3S)-3-{4-[(4,6-Dichloro-2,3-dihydro-1H-inden-1-yl)oxy]phenyl}-3-ethoxypropionic acid (Illustrative Compound No: 1-201)

$^1$H NMR (CDCl$_3$, 400 MHz): δ1.21 (3H, t, J=7.1 Hz), 2.19-2.29 (1H, m), 2.66 (1H, dd, J=4.0, 15.8 Hz), 2.58-2.69 (1H, m), 2.86 (1H, dd, J=9.4, 15.8 Hz), 2.88-2.97 (1H, m), 3.08-3.17 (1H, m), 3.37-3.52 (2H, m), 4.71 (1H, dd, J=4.0, 9.4 Hz), 5.74 (1H, dd, J=4.9, 6.8 Hz), 6.98 (2H, d, J=8.7 Hz), 7.28-7.32 (3H, m), 7.34 (1H, d, J=2.0 Hz)
MS (FAB) m/z: 417 (M+Na)$^+$

Example 54-32

3-Ethoxy-3-{4-[(4-fluorobiphenyl-2-yl)oxy]phenyl}propionic acid (Illustrative Compound No: 1-20)

$^1$H NMR (CDCl$_3$, 400 MHz): δ1.19 (3H, t, J=7.0 Hz), 2.62 (1H, dd, J=4.0, 15.8 Hz), 2.82 (1H, dd, J=9.4, 15.8 Hz), 3.34-3.47 (2H, m), 4.69 (1H, dd, J=4.0, 9.4 Hz), 6.71 (1H, dd, J=2.5, 10.0 Hz), 6.92 (1H, dd, J=2.5, 8.5 Hz), 6.96 (2H, d, J=9.0 Hz), 7.25-7.33 (3H, m), 7.34-7.44 (3H, m), 7.48-7.53 (2H, m)
MS (FAB) m/z: 403 (M+Na)$^+$

Example 54-33

3-Ethoxy-3-(4-{[6-(trifluoromethyl)pyridine-3-yl]methoxy}phenyl)propionic acid (Illustrative Compound No: 1-141)

$^1$H NMR (CDCl$_3$, 500 MHz): δ1.19 (3H, t, J=7.1 Hz), 2.63 (1H, dd, J=4.2, 15.7 Hz), 2.84 (1H, dd, J=9.3, 15.7 Hz), 3.47-3.35 (2H, m), 4.69 (1H, dd, J=4.2, 9.3 Hz), 5.17 (2H, s), 6.97 (2H, d, J=8.7 Hz), 7.29 (2H, d, J=8.7 Hz), 7.73 (1H, d, J=7.8 Hz), 7.98 (1H, d, J=7.8 Hz), 8.80 (1H, s)
MS (FAB) m/z: 370 (M+H)$^+$

Example 54-34

3-Ethoxy-3-(4-{[5-(trifluoromethyl)-2-furyl] methoxy}phenyl)propionic acid (Illustrative Compound No: 1-168)

$^1$H NMR (CDCl$_3$, 400 MHz): δ1.20 (3H, t, J=7.0 Hz), 2.63 (1H, dd, J=4.0, 15.7 Hz), 2.84 (1H, dd, J=9.6, 15.7 Hz), 3.35-3.49 (2H, m), 4.69 (1H, dd, J=4.0, 9.6 Hz), 5.04 (2H, s), 6.51 (1H, d, J=3.5 Hz), 6.78-6.81 (1H, m), 6.97 (2H, d, J=9.0 Hz), 7.28 (2H, d, J=9.0 Hz)
MS (FAB) m/z: 397 (M+K)$^+$

Example 54-35

(3S)-3-Ethoxy-3-{4-[(1R)-1,2,3,4-tetrahydronaphthalen-1-yloxy]phenyl}propionic acid (Illustrative Compound No: 1-158)

$^1$H NMR (CDCl$_3$, 500 MHz): δ1.21 (3H, t, J=7.1 Hz), 1.75-1.84 (1H, m), 1.97-2.07 (2H, m), 2.12-2.21 (1H, m), 2.66 (1H, dd, J=3.9, 15.6 Hz), 2.73-2.82 (1H, m), 2.86 (1H, dd, J=9.8, 15.6 Hz), 2.87-2.95 (1H, m), 3.38-3.52 (2H, m), 4.69 (1H, dd, J=3.9, 9.8 Hz), 5.38 (1H, dd, J=4.1, 4.1 Hz), 7.02 (2H, d, J=8.3 Hz), 7.14-7.22 (2H, m), 7.24 (1H, dd, J=1.5, 7.4 Hz), 7.27 (2H, d, J=8.3 Hz), 7.36 (1H, dd, J=1.0, 7.3 Hz)
MS (FAB) m/z: 379 (M+K)$^+$

Example 54-36

3-Ethoxy-3-(4-{[4-(trifluoromethyl)-1,3-thiazol-2-yl]methoxy}phenyl)propionic acid (Illustrative Compound No: 1-167)

$^1$H NMR (CDCl$_3$, 400 MHz): δ1.20 (3H, t, J=7.0 Hz), 2.63 (1H, dd, J=4.1, 15.9 Hz), 2.84 (1H, dd, J=9.5, 15.9 Hz), 3.35-3.48 (2H, m), 4.70 (1H, dd, J=4.1, 9.5 Hz), 5.39 (2H, s), 7.01 (2H, d, J=8.6 Hz), 7.31 (2H, d, J=8.6 Hz), 7.82 (1H, d, J=0.8 Hz).
MS (FAB) m/z: 414 (M+K)$^+$

Example 54-37

(3S)-3-Ethoxy-3-(4-{[5-(trifluoromethyl)-2,3-dihydro-1H-inden-1-yl]oxy}phenyl)propionic acid (Illustrative Compound No: 1-202)

$^1$H NMR (CDCl$_3$, 400 MHz): δ1.22 (3H, t, J=7.1 Hz), 2.21-2.31 (1H, m), 2.59-2.70 (2H, m), 2.87 (1H, dd, J=9.8, 15.7 Hz), 2.94-3.04 (1H, m), 3.15-3.25 (1H, m), 3.37-3.53 (2H, m), 4.71 (1H, dd, J=3.9, 9.8 Hz), 5.78 (1H, dd, J=4.7, 6.6 Hz), 7.01 (2H, d, J=8.6 Hz), 7.30 (2H, d, J=8.6 Hz), 7.42 (1H, d, J=8.0 Hz), 7.59 (1H, d, J=8.0 Hz), 7.67 (1H, s)
MS (FAB) m/z: 417 (M+Na)$^+$

Example 54-38

(3S)-3-Ethoxy-3-{4-[(4-fluoro-2,3-dihydro-1H-inden-1-yl)oxy]phenyl}propionic acid (Illustrative Compound No: 1-181)

$^1$H NMR (CDCl$_3$, 400 MHz): δ1.22 (3H, t, J=7.1 Hz), 2.21-2.31 (1H, m), 2.56-2.66 (1H, m), 2.66 (1H, dd, J=4.0, 15.9 Hz), 2.86 (1H, dd, J=9.7, 15.9 Hz), 2.91-3.02 (1H, m), 3.13-3.22 (1H, m), 3.38-3.53 (2H, m), 4.70 (1H, dd, J=4.0, 9.7 Hz), 5.77 (1H, dd, J=4.7, 6.3 Hz), 7.00 (2H, d, J=8.6 Hz), 6.97-7.05 (1H, m), 7.29 (2H, d, J=8.6 Hz), 7.20-7.33 (2H, m)
MS (FAB) m/z: 367 (M+Na)$^+$

Example 54-39

(3S)-3-(4-{[(2S)-4,6-Dichloro-2,3-dihydro-1H-inden-1-yl]oxy}phenyl)-3-ethoxypropionic acid (Illustrative Compound No: 1-201)

$^1$H NMR (CDCl$_3$, 400 MHz): δ1.21 (3H, t, J=7.1 Hz), 2.19-2.29 (1H, m), 2.66 (1H, dd, J=4.0, 15.8 Hz), 2.58-2.69 (1H, m), 2.86 (1H, dd, J=9.4, 15.8 Hz), 2.88-2.97 (1H, m), 3.08-3.17 (1H, m), 3.37-3.52 (2H, m), 4.71 (1H, dd, J=4.0, 9.4 Hz), 5.74 (1H, dd, J=4.9, 6.8 Hz), 6.98 (2H, d, J=8.7 Hz), 7.28-7.32 (3H, m), 7.34 (1H, d, J=2.0 Hz)
MS (FAB) m/z: 433 (M+K)$^+$

Example 54-40

(3S)-3-{4-[(4,6-Difluoro-2,3-dihydro-1H-inden-1-yl)oxy]phenyl}-3-ethoxypropionic acid (Illustrative Compound No: 1-182)

$^1$H NMR (CDCl$_3$, 400 MHz): δ1.21 (3H, t, J=7.0 Hz), 2.20-2.31 (1H, m), 2.66 (1H, dd, J=4.1, 15.9 Hz), 2.60-2.70 (1H, m), 2.86 (1H, dd, J=9.5, 15.9 Hz), 2.86-2.96 (1H, m), 3.07-3.17 (1H, m), 3.37-3.51 (2H, m), 4.71 (1H, dd, J=4.1, 9.5 Hz), 5.73 (1H, dd, J=5.0, 6.2 Hz), 6.78 (1H, dt, J=2.0, 9.0 Hz), 6.94 (1H, dd, J=2.0, 7.8 Hz), 6.98 (2H, d, J=8.6 Hz), 7.30 (2H, d, J=8.6 Hz)
MS (FAB) m/z: 401 (M+K)$^+$

Example 54-41

3-Ethoxy-3-{4-[(6-methoxypyridine-2-yl)methoxy] phenyl}propionic acid (Illustrative Compound No: 1-145)

$^1$H NMR (CDCl$_3$, 400 MHz): δ1.18 (3H, t, J=7.0 Hz), 2.63 (1H, dd, J=4.3, 16.0 Hz), 2.83 (1H, dd, J=9.4, 16.0 Hz), 3.33-3.47 (2H, m), 3.94 (3H, s), 4.68 (1H, dd, J=4.3, 9.4 Hz), 5.09 (2H, s), 6.66 (1H, d, J=8.2 Hz), 6.99 (2H, d, J=8.6 Hz), 7.07 (1H, d, J=7.4 Hz), 7.25 (2H, d, J=8.6 Hz), 7.58 (1H, dd, J=7.4, 8.2 Hz)

Example 54-42

3-{4-[(3-{[1-(tert-Butoxycarbonyl)piperidin-4-yl] oxy}benzyl)oxy]phenyl}-3-ethoxypropionic acid (Illustrative Compound No: 1-148)

$^1$H NMR (CDCl$_3$, 400 MHz): δ1.17 (3H, t, J=7.0 Hz), 1.57-1.88 (4H, m), 2.65 (1H, dd, J=5.5, 15.6 Hz), 2.86 (1H, dd, J=8.6, 15.6 Hz), 3.26-3.42 (4H, m), 3.53-3.67 (2H, m), 4.45 (1H, m), 4.66 (1H, dd, J=5.5, 8.6 Hz), 5.07 (2H, s), 6.84-6.99 (5H, m), 7.23-7.31 (3H, m)

Example 54-43

3-[6-(3,4-Dichlorobenzyloxy)pyridine-3-yl]-3-ethoxypropionic acid (Illustrative Compound No: 2-15)

$^1$H NMR (CDCl$_3$, 500 MHz): δ1.18 (3H, t, J=7.0 Hz), 2.63 (1H, dd, J=5.4, 15.6 Hz), 2.88 (1H, dd, J=9.3, 15.6 Hz), 3.40

(2H, q, J=7.0 Hz), 4.71 (1H, dd, J=5.4, 9.3 Hz), 5.33 (2H, s), 6.84 (1H, d, J=8.8 Hz), 7.28 (1H, m), 7.44 (1H, d, J=8.8 Hz), 7.55 (1H, m), 7.62 (1H, m), 8.10 (1H, s)

Example 54-44

3-[4-(1,3-Benzothiazol-2-ylmethoxy)phenyl]-3-ethoxypropionic acid (Illustrative Compound No: 1-164)

$^1$H NMR (CDCl$_3$, 400 MHz): δ1.18 (3H, t, J=7.0 Hz), 2.62 (1H, dd, J=4.3, 16.0 Hz), 2.82 (1H, dd, J=9.4, 16.0 Hz), 3.33-3.46 (2H, m), 5.49 (2H, s), 7.04 (2H, d, J=9.0 Hz), 7.28 (2H, d, J=9.0 Hz), 7.41 (1H, m), 7.51 (1H, m), 7.90 (1H, m), 8.04 (1H, m)

Example 54-45

3-Ethoxy-3-{4-[(5-methyl-2-phenyl-2H-1,2,3-triazol-4-yl)methoxy]phenyl}propionic acid (Illustrative Compound No: 1-165)

$^1$H NMR (CDCl$_3$, 400 MHz): δ1.18 (3H, t, J=7.0 Hz), 2.44 (3H, s), 2.63 (1H, dd, J=4.3, 15.6 Hz), 2.84 (1H, dd, J=9.4, 15.6 Hz), 3.33-3.46 (2H, m), 4.69 (1H, dd, J=4.3, 9.4 Hz), 5.20 (2H, s), 7.02 (2H, d, J=8.6 Hz), 7.27 (2H, d, J=8.6 Hz), 7.32 (1H, t, J=7.8 Hz), 7.46 (2H, dd, J=7.8, 7.8 Hz), 8.01 (2H, d, J=7.8 Hz)

Example 54-46

3-[4-(3,4-Dichlorobenzyloxy)phenyl]-3-(2,2-difluoroethoxy)propionic acid (Illustrative Compound No: 1-77)

$^1$H NMR (CDCl$_3$, 400 MHz): δ2.66 (1H, dd, J=4.7, 16.0 Hz), 2.90 (1H, dd, J=9.0, 16.0 Hz), 3.52 (2H, dt, J=4.3, 14.1 Hz), 4.79 (1H, dd, J=4.7, 9.0 Hz), 5.02 (2H, s), 5.82 (1H, m), 6.95 (2H, d, J=8.6 Hz), 7.26 (1H, m), 7.28 (2H, d, J=8.6 Hz), 7.46 (1H, d, J=8.2 Hz), 7.54 (1H, d, J=2.0 Hz)

Example 54-47

(3S)-3-Ethoxy-3-(4-{[(1R)-4-(trifluoromethyl)-2,3-dihydro-1H-inden-1-yl]amino}phenyl)propionic acid (Illustrative Compound No: 1-227)

$^1$H NMR (CDCl$_3$, 400 MHz): δ1.18 (3H, t, J=7.0 Hz), 1.95 (1H, m), 2.63 (1H, dd, J=3.9, 16.0 Hz), 2.63 (1H, m), 2.84 (1H, dd, J=9.8, 16.0 Hz), 3.03 (1H, m), 3.21 (1H, m), 3.38 (1H, m), 3.46 (1H, m), 4.62 (1H, dd, J=3.9, 9.8 Hz), 5.01 (1H, dd, J=6.9, 7.1 Hz), 6.68 (2H, d, J=8.6 Hz), 7.15 (2H, d, J=8.6 Hz), 7.30 (1H, dd, J=7.8, 7.8 Hz), 7.51 (1H, d, J=7.8 Hz), 7.52 (1H, d, J=7.8 Hz)

Example 54-48

(3S)-3-Ethoxy-3-(4-{[(1R)-6-methyl-4-(trifluoromethyl)-2,3-dihydro-1H-inden-1-yl]oxy}phenyl)-propionic acid (Illustrative Compound No: 1-215)

$^1$H NMR (CDCl$_3$, 400 MHz): δ1.21 (3H, t, J=7.0 Hz), 2.24 (1H, m), 2.41 (3H, s), 2.61 (1H, m), 2.66 (1H, dd, J=4.3, 15.6 Hz), 2.86 (1H, dd, J=9.4, 15.6 Hz), 3.05 (1H, m), 3.25 (1H, m), 3.37-3.51 (2H, m), 4.70 (1H, dd, J=4.3, 9.4 Hz), 5.72 (1H, dd, J=4.7, 6.6 Hz), 6.99 (2H, d, J=8.6 Hz), 7.28 (2H, d, J=8.6 Hz), 7.40 (2H, m)

Example 54-49

(3S)-3-Ethoxy-3-(4-{[(1R,3R)-3-methyl-4-(trifluoromethyl)-2,3-dihydro-1H-inden-1-yl]oxy}phenyl)-propionic acid (Illustrative Compound No: 1-216)

$^1$H NMR (CDCl$_3$, 400 MHz): δ1.19 (3H, t, J=7.0 Hz), 1.33 (3H, d, J=7.0 Hz), 2.33 (1H, ddd, J=7.4, 8.2, 12.9 Hz), 2.48 (1H, ddd, J=1.6, 7.0, 12.9 Hz), 2.66 (1H, dd, J=9.4, 15.6 Hz), 2.86 (1H, dd, J=4.3, 15.6 Hz), 3.36-3.49 (2H, m), 3.73 (1H, m), 4.72 (1H, dd, J=4.3, 9.4 Hz), 5.92 (1H, dd, J=7.0, 7.4 Hz), 7.03 (2H, d, J=8.6 Hz), 7.30 (2H, d, J=8.6 Hz), 7.38 (1H, dd, J=8.2, 8.2 Hz) 7.58 (1H, d, J=8.2 Hz), 7.60 (1H, d, J=8.2 Hz)

Example 54-50

(3S)-3-Ethoxy-3-(4-{[(1R,3S)-3-methyl-4-(trifluoromethyl)-2,3-dihydro-1H-inden-1-yl]oxy}phenyl)-propionic acid (Illustrative Compound No: 1-216)

$^1$H NMR (CDCl$_3$, 400 MHz): δ1.20 (3H, t, J=7.0 Hz), 1.41 (3H, d, J=7.0 Hz), 2.07 (1H, ddd, J=1.2, 1.8, 14.1 Hz), 2.61 (1H, m), 2.66 (1H, dd, J=4.3, 15.6 Hz), 2.86 (1H, dd, J=9.4, 15.6 Hz), 3.36-3.51 (2H, m), 3.63 (1H, m), 4.71 (1H, dd, J=4.3, 9.4 Hz), 5.61 (1H, dd, J=1.2, 6.3 Hz), 6.97 (2H, d, J=8.6 Hz), 7.29 (2H, d, J=8.6 Hz), 7.38 (1H, dd, J=8.2, 8.2 Hz) 7.60 (1H, d, J=8.2 Hz), 7.62 (1H, d, J=8.2 Hz)

Example 54-51

(3S)-3-Ethoxy-3-(4-{[(1R)-5-methyl-4-(trifluoromethyl)-2,3-dihydro-1H-inden-1-yl]oxy}phenyl)-propionic acid (Illustrative Compound No: 1-217)

$^1$H NMR (CDCl$_3$, 400 MHz): δ1.19 (3H, t, J=7.0 Hz), 2.22 (1H, m), 2.51 (3H, s), 2.55 (1H, m), 2.65 (1H, dd, J=4.3, 15.6 Hz), 2.85 (1H, dd, J=9.4, 15.6 Hz), 3.13 (1H, m), 3.33 (1H, m), 3.33-3.51 (2H, m), 4.70 (1H, dd, J=4.3, 9.4 Hz), 5.69 (1H, dd, J=3.9, 6.3 Hz), 6.97 (2H, d, J=9.0 Hz), 7.18 (1H, d, J=7.8 Hz), 7.28 (2H, d, J=9.0 Hz), 7.45 (1H, d, J=7.8 Hz)

Example 54-52

(3S)-3-(4-{[(1R)-5-Chloro-4-(trifluoromethyl)-2,3-dihydro-1H-inden-1-yl]oxy}phenyl)-3-ethoxypropionic acid (Illustrative Compound No: 1-218)

$^1$H NMR (CDCl$_3$, 400 MHz): δ1.18 (3H, t, J=7.0 Hz), 2.25 (1H, m), 2.60 (1H, m), 2.65 (1H, dd, J=4.3, 15.6 Hz), 2.85 (1H, dd, J=9.4, 15.6 Hz), 3.17 (1H, m), 3.30-3.48 (3H, m), 4.71 (1H, dd, J=4.3, 9.4 Hz), 5.68 (1H, dd, J=4.3, 6.3 Hz), 6.96 (2H, d, J=8.6 Hz), 7.29 (2H, d, J=8.6 Hz), 7.41 (1H, d, J=8.2 Hz), 7.49 (1H, d, J=8.2 Hz)

Example 54-53

(3S)-3-(4-{[(1R)-5-(trifluoromethyl)-2,3-dihydro-1H-inden-1-yl]oxy}phenyl)propionic acid (Illustrative Compound No: 1-222)

$^1$H NMR (CDCl$_3$, 400 MHz): δ1.21 (3H, t, J=7.0 Hz), 2.25 (1H, m), 2.63 (1H, m), 2.65 (1H, dd, J=4.3, 15.6 Hz), 2.85 (1H, dd, J=9.4, 15.6 Hz), 2.98 (1H, m), 3.19 (1H, m), 3.37-3.51 (2H, m), 4.70 (1H, dd, J=4.3, 9.4 Hz), 5.77 (1H, dd, J=4.7, 6.6 Hz), 6.99 (2H, d, J=8.6 Hz), 7.29 (2H, d, J=8.6 Hz), 7.50-7.52 (2H, m), 7.56 (1H, m)

Example 54-54

(3S)-3-Ethoxy-3-(4-{[4-(trifluoromethyl)-6,7-dihydro-5H-cyclopenta[b]pyridine-7-yl]oxy}phenyl)-propionic acid (Illustrative Compound No: 1-207)

¹H NMR (CDCl₃, 400 MHz): δ1.19 (3H, t, J=7.0 Hz), 2.36 (1H, m), 2.53 (1H, m), 2.65 (1H, m), 2.81 (1H, m), 3.13 (1H, m), 3.33 (1H, m), 3.35-3.49 (2H, m), 4.68 (1H, m), 5.75 (1H, m), 7.09 (2H, m), 7.27 (2H, d, J=8.6 Hz), 7.45 (1H, d, J=5.5 Hz) 8.71 (1H, d, J=5.5 Hz)

Example 54-55

(3S)-3-Ethoxy-3-(4-{[(1R)-7-methyl-4-(trifluoromethyl)-2,3-dihydro-1H-inden-1-yl]oxy}phenyl)-propionic acid (Illustrative Compound No: 1-223)

¹H NMR (CDCl₃, 400 MHz): δ1.16 (3H, t, J=7.0 Hz), 2.33 (1H, m), 2.39 (3H, s), 2.50 (1H, m), 2.59 (1H, dd, J=4.7, 15.2 Hz), 2.82 (1H, dd, J=9.0, 15.2 Hz), 3.13 (1H, m), 3.29 (1H, m), 3.31-3.45 (2H, m), 4.72 (1H, dd, J=4.7, 9.0 Hz), 5.76 (1H, m), 6.95 (2H, d, J=8.2 Hz), 7.17 (1H, d, J=8.2 Hz), 7.29 (2H, d, J=8.2 Hz), 7.51 (1H, d, J=8.2 Hz)

Example 54-56

(3S)-3-(4-{[(1R)-6-Chloro-4-methyl-2,3-dihydro-1H-inden-1-yl]oxy}phenyl)-3-ethoxypropionic acid (Illustrative Compound No: 1-224)

¹H NMR (CDCl₃, 400 MHz): δ1.20 (3H, t, J=7.0 Hz), 2.22 (1H, m), 2.27 (3H, s), 2.59 (1H, m), 2.66 (1H, dd, J=4.3, 15.6 Hz), 2.80 (1H, ddd, J=5.5, 8.6, 16.0 Hz), 2.85 (1H, dd, J=9.8, 15.6 Hz), 3.00 (1H, ddd, J=5.5, 9.0, 16.0 Hz), 3.36-3.50 (2H, m), 4.70 (1H, dd, J=4.3, 9.8 Hz), 5.70 (1H, dd, J=4.3, 6.6 Hz), 6.98 (2H, d, J=8.6 Hz), 7.13 (1H, d, J=1.6 Hz), 7.23 (1H, d, J=1.6 Hz), 7.28 (2H, d, J=8.6 Hz)

Example 54-57

(3S)-3-Ethoxy-3-(4-{[(1R)-5-fluoro-4-methyl-2,3-dihydro-1H-inden-1-yl]oxy}phenyl)propionic acid (Illustrative Compound No: 1-225)

¹H NMR (CDCl₃, 400 MHz): δ1.21 (3H, t, J=7.0 Hz), 2.21 (3H, d, J=1.6 Hz), 2.26 (1H, m), 2.58 (1H, m), 2.65 (1H, dd, J=3.9, 15.6 Hz), 2.85 (1H, dd, J=9.4, 15.6 Hz), 2.85 (1H, m), 3.06 (1H, m), 3.37-3.51 (2H, m), 4.69 (1H, dd, J=3.9, 9.4 Hz), 5.71 (1H, dd, J=3.5, 7.0 Hz), 6.92 (1H, dd, J=8.2, 10.2 Hz), 6.98 (2H, d, J=8.6 Hz), 7.20 (1H, dd, J=5.1, 8.2 Hz), 7.27 (2H, d, J=8.6 Hz)

Example 54-58

(3S)-3-(4-{[(1R)-5-Chloro-4-methyl-2,3-dihydro-1H-inden-1-yl]oxy}phenyl)-3-ethoxypropionic acid (Illustrative Compound No: 1-226)

¹H NMR (CDCl₃, 400 MHz): δ1.21 (3H, t, J=7.0 Hz), 2.25 (1H, m), 2.33 (3H, s), 2.58 (1H, m), 2.65 (1H, dd, J=3.9, 15.6 Hz), 2.85 (1H, dd, J=9.4, 15.6 Hz), 2.89 (1H, m), 3.09 (1H, m), 3.36-3.51 (2H, m), 4.69 (1H, dd, J=3.9, 9.4 Hz), 5.72 (1H, dd, J=3.9, 6.6 Hz), 6.98 (2H, d, J=8.6 Hz), 7.18 (1H, d, J=8.2 Hz), 7.25-7.29 (3H, m)

Example 54-59

(3S)-3-Ethoxy-3-(4-{[(3S)-7-ethyl-2,3-dihydro-1-benzofuran-3-yl]oxy}phenyl)propionic acid (Illustrative Compound No: 1-209)

¹H NMR (CDCl₃, 400 MHz): δ1.24 (3H, t, J=7.8 Hz), 1.26 (3H, t, J=7.1 Hz), 2.62-2.69 (3H, m), 2.85 (1H, dd, J=9.4, 15.6 Hz), 3.48-3.36 (2H, m), 4.62 (1H, dd, J=2.8, 11.0 Hz), 4.72-4.67 (2H, m), 5.90 (1H, dd, J=2.4, 6.3 Hz), 6.90 (1H, dd, J=7.4, 7.4 Hz), 6.92 (2H, d, J=8.6 Hz), 7.17 (1H, d, J=7.5 Hz), 7.25 (1H, d, J=7.0 Hz), 7.29 (2H, d, J=8.6 Hz)

Example 54-60

(3S)-3-Ethoxy-3-(4-{[(1R)-6-hydroxy-4-(trifluoromethyl)-2,3-dihydro-1H-inden-1-yl]oxy}phenyl)-propionic acid (Illustrative Compound No: 1-219)

¹H NMR (CDCl₃, 400 MHz): δ1.21 (3H, t, J=7.1 Hz), 1.64 (1H, brs), 2.21-2.29 (1H, m), 2.58-2.69 (2H, m), 2.87 (1H, dd, J=9.0, 15.7 Hz), 2.97-3.04 (1H, m), 3.18-3.25 (1H, m), 3.40-3.49 (2H, m), 4.71 (1H, dd, J=4.3, 9.0 Hz), 5.69 (1H, dd, J=4.7, 6.7 Hz), 6.96 (1H, s), 6.98 (1H, d, J=8.6 Hz), 7.08 (1H, d, J=2.3 Hz), 7.28 (2H, d, J=8.6 Hz)

Example 54-61

(3S)-3-Ethoxy-3-(4-{[(1S,2S)-2-fluoro-4-(trifluoromethyl)-2,3-dihydro-1H-inden-1-yl]oxy}phenyl)-propionic acid (Illustrative Compound No: 1-220)

¹H NMR (CDCl₃, 400 MHz): δ1.20 (3H, t, J=7.0 Hz), 2.66 (1H, dd, J=4.7, 15.7 Hz), 2.87 (1H, dd, J=9.0, 15.6 Hz), 3.37-3.47 (3H, m), 3.70 (1H, ddd, $J_{H,F}$=19.6 Hz, J=6.7, 19.6 Hz), 4.73 (1H, dd, J=4.3, 9.0 Hz), 2.85 (1H, dtd, $J_{H,F}$=51.2 Hz, J=3.1, 5.9 Hz), 5.80 (1H, dd, $J_{H,F}$=16.4 Hz, J=2.0 Hz), 7.08 (2H, d, J=8.6 Hz), 7.33 (1H, d, J=8.6 Hz), 7.43 (1H, dd, J=7.6, 7.7 Hz), 7.62 (1H, d, J=7.4 Hz), 7.66 (1H, d, J=7.8 Hz)

Example 54-62

(3S)-3-Ethoxy-3-(4-{[(1R)-6-methoxy-4-(trifluoromethyl)-2,3-dihydro-1H-inden-1-yl]oxy}phenyl)-propionic acid (Illustrative Compound No: 1-221)

¹H NMR (CDCl₃, 400 MHz): δ1.21 (3H, t, J=7.0 Hz), 2.19-2.28 (1H, m), 2.59-2.66 (1H, m), 2.66 (1H, dd, J=3.9, 15.6 Hz), 2.86 (1H, dd, J=9.4, 15.6 Hz), 2.97-3.07 (1H, m), 3.18-3.27 (1H, m), 3.38-3.51 (2H, m), 3.83 (3H, s), 4.70 (1H, dd, J=3.9, 9.4 Hz), 5.71 (1H, dd, J=5.0, 7.0 Hz), 7.00 (2H, d, J=8.6 Hz), 7.11 (1H, d, J=2.4 Hz), 7.13 (1H, d, J=2.4 Hz), 7.29 (2H, d, J=8.6 Hz)

MS (ESI) m/z: 423 (M−H)⁻

Example 54-63

(3S)-3-Ethoxy-3-(4-{[(1S)-4-(trifluoromethyl)-2,3-dihydro-1H-inden-1-yl]oxy}phenyl)propionic acid (Illustrative Compound No: 1-202)

¹H NMR (CDCl₃, 400 MHz): δ1.22 (3H, t, J=7.0 Hz), 2.22-2.30 (1H, m), 2.59-2.67 (1H, m), 2.65 (1H, dd, J=4.3, 16.0 Hz), 2.86 (1H, dd, J=9.4, 16.0 Hz), 3.07-3.15 (1H, m), 3.28-3.37 (1H, m), 3.38-3.52 (2H, m), 4.70 (1H, dd, J=3.9, 9.4 Hz), 5.77 (1H, dd, J=4.3, 7.0 Hz), 7.00 (2H, d, J=8.6 Hz), 7.29 (2H, d, J=8.6 Hz), 7.37 (1H, t, J=7.8 Hz), 7.61 (1H, d, J=7.8 Hz), 7.61 (1H, d, J=7.8 Hz)

Example 55

(3S)-3-Ethoxy-3-(4-{[(3S)-7-(trifluoromethoxy)-2,3-dihydro-1-benzofuran-3-yl]oxy}phenyl)propionic acid (Illustrative Compound No: 1-208)

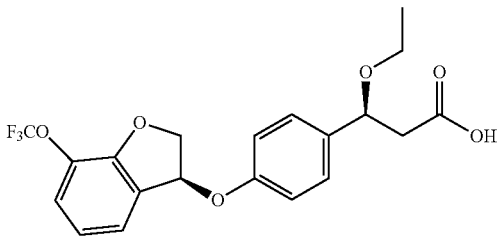

(55A) [2-(Trifluoromethoxy)phenoxy]acetic acid 2-(Trifluoromethoxy)phenol (1.00 g, 5.61 mmol) was dissolved in dimethylformamide (5 mL), and sodium hydride (63%, 320 mg, 8.40 mmol) was added thereto at 0° C., and then, the resulting mixture was stirred under a nitrogen atmosphere for 10 minutes. Bromoacetic acid (0.95 g, 6.84 mmol) and a dimethylformamide (5 mL) suspension of sodium hydride (63%, 425 mg, 11.2 mmol) were added thereto at room temperature, and the resulting mixture was stirred under a nitrogen atmosphere at room temperature for 6 hours.

To the reaction solution, 1 N hydrochloric acid was added, and the organic matter was extracted with ethyl acetate. The organic layer was washed with a saturated sodium chloride solution, then dried over anhydrous sodium sulfate and filtered. Then, the solvent was distilled off under reduced pressure, and the resulting residue was purified by silica gel column chromatography (dichloromethane:methanol=95:5 to 84:16 (v/v)), whereby the objective title compound was obtained as a white solid (1.16 g, yield: 88%).

$^1$H NMR (CDCl$_3$, 500 MHz): δ4.73 (2H, s), 6.96 (1H, dd, J=1.2, 8.2 Hz), 7.05 (1H, m), 7.24-7.31 (2H, m)

(55B) 7-(Trifluoromethoxy)-1-benzofuran-3 (2H)-one

[2-(Trifluoromethoxy) phenoxy]acetic acid (200 mg, 0.847 mmol) produced in (55A) was dissolved in dichloromethane (5 mL), and oxalyl chloride (0.11 mL, 1.26 mmol) and dimethylformamide (one drop) were added thereto at room temperature, and then, the resulting mixture was stirred under a nitrogen atmosphere for 2 hours.

The solvent was distilled off under reduced pressure, and the resulting residue was dissolved in dichloromethane (5 mL), and aluminum chloride (340 mg, 2.55 mmol) was added thereto at 0° C., and then, the resulting mixture was stirred at room temperature for 3 hours.

The reaction solution was added to ice water to stop the reaction. The organic matter was extracted with ethyl acetate, and the organic layer was washed with a saturated aqueous solution of sodium hydrogen carbonate and a saturated sodium chloride solution, then dried over anhydrous sodium sulfate and filtered. Then, the solvent was distilled off under reduced pressure, whereby a crude product was obtained.

This crude product was purified by silica gel column chromatography (hexane:ethyl acetate=95:5 to 90:10 (v/v)), whereby the objective title compound was obtained as a white solid (7 mg, yield: 4%).

$^1$H NMR (CDCl$_3$, 400 MHz): δ4.77 (2H, s), 7.15 (1H, dd, J=7.8, 7.8 Hz), 7.56 (1H, m), 7.67 (1H, dd, J=1.5, 7.8 Hz)

(55C) (3R)-7-(Trifluoromethoxy)-2,3-dihydro-1-benzofuran-3-ol

To a mixture of formic acid (0.20 mL, 5.3 mmol) and triethylamine (450 mg, 4.45 mmol), 7-(trifluoromethoxy)-1-benzofuran-3(2H)-one (160 mg, 0.734 mmol) produced in (55B) was added, and chloro[(1S,2S)—N-(p-toluenesulfonyl)-1,2-diphenylethanediamine](mesitylene)ruthenium (II) (22.0 mg, 0.0350 mmol) was added thereto at room temperature, and then, the resulting mixture was stirred under a nitrogen atmosphere at room temperature for 40 minutes.

The reaction solution was directly purified by silica gel column chromatography (hexane:ethyl acetate=100:0 to 50:50 (v/v)), whereby the objective title compound was obtained as a white solid (160 mg, yield: 99%).

$^1$H NMR (CDCl$_3$, 500 MHz): δ2.11 (1H, br), 4.55 (1H, dd, J=2.9, 10.7 Hz), 4.65 (1H, dd, J=6.8, 10.7 Hz), 5.43 (1H, dd, J=2.9, 6.8 Hz), 6.95 (1H, dd, J=7.3, 8.3 Hz), 7.20 (1H, d, J=8.3 Hz), 7.36 (1H, d, J=7.3 Hz)

(55D) {[(3S)-3-Ethoxy-3-(4-{[(1R)-4-(trifluoromethoxy)-2,3-dihydro-1H-inden-1-yl]oxy}phenyl)propyl]oxy}(triisopropyl)silane (3R)-7-(Trifluoromethoxy)-2,3-dihydro-1-benzofuran-3-ol (155 mg, 0.704 mmol) produced in (55C) and 4-{(1S)-1-ethoxy-3-[(triisopropylsilyl)oxy]propyl}phenol (207 mg, 0.587 mmol) produced in Example 50 (50E) were dissolved in tetrahydrofuran (5 mL), and triphenylphosphine (185 mg, 0.705 mmol) and a 40% diethyl azodicarboxylate toluene solution (0.32 mL, 0.704 mmol) were added thereto at room temperature, and then, the resulting mixture was stirred under a nitrogen atmosphere at 50° C. for 3 hours.

The solvent was distilled off under reduced pressure, and the resulting residue was purified by silica gel column chromatography (hexane:ethyl acetate=100:0 to 90:10 (v/v)), whereby the objective title compound was obtained as a colorless oily substance (110 mg, yield: 34%).

$^1$H NMR (CDCl$_3$, 400 MHz): δ1.05-1.09 (21H, m), 1.17 (3H, t, J=7.0 Hz), 1.78 (1H, m), 2.00 (1H, m), 3.27-3.43 (2H, m), 3.64 (1H, m), 3.85 (1H, m), 4.47 (1H, dd, J=5.1, 8.2 Hz), 4.73 (1H, dd, J=3.1, 10.9 Hz), 4.79 (1H, dd, J=6.6, 10.9 Hz), 5.94 (1H, dd, J=3.1, 6.6 Hz), 6.88 (2H, d, J=8.6 Hz), 6.93 (1H, dd, J=7.4, 8.2 Hz), 7.23 (1H, m), 7.27 (2H, d, J=8.6 Hz), 7.33 (1H, d, J=7.4 Hz)

(55E) (3S)-3-Ethoxy-3-(4-{[(1R)-4-(trifluoromethoxy)-2,3-dihydro-1H-inden-1-yl]oxy}phenyl)propan-1-ol {[(3S)-3-Ethoxy-3-(4-{[(1R)-4-(trifluoromethoxy)-2,3-dihydro-1H-inden-1-yl]oxy}phenyl)propyl]oxy}-(triisopropyl)silane (110 mg, 0.198 mmol) produced in (55D) was dissolved in tetrahydrofuran (5 mL), and a 1.0 M tetra-n-butylammonium fluoride tetrahydrofuran solution (0.40 mL, 0.40 mmol) was added thereto at 0° C., and then, the resulting mixture was stirred under a nitrogen atmosphere at 50° C. for 6 hours.

To the reaction solution, a saturated aqueous solution of ammonium chloride was added, and the organic matter was extracted with ethyl acetate. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=100:0 to 60:40 (v/v)), whereby the objective title compound was obtained as a colorless oily substance (60.0 mg, yield: 76%).

$^1$H NMR (CDCl$_3$, 500 MHz): δ1.19 (3H, t, J=6.8 Hz), 1.84 (1H, m), 2.04 (1H, m), 2.80 (1H, br), 3.31-3.44 (2H, m), 3.76-3.81 (2H, m), 4.48 (1H, dd, J=3.9, 9.3 Hz), 4.72 (1H, dd, J=2.9, 10.7 Hz), 4.81 (1H, dd, J=6.3, 10.7 Hz), 5.95 (1H, dd, J=2.9, 6.3 Hz), 6.90 (2H, d, J=8.8 Hz), 6.95 (1H, dd, J=7.3, 7.3 Hz), 7.24 (1H, m), 7.27 (2H, d, J=8.8 Hz), 7.34 (1H, d, J=7.3 Hz)

(55F) (3S)-3-Ethoxy-3-(4-{[(3S)-7-(trifluoromethoxy)-2,3-dihydro-1-benzofuran-3-yl]oxy}phenyl)propionic acid (3S)-3-Ethoxy-3-(4-{[(1R)-4-(trifluoromethoxy)-2,3-dihydro-1H-inden-1-yl]oxy}phenyl)propan-1-ol (60.0 mg, 0.151 mmol) produced in (55E) was dissolved in acetonitrile (2 mL), and a phosphate buffer (pH 6.9, 2 mL), 2,2,6,6-tetramethyl piperidine-N-oxyl (8.0 mg, 0.51 mmol), sodium chlorite (80%, mg, 0.71 mmol), and an aqueous solution of sodium hypochlorite (effective chlorine concentration: 5%) (0.06 mL) were sequentially added thereto at 0° C., and then, the resulting mixture was stirred at 10° C. for 3 hours.

To the reaction solution, a 1 N aqueous solution of sodium hydroxide was added at 0° C. to adjust the pH of the solution to 8 to 9, and an aqueous solution of sodium sulfite was added thereto. Then, the pH of the solution was adjusted to 3 to 4 with 1 N hydrochloric acid, and the organic matter was extracted with ethyl acetate. The organic layer was washed with a saturated sodium chloride solution, then dried over anhydrous sodium sulfate and filtered. Then, the solvent was distilled off under reduced pressure, and the resulting residue was purified by silica gel column chromatography (hexane: ethyl acetate=100:0 to 50:50 (v/v)), whereby the objective title compound was obtained as a white solid (46 mg, yield: 74%).

$^1$H NMR (CDCl$_3$, 400 MHz): δ1.19 (3H, t, J=7.0 Hz), 2.64 (1H, dd, J=4.3, 15.6 Hz), 2.85 (1H, dd, J=9.0, 15.6 Hz), 3.35-3.48 (2H, m), 4.71 (1H, dd, J=4.3, 9.0 Hz), 4.72 (1H, dd, J=3.1, 10.9 Hz), 4.80 (1H, dd, J=6.3, 10.9 Hz), 5.95 (1H, dd, J=3.1, 6.3 Hz), 6.91 (2H, d, J=8.6 Hz), 6.95 (1H, dd, J=7.4, 8.2 Hz), 7.24 (1H, d, J=8.2 Hz), 7.30 (2H, d, J=8.6 Hz), 7.33 (1H, d, J=7.4 Hz)

Example 56

(3S)-3-Ethoxy-3-(4-{[(1R)-5-fluoro-4-(trifluoromethyl)-2,3-dihydro-1H-inden-1-yl]oxy}phenyl)-propionic acid (Illustrative Compound No: 1-210)

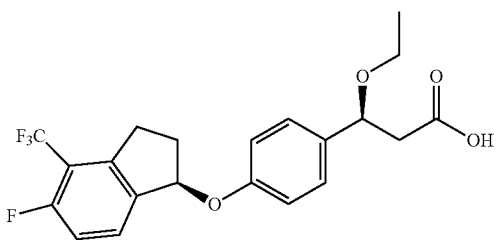

(56A) 3-[3-Fluoro-2-(trifluoromethyl)phenyl]propionic acid

Ethyl diethylphosphonoacetate (4.71 g, 21.0 mmol) was dissolved in tetrahydrofuran (20 mL), and sodium hydride (63%, 0.75 g, 19.7 mmol) was added thereto at 0° C., and then, the resulting mixture was stirred under a nitrogen atmosphere for 30 minutes. A tetrahydrofuran (3 mL) solution of 3-fluoro-2-(trifluoromethyl)benzaldehyde (2.88 g, 15.0 mmol) was added thereto at 0° C., and the resulting mixture was stirred under a nitrogen atmosphere for 30 minutes.

A saturated aqueous solution of ammonium chloride was added thereto, and the organic matter was extracted with diethyl ether. The organic layer was washed with a saturated sodium chloride solution, then dried over anhydrous sodium sulfate and filtered. Then, the solvent was distilled off under reduced pressure.

The resulting light yellow oily substance was dissolved in ethanol (20 mL), and 25% palladium hydroxide on carbon (2 g) was added thereto at room temperature, and then, the resulting mixture was stirred under a hydrogen atmosphere at room temperature for 2 hours. The reaction solution was filtered through a Celite filter, and the solvent was distilled off under reduced pressure.

The resulting light yellow oily substance was dissolved in methanol (15 mL) and tetrahydrofuran (5 mL), and a 2 N aqueous solution of sodium hydroxide (15 mL) was added thereto at room temperature, and then, the resulting mixture was stirred at room temperature for 10 hours.

2 N Hydrochloric acid was added thereto, and the solvent was distilled off under reduced pressure, and the organic matter was extracted with ethyl acetate. The organic layer was washed with a saturated sodium chloride solution, then dried over anhydrous sodium sulfate and filtered. Then, the solvent was distilled off under reduced pressure, whereby a crude product was obtained. This crude product was washed with hexane/ethyl acetate (95/5 (v/v)), whereby the objective title compound was obtained as a white solid (2.21 g, yield: 62%).

$^1$H NMR (CDCl$_3$, 400 MHz): δ2.65-2.77 (2H, m), 3.13-3.26 (2H, m), 7.04-7.23 (2H, m), 7.47 (1H, m)

(56B) 5-Fluoro-4-(trifluoromethyl)indan-1-one

To 3-[3-fluoro-2-(trifluoromethyl)phenyl]propionic acid (1.00 g, 4.23 mmol) produced in (56A), chlorosulfonic acid (5 mL) was added dropwise at 0° C., and the resulting mixture was stirred at 45° C. for 6 hours.

The reaction solution was added to ice water to stop the reaction, and the organic matter was extracted with ethyl acetate. The organic layer was washed with a saturated aqueous solution of sodium hydrogen carbonate and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=95:5 to 80:20 (v/v)), whereby the objective title compound was obtained as a colorless oily substance (740 mg, yield: 80%).

$^1$H NMR (CDCl$_3$, 400 MHz): δ2.74-2.78 (2H, m), 3.32-3.37 (2H, m), 7.24 (1H, m), 7.95 (1H, m)

(56C) (1S)-5-Fluoro-4-(trifluoromethyl)indan-1-ol

To a mixture of formic acid (1.00 mL, 26.5 mmol) and triethylamine (2.35 g, 23.2 mmol), 5-fluoro-4-(trifluoromethyl)indan-1-one (740 mg, 3.39 mmol) produced in (56B) was added, and chloro[(1S,2S)—N-(p-toluenesulfonyl)-1,2-diphenylethanediamine](mesitylene)ruthenium(II) (70.0 mg, 0.133 mmol) was added thereto at room temperature, and then, the resulting mixture was stirred under a nitrogen atmosphere at room temperature for 4 hours.

The reaction solution was directly purified by silica gel column chromatography (hexane:ethyl acetate=100:0 to 50:50 (v/v)), whereby the objective title compound was obtained as a white solid (710 mg, yield: 95%).

$^1$H NMR (CDCl$_3$, 400 MHz): 1.83 (1H, br), 1.99 (1H, m), 2.53 (1H, m), 3.05 (1H, m), 3.31 (1H, m), 5.22 (1H, m), 7.07 (1H, m), 7.53 (1H, m)

(56D) {[(3S)-3-Ethoxy-3-(4-{[(1R)-5-fluoro-4-(trifluoromethyl)-2,3-dihydro-1H-inden-1-yl]oxy}phenyl)propyl]oxy}-(triisopropyl)silane (1S)-5-Fluoro-4-(trifluoromethyl)indan-1-ol (519 mg, 2.36 mmol) produced in (56C) and 4-{(1S)-1-ethoxy-3-[(triisopropylsilyl)oxy]propyl}phenol (650 mg, 1.84 mmol) produced in Example 50 (50E) were dissolved in tetrahydrofuran (10 mL), and triphenylphosphine (655 mg, 2.50 mmol) and a 40% diethyl azodicarboxylate toluene solution (1.13 mL, 2.49 mmol) were added thereto at room temperature, and then, the resulting mixture was stirred under a nitrogen atmosphere at room temperature for 1.5 hours.

The solvent was distilled off under reduced pressure, and the resulting residue was purified by silica gel column chromatography (hexane:ethyl acetate=100:0 to 90:10 (v/v)), whereby the objective title compound was obtained as a colorless oily substance (850 mg, yield: 83%).

$^1$H NMR (CDCl$_3$, 400 MHz): δ1.05-1.09 (21H, m), 1.17 (3H, t, J=7.0 Hz), 1.78 (1H, m), 2.00 (1H, m), 2.27 (1H, m), 2.60 (1H, m), 3.13 (1H, m), 3.24-3.44 (2H, m), 3.31 (1H, m), 3.64 (1H, m), 3.85 (1H, m), 4.48 (1H, dd, J=4.6, 8.6 Hz), 5.68 (1H, dd, J=4.3, 6.6 Hz), 6.94 (2H, d, J=8.6 Hz), 7.09 (1H, m), 7.28 (2H, d, J=8.6 Hz), 7.55 (1H, m)

(56E) (3S)-3-Ethoxy-3-(4-{[(1R)-5-fluoro-4-(trifluoromethyl)-2,3-dihydro-1H-inden-1-yl]oxy}phenyl)propan-1-ol {[(3S)-3-Ethoxy-3-(4-{[(1R)-5-fluoro-4-(trifluoromethyl)-2,3-dihydro-1H-inden-1-yl]oxy}phenyl)propyl]oxy}(triisopropyl)silane (850 mg, 1.53 mmol) produced in (56D) was dissolved in tetrahydrofuran (6 mL), and a 1.0 M tetra-n-butylammonium fluoride tetrahydrofuran solution (2.00 mL, 2.00 mmol) was added thereto at 0° C., and then, the resulting mixture was stirred under a nitrogen atmosphere at room temperature for 3 hours.

To the reaction solution, a saturated aqueous solution of ammonium chloride was added, and the organic matter was extracted with ethyl acetate. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=100:0 to 60:40 (v/v)), whereby the objective title compound was obtained as a colorless oily substance (570 mg, yield: 94%).

$^1$H NMR (CDCl$_3$, 40 MHz): δ1.19 (3H, t, J=7.0 Hz), 1.84 (1H, m), 2.04 (1H, m), 2.28 (1H, m), 2.60 (1H, m), 3.13 (1H, m), 3.32 (1H, m), 3.32-3.45 (2H, m), 3.76-3.81 (2H, m), 4.47 (1H, dd, J=3.9, 9.3 Hz), 5.69 (1H, dd, J=4.3, 6.6 Hz), 6.95 (2H, d, J=8.6 Hz), 7.09 (1H, m), 7.28 (2H, d, J=8.6 Hz), 7.54 (1H, m)

(56F) (3S)-3-Ethoxy-3-(4-{[(1R)-5-fluoro-4-(trifluoromethyl)-2,3-dihydro-1H-inden-1-yl]oxy}phenyl)propionic acid (3S)-3-Ethoxy-3-(4-{[(1R)-5-fluoro-4-(trifluoromethyl)-2,3-dihydro-1H-inden-1-yl]oxy}phenyl)propan-1-ol (570 mg, 1.43 mmol) produced in (56E) was dissolved in acetonitrile (6 mL), and a phosphate buffer (pH 6.9, 6 mL), 2,2,6,6-tetramethylpiperidine-N-oxyl (23 mg, 0.15 mmol), sodium chlorite (80%, 390 mg, 3.45 mmol), and an aqueous solution of sodium hypochlorite (effective chlorine concentration: 5%) (0.55 mL) were sequentially added thereto at 0° C., and then, the resulting mixture was stirred at 10° C. for 1.5 hours.

To the reaction solution, a 1 N aqueous solution of sodium hydroxide was added at 0° C. to adjust the pH of the solution to 8 to 9, and an aqueous solution of sodium sulfite was added thereto. Then, the pH of the solution was adjusted to 3 to 4 with 1 N hydrochloric acid, and the organic matter was extracted with ethyl acetate. The organic layer was washed with a saturated sodium chloride solution, then dried over anhydrous sodium sulfate and filtered. Then, the solvent was distilled off under reduced pressure, and the resulting residue was purified by silica gel column chromatography (hexane:ethyl acetate=100:0 to 50:50 (v/v)), whereby the objective title compound was obtained as a white solid (410 mg, yield: 70%).

$^1$H NMR (CDCl$_3$, 400 MHz): δ1.20 (3H, t, J=7.0 Hz), 2.28 (1H, m), 2.61 (1H, m), 2.65 (1H, dd, J=4.3, 15.6 Hz), 2.85 (1H, dd, J=9.4, 15.6 Hz), 3.14 (1H, m), 3.32 (1H, m), 3.36-3.50 (2H, m), 4.70 (1H, dd, J=4.3, 9.4 Hz), 5.69 (1H, dd, J=4.3, 6.6 Hz), 6.96 (2H, d, J=8.6 Hz), 7.09 (1H, dd, J=8.6, 10.6 Hz), 7.29 (2H, d, J=8.6 Hz), 7.55 (1H, dd, J=4.3, 8.6 Hz)

Example 57

(3S)-3-Ethoxy-3-(4-{[(1R)-4-ethyl-2,3-dihydro-1H-inden-1-yl]oxy}phenyl)propionic acid (Illustrative Compound No: 1-187)

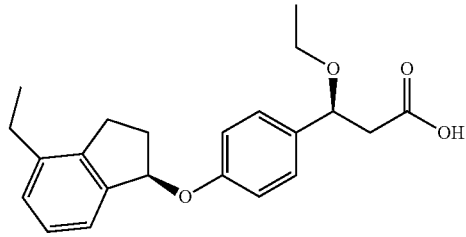

(57A) 4-Ethylindanone

4-Bromo-1-indanone (600 mg, 2.84 mmol) was dissolved in toluene (10 mL), and ethyl boronate (105 mg, 8.52 mmol), silver oxide (I) (274 mg, 7.10 mmol), potassium carbonate (196 mg, 8.52 mmol), and a [1,1'-bis(diphenylphosphino)ferrocene]palladium(II) dichloride dichloromethane complex (46 mg, 0.0568 mmol) were added thereto, and then, the resulting mixture was heated to reflux under a nitrogen atmosphere at 100° C. for 4 hours. After cooling to room temperature, the reaction solution was filtered, and the solvent was distilled off, whereby a crude product was obtained. This crude product was purified by silica gel column chromatography (hexane:ethyl acetate=100:0 to 80:20 (v/v)), whereby the title compound was obtained as a colorless oily substance (421 mg, yield: 92%).

$^1$H NMR (CDCl$_3$, 400 MHz): δ1.28 (3H, t, J=7.4 Hz), 2.70-2.75 (4H, m), 3.08 (2H, t, J=5.9 Hz), 7.34 (1H, t, J=7.4 Hz), 7.44 (1H, d, J=7.0 Hz), 7.62 (1H, d, J=7.4 Hz)

(57B) (1S)-4-Ethylindan-1-ol

To a mixture of formic acid (0.20 mL, 5.11 mmol) and triethylamine (0.61 mL, 4.38 mmol), a dichloromethane (6.0 mL) solution of 4-ethylindan-1-one (234 mg, 1.46 mmol) produced in (57A) was added, and chloro[(1S,2S)—N-(p-toluenesulfonyl)-1,2-diphenylethanediamine](mesitylene)ruthenium (II) (45 mg, 0.073 mmol) was added thereto at room temperature, and then, the resulting mixture was stirred under a nitrogen atmosphere at room temperature for 2 hours. Water was added to the reaction solution, and the organic matter was extracted with ethyl acetate. The organic layer was washed with a saturated sodium bicarbonate solution and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=100:0 to 90:10 (v/v)), whereby the objective title compound was obtained as a white solid (232 mg, yield: 98%).

$^1$H NMR (CDCl$_3$, 400 MHz): δ1.22 (3H, t, J=7.4 Hz), 1.71 (1H, brs), 1.92-2.00 (1H, m), 2.45-2.54 (1H, m), 2.62 (2H, q, J=7.8 Hz), 2.78 (1H, ddd, J=6.6, 8.2, 15.2 Hz), 3.03 (1H, ddd, J=4.7, 8.6, 16.0 Hz), 5.25 (1H, dd, J=6.2, 11.7 Hz), 7.12 (1H, d, J=7.5 Hz), 7.22 (1H, dd, J=7.4, 7.4 Hz), 7.27 (1H, d, J=8.2 Hz)

(57C) (3S)-3-Ethoxy-3-(4-{[(1R)-4-ethyl-2,3-dihydro-1H-inden-1-yl]oxy}phenyl)propan-1-ol (1S)-4-Ethylindan-1-ol (193 mg, 1.19 mmol) produced in (57B) and 4-{(1S)-1-ethoxy-3-[(triisopropylsilyl)oxy]propyl}phenol (350 mg, 0.99 mmol) produced in Example 50 (50E) were dissolved in tetrahydrofuran (40 mL), and triphenylphosphine (337 mg, 1.29 mmol) and a 40% diethyl azodicarboxylate toluene solution (0.59 mL, 1.29 mmol) were added thereto at room temperature, and then, the resulting mixture was stirred under a nitrogen atmosphere at 50° C. for 8 hours.

After the reaction solution was cooled to room temperature, the solvent was distilled off under reduced pressure, and the resulting residue was roughly purified by silica gel column chromatography (hexane:ethyl acetate=100:0 to 95:5 (v/v)), whereby a crude product was obtained. This crude product was dissolved in tetrahydrofuran (30 mL), and a 1.0 M tetra-n-butylammonium fluoride tetrahydrofuran solution (0.98 mL, 0.98 mmol) was added thereto at 0° C., and then, the resulting mixture was stirred under a nitrogen atmosphere at room temperature for 2 hours. To the reaction solution, a saturated aqueous solution of ammonium chloride was added, and the organic matter was extracted with ethyl acetate. The organic layer was washed with water and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=100:0 to 70:30 (v/v)), whereby the objective title compound was obtained as a colorless oily substance (220 mg, yield: 65%).

$^1$H NMR (CDCl$_3$, 400 MHz): δ1.19 (3H, t, J=7.0 Hz), 1.24 (3H, t, J=7.8 Hz), 1.81-1.88 (1H, m), 2.01-2.10 (1H, m), 2.19-2.27 (1H, m), 2.53-2.60 (1H, m), 2.65 (2H, q, J=7.4 Hz), 2.85 (1H, m), 3.10 (1H, ddd, J=5.4, 8.6, 14.0 Hz), 3.30-3.46 (2H, m), 3.80 (2H, dd, J=3.5, 7.8 Hz), 4.48 (1H, dd, J=3.9, 9.0 Hz), 5.76 (1H, dd, J=4.3, 7.0 Hz), 6.69 (2H, d, J=8.6 Hz), 7.17 (1H, d, J=6.6 Hz), 7.21-7.30 (4H, m)

(57D) (3S)-3-Ethoxy-3-(4-{[(1R)-4-ethyl-2,3-dihydro-1H-inden-1-yl]oxy}phenyl)propionic acid (3S)-3-Ethoxy-3-(4-{[(1R)-4-ethyl-2,3-dihydro-1H-inden-1-yl]oxy}phenyl)propan-1-ol (220 mg, 0.65 mmol) produced in (57C) was dissolved in acetonitrile (25 mL), and a phosphate buffer (pH 6.8, 25 mL), 2,2,6,6-tetramethylpiperidine-N-oxyl (10 mg, 0.065 mmol), sodium chlorite (80%, 118 mg, 1.30 mmol), and an aqueous solution of sodium hypochlorite (effective chlorine concentration: 5%) (0.13 mL, 0.065 mmol) were sequentially added thereto at 0° C., and then, the resulting mixture was stirred at room temperature for 2 hours. To the reaction solution, ethyl acetate was added, and the organic layer was washed with 1 N hydrochloric acid, water, and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=100:0 to 80:20 (v/v)), whereby the objective title compound was obtained as a white solid (218 mg, yield: 95%).

$^1$H NMR (CDCl$_3$, 400 MHz): δ1.19 (3H, t, J=7.1 Hz), 1.24 (3H, t, J=7.4 Hz), 2.18-2.26 (1H, m), 2.53-2.60 (1H, m), 2.62-2.67 (3H, m), 2.86 (1H, dd, J=9.4, 15.7 Hz), 2.87-2.92 (1H, m), 3.10 (1H, ddd, J=5.5, 8.6, 14.4 Hz), 3.35-3.49 (2H, m), 4.71 (1H, dd, J=4.3, 9.4 Hz), 5.76 (1H, dd, J=3.9, 6.6 Hz), 7.00 (2H, d, J=8.6 Hz), 7.17 (1H, d, J=7.0 Hz), 7.23 (1H, dd, J=7.5, 7.5 Hz), 7.26-7.29 (3H, m)

Example 58

(3S)-3-Ethoxy-3-(4-{[(1R)-4-methyl-2,3-dihydro-1H-inden-1-yl]oxy}phenyl)propionic acid (Illustrative Compound No: 1-183)

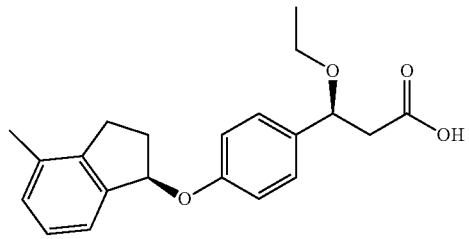

(58A) (1S)-4-Methylindan-1-ol

To a mixture of formic acid (0.91 mL, 23.9 mmol) and triethylamine (0.29 mL, 21.0 mmol), a dichloromethane (6.0 mL) solution of 4-methylindan-1-one (1.00 g, 6.84 mmol) was added, and chloro[(1S,2S)—N-(p-toluenesulfonyl)-1,2-diphenyl ethanediamine](mesitylene)ruthenium(II) (128 mg, 0.210 mmol) was added thereto at room temperature, and then, the resulting mixture was stirred under a nitrogen atmosphere at room temperature for 2 hours. Water was added to the reaction solution, and the organic matter was extracted with ethyl acetate. The organic layer was washed with a saturated sodium bicarbonate solution and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=100:0 to 75:25 (v/v)), whereby the objective title compound was obtained as a white solid (0.94 g, yield: 93%).

$^1$H NMR (CDCl$_3$, 400 MHz): δ1.68 (1H, d, J=7.1 Hz), 1.92-2.00 (1H, m), 2.26 (3H, s), 2.45-2.54 (1H, m), 2.74 (1H, ddd, J=6.2, 8.2, 14.8 Hz), 2.99 (1H, ddd, J=5.1, 8.6, 13.7 Hz), 5.26 (1H, dd, J=7.0, 12.1 Hz), 7.09 (1H, d, J=7.5 Hz), 7.17 (1H, dd, J=7.4, 7.4 Hz), 7.26 (1H, d, J=7.4 Hz)

(58B) (3S)-3-Ethoxy-3-(4-{[(1R)-4-methyl-2,3-dihydro-1H-inden-1-yl]oxy}phenyl)propan-1-ol (1S)-4-Methylindan-1-ol (252 mg, 1.70 mmol) produced in (58A) and 4-{(1S)-1-ethoxy-3-[(triisopropylsilyl)oxy]propyl}phenol (500 mg, 1.42 mmol) produced in Example 50 (50E) were dissolved in tetrahydrofuran (50 mL), and triphenylphosphine (484 mg, 1.85 mmol) and a 40% diethyl azodicarboxylate toluene solution (0.84 mL, 1.85 mmol) were added thereto at room temperature, and then, the resulting mixture was stirred under a nitrogen atmosphere at 50° C. for 8 hours.

After the reaction solution was cooled to room temperature, the solvent was distilled off under reduced pressure, and the resulting residue was roughly purified by silica gel column chromatography (hexane:ethyl acetate=100:0 to 95:5 (v/v)), whereby a crude product was obtained. This crude product was dissolved in tetrahydrofuran (30 mL), and a 1.0 M tetra-n-butylammonium fluoride tetrahydrofuran solution (1.3 mL, 1.30 mmol) was added thereto at 0° C., and then, the resulting mixture was stirred under a nitrogen atmosphere at room temperature for 2 hours. To the reaction solution, a saturated aqueous solution of ammonium chloride was added, and the organic matter was extracted with ethyl acetate. The organic layer was washed with water and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=100:0 to 75:25 (v/v)), whereby the objective title compound was obtained as a colorless oily substance (228 mg, yield: 49%).

$^1$H NMR (CDCl$_3$, 400 MHz): δ1.19 (3H, t, J=7.1 Hz), 1.81-1.88 (1H, m), 2.01-2.10 (1H, m), 2.19-2.27 (1H, m), 2.34 (3H, s), 2.53-2.61 (1H, m), 2.81-2.89 (2H, m), 3.06 (1H, ddd, J=5.4, 8.6, 14.5 Hz), 3.30-3.46 (2H, m), 3.79-3.81 (2H, m), 4.48 (1H, dd, J=3.9, 9.0 Hz), 5.76 (1H, dd, J=3.9, 6.6 Hz), 6.99 (2H, d, J=8.6 Hz), 7.14 (1H, d, J=7.4 Hz), 7.19 (1H, dd, J=7.4, 7.4 Hz), 7.24-7.28 (3H, m)

(58C) (3S)-3-Ethoxy-3-(4-{[(1R)-4-methyl-2,3-dihydro-1H-inden-1-yl]oxy}phenyl)propionic acid (3S)-3-Ethoxy-3-(4-{[(1R)-4-methyl-2,3-dihydro-1H-inden-1-yl]oxy}phenyl)propan-1-ol (228 mg, 0.70 mmol) produced in (58B) was dissolved in acetonitrile (25 mL), and a phosphate buffer (pH 6.8, 25 mL), 2,2,6,6-tetramethylpiperidine-N-oxyl (11 mg, 0.070 mmol), sodium chlorite (80%, 127 mg, 1.40 mmol), and an aqueous solution of sodium hypochlorite (effective chlorine concentration: 5%) (0.14 mL, 0.07 mmol) were sequentially added thereto at 0° C., and then, the resulting mixture was stirred at room temperature for 2 hours. To the reaction solution, ethyl acetate was added, and the organic layer was washed with 1 N hydrochloric acid, water, and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=100:0 to 65:35 (v/v)), whereby the objective title compound was obtained as a white solid (155 mg, yield: 65%).

$^1$H NMR (CDCl$_3$, 400 MHz): δ1.19 (3H, t, J=7.1 Hz), 2.17-2.26 (1H, m), 2.30 (3H, s), 2.52-2.61 (1H, m), 2.65 (1H, dd, J=4.3, 15.6 Hz), 2.81-2.89 (2H, m), 3.06 (1H, ddd, J=5.5, 8.6, 14.5 Hz), 3.36-3.49 (2H, m), 4.71 (1H, dd, J=4.3, 9.4 Hz), 5.77 (1H, dd, J=3.9, 6.6 Hz), 6.99 (2H, d, J=8.6 Hz), 7.14 (1H, d, J=7.4 Hz), 7.18 (1H, dd, J=7.4, 7.4 Hz), 7.26-7.28 (3H, m)

Example 59

(3S)-3-(4-{[(1R)-4-(Difluoromethyl)-2,3-dihydro-1H-inden-1-yl]oxy}phenyl)-3-ethoxypropionic acid (Illustrative Compound No: 1-211)

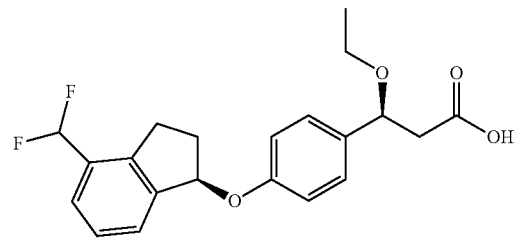

(59A) (1S)-4-Bromoindan-1-ol

To a mixture of formic acid (1.20 mL, 31.5 mmol) and triethylamine (3.76 mL, 27.0 mmol), a dichloromethane (6.0 mL) solution of 4-bromoindan-1-one (1.90 g, 9.00 mmol) was added, and chloro[(1S,2S)—N-(p-toluenesulfonyl)-1,2-diphenylethanediamine](mesitylene)ruthenium(II) (168 mg, 0.270 mmol) was added thereto at room temperature, and then, the resulting mixture was stirred under a nitrogen atmosphere at room temperature for 2 hours. Water was added to the reaction solution, and the organic matter was extracted with ethyl acetate. The organic layer was washed with a saturated sodium bicarbonate solution and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=95:5 to 65:35 (v/v)), whereby the objective title compound was obtained as a white solid (1.90 g, yield: 99%).

$^1$H NMR (CDCl$_3$, 400 MHz): δ1.77 (1H, d, J=7.4 Hz), 1.93-2.01 (1H, m), 2.49-2.57 (1H, m), 2.83 (1H, dt, J=8.2, 16.4 Hz), 3.08 (1H, ddd, J=4.3, 8.6, 16.5 Hz), 5.32 (1H, dd, J=7.0, 12.5 Hz), 7.13 (1H, dd, J=7.8, 7.8 Hz), 7.36 (1H, d, J=7.4 Hz), 7.43 (1H, d, J=7.8 Hz)

(59B) (1S)-1-(Allyloxy)-4-bromoindan (1S)-4-Bromoindan-1-ol (1.82 g, 8.54 mmol) produced in (59A) was dissolved in tetrahydrofuran (30 mL), and the resulting solution was cooled to 0° C. Then, sodium hydride (358 mg, 9.40 mmol) was added thereto, and the resulting mixture was stirred for 1 hour. Thereafter, allyl bromide (0.82 mL, 9.40 mmol) was added dropwise thereto, and the resulting mixture was stirred at room temperature for 5 hours.

Water was added to the reaction solution, and the organic matter was extracted with ethyl acetate. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=100:0 to 90:10 (v/v)), whereby the objective title compound was obtained as a colorless oily substance (2.16 g, yield: 100%).

$^1$H NMR (CDCl$_3$, 400 MHz): δ2.05-2.14 (1H, m), 2.33-2.41 (1H, m), 2.83 (1H, ddd, J=5.5, 8.6, 16.4 Hz), 3.09 (1H, ddd, J=5.9, 8.6, 16.8 Hz), 4.04-4.13 (2H, m), 5.04 (1H, dd, J=4.3, 6.6 Hz), 5.20 (1H, dd, J=1.6, 10.2 Hz), 5.33 (1H, dd, J=1.6, 17.2 Hz), 5.91-6.01 (1H, m), 7.09 (1H, dd, J=7.7, 7.8 Hz), 7.33 (1H, d, J=7.4 Hz), 7.41 (1H, d, J=7.8 Hz)

(59C) (1S)-1-(Allyloxy)indan-4-carbaldehyde (1S)-1-(Allyloxy)-4-bromoindan (2.16 g, 8.53 mmol) produced in (59B) was dissolved in tetrahydrofuran (30 mL), and the resulting solution was cooled to −78° C. Then, n-butyllithium (1.55 M, 10.2 mmol, 7.13 mL) was added dropwise thereto, and then, the resulting mixture was stirred under a nitrogen stream for 1 hour. Then, N, N-dimethylformamide (1.07 mL, 12.8 mmol) was added dropwise thereto, and the resulting mixture was stirred for 2 hours.

After the temperature of the reaction solution was raised to room temperature, water was added thereto, and the organic matter was extracted with ethyl acetate. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=100:0 to 60:40 (v/v)), whereby the objective title compound was obtained as a yellow oily substance (0.89 g, yield: 52%).

$^1$H NMR (CDCl$_3$, 400 MHz): δ2.12-2.20 (1H, m), 2.39-2.47 (1H, m), 3.20 (1H, ddd, J=5.5, 8.6, 14.1 Hz), 3.46 (1H, ddd, J=5.5, 8.6, 14.1 Hz), 4.07-4.17 (2H, m), 5.01 (1H, dd, J=4.7, 7.1 Hz), 5.22 (1H, dd, J=1.9, 10.5 Hz), 5.34 (1H, dd, J=1.5, 17.2 Hz), 5.93-6.03 (1H, m), 7.42 (1H, dd, J=7.4, 7.4 Hz), 7.66 (1H, d, J=7.4 Hz), 7.75 (1H, d, J=7.8 Hz), 10.2 (1H, s)

(59D) (1S)-1-(Allyloxy)-4-(difluoromethyl)indan (1S)-1-(Allyloxy)indan-4-carbaldehyde (0.89 g, 4.40 mmol) produced in (59C) and bis(2-methoxyethyl)aminosulfur trifluoride (1.38 mL, 7.48 mmol) were dissolved in dichloromethane (30 mL), and ethanol (0.88 mmol, 0.051 mL) was added dropwise thereto, and then, the resulting mixture was stirred at room temperature for 5 hours.

Water was added to the reaction solution, and the organic matter was extracted with ethyl acetate. The organic layer was washed with a saturated sodium bicarbonate solution and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=100:0 to 90:10 (v/v)), whereby the objective title compound was obtained as a yellow oily substance (0.66 g, yield: 67%).

$^1$H NMR (CDCl$_3$, 400 MHz): δ2.12-2.18 (1H, m), 2.36-2.44 (1H, m), 2.90-2.98 (1H, m), 3.17-3.24 (1H, m), 4.06-4.16 (2H, m), 4.99 (1H, dd, J=4.3, 6.6 Hz), 5.21 (1H, dd, J=1.6, 10.6 Hz), 5.34 (1H, dd, J=1.6, 17.2 Hz), 5.93-6.02 (1H, m), 6.68 (1H, t, J$_{H-F}$=55.5 Hz), 7.31 (1H, dd, J=7.4, 7.4 Hz), 7.41 (1H, d, J=7.8 Hz), 7.52 (1H, d, J=7.4 Hz)

(59E) (1S)-4-(Difluoromethyl)indan-1-ol (1S)-1-(Allyloxy)-4-(difluoromethyl)indan (0.60 g, 2.68 mmol) produced in (59D) and dihydridotetrakis(triphenylphosphine)ruthenium (154 mg, 0.13 mmol) were dissolved in ethanol (10 mL), and the resulting mixture was heated to reflux for 2 hours.

The solvent was distilled off under reduced pressure, and the resulting residue was dissolved in methanol (5.0 mL), and p-toluenesulfonic acid (46 mg, 0.26 mmol) was added thereto, and then, the resulting mixture was stirred at room temperature for 2 hours.

Water was added to the reaction solution, and the organic matter was extracted with ethyl acetate. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=100:0 to 80:20 (v/v)), whereby the objective title compound was obtained as a yellow oily substance (0.39 g, yield: 79%).

$^1$H NMR (CDCl$_3$, 400 MHz): δ1.86 (1H, brs), 1.96-2.03 (1H, m), 2.50-2.59 (1H, m), 2.94 (1H, td, J=8.6, 7.4 Hz), 3.16-3.24 (1H, m), 5.26 (1H, dd, J=5.9, 6.2 Hz), 6.68 (1H, t, J$_{H-F}$=55.5 Hz), 7.34 (1H, dd, J=7.4, 7.4 Hz), 7.42 (1H, d, J=7.1 Hz), 7.53 (1H, d, J=7.5 Hz)

(59F) (3S)-3-(4-{[(1R)-4-(Difluoromethyl)-2,3-dihydro-1H-inden-1-yl]oxy}phenyl)-3-ethoxypropan-1-ol (1S)-4-(Difluoromethyl)indan-1-ol (313 mg, 1.70 mmol) produced in (59E) and 4-{(1S)-1-ethoxy-3-[(triisopropyl silyl)oxy]propyl}phenol (499 mg, 1.42 mmol) produced in Example 50 (50E) were dissolved in tetrahydrofuran (40 mL), and triphenylphosphine (558 mg, 2.13 mmol) and a 40% diethyl azodicarboxylate toluene solution (0.97 mL, 2.13 mmol) were added thereto at room temperature, and then, the resulting mixture was stirred under a nitrogen atmosphere at 50° C. for 8 hours.

After the reaction solution was cooled to room temperature, the solvent was distilled off under reduced pressure, and the resulting residue was roughly purified by silica gel column chromatography (hexane:ethyl acetate=100:0 to 95:5 (v/v)), whereby a crude product was obtained. This crude product was dissolved in tetrahydrofuran (30 mL), and a 1.0 M tetra-n-butylammonium fluoride tetrahydrofuran solution (2.0 mL, 2.02 mmol) was added thereto at 0° C., and then, the resulting mixture was stirred under a nitrogen atmosphere at room temperature for 2 hours. To the reaction solution, a saturated aqueous solution of ammonium chloride was added, and the organic matter was extracted with ethyl acetate. The organic layer was washed with water and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=100:0 to 70:30 (v/v)), whereby the objective title compound was obtained as a colorless oily substance (447 mg, yield: 87%).

$^1$H NMR (CDCl$_3$, 400 MHz): δ1.20 (3H, t, J=7.1 Hz), 1.82-1.89 (1H, m), 2.01-2.10 (1H, m), 2.23-2.31 (1H, m), 2.59-2.67 (1H, m), 2.85 (1H, t, J=4.7 Hz), 3.07 (1H, dt, J=7.8, 7.0 Hz), 3.24-3.46 (3H, m), 3.78-3.82 (2H, m), 4.49 (1H, dd, J=3.9, 9.0 Hz), 5.76 (1H, dd, J=4.7, 7.0 Hz), 6.71 (1H, t, J$_{H-F}$=56.0 Hz), 6.99 (2H, d, J=8.6 Hz), 7.26 (2H, d, J=8.2 Hz), 7.35 (1H, dd, J=7.5, 7.5 Hz), 7.47 (1H, d, J=7.9 Hz), 7.55 (1H, d, J=7.8 Hz)

(59G) (3S)-3-(4-{[(1R)-4-(Difluoromethyl)-2,3-dihydro-1H-inden-1-yl]oxy}phenyl)-3-ethoxypropionic acid (3S)-3-(4-{[(1R)-4-(Difluoromethyl)-2,3-dihydro-1H-inden-1-yl]oxy}phenyl)-3-ethoxypropan-1-ol (447 mg, 1.23 mmol) produced in (59F) was dissolved in acetonitrile (25 mL), and a phosphate buffer (pH 6.8, 25 mL), 2,2,6,6-tetramethyl piperidine-N-oxyl (19 mg, 0.123 mmol), sodium chlorite (80%, 223 mg, 2.46 mmol), and an aqueous solution of sodium hypochlorite (effective chlorine concentration: 5%) (0.24 mL, 0.123 mmol) were sequentially added thereto at 0° C., and then, the resulting mixture was stirred at room temperature for 2 hours. To the reaction solution, ethyl acetate was added, and the organic layer was washed with 1 N hydrochloric acid, water, and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=100:0 to 65:35 (v/v)), whereby the objective title compound was obtained as a white solid (404 mg, yield: 87%).

$^1$H NMR (CDCl$_3$, 400 MHz): δ1.26 (3H, t, J=7.5 Hz), 2.31-2.24 (1H, m), 2.58-2.65 (1H, m), 2.66 (1H, dd, J=4.3, 16 Hz), 2.86 (1H, dd, J=4.3, 16 Hz), 3.03-3.11 (1H, m), 3.24-3.31 (1H, m), 3.39-3.49 (2H, m), 4.71 (1H, dd, J=4.3, 9.4 Hz), 5.77 (1H, dd, J=4.3, 6.6 Hz), 6.71 (1H, t, J$_{H-F}$=54.6 Hz), 7.00 (2H, d, J=9.0 Hz), 7.29 (2H, d, J=8.6 Hz), 7.35 (1H, dd, J=7.9, 7.9 Hz), 7.47 (1H, d, J=7.8 Hz), 7.55 (1H, d, J=7.4 Hz)

Example 60

(3S)-3-Ethoxy-3-(4-{[(3S)-7-(trifluoromethyl)-2,3-dihydro-1-benzofuran-3-yl]oxy}phenyl)propionic acid (Illustrative Compound No: 1-170)

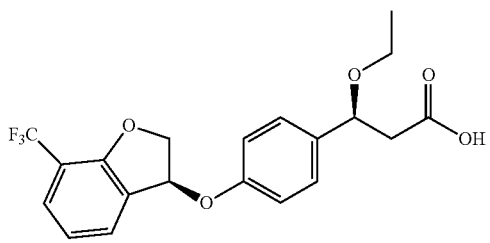

(60A) (3R)-7-(Trifluoromethyl)-2,3-dihydro-1-benzofuran-3-ol

To a mixture of formic acid (60 µL, 1.56 mmol) and triethylamine (186 µL, 1.33 mmol), a dichloromethane (2.0 mL) solution of 7-(trifluoromethyl)-1-benzofuran-3-one (90 mg, 0.445 mmol) produced in Example 47 (47E) was added, and chloro[(1S,2S)—N-(p-toluenesulfonyl)-1,2-diphenylethanediamine](mesitylene)ruthenium(II) (8.4 mg, 0.013 mmol) was added thereto at room temperature, and then, the resulting mixture was stirred overnight under a nitrogen atmosphere at room temperature.

The reaction solution was directly purified by silica gel column chromatography (hexane:ethyl acetate=100:0 to 30:70 (v/v)), whereby the objective title compound was obtained as a white solid (86 mg, yield: 95%).

$^1$H NMR (CDCl$_3$, 400 MHz): 1.95 (1H, d, J=7.43 Hz), 4.60 (1H, dd, J=2.7, 11.0 Hz), 4.69 (1H, dd, J=6.7, 11.0 Hz), 5.43 (1H, dt, J=2.7, 7.0 Hz), 7.03 (1H, t, J=7.4 Hz), 7.51 (1H, d, J=7.4 Hz), 7.60 (1H, d, J=7.4 Hz)

(60B) Methyl (3S)-3-ethoxy-3-(4-{[(3S)-7-(trifluoromethyl)-2,3-dihydro-1-benzofuran-3-yl]oxy}phenyl)propionate Methyl (3S)-3-ethoxy-3-(4-hydroxyphenyl)propionate (80 mg, 0.357 mmol) produced in Example 41 (41C) and (3R)-7-(trifluoromethyl)-2,3-dihydro-1-benzofuran-3-ol (77 mg, 0.357 mmol) produced in (60A) were dissolved in tetrahydrofuran (5 mL), and triphenylphosphine (140 mg, 0.535 mmol) and a 40% diethyl azodicarboxylate toluene solution (250 µL, 0.535 mmol) were added thereto at room temperature, and then, the resulting mixture was stirred under a nitrogen atmosphere at 60° C. for 3 hours. After the reaction solution was cooled to room temperature, the solvent was distilled off under reduced pressure, and the resulting residue was purified by silica gel column chromatography (hexane:ethyl acetate=100:0 to 60:40 (v/v)), whereby the objective title compound was obtained as a colorless oily substance (50 mg, yield: 34%).

$^1$H NMR (CDCl$_3$, 400 MHz): δ1.16 (3H, t, J=7.0 Hz), 2.58 (1H, dd, J=5.1, 15.3 Hz), 2.82 (1H, dd, J=9.0, 15.3 Hz), 3.33-3.42 (2H, m), 3.69 (3H, s), 4.71 (1H, dd, J=5.1, 9.0 Hz), 4.76 (1H, dd, J=2.7, 11.0 Hz), 4.83 (1H, dd, J=6.7, 11.0 Hz), 5.92 (1H, dd, J=2.7, 6.7 Hz), 6.89 (2H, d, J=8.6 Hz), 7.02 (1H, t, J=7.4 Hz), 7.30 (2H, d, J=8.6 Hz), 7.56 (1H, t, J=7.4 Hz), 7.56 (1H, t, J=7.4 Hz)

(60C) (3S)-3-Ethoxy-3-(4-{[(3S)-7-(trifluoromethyl)-2,3-dihydro-1-benzofuran-3-yl]oxy}phenyl)propionic acid Methyl (3S)-3-ethoxy-3-(4-{[(3S)-7-(trifluoromethyl)-2,3-dihydro-1-benzofuran-3-yl]oxy}phenyl)propionate (50 mg, 0.12 mmol) produced in (60B) was dissolved in methanol (5 mL), and a 1 N aqueous solution of sodium hydroxide (2 mL) was added thereto at room temperature, and then, the resulting mixture was stirred at room temperature for 1 hour.

The solvent was distilled off under reduced pressure, and to the resulting residue, 1 N hydrochloric acid was added, and the organic matter was extracted with ethyl acetate. The organic layer was washed with a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 0:100 (v/v)), whereby the objective title compound was obtained as a colorless oily substance (32 mg, yield: 66%).

$^1$H NMR (CDCl$_3$, 400 MHz): δ1.20 (3H, t, J=7.3 Hz), 2.63 (1H, dd, J=4.4, 15.6 Hz), 2.85 (1H, dd, J=9.3, 15.6 Hz), 3.37-3.47 (2H, m), 4.70 (1H, dd, J=4.4, 9.3 Hz), 4.75 (1H, dd,

J=2.9, 10.7 Hz), 4.83 (1H, dd, J=6.4, 10.7 Hz), 5.92-5.94 (1H, m), 6.91 (2H, d, J=8.8 Hz), 7.03 (1H, t, J=7.3 Hz), 7.30 (2H, d, J=8.8 Hz), 7.55 (1H, t, J=7.3 Hz), 7.57 (1H, t, J=7.3 Hz)
MS (ESI) m/z: 395 (M−H)⁻

Example 61

(3S)-3-Ethoxy-3-(4-{[(1R)-6-fluoro-4-(trifluoromethyl)-2,3-dihydro-1H-inden-1-yl]oxy}phenyl)-propionic acid (Illustrative Compound No: 1-212)

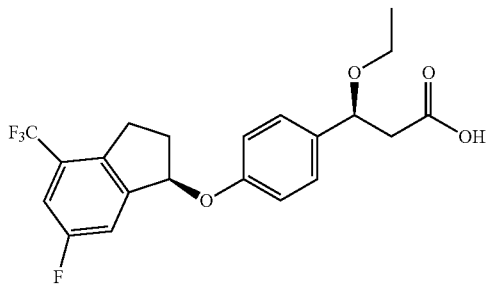

(61A) Ethyl (2E)-3-[4-fluoro-2-(trifluoromethyl) phenyl]acrylate

Ethyl diethylphosphonoacetate (8.75 g, 39.0 mmol) was dissolved in tetrahydrofuran (100 mL), and sodium hydride (60%, 1.98 g, 52.0 mmol) was added thereto at 0° C., and then, the resulting mixture was stirred under a nitrogen atmosphere for 30 minutes. 4-Fluoro-2-(trifluoromethyl)benzaldehyde (5.00 g, 26.0 mmol) was added thereto at 0° C., and the resulting mixture was stirred under a nitrogen atmosphere for 1 hour.

1 N Hydrochloric acid was added thereto, and the organic matter was extracted with ethyl acetate. The organic layer was washed with a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 70:30 (v/v)), whereby the objective title compound was obtained as a colorless oily substance (3.72 g, yield: 54%).

¹H NMR (CDCl₃, 400 MHz): 1.35 (3H, d, J=7.0 Hz), 4.28 (2H, q, J=7.0 Hz), 6.36 (1H, d, J=15.6 Hz), 7.25-7.30 (1H, m), 7.42 (1H, dd, J=2.7, 9.0 Hz), 7.70 (1H, dd, J=5.0, 9.0 Hz), 7.98 (1H, dd, J=2.0, 15.6 Hz)

(61B)
3-[4-Fluoro-2-(trifluoromethyl)phenyl]propionic acid

Ethyl (2E)-3-[4-fluoro-2-(trifluoromethyl)phenyl]acrylate (3.72 g, 14.2 mmol) produced in (61A) was dissolved in ethanol (50 mL), and 10% palladium hydroxide on carbon (500 mg) was added thereto at room temperature, and then, the resulting mixture was stirred under a hydrogen atmosphere at room temperature for 2 hours. The reaction solution was filtered through a Celite filter, and the solvent was distilled off under reduced pressure, whereby a colorless oily substance (3.88 g) was obtained.

The obtained colorless oily substance was dissolved in ethanol (100 mL), and a 2 N aqueous solution of sodium hydroxide (30 mL) was added thereto at room temperature, and then, the resulting mixture was stirred at room temperature for 1 hour.

The solvent was distilled off under reduced pressure, and to the resulting residue, 2 N hydrochloric acid was added, and the organic matter was extracted with ethyl acetate. The organic layer was washed with a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 0:100 (v/v)), whereby the objective title compound was obtained as a white solid (3.56 g, yield: 100%).

¹H NMR (CDCl₃, 400 MHz): δ2.67 (2H, t, J=7.4 Hz), 3.12 (2H, t, J=7.4 Hz), 7.19 (1H, dt, J=2.7, 8.2 Hz), 7.34-7.38 (2H, m)

(61C) 6-Fluoro-4-(trifluoromethyl)indan-1-one

To 3-[4-fluoro-2-(trifluoromethyl)phenyl]propionic acid (3.40 g, 14.4 mmol) produced in (61B), chlorosulfonic acid (30 mL) was added dropwise at 0° C., and the resulting mixture was stirred at 60° C. for 20 minutes.

The reaction solution was added to ice water to stop the reaction, and the organic matter was extracted with ethyl acetate. The organic layer was washed with a saturated aqueous solution of sodium hydrogen carbonate and a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 50:50 (v/v)), whereby the objective title compound was obtained as a white solid (2.58 g, yield: 82%).

¹H NMR (CDCl₃, 400 MHz): δ2.79-2.82 (2H, m), 3.29-3.31 (2H, m), 7.58 (1H, s), 7.60 (1H, s)

(61D) (1S)-6-Fluoro-4-(trifluoromethyl)indan-1-ol

To a mixture of formic acid (391 μL, 10.2 mmol) and triethylamine (1.21 mL, 8.71 mmol), a dichloromethane (5 mL) solution of 6-fluoro-4-(trifluoro methyl)indan-1-one (633 mg, 2.90 mmol) produced in (61C) was added, and chloro[(1S,2S)—N-(p-toluenesulfonyl)-1,2-diphenylethanediamine](mesitylene)ruthenium(II) (54.8 mg, 0.087 mmol) was added thereto at room temperature, and then, the resulting mixture was stirred under a nitrogen atmosphere at room temperature for 1 hour.

Water was added to the reaction solution, and the organic matter was extracted with ethyl acetate. The organic layer was washed with a saturated aqueous solution of sodium hydrogen carbonate and a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 0:100 (v/v)), whereby the objective title compound was obtained as a white solid (573 mg, yield: 90%).

¹H NMR (CDCl₃, 500 MHz): 1.86 (1H, d, J=6.8 Hz), 1.99-2.06 (1H, m), 2.57-2.63 (1H, m), 2.90-2.96 (1H, m), 3.17-3.22 (1H, m), 5.23 (1H, dt, J=6.4, 6.8 Hz), 7.24-7.30 (2H, m)

(61E) {[(3S)-3-Ethoxy-3-(4-{[(1R)-6-fluoro-4-(trifluoromethyl)-2,3-dihydro-1H-inden-1-yl]oxy}phenyl)propyl]oxy}(triisopropyl)silane (1S)-6-Fluoro-4-(trifluoromethyl)indan-1-ol (573 mg, 2.60 mmol) produced in (61D) and 4-{(1S)-1-ethoxy-3-[(triisopropylsilyl)oxy]propyl}phenol (918 mg, 2.60 mmol) produced in Example 50 (50E) were dissolved in tetrahydrofuran (10 mL), and triphenylphosphine (1.37 g, 5.20 mmol) and a 40% diethyl azodicarboxylate toluene solution (2.00 mL, 4.32 mmol) were added thereto at room temperature, and then, the resulting mixture was stirred under a nitrogen atmosphere at room temperature for 1 hour.

The solvent was distilled off under reduced pressure, and the resulting residue was roughly purified by silica gel column chromatography (hexane:ethyl acetate=100:0 to 50:50 (v/v)), whereby the objective title compound was obtained as a colorless oily substance (1.27 g, yield: 88%).

$^1$H NMR (CDCl$_3$, 500 MHz): δ1.07-1.09 (21H, m), 1.17 (3H, t, J=6.8 Hz), 1.76-1.82 (1H, m), 1.97-2.04 (1H, m), 2.25-2.32 (1H, m), 2.63-2.70 (1H, m), 3.00-3.08 (1H, m), 3.23-3.30 (1H, m), 3.29-3.35 (1H, m), 3.37-3.43 (1H, m), 3.63-3.67 (1H, m), 3.83-3.88 (1H, m), 4.47 (1H, dd, J=5.4, 8.3 Hz), 5.72 (1H, t, J=6.8 Hz), 6.95 (2H, d, J=8.8 Hz), 7.26-7.33 (4H, m)

(61F) (3S)-3-Ethoxy-3-(4-{[(1R)-6-fluoro-4-(trifluoromethyl)-2,3-dihydro-1H-inden-1-yl]oxy}phenyl)propan-1-ol {[(3S)-3-Ethoxy-3-(4-{[(1R)-6-fluoro-4-(trifluoromethyl)-2,3-dihydro-1H-inden-1-yl]oxy}phenyl)propyl]oxy}(triisopropyl)silane (1.20 g, 2.16 mmol) produced in (61E) was dissolved in tetrahydrofuran (5 mL), and a 1.0 M tetra-n-butylammonium fluoride tetrahydrofuran solution (4.5 mL, 4.50 mmol) was added thereto, and then, the resulting mixture was stirred under a nitrogen atmosphere at room temperature for 2 hours.

Water was added to the reaction solution, and the organic matter was extracted with ethyl acetate. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=100:0 to 0:100 (v/v)), whereby the objective title compound was obtained as a colorless oily substance (0.647 g, yield: 75%).

$^1$H NMR (CDCl$_3$, 500 MHz): δ1.19 (3H, t, J=6.8 Hz), 1.82-1.88 (1H, m), 2.01-2.09 (1H, m), 2.25-2.31 (1H, m), 2.64-2.71 (1H, m), 2.79 (1H, t, J=5.4 Hz), 3.02-3.08 (1H, m), 3.23-3.29 (1H, m), 3.32-3.38 (1H, m), 3.39-3.45 (1H, m), 3.78-3.81 (2H, m), 4.48 (1H, dd, J=3.9, 9.3 Hz), 5.72 (1H, t, J=5.8 Hz), 6.97 (2H, d, J=8.8 Hz), 7.26-7.31 (4H, m)

(61G) (3S)-3-Ethoxy-3-(4-{[(1R)-6-fluoro-4-(trifluoromethyl)-2,3-dihydro-1H-inden-1-yl]oxy}phenyl)propionic acid (3S)-3-Ethoxy-3-(4-{[(1R)-6-fluoro-4-(trifluoromethyl)-2,3-dihydro-1H-inden-1-yl]oxy}phenyl)propan-1-ol (587 mg, 1.47 mmol) produced in (61F) was dissolved in acetonitrile (14 mL), and a phosphate buffer (pH 6.8, 14 mL), 2,2,6,6-tetramethylpiperidine-N-oxyl (23 mg, 0.147 mmol), sodium chlorite (80%, 328 mg, 2.94 mmol), and an aqueous solution of sodium hypochlorite (effective chlorine concentration: 5%) (0.280 mL, 0.147 mmol) were sequentially added thereto at 0° C., and then, the resulting mixture was stirred at room temperature for 5 hours.

To the reaction solution, a 1 N aqueous solution of sodium hydroxide was added at 0° C. to adjust the pH of the solution to 8 to 9, and an aqueous solution of sodium sulfite was added thereto. Then, the pH of the solution was adjusted to 3 to 4 with 1 N hydrochloric acid, and the organic matter was extracted with ethyl acetate. The organic layer was washed with a saturated sodium chloride solution, then dried over anhydrous sodium sulfate and filtered. Then, the solvent was distilled off under reduced pressure, and the resulting residue was purified by silica gel column chromatography (hexane:ethyl acetate=100:0 to 0:100 (v/v)), whereby a crude product was obtained as a solid. This solid was washed with hexane/ethyl acetate, whereby the objective title compound was obtained as a white solid (370 mg, yield: 61%).

$^1$H NMR (CDCl$_3$, 400 MHz): δ1.21 (3H, t, J=7.0 Hz), 2.23-2.32 (1H, m), 2.66 (1H, dd, J=3.9, 15.6 Hz), 2.64-2.72 (1H, m), 2.86 (1H, dd, J=9.8, 15.6 Hz), 3.01-3.10 (1H, m), 3.22-3.31 (1H, m), 3.37-3.52 (2H, m), 4.70 (1H, dd, J=3.9, 9.8 Hz), 5.73 (1H, dd, J=5.5, 6.7 Hz), 6.98 (2H, d, J=9.0 Hz), 7.26-7.32 (4H, m)

MS (ESI) m/z: 411 (M−H)$^−$

Example 62

(3S)-3-(4-{[(1R)-4,6-Dimethyl-2,3-dihydro-1H-inden-1-yl]oxy}phenyl)-3-ethoxypropionic acid (Illustrative Compound No: 1-213)

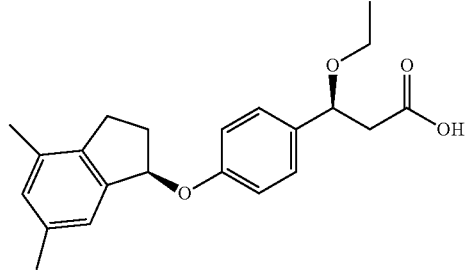

(62A) Ethyl (2E)-3-(2,4-dimethylphenyl)acrylate

Ethyl diethylphosphonoacetate (10.0 g, 44.7 mmol) was dissolved in tetrahydrofuran (100 mL), and sodium hydride (60%, 2.10 g, 55.9 mmol) was added thereto at 0° C., and then, the resulting mixture was stirred under a nitrogen atmosphere for 30 minutes. 2,4-Dimethylbenzaldehyde (5.00 g, 37.3 mmol) was added thereto at 0° C., and the resulting mixture was stirred under a nitrogen atmosphere for 1 hour.

1 N Hydrochloric acid was added thereto, and the organic matter was extracted with ethyl acetate. The organic layer was washed with a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 50:50 (v/v)), whereby the objective title compound was obtained as a colorless oily substance (6.87 g, yield: 90%).

$^1$H NMR (CDCl$_3$, 400 MHz): 1.34 (3H, d, J=7.0 Hz), 2.33 (3H, s), 2.41 (3H, s), 4.26 (2H, q, J=7.0 Hz), 6.33 (1H, d,

J=16.0 Hz), 7.02 (1H, d, J=8.2 Hz), 7.03 (1H, s), 7.46 (1H, d, J=8.2 Hz), 7.94 (1H, d, J=16.0 Hz)

(62B) 3-(2,4-Dimethylphenyl)propionic acid

Ethyl (2E)-3-(2,4-dimethylphenyl)acrylate (6.87 g, 33.6 mmol) produced in (62A) was dissolved in ethanol (100 mL), and 5% palladium carbon (1.20 g) was added thereto at room temperature, and then, the resulting mixture was stirred under a hydrogen atmosphere at room temperature for 3 hours. The reaction solution was filtered through a Celite filter, and the solvent was distilled off under reduced pressure, whereby a colorless oily substance was obtained.

The obtained colorless oily substance was dissolved in tetrahydrofuran (50 mL) and methanol (50 mL), and a 2N aqueous solution of sodium hydroxide (30 mL) was added thereto at room temperature, and then, the resulting mixture was stirred at room temperature for 1 hour.

The solvent was distilled off under reduced pressure, and to the resulting residue, 2 N hydrochloric acid was added, and the organic matter was extracted with ethyl acetate. The organic layer was washed with a saturated sodium chloride solution, then dried over anhydrous magnesium sulfate and filtered. Then, the solvent was distilled off under reduced pressure, whereby the objective title compound was obtained as a white solid (5.63 g, yield: 94%).

$^1$H NMR (CDCl$_3$, 400 MHz): 2.29 (6H, s), 2.62 (2H, t, J=7.4 Hz), 2.92 (2H, t, J=7.4 Hz), 6.96 (1H, d, J=7.8 Hz), 6.98 (1H, s), 7.04 (1H, d, J=7.8 Hz)

(62C) 4,6-Dimethylindan-1-one

To 3-(2,4-dimethylphenyl)propionic acid (5.63 g, 14.4 mmol) produced in (62B), polyphosphoric acid (138 g) was added, and the resulting mixture was stirred at 90° C. for 1 hour.

The reaction solution was added to ice water to stop the reaction, and the organic matter was extracted with dichloromethane. The organic layer was washed with water and a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 0:100 (v/v)), whereby the objective title compound was obtained as a white solid (4.62 g, yield: 91%).

$^1$H NMR (CDCl$_3$, 400 MHz): δ2.32 (3H, s), 2.37 (3H, s), 2.68-2.71 (2H, m), 2.96-2.99 (2H, m), 7.24 (1H, s), 7.40 (1H, s)

(62D) (1S)-4,6-Dimethylindan-1-ol

To a mixture of formic acid (395 μL, 10.5 mmol) and triethylamine (1.25 mL, 9.00 mmol), a dichloromethane (5 mL) solution of 4,6-dimethylindan-1-one (480 mg, 3.00 mmol) produced in (62C) was added, and chloro[(1S,2S)—N-(p-toluenesulfonyl)-1,2-diphenylethanediamine](mesitylene)ruthenium(II) (37 mg, 0.060 mmol) was added thereto at room temperature, and then, the resulting mixture was stirred under a nitrogen atmosphere at 40° C. for 3 hours.

The reaction solution was purified by silica gel column chromatography (hexane:ethyl acetate=100:0 to 50:50 (v/v)), whereby the objective title compound was obtained as a white solid (423 mg, yield: 87%).

$^1$H NMR (CDCl$_3$, 500 MHz): 1.63 (1H, d, J=6.8 Hz), 1.92-1.98 (1H, m), 2.24 (3H, s), 2.33 (3H, s), 2.45-2.52 (1H, m), 2.66-2.72 (1H, m), 2.91-2.97 (1H, m), 5.22 (1H, dt, J=4.9, 6.8 Hz), 6.92 (1H, s), 7.07 (1H, s)

(62E) {[(3S)-3-(4-{[(1R)-4,6-Dimethyl-2,3-dihydro-1H-inden-1-yl]oxy}phenyl)-3-ethoxypropyl]oxy}(triisopropyl)silane (1S)-4,6-Dimethylindan-1-ol (423 mg, 2.60 mmol) produced in (62D) and 4-{(1S)-1-ethoxy-3-[(triisopropyl silyl)oxy]propyl}phenol (835 mg, 2.37 mmol) produced in Example 50 (50E) were dissolved in tetrahydrofuran (10 mL), and triphenylphosphine (932 mg, 3.55 mmol) and a 40% diethyl azodicarboxylate toluene solution (1.60 mL, 3.55 mmol) were added thereto at room temperature, and then, the resulting mixture was stirred under a nitrogen atmosphere at room temperature for 30 minutes.

The solvent was distilled off under reduced pressure, and the resulting residue was purified by silica gel column chromatography (hexane:ethyl acetate=100:0 to 50:50 (v/v)), whereby the objective title compound was obtained as a colorless oily substance (669 mg, yield: 57%).

$^1$H NMR (CDCl$_3$, 400 MHz): δ1.06-1.07 (21H, m), 1.17 (3H, t, J=7.0 Hz), 1.76-1.84 (1H, m), 1.98-2.06 (1H, m), 2.17-2.25 (1H, m), 2.26 (3H, s), 2.32 (3H, s), 2.51-2.59 (1H, m), 2.75-2.83 (1H, m), 2.97-3.04 (1H, m), 3.27-3.35 (1H, m), 3.36-3.43 (1H, m), 3.62-3.67 (1H, m), 3.82-3.88 (1H, m), 4.45 (1H, dd, J=5.1, 8.2 Hz), 5.71 (1H, dd, J=4.3, 7.0 Hz), 6.96 (1H, s), 6.97 (2H, d, J=8.6 Hz), 7.09 (1H, s), 7.25 (2H, d, J=8.6 Hz)

(62F) (3S)-3-(4-{[(1R)-4,6-Dimethyl-2,3-dihydro-1H-inden-1-yl]oxy}phenyl)-3-ethoxypropan-1-ol {[(3S)-3-(4-{[(1R)-4,6-Dimethyl-2,3-dihydro-1H-inden-1-yl]oxy}phenyl)-3-ethoxypropyl]oxy}(triisopropyl)silane (669 mg, 1.35 mmol) produced in (62E) was dissolved in tetrahydrofuran (5 mL), and a 1.0 M tetra-n-butylammonium fluoride tetrahydrofuran solution (3.0 mL, 3.00 mmol) was added thereto, and then, the resulting mixture was stirred under a nitrogen atmosphere at room temperature for 2 hours.

Water was added to the reaction solution, and the organic matter was extracted with ethyl acetate. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=100:0 to 30:70 (v/v)), whereby the objective title compound was obtained as a colorless oily substance (316 mg, yield: 69%).

$^1$H NMR (CDCl$_3$, 500 MHz): δ1.19 (3H, t, J=6.8 Hz), 1.82-1.88 (1H, m), 2.02-2.09 (1H, m), 2.19-2.24 (1H, m), 2.26 (3H, s), 2.32 (3H, s), 2.52-2.59 (1H, m), 2.77-2.83 (1H, m), 2.84 (1H, dd, J=3.9, 6.4 Hz), 2.97-3.03 (1H, m), 3.31-3.37 (1H, m), 3.39-3.45 (1H, m), 3.78-3.81 (2H, m), 4.48 (1H, dd, J=3.9, 8.8 Hz), 5.72 (1H, dd, J=3.9, 6.8 Hz), 6.97 (1H, s), 6.98 (2H, d, J=8.8 Hz), 7.08 (1H, s), 7.25 (2H, d, J=8.8 Hz)

(62G) (3S)-3-(4-{[(1R)-4,6-Dimethyl-2,3-dihydro-1H-inden-1-yl]oxy}phenyl)-3-ethoxypropionic acid (3S)-3-(4-{[(1R)-4,6-Dimethyl-2,3-dihydro-1H-inden-1-yl]oxy}phenyl)-3-ethoxypropan-1-ol (316 mg, 0.928 mmol) produced in (62F) was dissolved in acetonitrile (8 mL), and a phosphate buffer (pH 6.8, 8 mL), 2,2,6,6-tetramethylpiperidine-N-oxyl (15 mg, 0.093 mmol), sodium chlorite (80%, 226 mg, 1.86 mmol), and an aqueous solution of sodium hypochlorite (effective chlorine concentration: 5%) (0.19 mL, 0.093 mmol) were sequentially added thereto at 0° C., and then, the resulting mixture was stirred at room temperature for 5 hours.

To the reaction solution, a 1 N aqueous solution of sodium hydroxide was added at 0° C. to adjust the pH of the solution to 8 to 9, and an aqueous solution of sodium sulfite was added thereto. Then, the pH of the solution was adjusted to 3 to 4 with 1 N hydrochloric acid, and the organic matter was extracted with ethyl acetate. The organic layer was washed with a saturated sodium chloride solution, then dried over anhydrous sodium sulfate and filtered. Then, the solvent was distilled off under reduced pressure, and the resulting residue was purified by silica gel column chromatography (hexane:ethyl acetate=100:0 to 0:100 (v/v)), whereby a crude product was obtained as a solid. This solid was washed with hexane, whereby the objective title compound was obtained as a white solid (212 mg, yield: 64%).

$^1$H NMR (CDCl$_3$, 500 MHz): δ1.21 (3H, t, J=7.0 Hz), 2.18-2.23 (1H, m), 2.26 (3H, s), 2.32 (3H, s), 2.52-2.59 (1H, m), 2.65 (1H, dd, J=3.9, 15.6 Hz), 2.77-2.82 (1H, m), 2.86 (1H, dd, J=9.8, 15.6 Hz), 2.97-3.04 (1H, m), 3.39-3.45 (1H, m), 3.45-3.51 (1H, m), 4.68 (1H, dd, J=3.9, 9.8 Hz), 5.71 (1H, dd, J=3.9, 6.4 Hz), 6.97 (1H, s), 7.00 (2H, d, J=8.8 Hz), 7.08 (1H, s), 7.26 (2H, d, J=8.8 Hz)
MS (ESI) m/z: 353 (M−H)$^−$

Example 63

(3S)-3-Ethoxy-3-(4-{[(1R)-4-(trifluoromethoxy)-2,3-dihydro-1H-inden-1-yl]oxy}phenyl)propionic acid
(Illustrative Compound No: 1-214)

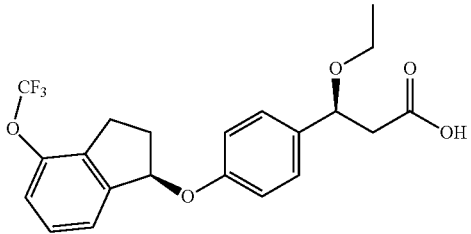

(63A) Methyl (2E)-3-[2-(trifluoromethoxy)phenyl]acrylate

A tetrahydrofuran (40 mL) solution of methyl dimethyl phosphonoacetate (7.3 mL, 50.6 mmol) was slowly added to a suspension of sodium hydride (about 63%, oily, 1.93 g, 50.6 mmol) and tetrahydrofuran (80 mL) at 0° C., and the resulting mixture was stirred under a nitrogen atmosphere for 30 minutes. A tetrahydrofuran (40 mL) solution of 2-(trifluoromethoxy)benzaldehyde (8.01 g, 42.1 mmol) was slowly added thereto, and the resulting mixture was stirred under a nitrogen atmosphere at room temperature for 2 hours. To the reaction solution, a saturated aqueous solution of ammonium chloride was added, and the organic matter was extracted with ethyl acetate. The organic layer was washed with a saturated sodium chloride solution, then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 85:15 (v/v)), whereby the objective title compound was obtained as a colorless oily substance (12.2 g, quantitative).

$^1$H NMR (CDCl$_3$, 500 MHz): δ3.83 (3H, s), 6.49 (1H, d, J=16.1 Hz), 7.35-7.28 (2H, m), 7.40-7.45 (1H, m), 7.66 (1H, dd, J=7.8, 1.5 Hz), 7.92 (1H, d, J=16.1 Hz)

(63B) 3-[2-(Trifluoromethoxy)phenyl]propionic acid

To a methanol solution of methyl (2E)-3-[2-(trifluoromethoxy)phenyl]acrylate (12.2 g, 49.6 mmol) produced in (63A), 10% palladium carbon (1.10 g) was added under a nitrogen atmosphere, and the resulting mixture was stirred under a hydrogen atmosphere at room temperature for 1.5 hours. After the reaction system was replaced with nitrogen, dichloromethane (90 mL) was added thereto, and the resulting mixture was filtered through a Celite filter. Then, the solvent was distilled off under reduced pressure, whereby a crude product was obtained. This crude product was used in the subsequent reaction step without performing further purification procedures.

The obtained crude product was dissolved in methanol (80 mL), and a 2 N aqueous solution of sodium hydroxide (42 mL, 84 mmol) was added thereto at room temperature, and then, the resulting mixture was stirred at room temperature for 30 minutes. After water was added to the reaction solution, 2 N hydrochloric acid (42 mL, 84 mmol) was added thereto, and the organic matter was extracted with dichloromethane. The organic layer was washed sequentially with water and a saturated sodium chloride solution, then dried over anhydrous sodium sulfate and filtered. Then, the solvent was distilled off under reduced pressure, whereby the objective title compound was obtained as a white solid (8.86 g, yield: 76%).

H NMR (CDCl$_3$, 400 MHz): δ2.69 (2H, t, J=7.7 Hz), 3.03 (2H, t, J=7.7 Hz), 7.20-7.33 (4H, m)

(63C) 4-(Trifluoromethoxy)indan-1-one

To 3-[2-(trifluoromethoxy)phenyl]propionic acid (1.06 g, 4.53 mmol) produced in (63B), polyphosphoric acid (20 g) was added, and the resulting mixture was heated and stirred at 70 to 80° C. for 2 hours. After ice water was added to the reaction solution, the organic matter was extracted with ethyl acetate. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=100:0 to 50:50 (v/v)), whereby the objective title compound was obtained as a light orange oily substance (336 mg, yield: 34%).

$^1$H NMR (CDCl$_3$, 400 MHz): δ2.75 (2H, t, J=5.9 Hz), 3.19 (2H, t, J=5.9 Hz), 7.51-7.42 (2H, m), 7.73 (1H, dd, J=7.1, 1.6 Hz)

(63D) (1S)-4-(Trifluoromethoxy)indan-1-ol

To a mixture of formic acid (0.225 mL, 5.85 mmol) and triethylamine (0.70 mL, 5.02 mmol), a dichloromethane (1.2 mL) solution of 4-(trifluoromethoxy)indan-1-one (362 mg, 1.67 mmol) produced in (63C) was added, and chloro[(1S, 2S)—N-(p-toluenesulfonyl)-1,2-diphenylethanediamine](mesitylene)ruthenium(II) (50 mg, 0.084 mmol) was added thereto at room temperature, and then, the resulting mixture was stirred under a nitrogen atmosphere at room temperature for 2 hours. The reaction solution was distilled off under reduced pressure, and the resulting crude product was purified by silica gel column chromatography (hexane:ethyl acetate=100:0 to 70:30 (v/v)), whereby the objective title compound was obtained as a white solid (361 mg, yield: 99%).

¹H NMR (CDCl₃, 400 MHz): δ1.79 (1H, brs), 1.94-2.03 (1H, m), 2.50-2.60 (1H, m), 2.81-2.90 (1H, m), 3.08-3.17 (1H, m), 5.30 (1H, t, J=6.0 Hz), 7.15 (1H, brd, J=7.9 Hz), 7.30 (1H, t like, J=7.6 Hz), 7.37 (1H, d, J=7.4 Hz)

(63E) Methyl (3S)-3-ethoxy-3-(4-{[(1R)-4-(trifluoromethoxy)-2,3-dihydro-1H-inden-1-yl]oxy}phenyl)propionate (1S)-4-(Trifluoromethoxy)indan-1-ol (143 mg, 0.655 mmol) produced in (63D) and methyl (3S)-3-ethoxy-3-(4-hydroxyphenyl)propionate (110 mg, 0.504 mmol) produced in Example 41 (41C) were dissolved in tetrahydrofuran (2.5 mL), and triphenylphosphine (175 mg, 0.655 mmol) and a 40% diethyl azodicarboxylate toluene solution (0.300 mL, 0.655 mmol) were added thereto at room temperature, and then, the resulting mixture was stirred under a nitrogen atmosphere at 60° C. for 4 hours. After the reaction solution was cooled to room temperature, the solvent was distilled off under reduced pressure, and the resulting residue was purified by silica gel column chromatography (hexane:ethyl acetate=95:5 to 75:25 (v/v)), whereby the objective title compound was obtained as a colorless oily substance (141 mg, yield: 66%).

¹H NMR (CDCl₃, 400 MHz): δ1.16 (3H, t, J=7.1 Hz), 2.19-2.29 (1H, m), 2.59 (1H, dd, J=15.1, 4.9 Hz), 2.54-2.67 (1H, m), 2.83 (1H, dd, J=15.1, 8.9 Hz), 2.93-3.04 (1H, m), 3.15-3.24 (1H, m), 3.31-3.45 (2H, m), 3.69 (3H, s), 4.72 (1H, dd, J=8.9, 4.9 Hz), 5.78 (1H, dd, J=7.0, 4.7 Hz), 6.98 (2H, d, J=9.0 Hz), 7.20 (1H, brd, J=7.8 Hz), 7.30 (2H, d, J=9.0 Hz), 7.26-7.33 (1H, m), 7.38 (1H, d, J=7.4 Hz)

(63F) (3S)-3-Ethoxy-3-(4-{[(1R)-4-(trifluoromethoxy)-2,3-dihydro-1H-inden-1-yl]oxy}phenyl)propionic acid Methyl (3S)-3-ethoxy-3-(4-{[(1R)-4-(trifluoromethoxy)-2,3-dihydro-1H-inden-1-yl]oxy}phenyl)propionate (141 mg, 0.332 mmol) produced in (63E) was dissolved in tetrahydrofuran (1.5 mL) and methanol (1.5 mL), and a 2 N aqueous solution of sodium hydroxide (0.500 mL, 1.00 mmol) and water (0.500 mL) were added thereto at room temperature, and then, the resulting mixture was stirred at room temperature for 1.5 hours. After water was added to the reaction solution, 2 N hydrochloric acid (0.500 mL, 1.00 mmol) was added thereto, and the organic matter was extracted with ethyl acetate. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=90:10 to 50:50 (v/v)), whereby the objective title compound was obtained as a white solid (135 mg, yield: 99%).

¹H NMR (CDCl₃, 400 MHz): δ1.21 (3H, t, J=7.0 Hz), 2.20-2.29 (1H, m), 2.66 (1H, dd, J=15.8, 4.0 Hz), 2.58-2.69 (1H, m), 2.86 (1H, dd, J=15.8, 9.6 Hz), 2.94-3.04 (1H, m), 3.15-3.25 (1H, m), 3.38-3.52 (2H, m), 4.71 (1H, dd, J=9.6, 4.0 Hz), 5.79 (1H, dd, J=6.9, 4.5 Hz), 7.00 (2H, d, J=8.6 Hz), 7.21 (1H, brd, J=7.8 Hz), 7.29 (2H, d, J=8.6 Hz), 7.27-7.34 (1H, m), 7.38 (1H, d, J=7.4 Hz)

MS (FAB) m/z: 449 (M+K)⁺

Example 64

(3S)-3-(4-{[(1R)-4-Cyclopropyl-2,3-dihydro-1H-inden-1-yl]oxy}phenyl)-3-ethoxypropionic acid (Illustrative Compound No: 1-190)

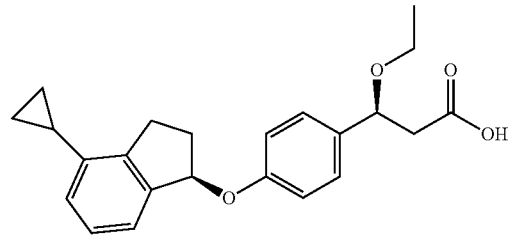

(64A) 4-Cyclopropylindan-1-one

To a toluene (6.0 mL) solution of 4-bromoindan-1-one (300 mg, 1.42 mmol), water (0.30 mL), cyclopropyl borate (158 mg, 1.85 mmol), potassium phosphate (1.05 g, 4.97 mmol), tricyclohexylphosphine (a 0.48 M toluene solution, 0.295 mL, 0.142 mmol), and palladium acetate (16 mg, 0.071 mmol) were sequentially added, and the resulting mixture was stirred under a nitrogen atmosphere at 100° C. for 4 hours. After the reaction solution was cooled to room temperature, water was added thereto, and the organic matter was extracted with ethyl acetate. The organic layer was washed with a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=100:0 to 80:20 (v/v)), whereby the objective title compound was obtained as a light yellow solid (211 mg, yield: 86%).

¹H NMR (CDCl₃, 400M Hz): δ0.71-0.77 (2H, m), 1.01-1.07 (2H, m), 1.92-2.01 (1H, m), 2.73 (2H, t, J=5.7 Hz), 3.20 (2H, t, J=5.7 Hz), 7.14 (1H, d, J=7.4 Hz), 7.31 (1H, t, J=7.4 Hz), 7.59 (1H, d, J=7.4 Hz)

(64B) (1S)-4-Cyclopropylindan-1-ol

To a mixture of formic acid (0.164 mL, 4.31 mmol) and triethylamine (0.510 mL, 3.68 mmol), a dichloromethane (1.5 mL) solution of 4-cyclopropylindan-1-one (211 mg, 1.23 mmol) produced in (64A) was added, and chloro[(1S,2S)—N-(p-toluenesulfonyl)-1,2-diphenylethanediamine](mesitylene)ruthenium(II) (23 mg, 0.037 mmol) was added thereto at room temperature, and then, the resulting mixture was stirred under a nitrogen atmosphere at room temperature for 1 hour. To the reaction solution, chloro[(1S,2S)—N-(p-toluenesulfonyl)-1,2-diphenylethanediamine](mesitylene)ruthenium (II) (15 mg, 0.025 mmol) was added again at room temperature, and the resulting mixture was stirred under a nitrogen atmosphere at room temperature for 3.5 hours. The reaction solution was distilled off under reduced pressure, and the resulting crude product was purified by silica gel column chromatography (hexane:ethyl acetate=100:0 to 75:25 (v/v)), whereby the objective title compound was obtained as a white solid (207 mg, yield: 97%).

¹H NMR (CDCl₃, 400 MHz): δ0.66-0.71 (2H, m), 0.91-0.98 (2H, m), 1.66 (1H, brs), 1.84-1.92 (1H, m), 1.94-2.03

(1H, m), 2.48-2.57 (1H, m), 2.84-2.93 (1H, m), 3.12-3.21 (1H, m), 5.26 (1H, brs), 6.82 (1H, d, J=7.4 Hz), 7.19 (1H, t, J=7.4 Hz), 7.24 (1H, d, J=7.4 Hz)

(64C) (3S)-3-(4-{[(1R)-4-Cyclopropyl-2,3-dihydro-1H-inden-1-yl]oxy}phenyl)-3-ethoxypropan-1-ol (1S)-4-Cyclopropylindan-1-ol (207 mg, 1.19 mmol) produced in (64B) and 4-{(1S)-1-ethoxy-3-[(triisopropyl silyl)oxy]propyl}phenol (504 mg, 1.43 mmol) produced in Example 50 (50E) were dissolved in tetrahydrofuran (5.0 mL), and triphenylphosphine (375 mg, 1.43 mmol) and a 40% diethyl azodicarboxylate toluene solution (0.650 mL, 1.43 mmol) were added thereto at room temperature, and then, the resulting mixture was stirred under a nitrogen atmosphere at 50° C. for 4 hours. After the reaction solution was cooled to room temperature, the solvent was distilled off under reduced pressure, and the resulting residue was roughly purified by silica gel column chromatography (hexane:ethyl acetate=100:0 to 91:9 (v/v)), whereby a crude product was obtained. This crude product was used in the subsequent reaction step without performing further purification procedures.

The crude product was dissolved in tetrahydrofuran (5.0 mL), and a 1.0 M tetra-n-butylammonium fluoride tetrahydrofuran solution (1.40 mL, 1.40 mmol) was added thereto at 0° C., and then, the resulting mixture was stirred under a nitrogen atmosphere at 40° C. for 2 hours. To the reaction solution, a saturated aqueous solution of ammonium chloride was added, and the organic matter was extracted with ethyl acetate. The organic layer was washed with water and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=90:10 to 40:60 (v/v)), whereby the objective title compound was obtained as a white solid (198 mg, yield: 47%).

$^1$H NMR (CDCl$_3$, 400 MHz): δ0.67-0.72 (2H, m), 0.93-0.98 (2H, m), 1.19 (3H, t, J=7.1 Hz), 1.81-1.94 (2H, m), 2.01-2.11 (1H, m), 2.20-2.30 (1H, m), 2.54-2.65 (1H, m), 2.88 (1H, brs), 2.97-3.06 (1H, m), 3.17-3.27 (1H, m), 3.30-3.47 (2H, m), 3.77-3.84 (2H, m), 4.48 (1H, dd, J=9.2, 4.1 Hz), 5.77 (1H, dd, J=6.8, 4.1 Hz), 6.88 (1H, d, J=7.5 Hz), 7.00 (2H, d, J=8.6 Hz), 7.19 (1H, t, J=7.5 Hz), 7.26 (2H, d, J=8.6 Hz), 7.23-7.28 (1H, m)

(64D) (3S)-3-(4-{[(1R)-4-Cyclopropyl-2,3-dihydro-1H-inden-1-yl]oxy}phenyl)-3-ethoxypropionic acid (3S)-3-(4-{[(1R)-4-Cyclopropyl-2,3-dihydro-1H-inden-1-yl]oxy}phenyl)-3-ethoxypropan-1-ol (198 mg, 0.562 mmol) produced in (64C) was dissolved in acetonitrile (6.0 mL), and a phosphate buffer (pH 6.8, 6.0 mL), 2,2,6,6-tetramethyl piperidine-N-oxyl (17.5 mg, 0.112 mmol), sodium chlorite (80%, 318 mg, 2.81 mmol), and an aqueous solution of sodium hypochlorite (effective chlorine concentration: 5%) (0.215 mL, 0.112 mmol) were sequentially added thereto at 0° C., and then, the resulting mixture was stirred at 0° C. for 1 hour. To the reaction solution, water (6 mL) and a 2 N aqueous solution of NaOH (1 mL) were added, and the resulting mixture was poured into a saturated aqueous solution of sodium sulfite at 0° C. 2 N Hydrochloric acid was added thereto to adjust the pH of the solution to 3 to 4, and the organic matter was extracted with ethyl acetate. The organic layer was washed with water and a saturated sodium chloride solution, then dried over anhydrous sodium sulfate and filtered. Then, the solvent was distilled off under reduced pressure, whereby a crude product was obtained. This crude product was purified by silica gel column chromatography (hexane:ethyl acetate=90:10 to 50:50 (v/v)), whereby the objective title compound was obtained as a white solid (186 mg, yield: 90%).

$^1$H NMR (CDCl$_3$, 400 MHz): δ0.67-0.73 (2H, m), 0.92-0.99 (2H, m), 1.21 (3H, t, J=7.1 Hz), 1.86-1.94 (1H, m), 2.20-2.29 (1H, m), 2.54-2.65 (1H, m), 2.66 (1H, dd, J=16.0, 3.8 Hz), 2.86 (1H, dd, J=16.0, 9.6 Hz), 2.97-3.06 (1H, m), 3.17-3.27 (1H, m), 3.36-3.53 (2H, m), 4.70 (1H, dd, J=9.6, 3.8 Hz), 5.77 (1H, dd, J=6.9, 4.1 Hz), 6.88 (1H, d, J=7.5 Hz), 7.01 (2H, d, J=8.6 Hz), 7.19 (1H, t, J=7.5 Hz), 7.28 (2H, d, J=8.6 Hz), 7.23-7.31 (1H, m)

MS (FAB) m/z: 405 (M+K)$^+$

Test Example 1

Oral Glucose Tolerance Test (1) Animal Used

Commercially available genetically obese impaired glucose tolerance rats (Crlj:ZUC-Lepr$^{fa}$/Lepr$^{fa}$ rats, male, 11 weeks of age at the time of use, purchased from Charles River Laboratories Japan, Inc.)

(2) Experimental Method and Results

The rats were preliminarily reared for 2 weeks by feeding them laboratory chow (FR-2, Funabashi Farm Co., Ltd.) ad libitum. Then, the rats were fasted for 15 to 18 hours and used as test animals. A suspension was prepared such that the concentration of a test compound fell within a range from 0.075 to 0.25 mg/mL using a 0.5% solution of methyl cellulose (Wako Pure Chemical Industries, Ltd.). The test compound was orally administered by gavage to the rats (6 rats in each group) at a dose of 0.3 to 1 mg/kg. To the rats in the control group, a 0.5% solution of methyl cellulose was orally administered at a dose of 4 mL/kg. The oral glucose loading was performed such that a glucose solution (Otsuka Glucose Injection 50%, Otsuka Pharmaceutical Co., Ltd.) was orally administered at a dose of 2 g/kg after 30 minutes from administration of the test compound.

The blood was collected from the tail vein of each rat, and the blood glucose level was measured after 30 minutes from the oral glucose loading using a fully automatic blood glucose meter (Glucoroder GXT, A& T Corporation), and the blood glucose lowering index (%) was calculated from the following equation. The blood glucose lowering index is shown in Table 3.

Blood glucose lowering index (%)=[1−(blood glucose level in test compound administration group)/(blood glucose level in control group)]×100

TABLE 3

| Example | Dose (mg/kg) | Blood glucose lowering index (%) |
|---|---|---|
| 1 | 1 | 25 |
| 16 | 1 | 39 |
| 17 | 1 | 38 |
| 18 | 1 | 35 |
| 20 | 1 | 15 |
| 23 | 1 | 16 |
| 24 | 1 | 37 |
| 25 | 1 | 39 |
| 49 | 1 | 37 |
| 50 | 1 | 38 |
| 51 | 1 | 42 |
| 52 | 1 | 15 |

TABLE 3-continued

| Example | Dose (mg/kg) | Blood glucose lowering index (%) |
|---|---|---|
| 53 | 1 | 41 |
| 55 | 0.3 | 38 |
| 56 | 0.3 | 40 |
| 57 | 1 | 50 |
| 58 | 1 | 35 |
| 59 | 0.3 | 32 |
| 60 | 1 | 48 |
| 61 | 0.3 | 34 |
| 62 | 0.3 | 33 |
| 63 | 1 | 45 |
| 64 | 0.3 | 30 |

Further, the collected blood is centrifuged, and the plasma is separated. The plasma is deproteinized and then, subjected to liquid chromatography and mass spectrometer systems, and the concentration of the compound is calculated. On the basis of the obtained concentration of the compound, the maximum blood concentration of the compound, AUC, half life, and the like can be calculated using analysis software such as WinNonlin (Pharsight, Inc.).

Test Example 2

Test for Evaluation of Enhancing Effect on Insulin Secretion

The plasma insulin level is measured for each of the blood samples collected at the time of the oral glucose tolerance test. The insulin level is measured by a radioimmunoassay using Rat Insulin RIA kit (Millipore Corporation).

From the above tests, it is found that the compound of the invention has an enhancing effect on insulin secretion.

From the above tests, it is found that the compound of the invention has an excellent blood glucose lowering effect, enhancing effect on insulin secretion, inhibitory effect on postprandial blood glucose, improving effect on impaired glucose tolerance, and the like. Further, it can be confirmed by a common procedure that the compound of the invention has excellent in vivo kinetics, is less likely to form a reactive metabolite, has a low plasma protein binding ratio, has a high water solubility, is less likely to be metabolized by an enzyme such as UDP-glucuronosyltransferase (UGT) or cytochrome P450 (CYP), can be sufficiently dissociated from cytochrome P450 (CYP) inhibitory effect, CYP inductive effect, or toxicity (such as cytotoxicity or respiratory chain inhibitory effect), and so on. Accordingly, the compound of the invention is considered to be useful as a preventive or therapeutic agent for hyperglycemia, diabetes mellitus, and pathological conditions or diseases associated with these diseases.

Preparation Examples

| (1) Capsule | |
|---|---|
| Example Compound 1 | 10 mg |
| Lactose | 110 mg |
| Cornstarch | 57 mg |
| Magnesium stearate | 3 mg |
| Total | 180 mg |

Powders of the respective components shown above are mixed well and packed in capsules, whereby a capsule preparation can be produced.

| (2) Tablet | |
|---|---|
| Example Compound 20 | 10 mg |
| Lactose | 86 mg |
| Cornstarch | 42 mg |
| Microcrystalline cellulose | 6 mg |
| Hydroxypropyl cellulose | 5 mg |
| Magnesium stearate | 1 mg |
| Total | 150 mg |

Powders of the respective components shown above are mixed well and compression molded into tablets each having a weight of 150 mg. If necessary, these tablets may be coated with a sugar or a film.

| (3) Granule | |
|---|---|
| Example Compound 52 | 10 mg |
| Lactose | 710 mg |
| Cornstarch | 210 mg |
| Microcrystalline cellulose | 40 mg |
| Hydroxypropyl cellulose | 30 mg |
| Total | 1000 mg |

Powders of the respective components shown above are mixed well, and an aqueous solution of a binder is added thereto and the resulting mixture is kneaded. Then, the kneaded material is formed into granules and dried. The dried granules are forcedly passed through a screen using a crushing, granulating and size reduction machine, whereby a granule preparation can be produced.

The invention claimed is:

1. A compound represented by the following general formula (I) or a pharmacologically acceptable salt thereof:

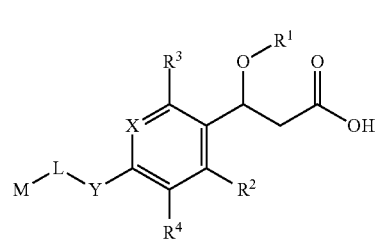

(I)

wherein X represents $=C(R^5)-$ or $=N-$; Y represents $-O-$ or $-NH-$; L represents a C1-C3 alkylene group optionally substituted with a halogen atom, a C1-C3 haloalkyl group or a C1-C3 alkyl group, or a bond; M represents a C3-C10 cycloalkyl group (the cycloalkyl group being optionally fused with one phenyl group or 4- to 10-membered heterocyclic ring containing 1 to 3 heteroatoms which may be the same or different and are selected from nitrogen, oxygen, and sulfur, and further optionally substituted with 1 to 5 substituents selected from substituent group α), a C6-C10 aryl group (the aryl group being optionally substituted with 1 to 5 substituents selected from substituent group α), or a 4- to 10-membered heterocyclic group containing 1 to 3 heteroatoms which may be the same or different and are selected from nitrogen, oxygen, and sulfur (the heterocyclic group being optionally substituted with 1 to 5 substituents selected from substituent group α); $R^1$ represents a C1-C6 alkyl group, a C3-C10 cycloalkyl group, a C1-C6 haloalkyl group, a C2-C6 alkenyl group, a C2-C6 alkynyl group, a C1-C6 aliphatic acyl group, a C1-C6 alkoxy C1-C6 alkyl group or a C6-C10 aryl group; $R^2$, $R^3$, $R^4$, and $R^5$ may be the same or different and each represents a hydrogen atom, a halogen atom, a C1-C3 alkyl group, a C1-C3 haloalkyl group, a C1-C3 alkoxy group or a nitro group; the alkyl group moieties of $R^1$ and $R^2$ being optionally bonded to each other to form a 5- to 6-membered heterocyclic ring containing one oxygen atom; and the substituent group α is selected from a halogen atom, a C1-C6 alkyl group, a C1-C6 haloalkyl group, a C1-C6 hydroxyalkyl group (the hydroxyalkyl group being optionally substituted with one C1-C6 alkyl group), a C1-C6 alkoxy C1-C6 alkyl group, a C1-C6 aminoalkyl group, a C1-C6 alkoxy group, a C1-C6 haloalkoxy group, a C6-C10 aryloxy group, a C1-C6 alkylthio group, a carboxy group, a C1-C6 alkoxycarbonyl group, a hydroxy group, a C1-C6 aliphatic acyl group, an amino group, a C1-C6 alkylamino group, a C3-C10 cycloalkylamino group, a C1-C6 dialkylamino group, a C1-C6 alkoxyamino group, a C1-C6 aliphatic acylamino group (the C1-C6 aliphatic acylamino group being optionally substituted with 1 to 3 halogen atoms), a cyano group, a nitro group, a C1-C6 alkylsulfonyl group, a C1-C6 dialkylaminosulfonyl group, a C3-C10 cycloalkyl group, and a C6-C10 aryl group (the aryl group being optionally substituted with one to five C1-C6 haloalkyl groups).

2. The compound according to claim 1, wherein X is =C($R^5$)— and $R^5$ is a hydrogen atom.

3. The compound according to claim 1, wherein Y is —O—.

4. The compound according to claim 1, wherein L is a bond or a C1-C3 alkylene group.

5. The compound according to claim 1, wherein M is a C3-C10 cycloalkyl group (the cycloalkyl group being optionally fused with one phenyl group, and further optionally substituted with 1 to 5 substituents selected from the substituent group α), a C6-C10 aryl group (the aryl group may be substituted with 1 to 5 groups selected from the substituent group α).

6. The compound according to claim 1, wherein $R^2$, $R^3$, and $R^4$ are each a hydrogen atom.

7. A compound represented by the following general formula (II) or a pharmacologically acceptable salt thereof:

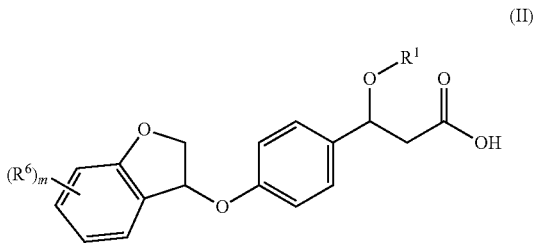

(II)

wherein $R^2$ represents a C1-C6 alkyl group, a C3-C10 cycloalkyl group, a C1-C6 haloalkyl group, a C2-C6 alkenyl group, a C2-C6 alkynyl group, a C1-C6 aliphatic acyl group, a C1-C6 alkoxy C1-C6 alkyl group or a C6-C10 aryl group; m represents an integer of any one of 0 to 3; $R^6$'s may be the same or different and each represents a halogen atom, a C1-C6 alkyl group, a C1-C6 haloalkyl group, a C1-C6 hydroxyalkyl group (the hydroxyalkyl group being optionally substituted with one C1-C6 alkyl group), a C1-C6 alkoxy C1-C6 alkyl group, a C1-C6 aminoalkyl group, a C1-C6 alkoxy group, a C1-C6 haloalkoxy group, a C6-C10 aryloxy group, a C1-C6 alkylthio group, a carboxy group, a C1-C6 alkoxycarbonyl group, a hydroxy group, a C1-C6 aliphatic acyl group, an amino group, a C1-C6 alkylamino group, a C3-C10 cycloalkylamino group, a C1-C6 dialkylamino group, a C1-C6 alkoxyamino group, a C1-C6 aliphatic acylamino group (the C1-C6 aliphatic acylamino group being optionally substituted with 1 to halogen atoms), a cyano group, a nitro group, a C1-C6 alkylsulfonyl group, a C1-C6 dialkylaminosulfonyl group, a C3-C10 cycloalkyl group, or a C6-C10 aryl group (the aryl group being optionally substituted with one to five C1-C6 haloalkyl groups).

8. The compound according to claim 7, wherein $R^1$ is a C1-C6 alkyl group.

9. The compound according to claim 7, wherein $R^1$ is an ethyl group.

10. The compound according to claim 7, wherein m is 1 or 2.

11. The compound according to claim 7, wherein $R^6$'s may be the same or different and are each a halogen atom, a C1-C6 alkyl group, a C1-C6 haloalkyl group, a C1-C6 alkoxy group, or a C1-C6 haloalkoxy group.

12. The compound according to claim 7, wherein $R^6$'s may be the same or different and are each a C1-C6 haloalkyl group or a C1-C6 haloalkoxy group.

13. A compound represented by the following general formula (III) or a pharmacologically acceptable salt thereof:

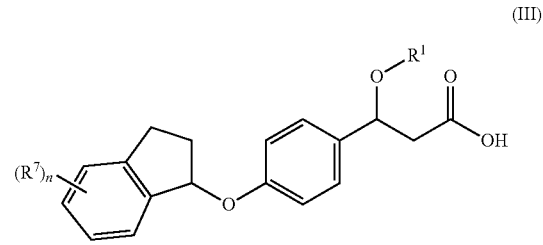

(III)

wherein $R^1$ represents a C1-C6 alkyl group, a C3-C10 cycloalkyl group, a C1-C6 haloalkyl group, a C2-C6 alkenyl group, a C2-C6 alkynyl group, a C1-C6 aliphatic acyl group, a C1-C6 alkoxy C1-C6 alkyl group or a C6-C10 aryl group; n represents an integer of any one of 0 to 3; $R^7$'s may be the same or different and each represents a halogen atom, a C1-C6 alkyl group, a C1-C6 haloalkyl group, a C1-C6 hydroxyalkyl group (the hydroxyalkyl group being optionally substituted with one C1-C6 alkyl group), a C1-C6 alkoxy C1-C6 alkyl group, a C1-C6 aminoalkyl group, a C1-C6 alkoxy group, a C1-C6 haloalkoxy group, a C6-C10 aryloxy group, a C1-C6 alkylthio group, a carboxy group, a C1-C6 alkoxycarbonyl group, a hydroxy group, a C1-C6 aliphatic acyl group, an amino group, a C1-C6 alkylamino group, a C3-C10 cycloalkylamino group, a C1-C6 dialkylamino group, a C1-C6 alkoxyamino group, a C1-C6 aliphatic acylamino group (the C1-C6 aliphatic acylamino group being optionally substituted with 1 to 3 halogen atoms), a cyano group, a nitro group, a C1-C6 alkylsulfonyl group, a C1-C6 dialkylaminosulfonyl group, a C3-C10 cycloalkyl group, or a C6-C10 aryl group (the aryl group being optionally substituted with one to five C1-C6 haloalkyl groups).

14. The compound according to claim 13, wherein $R^1$ is a C1-C6 alkyl group.

15. The compound according to claim 13, wherein $R^1$ is an ethyl group.

16. The compound according to claim 13, wherein n is 1 or 2.

17. The compound according to claim 13, wherein $R^7$'s may be the same or different and are each a halogen atom, a C1-C6 alkyl group, a C1-C6 haloalkyl group, a C1-C6 haloalkoxy group or a C3-C10 cycloalkyl group.

18. The compound according to claim 13, wherein $R^7$'s may be the same or different and are each a fluorine atom, a methyl group, an ethyl group, a difluoromethyl group, a trifluoromethyl group, or a trifluoromethoxy group.

19. A compound or a pharmacologically acceptable salt thereof, which is selected from the following 3-{4-[(3,4-Dichlorobenzyl)oxy]phenyl}-3-ethoxypropionic acid, (3S)-3-{4-[(3,4-dichlorobenzyl)oxy]phenyl}-3-ethoxypropionic acid, 3-ethoxy-3-(6-{[4-(trifluoromethyl)benzyl]oxy}pyridin-3-yl)propionic acid, (3S)-3-ethoxy-3-(6-{[4-(trifluoromethyl)benzyl]oxy}pyridin-3-yl)propionic acid, 3-ethoxy-3-{4-[(2-methylbenzyl)oxy]phenyl}propionic acid, 3-{4-[(4-cyano-1-naphthyl)oxy]phenyl}-3-ethoxypropionic acid, 3-[4-(3,5-dichlorophenoxy)phenyl]-3-ethoxypropionic acid, 3-[4-(2,5-dichlorophenoxy)phenyl]-3-ethoxypropionic acid, (3S)-3-ethoxy-3-(4-{[4-(trifluoromethyl)benzyl]oxy}phenyl)propionic acid, (3S)-3-(4-{[(1R)-4-chloro-2,3-dihydro-1H-inden-1-yl]oxy}-phenyl)-3-ethoxypropionic acid, (3S)-3-ethoxy-3-(4-{[(1R)-4-(trifluoromethyl)-2,3-dihydro-1H-inden-1-yl]oxy}phenyl)propionic acid, (3S)-3-(4-{[(1S)-4-chloro-2,3-dihydro-1H-inden-1-yl]oxy}-phenyl)-3-ethoxypropionic acid, or (3S)-3-ethoxy-3-(4-{[4-(trifluoromethyl)-2,3-dihydro-1H-inden-1-yl]oxy}phenyl)propionic acid.

20. A compound or a pharmacologically acceptable salt thereof, which is selected from the following (3S)-3-Ethoxy-3-(4-{[4-(trifluoromethyl)-2,3-dihydro-1H-inden-1-yl]oxy}phenyl)propionic acid, (3S)-3-Ethoxy-3-(4-{[(3S)-7-(trifluoromethoxy)-2,3-dihydro-1-benzofuran-3-yl]oxy}phenyl)propionic acid, (3S)-3-Ethoxy-3-(4-{[(1R)-5-fluoro-4-(trifluoromethyl)-2,3-dihydro-1H-inden-1-yl]oxy}phenyl)propionic acid, (3S)-3-Ethoxy-3-(4-{[(1R)-4-ethyl-2,3-dihydro-1H-inden-1-yl]oxy}phenyl)propionic acid, (3S)-3-(4-{[(1R)-4-(Difluoromethyl)-2,3-dihydro-1H-inden-1-yl]oxy}phenyl)-3-ethoxypropionic acid, (3S)-3-Ethoxy-3-(4-{[(1R)-6-fluoro-4-(trifluoromethyl)-2,3-dihydro-1H-inden-1-yl]oxy}phenyl)propionic acid, (3S)-3-(4-{[(1R)-4,6-Dimethyl-2,3-dihydro-1H-inden-1-yl]oxy}phenyl)-3-ethoxypropionic acid, or (3S)-3-Ethoxy-3-(4-{[(1R)-4-(trifluoromethoxy)-2,3-dihydro-1H-inden-1-yl]oxy}phenyl)propionic acid.

21. (3S)-3-Ethoxy-3-(4-{[(1R)-4-(trifluoromethyl)-2,3-dihydro-1H-inden-1-yl]oxy}phenyl)propionic acid.

22. (3S)-3-Ethoxy-3-(4-{[(1R)-4-methyl-2,3-dihydro-1H-inden-1-yl]oxy}phenyl)propionic acid.

23. (3S)-3-Ethoxy-3-(4-{[(3S)-7-(trifluoromethyl)-2,3-dihydro-1-benzofuran-3-yl]oxy}phenyl)propionic acid.

24. (3S)-3-(4-{[(1R)-4-Cyclopropyl-2,3-dihydro-1H-inden-1-yl]oxy}phenyl)-3-ethoxypropionic acid.

25. A pharmacologically acceptable salt of the compound according to any one of claims 21 to 24.

26. A pharmaceutical composition, comprising the compound or a pharmacologically acceptable salt thereof according to any one of claims 1, 7, 13, 19, or 20-24 as an active ingredient.

27. A method for treating a disease selected from diabetes mellitus, postprandial hyperglycemia, diabetic neuropathy, diabetic nephropathy, diabetic retinopathy, obesity relating to diabetes, comprising administering a pharmacologically effective amount of the compound or a pharmacologically acceptable salt thereof according to any one of claims 1, 7, 13, 19, or 20-24, or a pharmacologically acceptable ester thereof to a mammal.

\* \* \* \* \*